(12) United States Patent
Hattori et al.

(10) Patent No.: US 7,820,693 B2
(45) Date of Patent: Oct. 26, 2010

(54) 1-(2H)-ISOQUINOLONE DERIVATIVE

(75) Inventors: Kazuo Hattori, Kamakura (JP); Satoshi Niizuma, Kamakura (JP); Miyako Masubuchi, Kamakura (JP); Kohei Koyama, Kamakura (JP); Osamu Kondoh, Kamakura (JP); Toshiyuki Tsukaguchi, Kamakura (JP); Takehiro Okada, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 548 days.

(21) Appl. No.: 11/816,910

(22) PCT Filed: Feb. 22, 2006

(86) PCT No.: PCT/JP2006/303180

§ 371 (c)(1),
(2), (4) Date: Aug. 22, 2007

(87) PCT Pub. No.: WO2006/090743

PCT Pub. Date: Aug. 31, 2006

(65) Prior Publication Data
US 2009/0030195 A1 Jan. 29, 2009

(30) Foreign Application Priority Data
Feb. 22, 2005 (JP) ............................. 2005-045926
Aug. 17, 2005 (JP) ............................. 2005-236919

(51) Int. Cl.
A61K 31/47 (2006.01)
C07D 401/10 (2006.01)
(52) U.S. Cl. ........................................ 514/309; 546/141
(58) Field of Classification Search ........................ None
See application file for complete search history.

(56) References Cited

U.S. PATENT DOCUMENTS

| 4,461,773 A | 7/1984 | Gregory |
| 4,942,163 A | 7/1990 | Behrens |
| 2006/0205767 A1 | 9/2006 | Wong et al. |
| 2007/0185160 A1 | 8/2007 | Hattori et al. |

FOREIGN PATENT DOCUMENTS

| EP | 050827 A1 | 5/1982 |
| WO | 9851307 A1 | 11/1998 |
| WO | 9911624 A1 | 3/1999 |
| WO | 2005018568 A2 | 3/2005 |
| WO | 2005075431 A1 | 8/2005 |
| WO | 2005075432 A1 | 8/2005 |

OTHER PUBLICATIONS

Won-Jea Cho, et al. "Synthesis and Biological Evaluation of 3-Arylisoquinolines as Antitumor Agents." Bioorganic & Medicinal Chemistry Letters 8, 1998, p. 41-46.

Won-Jea Cho, et al. "Molecular Modeling of 3-Arylisoquinolines Antitumor Agents Active Against A-549. A Comparative Molecular Field Analysis Study." Bioorganic & Medicinal Chemistry Letters 10, 2002, p. 2953-2961.

Alain Rose, et al. "Oxygen Heterocycles. Part XIII. From 3-Arylisocoumarins to 3-Arlisoquinones and 4Aryl-5H-2,3-benzodiazepines."J. Chem. Soc. (C),1968, p. 2205-2208.

Graham S. Poindexter. "Convenient Preparation of 3-Substituted 1(2H)-Isoquinolinones." J. Org. Chem. 1982, 47, p. 3787-3788.

Won-Jea Gho. "Synthesis and Antitumor Activity of 3-Arylisoquinoline Derivatives." Arch. Pharm. Res. vol. 20, No. 3, 1997, p. 264-268.

Seung Hoon Cheon, et al. "Structure-Activity Relationship Studies of Isoquinolinone Type Anticancer Agent." Arch. Pharm. Res. vol. 24, No. 4, 2001, p. 276-208.

Thanh Nguyen Le, et al. "A Facile synthesis of benzo[c]phenanthiridine alkaloids: oxynitidine and oxysanguinarine using lithiated toluamide-benzonitrile cycloaddition." Tetrahedron Letters 45, 2004, p. 2763-2766.

Thanh Nguyen Le, et al. "A versatile total synthesis of benzo[c]phenanthridine alkaloids using lithiated toluamide-benzonitrile cycloaddition." J. Org. Chem., 2004, 69, 2768-2772.

John P. Wolfe, et al. "Simple, Efficient Catalyst System for the Palladium-Catalyzed Amination of Aryl Chlorides, Bromides, and Triflates." J. Org. Chem. 2000, 65, p. 1158-1174.

(Continued)

Primary Examiner—Zinna N Davis
(74) Attorney, Agent, or Firm—Browdy and Neimark, PLLC

(57) ABSTRACT

The present invention provides a compound having high antitumor activity, which is useful for therapeutic and preventive agents effective for proliferative diseases such as cancer; a production method thereof; an intermediate compound useful for such production; and a pharmaceutical composition comprising such a compound. The present invention provides a compound represented by the formula (1):

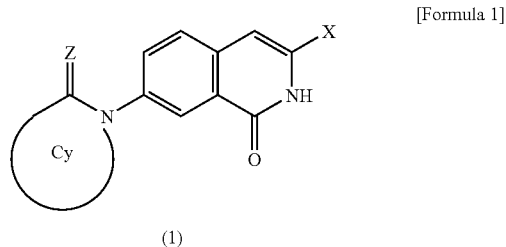

(1)

wherein X represents an aryl group or heteroaryl group which may be substituted, Cy represents a 4- to 7-membered monocyclic heterocyclic ring or a 8- to 10-membered condensed heterocyclic ring which may be substituted, and Z represents O, S, or NRa; or a prodrug thereof; or a pharmaceutically acceptable salt thereof; and a pharmaceutical and a pharmaceutical composition which comprise the compound.

16 Claims, No Drawings

OTHER PUBLICATIONS

Michele C. Harris, et al. "Improved Functional Group Compatibility in the Palladium-Catalyzed Synthesis of Aryl Amines." Org. Letters, 2002, 4, p. 2885-2888.

Xaohua Huang, et al. "New Ammonia Equivalents for the Pd-Catalyzed Aminaton of Ayl Halides." Org. Leters, 2001, 3, p. 3417-3419.

Kentaro Okano, et al. "Synthesis of Secondary Arylamines through Copper-Mediated Intermolecular Aryl Amination." Org. Letters, 2003, 5, p. 4987-4990.

Artis Klapars, et al. "A General and Efficient Copper Catalyst for the Amidation of Aryl Halides and the N-Arylation of Nitrogen Heterocycles." J. Am. Chem. Soc., 2001, 123, p. 7727-7729.

Artis Klapars, et al. "A General and Efficient Copper Catalyst for the Amidation of Aryl Halides." J. Am. Chem. Soc., 2002, 124, 7421-7428.

Teruo Umemoto, et al. "Synthesis, Properties, and Reactivity of N,N-Difluorobipyridinium and Related Salts and Their Applications as Reactive and Easy-to-Handle Electrophilic Fluorinating Agents with High Effective Fluorine Content." J. Org. Chem., 1998, 63, p. 3379-3385.

Noboru Yagi, et al. "Synthesis of N-Substituted-7-acylamino-3-phenylisocarbostyril and 6-Phenylbenzimidazor[2, 1-a]-isoquinoline Derivatives and their Fluorescence Spectra." Yuki Gosei Kagaku Kyokaishi, 1969, 27, p. 51-58.

Thanh Nguyen, et al. "Synthesis of Oxychelerythrine Using Lithiated Toluamide-Benzonitrile Cycloaddition." Chem. Pharm. Bull., 2005, 53, p. 118-120.

Thanh Nguyen, et al. "Total Synthesis of Oxyfagaronine, Phenolic Benza[c]phenanthridine and General Synthetic Way of 2,3,7,8- and 2,3,8,9-Tetrasubstituted Benzo[c]phenanthridine Alkaloids." Chem. Pahrm. Bull., 2006, 54, p. 476-480.

Tuanli Yao, et al. "Regio- and Stereoselective Synthesis of Isoindolin-1-ones via Electrophilic Cyclization." J. Org. Chem., 2005, 70, p. 1432-1437.

Jonathan L. Hartwell. "o-Chlorobromobenzene." Org. Synth. Collective, vol. 3, 1955, p. 185-187.

Peter J. Harrington, et al. "Palladium-Catalyzed Reactions in the Synthesis of 3- and 4-Substituted Indoles. Approaches to Ergot Alkaloids." J. Org. Chem., 1984, 49, p. 2657-2662.

Jingjun Yin, et al. "Palladium-Catalyzed Intermolecular Coupling of Aryl Halides and Amides." Org. Letters, 2000, 2, p. 1101-1104.

R. Greg Browning, et al. "Synhess of chra N-aryl pyrroidinones via a palladium-catayzed cross-couping reaction." Tetrahedron Letters, 2001, 42, p. 7155-7157.

Dominique Delaunay, et al. "Reactivity of β-Amino Alcohols with Carbon Disulfide. Study on the Synthesis of 2-Oxazolidinethiones and 2-Thiazolidinethiones." J. Org. Chem., 1995, 60, p. 6604-6607.

Mojmir Suchy, et al. "Synthesis, Absolute Configuration, and Enantiomeric Enrichment of a Cruciferous Oxindole Phytoalexin, (S)-(−)-Spirobrassinin, and Its Oxazoline Analog." J. Org. Chem., 2001, 66, p. 3940-3947.

Toshiya Morie, et al. "Asymmetric Synthesis of the Enantiomers of 2-Aminomethyl-4-(4-Fluorobenzyl) Morpholine, and Intermediate of Mosapride, a Gastroprokinetic Agent." Heterocycles, 1994, 38, p. 1033-1040.

Edwin J. Iwanowicz, et al. "Novel Guanidine-Based Inhibitors of Inosine Monophosphate Dehydrogenase." Bioorganic & Medicinal Chemistry Letters, 12, 2002, p. 2931-2934.

Qun Sun, et al. "Single Bead IR Monitoring or a Novel Benzimidazole Synthesis." Bioorganic & Medicinal Chemistry Letters, 8, 1998, p. 361-364.

John J. Baldwin, et al. "β1-Selective Adrenoceptor Antagonists: Example of the 2-[4-[3-(Substituted amino)-2-hydroxypropoxy]phenyl]imidazole Class. 2." J. Med. Chem., 1986, 29, p. 1065-1080.

Marlys Hammond, et al. "Structure-Activity Relationships in a Series of NPY Y5 Antagonists: 3-Amido-9-ethylcarazoles, Core-Modified Analogues and Amide Isosteres." Bioorganic & Medicinal Chemistry Letters, 13, 2001, p. 1989-1992.

P.C. Reeves, et al. Jikken Kagaku Koza, Fourth Series, vol. 22, 1992, p. 43-82.

Keisike Kurita, et al. "Trichloromethyl Chloroformate as a Phosgene Equivalent: 3-Isocyanatopopanoyl Chloride." Org. Synth. Collective, col. 6, 1988, p. 715-718.

Y. Watanabe, et al. Jikken Kagaku Koza, Fourth Series, vol. 20, 1992, p. 358-359.

Ulrike Peters, et al. "Platelet Activating Factor Synthetic Studies." Tetrahedron, 1987, 43, p. 3803-3816.

Edward J. Glamkowski, et al . "7-(Aminoacyl) and 7-(Aminoalkyl) Derivatives of 1, 2,6,7-Tetrahydoindolo [1,7-ab] ,[1,5]benzodiazepines as Potential Antidepressant Agents." Bioorg. Med. Chem., 1980, 23, p. 1380-1386.

N. Selvakumar, et al. "Influence of Ethylene-Oxy Spacer Group on the Activity of Linezolid: Synthesis of Potent Antibacterials Possessing a Thiocarbonyl Group." Bioorg. Med. Chem. Letters, 2003, 13, p. 4167-4172.

John Boot, et al. "Discovery and strucure-activity relationships of novel selectve norepinephrine and dual serotonin/norepinephrine reuptake inhibitors." Bioorg. Med. Chem. Letters, 2005, 15, p. 699-703.

Daniela Spera, et al. "Estradiol derivatives bearing sulfur-containing substituents at the 11β or 7α positions: versatile reagents for the preparation of estrogen conjugates." Bioorg. Med. Chem. Letters, 2004, 12, p. 4393-4401.

Jikken Kagaku Koza, Fourth Series, vol. 22, 1992, p. 137-173.

Munetaka Kunishima, et al. "Formation of carboxamides by direct condensation of carboxylic acides and amines in alcohols using a new alcohol- and water-soluble condensing agent: DMT-MM." Tetrahedron, 2001, 57, p. 1551-1558.

H.J. Zhu, et al. "Chiral Ligunds Derived from Abrine 8. An Experimental and Theoretical Study of Free Ligand Conformational Preferences and the Addition of Diethylzine to Benzaldehyde." J. Org. Chem., 2005, 70, p. 261-267.

Seung Hoon Cheon. et al, "Structure-Activity Relationship Studies of Isoquinolinone Type Anticancer Agent." Arch. Pharm. Res. vol. 24, No. 4, p. 276-280 (2001).

Fujioka et al, Tetrahedron Lett. vol. 46, pp. 2197-2199 (2005).

1-(2H)-ISOQUINOLONE DERIVATIVE

This application is a 371 of PCT JP2006/303180 filed Feb. 22, 2006.

FIELD OF THE INVENTION

The present invention relates to a novel 1-(2H)-isoquinolone derivative and a pharmaceutical comprising the same as an active ingredient. The present invention particularly relates to an antitumor agent useful as a therapeutic agent for diseases such as solid cancer.

DESCRIPTION OF THE RELATED ART

Regarding a method for synthesizing a 1-(2H)-isoquinolone derivative having a substituent at position 3, several reports have already been made. For example, in 1968, Rose et al, have reported a method of allowing ammonia to act on a 3-aryl isocoumarin derivative, so as to synthesize a 1-(2H)-isoquinolone derivative (see to Non-Patent Document 1). In addition, in 1982, Poindexter has reported a method of synthesizing a 1-(2H)-isoquinolone derivative by the reaction of N,2-dimethylbenzamide with a nitrile derivative (see to Non-Patent Document 2).

Moreover, the pharmacological activity of such an isoquinolone derivative has also been reported. Researchers of Octamer have reported an isoquinolone derivative having anti-inflammatory action (see to Patent Document 1). Also, researchers of Guilford have reported that 3-phenyl-1-(2H)-isoquinolone has an inhibitory activity on poly(ADP-ribose) polymerase, and that it can be used as a radiosensitizer (see to Patent Document 3). Moreover, with regard to an isoquinolone derivative having anticancer action, in 1989, researchers of Du Pont have reported that a 3-(1-naphthyl)-1-(2H)-isoquinolone derivative exhibits anticancer action (see to Patent Document 2). Furthermore, a patent application, which is pending simultaneously with the present application, discloses a 1-(2H)-isoquinolone derivative exhibiting anticancer action (published after the priority date of the present application; see to Patent Documents 4 and 5). Thereafter, Won-Jea Cho et al. have reported a 3-aryl isoquinolone derivative having anticancer action (see to Non-Patent Documents 3 to 8). However, among such isoquinolone derivatives, no compounds have been commercialized as anticancer agent to date. Thus, it has been desired that a compound having higher anticancer activity and also having preferred physical properties be developed.

[Patent Document 1] International Publication WO98/51307
[Patent Document 2] U.S. Pat. No. 4,942,163
[Patent Document 3] International Publication WO99/11624
[Patent Document 4] International Publication WO2005/075431
[Patent Document 5] International Publication WO2005/075432
[Non-Patent Document 1] J. Chem. Soc. (C), pp. 2205-2208 (1968)
[Non-Patent Document 2] J. Org. Chem., vol. 47, pp. 3787-3788 (1982)
[Non-Patent Document 3] Arch. Pharm. Res., vol. 20, pp. 264-268 (1997)
[Non-Patent Document 4] Bioorg. Med. Chem. Lett., vol. 8, pp. 41-46 (1998)
[Non-Patent Document 5] Arch. Pharm. Res., vol. 24, pp. 276-280 (2001)
[Non-Patent Document 6] Bioorg. Med. Chem., vol. 10, pp. 2953-2961 (2002)
[Non-Patent Document 7] Tetrahedron Lett., vol. 45, pp. 2763-2766 (2004)
[Non-Patent Document 8] J. Org. Chem., vol. 69, pp. 2768-2772 (2004)

DISCLOSURE OF THE INVENTION

Problems to be Solved by the Invention

It is an object of the present invention to provide a compound, which has high antitumor activity and is useful as a therapeutic and preventive agent effective for proliferative diseases such as cancer, a production method thereof, an intermediate compound useful for such production, and a pharmaceutical composition comprising such a compound.

Means for Solving the Problems

The present inventors have conducted intensive studies directed towards providing a novel therapeutic and preventive agent, which is effective for proliferative diseases such as cancer. As a result, the inventors have found that the compound of the present invention has excellent antitumor activity and is excellent in terms of solubility in water, and that it has preferred properties as a pharmaceutical in terms of safety or the like, thereby completing the present invention.

That is to say, in one aspect, the present invention provides a compound represented by the following formula (1):

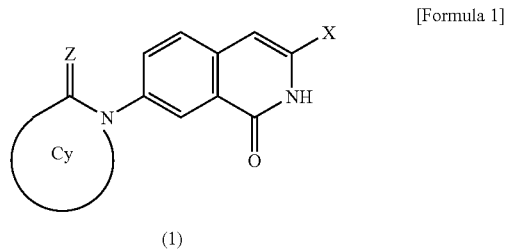

[Formula 1]

(1)

wherein X represents an aryl group or heteroaryl group, wherein the aryl group or heteroaryl group may be substituted with one or more substituents selected from Group A;

wherein Group A consists of a $C_{1-8}$ alkyl group (wherein the alkyl group may be substituted with one or more substituents selected from a halogen atom, an aryl group, a heteroaryl group, —$OR^{11}$, and —$NR^{12}R^{13}$), a $C_{2-7}$ alkenyl group (wherein the $C_{2-7}$ alkenyl group may be substituted with one or more substituents selected from a halogen atom, a $C_{1-8}$ alkyl group, an aryl $C_{1-6}$ alkyl group, an aryl group, and a heteroaryl group), a $C_{2-7}$ alkynyl group (wherein the $C_{2-7}$ alkynyl group may be substituted with one or more substituents selected from a halogen atom, a $C_{1-8}$ alkyl group, an aryl $C_{1-6}$ alkyl group, an aryl group, and a heteroaryl group), a halogen atom, a hydroxyl group, an aryl group, a heteroaryl group, a cyano group, an amino group (wherein the nitrogen atom of the amino group may be substituted with one or two substituents selected from a $C_{1-8}$ alkyl group, which may be substituted with —$OR^{11}$ or —$NR^{12}R^{13}$, an aryl group, an aryl $C_{1-6}$ alkyl group, and a heteroaryl group), —$S(O)_{n1}R^{14}$ (wherein n1 represents an integer from 0 to 2), a $C_{1-6}$ alkoxy group (wherein the alkoxy group may be substituted with one or more groups selected from an aryl group, a heteroaryl group, —$OR^{11}$, —$NR^{12}R^{13}$, and a halogen atom), a 4- to 7-membered heterocyclyl group (wherein the heterocyclyl group may be substituted with one or more substituents selected from a $C_{1-8}$ alkyl group, an aryl group, an aryl $C_{1-6}$ alkyl group, and a heteroaryl group), an aryloxy group, a heteroaryloxy group, and a $C_{1-6}$ alkylenedioxy group;

wherein each of $R^{11}$, $R^{12}$, $R^{13}$, and $R^{14}$ is independently selected from a hydrogen atom, a $C_{1-8}$ alkyl group (wherein the alkyl group may be substituted with one or more substituents selected from a hydroxyl group, a $C_{1-6}$ alkoxy group, an aryl $C_{1-6}$ alkoxy group, an aryl group, and a heteroaryl group), an aryl group, and a heteroaryl group; or $R^{12}$ and $R^{13}$, together with nitrogen to which they bind, may form a 4- to 7-membered heterocyclic ring containing at least one nitrogen atom;

Z represents O, S, or NRa, wherein Ra represents a hydrogen atom, a $C_{1-8}$ alkyl group, an aryl $C_{1-6}$ alkyl group, an aryl group, or a heteroaryl group;

Cy represents a 4- to 7-membered monocyclic heterocyclic ring or a 8- to 10-membered condensed heterocyclic ring, wherein the carbon atom(s) of the heterocyclic ring may be substituted with one or more substituents selected from Group Q1, and when the heterocyclic ring contains —NH—, the nitrogen atom may be substituted with a substituent selected from Group Q2;

wherein Group Q1 consists of a $C_{1-8}$ alkyl group, which may be substituted with one or more substituents selected from Group B, a $C_{2-7}$ alkenyl group, which may be substituted with one or more substituents selected from Group B, a hydroxyl group, a $C_{1-6}$ alkoxy group (wherein the alkoxy group may be substituted with one or more substituents selected from a halogen atom, a hydroxyl group, a $C_{1-6}$ alkoxy group, an amino group, a $C_{1-6}$ alkylamino group, a di($C_{1-6}$ alkyl)amino group, an aryl group, and a heteroaryl group), a $C_{1-6}$ alkylcarbonyl group, —CONR$^{21}$R$^{22}$, a carboxy group, a $C_{1-6}$ alkoxycarbonyl group, which may be substituted with an aryl group, an aryloxy group, a heteroaryloxy group, an amino group, a $C_{1-6}$ alkylamino group, a di($C_{1-6}$ alkyl)amino group, a 4- to 7-membered heterocyclyl group (wherein the heterocyclyl group may be substituted with one or two substituents selected from a $C_{1-8}$ alkyl group, an aryl group, an aryl $C_{1-6}$ alkyl group, and a heteroaryl group), an oxo group, and a thioxo group;

wherein each of $R^{21}$ and $R^{22}$ is independently selected from a hydrogen atom, a $C_{1-8}$ alkyl group (wherein the alkyl group may be substituted with one or more substituents selected from a halogen atom, a hydroxyl group, a $C_{1-6}$ alkoxy group, an aryl group, an amino group, a $C_{1-6}$ alkylamino group, and a di($C_{1-6}$ alkyl)amino group), an aryl group, and a heteroaryl group; or $R^{21}$ and $R^{22}$, together with a nitrogen atom to which they bind, may form a 4- to 7-membered heterocyclyl group containing at least one nitrogen atom (wherein the heterocyclyl group may be substituted with one or more substituents selected from a hydroxyl group, a $C_{1-8}$ alkyl group (wherein the alkyl group may be substituted with one or more substituents selected from a hydroxyl group, a $C_{1-8}$ alkoxy group, and an aryl group), an aryl group, and a heteroaryl group);

wherein Group Q2 consists of a $C_{1-8}$ alkyl group (wherein the alkyl group may be substituted with one or more substituents selected from a halogen atom, a hydroxyl group, a $C_{1-6}$ alkoxy group, an amino group, a $C_{1-6}$ alkylamino group, a di($C_{1-6}$ alkyl)amino group, an aryl group, and a heteroaryl group), a $C_{1-6}$ alkoxycarbonyl group, an aryl $C_{1-6}$ alkoxycarbonyl group, an aryl group, and a heteroaryl group;

wherein Group B consists of a halogen atom, an aryl group, a heteroaryl group, an oxo group, a $C_{1-6}$ alkylcarbonyl group, a $C_{1-6}$ alkylaminocarbonyl group, a di($C_{1-6}$ alkyl)aminocarbonyl group, a $C_{1-6}$ alkoxycarbonyl group, an azido group, —OR$^{31}$, —NR$^{32}$R$^{33}$, and —S(O)$_{n2}$R$^3$ (wherein n2 represents an integer from 0 to 2);

wherein $R^{31}$ is selected from a hydrogen atom, —PO(OR$^{41}$)OR$^{42}$, a $C_{1-8}$ alkyl group (wherein the alkyl group may be substituted with one or more substituents selected from a halogen atom, a hydroxyl group, a $C_{1-6}$ alkoxy group, which may be substituted with a $C_{1-6}$ alkoxy group, an aryl group, and —NR$^{34}$R$^{35}$), an aryl group, a heteroaryl group, a $C_{1-6}$ alkylcarbonyl group, a $C_{2-7}$ alkenylcarbonyl group, a $C_{3-8}$ cycloalkylcarbonyl group (wherein the $C_{1-6}$ alkylcarbonyl group, $C_{2-7}$alkenylcarbonyl group, and $C_{3-8}$ cycloalkylcarbonyl group may be substituted with one or more substituents selected from a hydroxyl group, —NR$^{37}$R$^{38}$, an aryl group, which may be substituted with a hydroxyl group, a heteroaryl group, a mercapto group, a $C_{1-6}$ alkylthio group, a guanidyl group, a carboxy group, a $C_{1-6}$ alkoxycarbonyl group, a $C_{1-6}$ alkylcarbonyloxy group, an aryl $C_{1-6}$ alkoxy group, an aminocarbonyl group, a $C_{1-6}$ alkylaminocarbonyl group, and a di($C_{1-6}$ alkyl)aminocarbonyl group (wherein the $C_{1-6}$ alkylaminocarbonyl group and di($C_{1-6}$ alkyl)aminocarbonyl group may be substituted with one or more substituents selected from an amino group, a $C_{1-6}$ alkylamino group, and a di($C_{1-6}$ alkyl)amino group), and —(OCHR$^{74}$CH$_2$)$_l$—OR$^{73}$ (wherein l represents an integer from 1 to 20), an arylcarbonyl group, a heteroarylcarbonyl group, a 4- to 12-membered heterocyclyl carbonyl group (wherein the arylcarbonyl group, heteroarylcarbonyl group, and heterocyclyl carbonyl group may be substituted with one or more substituents selected from a hydroxyl group, a carboxy group, a $C_{1-6}$ alkyl group, a $C_{1-6}$ alkoxycarbonyl group, a $C_{1-6}$ alkylcarbonyl group (wherein the $C_{1-6}$ alkoxycarbonyl group and $C_{1-6}$ alkylcarbonyl group may be substituted with one or more substituents selected from a hydroxyl group, —NR$^{84}$R$^{85}$, and a carboxy group), a $C_{1-6}$ alkoxycarbonyl group (wherein the $C_{1-6}$ alkoxycarbonyl group may be substituted with one or more 4- to 12-membered heterocyclyl groups), —CONR$^{71}$R$^{72}$, —CO(OCHR$^{76}$CH$_2$)$_k$—OR$^{75}$ (wherein k represents an integer from 1 to 20), and —S(O)$_{n3}$R$^{81}$ (wherein n3 represents an integer of 1 or 2);

each of $R^{32}$, $R^{33}$, $R^{34}$, $R^{35}$, $R^{37}$, $R^{38}$, $R^{71}$, $R^{72}$, $R^{84}$, and $R^5$ is independently selected from a hydrogen atom, a $C_{1-8}$ alkyl group (wherein the alkyl group may be substituted with one or more substituents selected from a halogen atom, a hydroxyl group, a $C_{1-6}$ alkoxy group, —(OCH$_2$CH$_2$)$_m$—OH (wherein m represents an integer from 1 to 20), a $C_{1-6}$ alkoxycarbonyl group, an aryl group, an amino group, a $C_{1-6}$ alkylamino group, and a di($C_{1-6}$ alkyl)amino group), —S(O)$_{n4}$R$^{83}$ (wherein n4 represents an integer of 1 or 2), a $C_{1-6}$ alkylcarbonyl group (wherein the $C_{1-6}$ alkylcarbonyl group may be substituted with one or more substituents selected from an amino group, a $C_{1-6}$ alkylamino group, a di($C_{1-6}$ alkyl)amino group, an aminocarbonyl group, an aryl group, which may be substituted with a hydroxyl group, a heteroaryl group, a hydroxyl group, a mercapto group, a $C_{1-6}$ alkylthio group, a guanidyl group, and a carboxy group), a $C_{1-6}$ alkylaminocarbonyl group, a $C_{1-6}$ alkoxycarbonyl group, a 4- to 7-membered heterocyclyl carbonyl group, an aryl group, and a heteroaryl group; or $R^{32}$ and $R^{33}$, $R^{34}$ and $R^{35}$, $R^{37}$ and $R^{38}$, and $R^{84}$ and $R^{85}$, together with a nitrogen atom to which they bind, may form a 4- to 7-membered heterocyclyl group containing at least one nitrogen atom (wherein the heterocyclyl group may be substituted with one or more substituents selected from a hydroxyl group, a $C_{1-8}$ alkyl group (wherein the alkyl group may be substituted with one or more substituents selected from a hydroxyl group, a $C_{1-8}$ alkoxy group, and an aryl group), a $C_{1-8}$ alkoxy group (wherein the alkoxy group may be substituted with one or more substituents selected from a hydroxyl group, a $C_{1-8}$ alkoxy group, and an aryl group), an aryl group, and a heteroaryl group);

each of $R^{39}$ and $R^{83}$ is independently selected from a hydrogen atom, a $C_{1-8}$ alkyl group (wherein the alkyl group may be substituted with one or more substituents selected from a hydroxyl group, a $C_{1-6}$ alkoxy group, an aryl $C_{1-6}$ alkoxy group, an aryl group, and a heteroaryl group), a $C_{2-8}$ alkenyl group, a $C_{3-6}$ cycloalkyl group, an aryl group, and a heteroaryl group;

each of $R^{41}$ and $R^{42}$ is independently selected from a hydrogen atom, an aryl $C_{1-6}$ alkyl group, and a $C_{1-8}$ alkyl group;

each of $R^{73}$ and $R^{75}$ is independently selected from a hydrogen atom, a $C_{1-6}$ alkyl group, which may be substituted with one or more hydroxyl groups, and an aryl $C_{1-6}$ alkyl group;

each occurrence of $R^{74}$ and $R^{76}$ is independently selected from a hydrogen atom, a $C_{1-6}$ alkyl group, a $C_{1-6}$ alkyl group, which is substituted with a hydroxyl group, and —CH$_2$(OCH$_2$CH$_2$)$_i$—OR$^{80}$ (wherein i represents an integer from 1 to 20);

$R^{80}$ is selected from a hydrogen atom, an aryl $C_{1-6}$ alkyl group, and a $C_{1-6}$ alkyl group, which may be substituted with one or more hydroxyl groups; and $R^{81}$ represents a $C_{1-6}$ alkyl group, or a prodrug thereof, or a pharmaceutically acceptable salt thereof.

In one aspect of the present invention, Cy is not particularly limited. It may be a heterocyclic ring selected from the following group, for example:

[Formula 2]

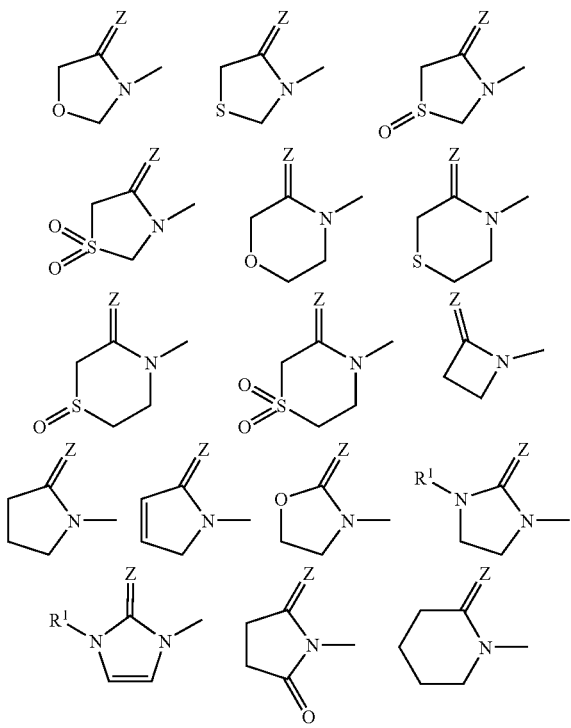

-continued

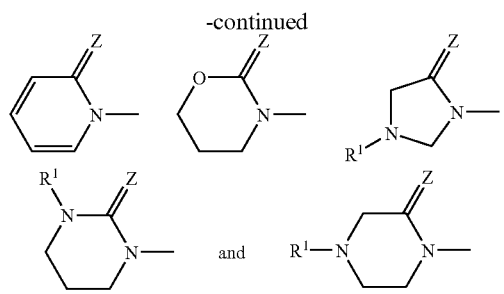

wherein the carbon atom(s) of the heterocyclic ring may be substituted with one or more substituents selected from Group Q1; and $R^1$ represents a hydrogen atom, a $C_{1-8}$ alkyl group (wherein the alkyl group may be substituted with one or more substituents selected from a halogen atom, a hydroxyl group, a $C_{1-6}$ alkoxy group, an amino group, a $C_{1-6}$ alkylamino group, a di($C_{1-6}$ alkyl)amino group, an aryl group, and a heteroaryl group), a $C_{1-6}$ alkoxycarbonyl group, an aryl $C_{1-6}$ alkoxycarbonyl group, an aryl group, or a heteroaryl group.

In another aspect of the present invention, Cy may be a heterocyclic ring selected from the following group:

[Formula 3]

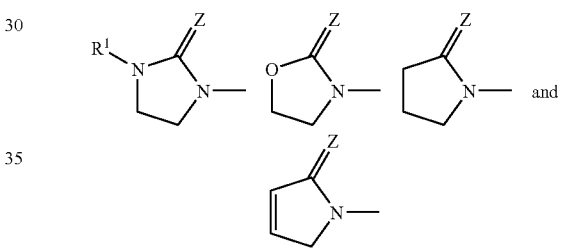

In another aspect of the present invention, the carbon atom(s) of Cy are substituted with one or two groups selected from a hydroxyl group, and the groups —C(=O)—OR$^{50}$, —CR$^{51}$R$^{52}$—OR$^{53}$, CR$^z$R$^q$CR$^{51}$R$^{52}$—OR$^{53}$, —C(=O)—NR$^{54}$R$^{55}$, and —CR$^{51}$R$^{52}$—NR$^{56}$R$^{57}$;

$R^{50}$ represents a hydrogen atom or a $C_{1-6}$ alkyl group (wherein the alkyl group may be substituted with a hydroxyl group or a $C_{1-6}$ alkoxy group);

each of $R^{51}$ and $R^{52}$ is independently selected from a hydrogen atom, a $C_{1-3}$ alkyl group (wherein the alkyl group may be substituted with one or more substituents selected from a hydroxyl group and an amino group), and a $C_{2-3}$ alkenyl group;

each of $R^z$ and $R^q$ is independently selected from a hydrogen atom and a $C_{1-3}$ alkyl group;

$R^{53}$ represents a hydrogen atom, a $C_{1-6}$ alkyl group (wherein the alkyl group may be substituted with 1 to 3 substituents selected from an aryl group, a hydroxyl group, a $C_{1-6}$ alkoxy group, a $C_{1-6}$ alkoxy $C_{1-6}$ alkoxy group, and —NR$^x$R$^y$), a $C_{1-6}$ alkylcarbonyl group (wherein the alkylcarbonyl group may be substituted with 1 to 3 substituents selected from a hydroxyl group, a $C_{1-3}$ alkoxy group, an aryl group, —NR$^{61}$R$^{62}$, a carboxy group, —CONR$^{63}$R$^{64}$, and —(OCHR$^{74}$CH$_2$)$_l$—OR$^{73}$ (wherein R$^{73}$, R$^{74}$, and l are the same as those defined above)), an arylcarbonyl group or a 4- to 7-membered heterocyclyl carbonyl group (wherein the arylcarbonyl group and heterocyclyl carbonyl group may be substituted with one or more substituents selected from a carboxy group, a $C_{1-6}$ alkoxycarbonyl group, and a $C_{1-6}$ alkylcarbonyl group (wherein the $C_{1-6}$ alkoxycarbonyl group and $C_{1-6}$ alkylcarbonyl group may be substituted with one or more substituents selected from —$NR^{61}R^{62}$, a carboxy group, and a hydroxyl group)), or —$CO(OCHR^{76}CH_2)_k$—$OR^{75}$ (wherein $R^{75}$, $R^{76}$, and k are the same as those defined above), each of $R^{54}$ and $R^{55}$ is independently selected from a hydrogen atom and a $C_{1-6}$ alkyl group (wherein the alkyl group may be substituted with a hydroxyl group or an amino group); or $R^{54}$ and $R^{55}$, together with a nitrogen atom to which they bind, may form a 4- to 7-membered heterocyclic ring (wherein the heterocyclic ring may be substituted with 1 to 3 substituents selected from a hydroxyl group and a hydroxy $C_{1-6}$ alkyl group);

each of $R^{56}$ and $R^{57}$ is independently selected from a hydrogen atom, a $C_{1-6}$ alkyl group (wherein the alkyl group may be substituted with a hydroxyl group or an amino group), and a $C_{1-6}$ alkylsulfonyl group (wherein the alkylsulfonyl group may be substituted with a hydroxyl group or an amino group); or $R^{56}$ and $R^{57}$, together with a nitrogen atom to which they bind, may form a 4- to 7-membered heterocyclic ring (wherein the heterocyclic ring may be substituted with 1 to 3 substituents selected from a hydroxyl group and a hydroxy $C_{1-6}$ alkyl group);

each of $R^{61}$ and $R^{62}$ is independently selected from a hydrogen atom, a $C_{1-6}$ alkyl group, and a $C_{1-6}$ alkylcarbonyl group (wherein the alkylcarbonyl group may be substituted with 1 to 3 substituents selected from a hydroxyl group, a $C_{1-3}$ alkoxy group, an aryl group, an amino group, a $C_{1-6}$ alkylamino group, a di($C_{1-6}$ alkyl)amino group, and a carboxy group); or $R^{61}$ and $R^{62}$, together with a nitrogen atom to which they bind, may form a 4- to 7-membered heterocyclic ring;

each of $R^x$ and $R^y$ is independently selected from a hydrogen atom and a $C_{1-6}$ alkyl group, and each of $R^{63}$ and $R^{64}$ is independently selected from a hydrogen atom and a $C_{1-6}$ alkyl group (wherein the alkyl group may be substituted with a hydroxyl group or an amino group); or $R^x$ and $R^y$, or $R^{63}$ and $R^{64}$, together with a nitrogen atom to which they bind, may form a 4- to 7-membered heterocyclic ring.

In another aspect of the present invention, the substituent(s) on the ring carbon atom(s) of Cy are selected from a hydroxyl group, a $C_{1-8}$ alkyl group (wherein the alkyl group may be substituted with one or more substituents selected from a hydroxyl group, a $C_{1-6}$ alkylamino group, a di($C_{1-6}$ alkyl)amino group, a 4- to 7-membered heterocyclyl group containing at least one nitrogen atom (wherein the heterocyclyl group may be substituted with a hydroxyl group, or a $C_{1-6}$ alkyl group, which may be substituted with a hydroxyl group), a $C_{1-6}$ alkylcarbonyloxy group (wherein the $C_{1-6}$ alkylcarbonyloxy group may be substituted with one or two substituents selected from a hydroxyl group and —$(OCH_2CH_2)_l$—$OR^{73}$ (wherein $R^{73}$ and l are the same as those defined above), —$OCO(OCHR^{76}CH_2)_k$—$OR^{75}$ (wherein $R^{75}$, $R^{76}$, and k are the same as those defined above)), and —$CONR^{91}R^{92}$;

wherein each of $R^{91}$ and $R^{92}$ is selected from a hydrogen atom and a $C_{1-6}$ alkyl group; or $R^{91}$ and $R^{92}$, together with nitrogen to which they bind, may form a 4- to 7-membered heterocyclic ring containing at least one nitrogen atom (wherein the heterocyclyl group may be substituted with a hydroxyl group).

In still another aspect of the present invention, the substituent(s) on the ring carbon atom(s) of Cy are selected from a hydroxyl group and a $C_{1-8}$ alkyl group (wherein the alkyl group may be substituted with one or more substituents selected from a hydroxyl group, a $C_{1-6}$ alkylamino group, a di($C_{1-6}$ alkyl)amino group, and a 4- to 7-membered heterocyclyl group containing at least one nitrogen atom (wherein the heterocyclyl group may be substituted with a hydroxyl group)).

In yet another aspect, the present invention provides the compound represented by the formula (1), a prodrug thereof, and a pharmaceutically acceptable salt thereof, wherein the carbon atom(s) of Cy are substituted with the group —$CR^{51}R^{52}$—$OR^{53}$;

wherein each of $R^{51}$ and $R^{52}$ is independently selected from a hydrogen atom, a $C_{1-3}$ alkyl group (wherein the alkyl group may be substituted with a hydroxyl group or an amino group), and a $C_{2-3}$ alkenyl group;

$R^{53}$ is selected from a hydrogen atom, —$PO(OR^{41})OR^{42}$, a $C_{1-6}$ alkylcarbonyl group, a $C_{3-8}$ cycloalkylcarbonyl group (wherein the $C_{1-6}$ alkylcarbonyl group and $C_{3-8}$ cycloalkylcarbonyl group may be substituted with one or more substituents selected from a hydroxyl group, —$NR^{37}R^{38}$, an aryl group, a carboxy group, a $C_{1-6}$ alkoxycarbonyl group, a $C_{1-6}$ alkylaminocarbonyl group, and a di($C_{1-6}$ alkyl)aminocarbonyl group (wherein the $C_{1-6}$ alkylaminocarbonyl group and di($C_{1-6}$ alkyl)aminocarbonyl group may be substituted with one or more substituents selected from an amino group, a $C_{1-6}$ alkylamino group, and a di($C_{1-6}$ alkyl)amino group)), an arylcarbonyl group, and a 4- to 7-membered heterocyclyl carbonyl group (wherein the arylcarbonyl group and heterocyclyl carbonyl group may be substituted with one or more substituents selected from a carboxy group, a $C_{1-6}$ alkoxycarbonyl group, a $C_{1-6}$ alkylcarbonyl group (wherein the $C_{1-6}$ alkoxycarbonyl group and $C_{1-6}$ alkylcarbonyl group may be substituted with one or more substituents selected from a hydroxyl group, —$NR^{37}R^{38}$, a carboxy group, and a hydroxyl group));

each of $R^{37}$ and $R^{38}$ is independently selected from a hydrogen atom, a $C_{1-8}$ alkyl group (wherein the alkyl group may be substituted with one or more substituents selected from a halogen atom, a hydroxyl group, a $C_{1-6}$ alkoxy group, an aryl group, an amino group, a $C_{1-6}$ alkylamino group, and a di($C_{1-6}$ alkyl)amino group), —$S(O)_{n2}R^{39}$ (wherein n2 represents an integer of 1 or 2), a $C_{1-6}$ alkylcarbonyl group (wherein the $C_{1-6}$ alkylcarbonyl group may be substituted with one or more substituents selected from an amino group, a $C_{1-6}$ alkylamino group, a di($C_{1-6}$ alkyl)amino group, and an aryl group), a $C_{1-6}$ alkylaminocarbonyl group, a $C_{1-6}$ alkoxycarbonyl group, an aryl group, and a heteroaryl group; or $R^{37}$ and $R^{38}$, together with a nitrogen atom to which they bind, may form a 4- to 7-heterocyclyl group containing at least one nitrogen atom (wherein the heterocyclyl group may be substituted with a hydroxyl group, a $C_{1-8}$ alkyl group (wherein the alkyl group may be substituted with a hydroxyl group, a $C_{1-8}$ alkoxy group, or an aryl group), a $C_{1-8}$ alkoxy group (wherein the alkoxy group may be substituted with a hydroxyl group, a $C_{1-8}$ alkoxy group, or an aryl group), an aryl group, or a heteroaryl group);

$R^{39}$ is selected from a hydrogen atom, a $C_{1-8}$ alkyl group (wherein the alkyl group may be substituted with one or more substituents selected from a hydroxyl group, a $C_{1-6}$ alkoxy group, an aryl $C_{1-6}$ alkoxy group, an aryl group, and a heteroaryl group), a $C_{2-8}$ alkenyl group, a $C_{3-6}$ cycloalkyl group, an aryl group, and a heteroaryl group; and each of $R^{41}$ and $R^{42}$ is independently selected from a hydrogen atom, an aryl $C_{1-6}$ alkyl group, and a $C_{1-8}$ alkyl group.

In still another aspect of the present invention, the substituent(s) on the ring carbon atom(s) of Cy are selected from a hydroxyl group, a hydroxymethyl group, and a 1-hydroxy-1-methylethyl group.

In still another aspect of the present invention, a substituent on the ring nitrogen atom of Cy is selected from an $C_{1-8}$ alkyl group (wherein the alkyl group may be substituted with a hydroxyl group).

In yet another aspect of the present invention, the substituent(s) on the ring carbon atom(s) of Cy are —$CH_2$—$OCOCH_2$—$(OCH_2CH_2)_l$—$OR^{73}$ (wherein $R^{73}$ and l are the same as those defined above), a propionyloxymethyl group, which is substituted with one or two hydroxyl groups, or —$CH_2$—$OCO(OCHR^{76}CH_2)_k$—$OR^{75}$ (wherein $R^{75}$, $R^{76}$, and k are the same as those defined above).

In one aspect of the present invention, Z is preferably O. In addition, the substituent(s) on the ring carbon atom(s) of Cy are not particularly limited. For example, it may be selected from a hydroxyl group and a $C_{1-8}$ alkyl group (wherein the alkyl group may be substituted with one or more substituents selected from a hydroxyl group, a $C_{1-6}$ alkylcarbonylamino group, and a 4- to 7-membered heterocyclyl group containing at least one nitrogen atom (wherein the heterocyclyl group may be substituted with a hydroxyl group), and in particular, it may be substituted with a hydroxyl group).

In one aspect of the present invention, X may be an aryl group, which may be substituted with one or more substituents selected from Group A1; wherein Group A1 consists of a $C_{1-8}$ alkyl group (wherein the alkyl group may be substituted with one or more substituents selected from a halogen atom and —$NR^{12}R^{13}$), a halogen atom, a hydroxyl group, an aryl group, an amino group (wherein the nitrogen atom of the amino group may be substituted with one or two substituents selected from a $C_{1-8}$ alkyl group and an aryl group), —$SR^{14}$, a $C_{1-6}$ alkoxy group (wherein the alkoxy group may be substituted with one or more substituents selected from —$OR^{11}$ and a halogen atom), and a 4- to 7-membered heterocyclyl group (wherein the heterocyclyl group may be substituted with one or two substituents selected from $C_{1-8}$ alkyl groups); wherein each of $R^{11}$, $R^{12}$, $R^{13}$, and $R^{14}$ is independently selected from a hydrogen atom, a $C_{1-8}$ alkyl group, and an aryl group; or $R^{12}$ and $R^{13}$, together with nitrogen to which they bind, may form a 4- to 7-membered heterocyclic ring containing at least one nitrogen atom.

In one aspect of the present invention, X may be an aryl group, which may be substituted with one or more substituents selected from a halogen atom, a $C_{1-6}$ alkyl group, a halo $C_{1-6}$ alkyl group, a $C_{1-6}$ alkoxy group, a halo $C_{1-6}$ alkoxy group, an aryl group, and a 4- to 7-membered heterocyclyl group. More specifically, X is an aryl group, and the aryl group may be substituted with an ethyl group, a trifluoromethyl group, a trifluoromethoxy group, an ethoxy group, a propoxy group, a phenyl group, or a morpholinyl group.

In another aspect, the present invention provides a pharmaceutical composition, which comprises, as an active ingredient, the compound represented by the formula (1), a prodrug thereof, or a pharmaceutically acceptable salt thereof.

In a further aspect, the present invention provides a therapeutic and preventive agent used for malignant tumor such as solid cancer, which comprises, as an active ingredient, the compound represented by the formula (1), a prodrug thereof, or a pharmaceutically acceptable salt thereof.

EMBODIMENTS OF THE INVENTION

The present invention provides a 1-(2H)-isoquinolone derivative, which has excellent antitumor action and also has preferred properties as a pharmaceutical in terms of water solubility and safety. In addition, the present invention provides a compound, which is useful as a therapeutic and preventive agent effective for proliferative diseases such as cancer, a production method thereof, an intermediate compound useful for such production, and a pharmaceutical composition comprising such a compound.

Embodiments of the Invention

In the present invention, the term "aryl group" is used to mean an aromatic hydrocarbon group containing 6 to 10 carbon atoms, which includes phenyl, 1-naphthyl, 2-naphthyl, and others.

In the present invention, the term "heteroaryl group" is used to mean a 5- to 10-membered aromatic heterocyclyl group containing one or more heteroatoms selected from an oxygen atom, a nitrogen atom, and a sulfur atom. Examples of such a heteroaryl group may include furyl, thienyl, pyrrolyl, imidazolyl, pyrazolyl, oxazolyl, isoxazolyl, thiazolyl, isothiazolyl, oxadiazolyl, thiadiazolyl, triazolyl, tetrazolyl, pyridinyl, pyrimidinyl, pyrazinyl, pyridazinyl, indolyl, quinolinyl, isoquinolyl, and benzimidazolyl.

In the present invention, the term "halogen atom" is used to mean a fluorine atom, a chlorine atom, a bromine atom, an iodine atom, or the like. A preferred example of such a halogen atom is a fluorine atom.

In the present invention, the term "$C_{1-8}$ alkyl group" is used to mean a linear or branched alkyl group containing 1 to 8 carbon atoms, or a cyclic or partially cyclic alkyl group containing 3 to 8 carbon atoms. Examples of such a $C_{1-8}$ alkyl group may include methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, 2-ethylbutyl, cyclopropyl, cyclobutyl, cyclopentyl, cyclohexyl, cycloheptyl, cyclooctyl, methylcyclopropyl, cyclopropylmethyl, and methylhexyl. A preferred example of such a $C_{1-8}$ alkyl group is a linear or branched $C_{1-8}$ alkyl group, and a more preferred example is a linear or branched $C_{1-6}$ alkyl group.

In the present invention, the term "$C_{2-7}$ alkenyl group" is used to mean a linear or branched alkenyl group containing 2 to 7 carbon atoms. Examples of such a $C_{2-7}$ alkenyl group may include ethenyl(vinyl), 1-propenyl, 2-propenyl(allyl), propen-2-yl, 3-butenyl(homoallyl), and 1,4-pentadien-3-yl.

In the present invention, the term "$C_{2-7}$ alkynyl group" is used to mean a linear or branched alkynyl group containing 2 to 7 carbon atoms. Examples of such a $C_{2-7}$ alkynyl group may include ethynyl, 1-propynyl, 2-propynyl, 1-butynyl, 2-butynyl, and 3-butynyl.

In the present invention, the term "$C_{1-6}$ alkoxy group" is used to mean an alkyloxy group having a linear or branched alkyl group containing 1 to 6 carbon atoms, and a cyclic or partially cyclic alkyl group containing 3 to 6 carbon atoms, as alkyl portions thereof. Examples of such a $C_{1-6}$ alkoxy group may include methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, 2-ethylbutoxy, cyclopropoxy, cyclobutoxy, cyclopentoxy, cyclohexyloxy, and cyclopropylmethoxy.

In the present invention, the term "aryloxy group" is used to mean an aryloxy group having, as an aryl portion thereof, an aromatic hydrocarbon group containing 6 to 10 carbon atoms, which has already been defined above. Examples of such an aryloxy group may include phenoxy, 1-naphthoxy, and 2-naphthoxy.

In the present invention, the term "heteroaryloxy group" is used to mean a heteroaryloxy group having, as a heteroaryl portion thereof, a 5- to 10-membered aromatic heterocyclyl group containing a heteroatom selected from at least one oxygen atom, nitrogen atom, and sulfur atom, which has already been defined above. Examples of such a heteroaryloxy group may include furyloxy, thienyloxy, pyrrolyloxy, imidazolyloxy, pyrazolyloxy, oxazolyloxy, isoxazolyloxy, thiazolyloxy, isothiazolyloxy, oxadiazolyloxy, thiadiazolyloxy, triazolyloxy, tetrazolyloxy, pyridinyloxy, pyrimidinyloxy, pyrazinyloxy, pyridazinyloxy, indolyloxy, quinolinyloxy, and isoquinolinyloxy.

In the present invention, the term "heteroarylcarbonyl group" is used to mean a heteroarylcarbonyl group having, as a heteroaryl portion thereof, a 5- to 10-membered aromatic heterocyclyl group containing a heteroatom selected from at least one oxygen atom, nitrogen atom, and sulfur atom, which has already been defined above. Examples of such a heteroarylcarbonyl group may include furylcarbonyl, thienylcarbonyl, pyrrolylcarbonyl, imidazolylcarbonyl, pyrazolylcarbonyl, oxazolylcarbonyl, isoxazolylcarbonyl, thiazolylcarbonyl, isothiazolylcarbonyl, oxadiazolylcarbonyl, thiadiazolylcarbonyl, triazolylcarbonyl, tetrazolylcarbonyl, pyridinylcarbonyl, pyrimidinylcarbonyl, pyrazinylcarbonyl, pyridazinylcarbonyl, indolylcarbonyl, quinolinylcarbonyl, and isoquinolinylcarbonyl.

In the present invention, the term "haloC$_{1-6}$ alkyl group" is used to mean an alkyl group substituted with one or more halogen atoms, which has, as alkyl portions thereof, a linear or branched alkyl group containing 1 to 6 carbon atoms, and a cyclic or partially cyclic alkyl group containing 3 to 6 carbon atoms. Examples of such a haloC$_{1-6}$ alkyl group may include trifluoromethyl, trichloromethyl, chlorodifluoromethyl, 2,2,2-trifluoroethyl, perfluoroethyl, 2,2,2-trichloroethyl, bromomethyl, dibromomethyl, tribromomethyl, iodomethyl, difluoromethyl, and dichloromethyl.

In the present invention, the term "haloC$_{1-6}$ alkoxy group" is used to mean an alkoxy group substituted with one or more halogen atoms, which has, as alkyl portions thereof, a linear or branched alkyl group containing 1 to 6 carbon atoms, and a cyclic or partially cyclic alkyl group containing 3 to 6 carbon atoms. Examples of such a haloC$_{1-6}$ alkoxy group may include trifluoromethoxy, trichloromethoxy, chlorodifluoromethoxy, 2,2,2-trifluoroethoxy, perfluoroethoxy, 2,2,2-trichloroethoxy, bromomethoxy, dibromomethoxy, tribromomethoxy, iodomethoxy, difluoromethoxy, and dichloromethoxy.

In the present invention, the term "C$_{1-6}$ alkylamino group" is used to mean an alkylamino group having, as alkyl portions thereof, a linear or branched alkyl group containing 1 to 6 carbon atoms, and a cyclic or partially cyclic alkyl group containing 3 to 6 carbon atoms. Examples of such a C$_{1-6}$ alkylamino group may include methylamino, ethylamino, n-propylamino, i-propylamino, n-butylamino, s-butylamino, i-butylamino, t-butylamino, n-pentylamino, 3-methylbutylamino, 2-methylbutylamino, 1-methylbutylamino, 1-ethylpropylamino, n-hexylamino, 4-methylpentylamino, 3-methylpentylamino, 2-methylpentylamino, 1-methylpentylamino, 3-ethylbutylamino, and 2-ethylbutylamino.

In the present invention, the term "di(C$_{1-6}$ alkyl)amino group" is used to mean a dialkylamino group having, as two alkyl portions, a linear or branched alkyl group containing 1 to 6 carbon atoms, and a cyclic or partially cyclic alkyl group containing 3 to 6 carbon atoms. The two alkyl portions may be either identical to or different from each other. Examples of such a "di(C$_{1-6}$ alkyl)amino group" may include dimethylamino, diethylamino, di-n-propylamino, di-i-propylamino, di-n-butylamino, methyl-n-butylamino, methyl-s-butylamino, methyl-i-butylamino, methyl-t-butylamino, ethyl-n-butylamino, ethyl-s-butylamino, ethyl-i-butylamino, and ethyl-t-butylamino.

In the present invention, the term "C$_{1-6}$ alkylcarbonyl group" is used to mean an alkylcarbonyl group having, as alkyl portions thereof, a linear or branched alkyl group containing 1 to 6 carbon atoms, and a cyclic or partially cyclic alkyl group containing 3 to 6 carbon atoms.

In addition, in the present invention, the term "C$_{1-6}$ alkoxycarbonyl group (wherein the alkoxycarbonyl group may be substituted with one or more substituents selected from an amino group, a guanidyl group, a carboxy group, a mercapto group, an aminocarbonyl group, a methylthio group, a phenyl group, which may be substituted with a hydroxyl group, a hydroxyl group, and an indolyl group)" also includes an α-amino acid-derived group (a group obtained by conversion of a carboxy group to a carbonyl group), such as alanine, arginine, asparagine, aspartic acid, cysteine, glutamine, glutamic acid, glycine, histidine, isoleucine, leusine, lysine, methionine, phenylalanine, serine, threonine, tryptophan, tyrosine, or valine.

In the present invention, the term "C$_{2-7}$ alkenylcarbonyl group" is used to mean an alkenylcarbonyl group having, as an alkenyl portion thereof, a linear or branched alkenyl group containing 2 to 7 carbon atoms. Examples of such a C$_{2-7}$ alkenylcarbonyl group may include ethenylcarbonyl(vinylcarbonyl), 1-propenylcarbonyl, 2-propenylcarbonyl(allylcarbonyl), propen-2-ylcarbonyl, 3-butenylcarbonyl(homoallylcarbonyl), and 1,4-pentadien-3-ylcarbonyl.

In the present invention, the term "C$_{1-6}$ alkylcarbonylamino group" is used to mean an alkylcarbonylamino group having, as alkyl portions thereof, a linear or branched alkyl group containing 1 to 6 carbon atoms, and a cyclic or partially cyclic alkyl group containing 3 to 6 carbon atoms.

In the present invention, the term "C$_{1-6}$ alkylcarbonyloxy group" is used to mean an alkylcarbonyloxy group having, as alkyl portions thereof, a linear or branched alkyl group containing 1 to 6 carbon atoms, and a cyclic or partially cyclic alkyl group containing 3 to 6 carbon atoms.

In the present invention, the term "C$_{1-6}$ alkoxycarbonyl group" is used to mean an alkoxycarbonyl group having, as alkoxy portions thereof, a linear or branched alkoxy group containing 1 to 6 carbon atoms, and a cyclic or partially cyclic alkoxy group containing 3 to 6 carbon atoms.

In the present invention, the term "C$_{1-6}$ alkylaminocarbonyl group" is used to mean an alkylaminocarbonyl group having, as alkyl portions thereof, a linear or branched alkyl group containing 1 to 6 carbon atoms, and a cyclic or partially cyclic alkyl group containing 3 to 6 carbon atoms.

In the present invention, the term "di(C$_{1-6}$ alkyl)aminocarbonyl group" is used to mean a dialkylaminocarbonyl group having, as two alkyl portions thereof, a linear or branched alkyl group containing 1 to 6 carbon atoms, and a cyclic or partially cyclic alkyl group containing 3 to 6 carbon atoms, which may be either identical to or different from each other.

In the present invention, the term "amino C$_{1-6}$ alkoxycarbonyl group" is used to mean an aminoalkoxycarbonyl group having, as alkoxy portions thereof, a linear or branched alkoxy group containing 1 to 6 carbon atoms, and a cyclic or partially cyclic alkoxy group containing 3 to 6 carbon atoms.

In the present invention, the term "hydroxy C$_{1-6}$ alkyl group" is used to mean a hydroxyalkyl group having, as alkyl portions thereof, a linear or branched alkyl group containing 1 to 6 carbon atoms, and a cyclic or partially cyclic alkyl group containing 3 to 6 carbon atoms.

In the present invention, the term "$C_{1-6}$ alkylthio group" is used to mean an alkylthio group having, as alkyl portions thereof, a linear or branched alkyl group containing 1 to 6 carbon atoms, and a cyclic or partially cyclic alkyl group containing 3 to 6 carbon atoms. Examples of such a $C_{1-6}$ alkylthio group may include methylthio, ethylthio, n-propylthio, i-propylthio, n-butylthio, s-butylthio, i-butylthio, t-butylthio, n-pentylthio, 3-methylbutylthio, 2-methylbutylthio, 1-methylbutylthio, 1-ethylpropylthio, n-hexylthio, 4-methylpentylthio, 3-methylpentylthio, 2-methylpentylthio, 1-methylpentylthio, 3-ethylbutylthio, and 2-ethylbutylthio.

In the present invention, the term "aryl $C_{1-6}$ alkyl group" is used to mean an aralkyl group, which has, as an aryl group thereof, the defined aromatic hydrocarbon group containing 6 to 10 carbon atoms, and as alkyl portions thereof, a linear or branched alkyl group containing 1 to 6 carbon atoms, and a cyclic or partially cyclic alkyl group containing 3 to 6 carbon atoms. Examples of such an aryl $C_{1-6}$ alkyl group may include benzyl, 1-phenethyl, and 2-phenethyl.

In the present invention, the term "aryl $C_{1-6}$ alkoxy group" is used to mean an aralkyloxy group, which has, as an aryl group thereof, the defined aromatic hydrocarbon group containing 6 to 10 carbon atoms, and as alkoxy portions thereof, a linear or branched alkoxy group containing 1 to 6 carbon atoms, and a cyclic or partially cyclic alkoxy group containing 3 to 6 carbon atoms. Examples of such an aryl $C_{1-6}$ alkoxy group may include benzyloxy, 1-phenethyloxy, and 2-phenethyloxy.

In the present invention, the term "a 4- to 7-membered heterocyclic ring containing at least one nitrogen atom" is used to mean a saturated or unsaturated heterocyclic ring containing 4 to 7 atoms in the ring thereof, which contains one or more nitrogen atoms and may also contain one or more heteroatoms selected from an oxygen atom and a sulfur atoms. Such a heterocyclic ring may have a monocyclic ring, condensed ring, or spiro ring skeleton. An aromatic heterocyclic ring is also included therein. Specific examples may include azetidine, pyrrolidine, piperidine, piperazine, pyrrole, imidazole, imidazoline, imidazolidine, pyrazole, pyrazoline, oxazoline, oxazolidine, morpholine, thiomorpholine, and hexamethyleneimine.

In the present invention, the term "4- to 7-heterocyclyl group containing at least one nitrogen atom" is used to mean a saturated or unsaturated heterocyclyl group containing 4 to 7 atoms in the ring thereof, which contains one or more nitrogen atoms and may also contain one or more heteroatoms selected from an oxygen atom and a sulfur atom. Such a heterocyclyl group may have a monocyclic ring, condensed ring, or spiro ring skeleton. An aromatic heterocyclyl group is also included therein. Specific examples may include azetidinyl, pyrrolidinyl, piperidinyl, piperazinyl, pyrrolyl, imidazolyl, imidazolinyl, imidazolidinyl, pyrazolyl, pyrazolinyl, oxazolinyl, oxazolidinyl, morpholinyl, thiomorpholinyl, pyridinyl, pyrazinyl, pyrimidinyl, pyridazinyl, oxazolidinyl, hexamethyleneimino, and octahydroisoquinolyl. The position of the heterocyclyl group to be substituted is not particularly limited, as long as it is a substitutable position on a carbon atom or nitrogen atom.

In the present invention, the term "4- to 12-membered heterocyclyl group" is used to mean a saturated or unsaturated heterocyclyl group containing 4 to 12 atoms in the ring thereof, which may contain one or more heteroatoms selected from a nitrogen atom, an oxygen atom, and a sulfur atom. The heterocyclic ring may have a monocyclic ring, condensed ring, or spiro ring skeleton. An aromatic heterocyclic ring is also included therein. Specific examples may include isobenzofuranyl, chromenyl, indolizinyl, indolyl, isoindolyl, indazolyl, puryl, quinolizinyl, isoquinolinyl, quinolinyl, phthalazinyl, naphthyridinyl, quinoxalinyl, quinazolinyl, cinnolinyl, pteridinyl, isochromanyl, chromanyl, quinuclidinyl, oxacycloheptyl, dioxacycloheptyl, thiacycloheptyl, diazacycloheptyl, oxacyclooctyl, dioxacyclooctyl, azacyclooctyl, diazacyclooctyl, azaoxacyclooctyl, thiacyclooctyl, dithiacyclooctyl, thiaoxacyclooctyl, azathiacyclooctyl, oxacyclononyl, dioxacyclononyl, trioxacyclononyl, azacyclononyl, azaoxacyclononyl, triazacyclononyl, thiacyclononyl, dithiacyclononyl, azadithiacyclononyl, oxacyclodecanyl, dioxacyclodecanyl, trioxacyclodecanyl, azacyclodecanyl, diazacyclodecanyl, azaoxacyclodecanyl, azadioxacyclodecanyl, diazaoxacyclodecanyl, thiacyclodecanyl, dithiacyclodecanyl, trithiacyclodecanyl, azathiacyclodecanyl, diazathiacyclodecanyl, oxacycloundecanyl, dioxacycloundecanyl, trioxacycloundecanyl, azacycloundecanyl, diazacycloundecanyl, triazacycloundecanyl, thiacycloundecanyl, dithiacycloundecanyl, trithiacycloundecanyl, azaoxacycloundecanyl, azathiacycloundecanyl, azadioxacycloundecanyl, diazaoxacycloundecanyl, azathiacycloundecanyl, diazathiacycloundecanyl, azadithiacycloundecanyl, oxacyclododecanyl, dioxacyclododecanyl, trioxacyclododecanyl, tetraoxacyclododecanyl, azacyclododecanyl, diazacyclododecanyl, triazacyclododecanyl, tetraazacyclododecanyl, thiacyclododecanyl, dithiacyclododecanyl, trithiacyclododecanyl, tetrathiacyclododecanyl, azaoxacyclododecanyl, azathiacyclododecanyl, diazaoxacyclododecanyl, azadioxacyclododecanyl, azatrioxacyclododecanyl, azadithiacyclododecanyl, diazadithiacyclododecanyl, azatrithiacyclododecanyl, as well as specific examples of "4- to 7-membered heterocyclyl group described later. The position of the heterocyclyl group to be substituted is not particularly limited, as long as it is a substitutable position on a carbon atom or nitrogen atom. In addition, when the heterocyclyl group has —NH— in the ring thereof, the substituent of the heterocyclic ring may be present on a carbon atom or a nitrogen atom, unless otherwise specified.

In the present invention, the term "4- to 7-membered heterocyclic ring" is used to mean a saturated or unsaturated heterocyclyl group containing 4 to 7 atoms in the ring thereof, which may contain one or more heteroatoms selected from a nitrogen atom, an oxygen atom, and a sulfur atom. The heterocyclic ring may have a monocyclic ring, condensed ring, or spiro ring skeleton. An aromatic heterocyclic ring is also included therein. Specific examples may include azetidinyl, pyrrolidinyl, piperidinyl, piperazinyl, pyrrolyl, imidazolyl, imidazolinyl, pyrazolyl, pyrazolinyl, oxazolinyl, morpholinyl, thiomorpholinyl, pyridinyl, pyrazinyl, pyrimidinyl, pyridazinyl, hexamethyleneimino, furyl, tetrahydrofuryl, thienyl, tetrahydrothienyl, dioxolanyl, oxathiolanyl, and dioxanyl. The position of the heterocyclyl group to be substituted is not particularly limited, as long as it is a substitutable position on a carbon atom or nitrogen atom. In addition, when the heterocyclyl group has —NH— in the ring thereof, the substituent of the heterocyclic ring may be present on a carbon atom or a nitrogen atom, unless otherwise specified. Specific examples of such a heterocyclic ring having a substituent(s) may include methyldioxolanyl, dimethyldioxolanyl, ethyldioxolanyl, diethyldioxolanyl, hydroxypiperidinyl, hydroxymethylpiperidinyl, hydroxyethylpiperidinyl, methoxypiperidinyl, ethoxypiperidinyl, methylthiopiperidinyl, carboxytetrahydrofuryl, hydroxytetrahydrofuryl, dihydroxytetrahydrofuryl, trihydroxytetrahydrofuryl, hydroxytetrahydropyranyl, dihydroxytetrahydropyranyl, trihydroxytetrahydropyranyl, tetrahydroxytetrahydropyranyl, phenyltetrahydrothienyl, methoxycarbonyldioxolanyl, and methylcarbonylpiperazinyl.

In the present invention, the term "4- to 7-membered monocyclic heterocyclic ring" is used to mean a saturated or unsaturated monocyclic heterocyclyl group containing 4 to 7 atoms in the ring thereof, which contains one or more heteroatoms selected from a nitrogen atom, an oxygen atom, and a sulfur atom. An aromatic monocyclic heterocyclic ring is also included therein. Further, when the heterocyclic ring has —NH— in the ring thereof, the substituent of the heterocyclic ring may be present on a carbon atom or a nitrogen atom, unless otherwise specified. When Cy in the formula (1) is a 4- to 7-membered monocyclic heterocyclic ring, examples of a group consisting of Cy substituted with the group Z= may include the following groups:

[Formula 4]

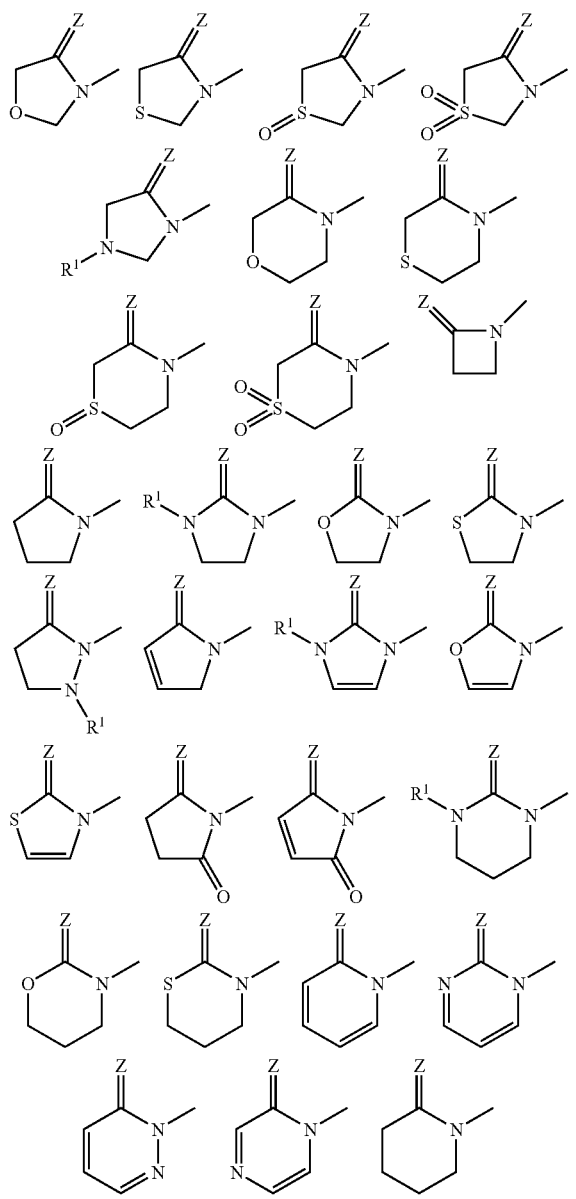

[Formula 5]

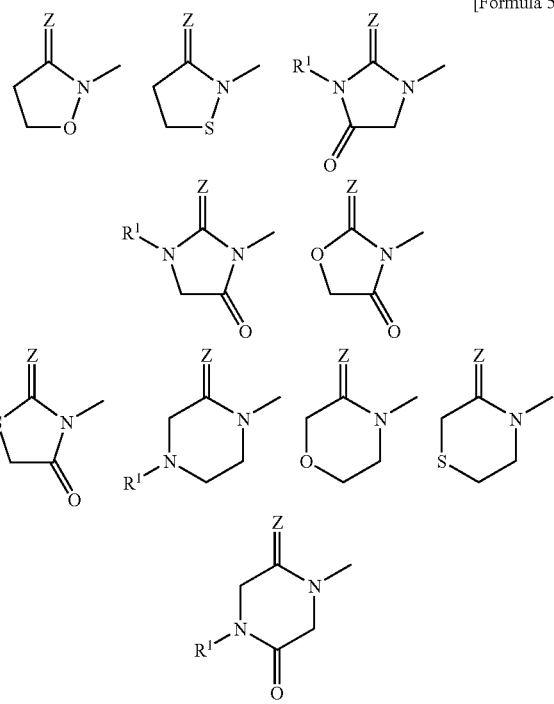

wherein $R^1$ is the same as defined above, and each heterocyclic ring may have a substituent as defined above.

In the present invention, the term "8- to 10-membered condensed heterocyclic ring" is used to mean a saturated or unsaturated cyclic heterocyclyl group containing to 10 atoms in the ring thereof, which contains one or more heteroatoms selected from a nitrogen atom, an oxygen atom, and a sulfur atom. An aromatic cyclic heterocyclic ring is also included therein. When Cy in the formula (1) is a 8- to 10-membered condensed heterocyclic ring, examples of a group consisting of Cy substituted with the group Z= may include the following groups:

[Formula 6]

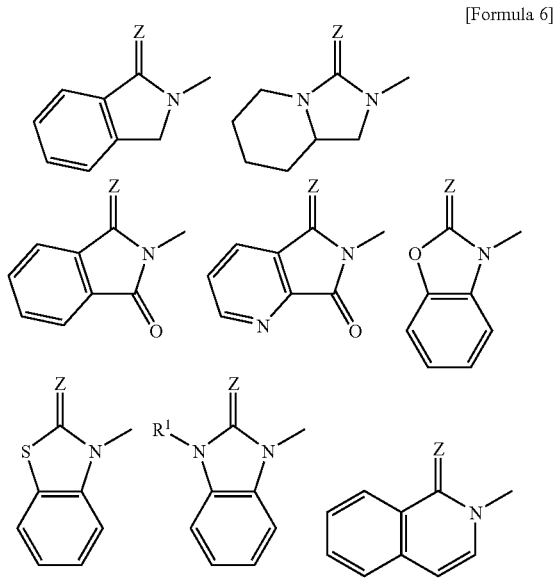

-continued

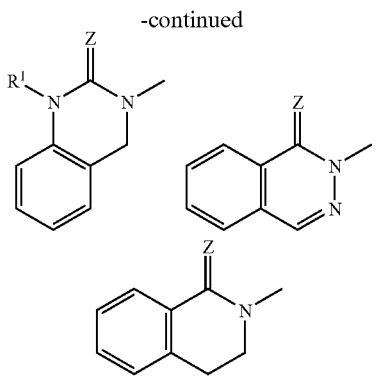

wherein $R^1$ is the same as defined above, and each heterocyclic ring may have a substituent as defined above.

In the present invention, the term "4- to 12-membered heterocyclyl carbonyl group" is used to mean a heterocyclyl carbonyl group having a saturated or unsaturated heterocyclyl group containing 4 to 12 atoms in the ring thereof, which may contain, as a 4- to 12-membered heterocyclic ring portion thereof, one or more heteroatoms selected from a nitrogen atom, an oxygen atom, and a sulfur atom, as defined above. Specific examples may include azetidinylcarbonyl, pyrrolidinylcarbonyl, piperidinylcarbonyl, piperazinylcarbonyl, pyrrolylcarbonyl, imidazolylcarbonyl, imidazolinylcarbonyl, pyrazolylcarbonyl, pyrazolinylcarbonyl, oxazolinylcarbonyl, morpholinylcarbonyl, thiomorpholinylcarbonyl, pyridinylcarbonyl, pyrazinylcarbonyl, pyrimidinylcarbonyl, pyridazinylcarbonyl, hexamethyleneiminocarbonyl, furylcarbonyl, tetrahydrofurylcarbonyl, thienylcarbonyl, tetrahydrothienylcarbonyl, dioxacyclopentylcarbonyl, isobenzofuranylcarbonyl, chromenylcarbonyl, indolizinylcarbonyl, indolylcarbonyl, isoindolylcarbonyl, indazolylcarbonyl, purylcarbonyl, quinolizinylcarbonyl, isoquinolinylcarbonyl, quinolinylcarbonyl, phthalazinylcarbonyl, naphthyridinylcarbonyl, quinoxalinylcarbonyl, quinazolinylcarbonyl, cinnolinylcarbonyl, pteridinylcarbonyl, isochromanylcarbonyl, chromanylcarbonyl, quinuclidinylcarbonyl, oxacycloheptylcarbonyl, dioxacycloheptylcarbonyl, thiacycloheptylcarbonyl, diazacycloheptylcarbonyl, oxacyclooctylcarbonyl, dioxacyclooctylcarbonyl, azacyclooctylcarbonyl, diazacyclooctylcarbonyl, azaoxacyclooctylcarbonyl, thiacyclooctylcarbonyl, dithiacyclooctylcarbonyl, thiaoxacyclooctylcarbonyl, azathiacyclooctylcarbonyl, oxacyclononylcarbonyl, dioxacyclononylcarbonyl, trioxacyclononylcarbonyl, azacyclononylcarbonyl, azaoxacyclononylcarbonyl, triazacyclononylcarbonyl, thiacyclononylcarbonyl, dithiacyclononylcarbonyl, azadithiacyclononylcarbonyl, oxacyclodecanylcarbonyl, dioxacyclodecanylcarbonyl, trioxacyclodecanylcarbonyl, azacyclodecanylcarbonyl, diazacyclodecanylcarbonyl, azaoxacyclodecanylcarbonyl, azadioxacyclodecanylcarbonyl, diazaoxacyclodecanylcarbonyl, thiacyclodecanylcarbonyl, dithiacyclodecanylcarbonyl, trithiacyclodecanylcarbonyl, azathiacyclodecanylcarbonyl, diazathiacyclodecanylcarbonyl, oxacycloundecanylcarbonyl, dioxacycloundecanylcarbonyl, trioxacycloundecanylcarbonyl, azacycloundecanylcarbonyl, diazacycloundecanylcarbonyl, triazacycloundecanylcarbonyl, thiacycloundecanylcarbonyl, dithiacycloundecanylcarbonyl, trithiacycloundecanylcarbonyl, azaoxacycloundecanylcarbonyl, azadioxacycloundecanylcarbonyl, diazaoxacycloundecanylcarbonyl, azathiacycloundecanylcarbonyl, diazathiacycloundecanylcarbonyl, azadithiacycloundecanylcarbonyl, oxacyclododecanylcarbonyl, dioxacyclododecanylcarbonyl, trioxacyclododecanylcarbonyl, tetraoxacyclododecanylcarbonyl, azacyclododecanylcarbonyl, diazacyclododecanylcarbonyl, triazacyclododecanylcarbonyl, tetraazacyclododecanylcarbonyl, thiacyclododecanylcarbonyl, dithiacyclododecanylcarbonyl, trithiacyclododecanylcarbonyl, tetrathiacyclododecanylcarbonyl, azaoxacyclododecanylcarbonyl, azathiacyclododecanylcarbonyl, diazaoxacyclododecanylcarbonyl, azadioxacyclododecanylcarbonyl, azatrioxacyclododecanylcarbonyl, azadithiacyclododecanylcarbonyl, diazadithiacyclododecanylcarbonyl, and azatrithiacyclododecanylcarbonyl.

In addition, uronic acid residues (groups obtained by conversion of a carboxy group to a carbonyl group) derived from monosaccharides capable of adopting a cyclic structure, such as alluronic acid, altruronic acid, glucuronic acid, mannuronic acid, guluronic acid, iduronic acid, galacturonic acid, or taluronic acid, are also included.

Moreover, a pyrrolidin-2-ylcarbonyl group derived from proline that is an α-amino acid is also included.

$R^{32}$, $R^{33}$, $R^{34}$, $R^{35}$, $R^{37}$, $R^{38}$, $R^{71}$, $R^{72}$, $R^{84}$, and $R^{85}$ are the same as those, which have already been defined above. Preferably, each of $R^{32}$, $R^{33}$, $R^{34}$, and $R^{35}$ is independently selected from a hydrogen atom, a $C_{1-8}$ alkyl group (wherein the alkyl group may be substituted with one or more substituents selected from a halogen atom, a hydroxyl group, a $C_{1-6}$ alkoxy group, an aryl group, an amino group, a $C_{1-6}$ alkylamino group, and a di($C_{1-6}$ alkyl)amino group), $-S(O)_{n4}R^{83}$ (wherein n4 and $R^{83}$ are the same as those defined above), a $C_{1-6}$ alkylcarbonyl group (wherein the $C_{1-6}$ alkylcarbonyl group may be substituted with one or more substituents selected from an amino group, a $C_{1-6}$ alkylamino group, a di($C_{1-6}$ alkyl)amino group, and an aryl group), a $C_{1-6}$ alkylaminocarbonyl group, a $C_{1-6}$ alkoxycarbonyl group, an aryl group, and a heteroaryl group; or preferably, $R^{32}$ and $R^{33}$, and $R^{34}$ and $R^{35}$, together with a nitrogen atom to which they bind, may form a 4- to 7-membered heterocyclyl group containing at least one nitrogen atom (wherein the heterocyclyl group may be substituted with one or more substituents selected from a hydroxyl group, a $C_{1-8}$ alkyl group (wherein the alkyl group may be substituted with one or more substituents selected from a hydroxyl group, a $C_{1-8}$ alkoxy group, and an aryl group), a $C_{1-8}$ alkoxy group (wherein the alkoxy group may be substituted with one or more substituents selected from a hydroxyl group, a $C_{1-8}$ alkoxy group, and an aryl group), an aryl group, and a heteroaryl group).

Furthermore, preferably, each of $R^{32}$ and $R^{33}$ is independently selected from a hydrogen atom, a $C_{1-8}$ alkyl group, and a $C_{1-6}$ alkylcarbonyl group, or $R^{32}$ and $R^{33}$, together with a nitrogen atom to which they bind, may form a 4- to 7-membered heterocyclyl group containing at least one nitrogen atom (wherein the heterocyclyl group may be substituted with a hydroxyl group or a $C_{1-8}$ alkyl group (wherein the alkyl group may be substituted with a substituent selected from a hydroxyl group and a $C_{1-8}$ alkoxy group)).

Still further, preferably, $R^{34}$ and $R^{35}$, together with a nitrogen atom to which they bind, may form a 4- to 7-membered heterocyclyl group containing at least one nitrogen atom.

Preferably, each of $R^{71}$ and $R^{72}$ is independently selected from a hydrogen atom, a $C_{1-8}$ alkyl group (wherein the $C_{1-8}$ alkyl group is substituted with $-(OCH_2CH_2)_m-OH$ or 1 to 5 hydroxyl groups), and a $C_{1-6}$ alkoxycarbonyl group.

In the present invention, the term "$-S(O)_{n1}R^{14}$" is used to mean $-SR^{14}$, $-SOR^{14}$, or $-SO_2R^{14}$. For example, such $-S(O)_{n1}R^{14}$ includes $-S(O)_{n1}$ ($C_{1-6}$ alkyl group), $-S(O)_{n1}$ (aryl group), and —S(O)$_{n1}$ (heteroaryl group). Specific examples of "—S(O)$_{n1}$R$^{14}$" may include methylthio, ethylthio, n-propylthio, isopropylthio, trifluoromethylthio, benzylthio, 4-methylphenylthio, phenylthio, methylsulfinyl, ethylsulfinyl, n-propylsulfinyl, isopropylsulfinyl, trifluoromethylsulfinyl, benzylsulfinyl, 4-methylphenylsulfinyl, phenylsulfinyl, methylsulfonyl, ethylsulfonyl, n-propylsulfonyl, isopropylsulfonyl, trifluoromethylsulfonyl, benzylsulfonyl, 4-methylphenylsulfonyl, and phenylsulfonyl.

In the present invention, the term "C$_{1-6}$ alkylenedioxy group" is a divalent group "—O—(C$_{1-6}$ alkylene)-O—," which contains a linear or branched alkylene group containing 1 to 6 carbon atoms and binds to a carbon atom adjacent thereto. Examples of such a C$_{1-6}$ alkylenedioxy group may include methylenedioxy, ethylenedioxy, methylmethylenedioxy, and dimethylmethylenedioxy.

In the present invention, the term "oxo group" is used to mean "=O." For example, a methylene group substituted with an oxo group forms a carbonyl group "—C(=O)—."

In the present invention, the term "thioxo group" is used to mean "=S." For example, a methylene group substituted with an thioxo group forms a thiocarbonyl group "—C(=S)—."

In the present invention, when any given group is substituted with one or more substituents, such substituents may be either identical to or different from one another. The number of such substituents ranges from 1 to the maximum number, which is substitutable on a chemical structure. The number of substituents is, for example, between 1 and 7, typically between 1 and 5, and particularly between 1 and 3.

n1 is preferably 0 or 2, and each of n3 and n4 is preferably 2.

Preferred examples of R$^{83}$ of —S(O)$_{n4}$R$^{83}$, which is a specific example of R$^{32}$ and R$^{33}$ in —NR$^{32}$R$^{33}$, may include a C$_{1-8}$ alkyl group (wherein the C$_{1-8}$ alkyl group may be substituted with one or more hydroxyl groups), a C$_{2-8}$ alkenyl group, a C$_{3-6}$ cycloalkyl group, and an aryl group.

Preferably, each of R$^{41}$ and R$^{42}$ is independently selected from a hydrogen atom and an aryl C$_{1-6}$ alkyl group. Among others, it is preferable to select from among a hydrogen atom and a benzyl group. In addition, R$^{41}$ and R$^{42}$ are preferably identical to each other.

The present invention includes a salt of the compound represented by the formula (1) and a pharmacologically acceptable salt of the prodrug of the compound. These salts are produced by allowing the compound or the prodrug thereof to come into contact with an acid or base, which can be used in production of a pharmaceutical. Examples of such a salt may include: hydrochloride, hydrobromide, hydroiodide, sulfate, sulfonate, methanesulfonate, toluenesulfonate, phosphate, phosphonate; carboxylates such as formate, acetate, oxalate, maleate, citrate, malate, succinate, malonate, benzoate, salicylate, fluoroacetate or trifluoroacetate, or alkali metal salts such as a sodium salt or a potassium salt; and alkali earth metal salts such as a magnesium salt or a calcium salt; and ammonium salts such as an ammonium salt, an alkylammonium salt, a dialkylammonium salt, a trialkylammonium salt, or a tetraalkylammonium salt.

The "prodrug" of the present invention means a derivative of the compound represented by the formula (1), which is converted to the compound represented by the formula (1) or a pharmaceutically acceptable salt thereof, as a result of enzymatic or nonenzymatic decomposition under physiological conditions. When such a prodrug is administered to a patient, it may be inactive. However, such a prodrug is converted to the compound of the formula (1) and exists in the form of the compound of the formula (1) in vivo. The compound represented by the formula (1) of the present invention may include those, which act as prodrugs by themselves. In order to impart preferred properties as a pharmaceutical, the "prodrug" of the present invention includes compounds obtained by further converting the compound to derivatives.

Examples of the "prodrug" of the present invention may include:

1) a compound wherein a hydroxyl group is protected by a protecting group, when the compound of the formula (1) has the hydroxyl group in the molecule thereof;

2) a compound wherein a —NH— group or amino group is protected by a protecting group, when the compound of the formula (1) has the —NH group or amino group in the molecule thereof; and 3) a compound wherein a carboxy group is converted to an ester group or an amino group, which may be substituted, when the compound of the formula (1) has the carboxy group in the molecule thereof.

Examples of such a protecting group for a hydroxyl group in the prodrug of the present invention, such as R$^{31}$ or R$^{53}$, may include —PO(OR$^{41}$)OR$^{42}$, a C$_{1-6}$ alkylcarbonyl group, a C$_{2-7}$ alkenylcarbonyl group, a C$_{3-8}$ cycloalkylcarbonyl group (wherein the C$_{1-6}$ alkylcarbonyl group, C$_{2-7}$ alkenylcarbonyl group, and a C$_{3-8}$ cycloalkylcarbonyl group may be substituted with one or more substituents selected from a hydroxyl group, —NR$^{37}$R$^{38}$, an aryl group, which may be substituted with a hydroxyl group, a heteroaryl group, a mercapto group, a C$_{1-6}$ alkylthio group, a guanidyl group, a carboxy group, a C$_{1-6}$ alkoxycarbonyl group, a C$_{1-6}$ alkylcarbonyloxy group, an aryl C$_{1-6}$ alkoxy group, an aminocarbonyl group, a C$_{1-6}$ alkylaminocarbonyl group, and a di(C$_{1-6}$ alkyl)aminocarbonyl group (wherein the C$_{1-6}$ alkylaminocarbonyl group and di(C$_{1-6}$ alkyl)aminocarbonyl group may be substituted with one or more substituents selected from an amino group, a C$_{1-6}$ alkylamino group, and a di(C$_{1-6}$ alkyl)amino group), and —(OCHR$^{74}$CH$_2$)$_l$—OR$^{73}$ (wherein l, R$^{73}$, and R$^{74}$ are the same as those defined above)), an arylcarbonyl group, a heteroarylcarbonyl group, a 4- to 12-membered heterocyclyl carbonyl group (wherein the arylcarbonyl group, heteroarylcarbonyl group, and heterocyclyl carbonyl group may be substituted with one or more substituents selected from a hydroxyl group, a carboxy group, a C$_{1-6}$ alkoxycarbonyl group, and a C$_{1-6}$ alkylcarbonyl group (wherein the C$_{1-6}$ alkoxycarbonyl group and C$_{1-6}$ alkylcarbonyl group may be substituted with one or more substituents selected from a hydroxyl group, —NR$^{84}$R$^{85}$, and a carboxy group)), a C$_{1-6}$ alkoxycarbonyl group (wherein the C$_{1-6}$ alkoxycarbonyl group may be substituted with a 4- to 12-membered heterocyclyl carbonyl group), —CONR$^{71}$R$^{72}$, and —CO(OCHR$^{76}$CH$_2$)$_k$—OR$^{75}$ (wherein k, R$^{75}$, and R$^{76}$ are the same as those defined above).

Herein, each of R$^{37}$, R$^{38}$, R$^{84}$, and R$^{85}$ is independently selected from a hydrogen atom, a C$_{1-8}$ alkyl group (wherein the alkyl group may be substituted with one or more substituents selected from a halogen atom, a hydroxyl group, a C$_{1-6}$ alkoxy group, —(OCH$_2$CH$_2$)$_m$—OH (wherein m is the same as that defined above), a C$_{1-6}$ alkoxycarbonyl group, an aryl group, an amino group, a C$_{1-6}$ alkylamino group, and a di(C$_{1-6}$ alkyl)amino group), —S(O)$_{n4}$R$^{83}$ (wherein n4 represents an integer of 1 or 2), a C$_{1-6}$ alkylcarbonyl group (wherein the C$_{1-6}$ alkylcarbonyl group may be substituted with one or more substituents selected from an amino group, a C$_{1-6}$ alkylamino group, a di(C$_{1-6}$ alkyl)amino group, an aminocarbonyl group, an aryl group, which may be substituted with a hydroxyl group, a heteroaryl group, a hydroxyl group, a mercapto group, a $C_{1-6}$ alkylthio group, a guanidyl group, and a carboxy group), a $C_{1-6}$ alkylaminocarbonyl group, a $C_{1-6}$ alkoxycarbonyl group, a 4- to 7-membered heterocyclyl carbonyl group, an aryl group, and a heteroaryl group; or $R^{37}$ and $R^{38}$, together with a nitrogen atom to which they bind, may form a 4- to 7-membered heterocyclyl group (wherein the heterocyclyl group may be substituted with a hydroxyl group, a $C_{1-8}$ alkyl group (wherein the alkyl group may be substituted with a hydroxyl group, a $C_{1-8}$ alkoxy group, or an aryl group), a $C_{1-8}$ alkoxy group (wherein the alkoxy group may be substituted with a hydroxyl group, a $C_{1-8}$ alkoxy group, or an aryl group), an aryl group, or a heteroaryl group);

$R^{83}$ is selected from a hydrogen atom, a $C_{1-8}$ alkyl group (wherein the alkyl group may be substituted with one or more substituents selected from a hydroxyl group, a $C_{1-6}$ alkoxy group, an aryl $C_{1-6}$ alkoxy group, an aryl group, and a heteroaryl group), a $C_{2-8}$ alkenyl group, a $C_{3-6}$ cycloalkyl group, an aryl group, or a heteroaryl group.

A protecting group for a hydroxyl group is preferably selected from a $C_{1-6}$ alkylcarbonyl group (wherein the $C_{1-6}$ alkylcarbonyl group may be substituted with 1 to 3 substituents selected from a hydroxyl group, —$NR^{37}R^{38}$, a carboxy group, a $C_{1-6}$ alkylcarbonyloxy group, a $C_{1-6}$ alkylaminocarbonyl group, which may be substituted with an amino group, and —$(OCHR^{74}CH_2)_l$—$OR^{73}$ (wherein l, $R^{73}$, $R^{74}$ are the same as those defined above)), an arylcarbonyl group, which may be substituted with a carboxy group, a heteroarylcarbonyl group, a $C_{1-6}$ alkoxycarbonyl group, which may be substituted with a 4- to 12-heterocyclyl group, —$CONR^{71}R^{72}$ (wherein $R^{71}$ and $R^{72}$ are the same as those defined above), and —$CO(OCHR^{76}CH_2)_k$—$OR^{75}$ (wherein k, $R^{75}$, and $R^{76}$ are the same as those defined above).

Preferably, each of $R^{37}$ and $R^{38}$ is independently selected from a hydrogen atom, a $C_{1-8}$ alkyl group (wherein the $C_{1-8}$ alkyl group may be substituted with an amino group), and an α-amino acid-derived group (a group obtained by conversion of a carboxy group to a carbonyl group).

In addition, such a protected hydroxyl group may be esters of naturally occurring type amino acids (namely, asparagine, aspartic acid, alanine, arginine, isoleucine, glycine, glutamine, glutamic acid, cysteine, serine, tyrosine, tryptophan, threonine, valine, histidine, phenylalanine, proline, methionine, lysine, and leucine), esters of non-naturally occurring type amino acids, dipeptide esters, tripeptide esters, or tetrapeptide esters.

Examples of a protecting group for an —NH— group or amino group may include a $C_{1-6}$ alkylcarbonyl group, an arylcarbonyl group, a heteroarylcarbonyl group, a $C_{1-6}$ alkoxycarbonyl group, a $C_{1-6}$ alkylaminocarbonyl group, a di($C_{1-6}$ alkyl)aminocarbonyl group, an aryl $C_{1-6}$ alkyl group, a heteroaryl $C_{1-6}$ alkyl group, an (aryl $C_{1-6}$ alkyl)aminocarbonyl group, —$P(=O)(OH)_2$, —$CH_2OP(=O)(OH)_2$, a $C_{1-6}$ alkyl group, and a $C_{1-6}$ alkylsulfonyl group. In addition, such a protected —NH— group or amino group may be amides of naturally occurring type or non-naturally occurring type amino acids, dipeptide amides, tripeptide esters, and tetrapeptide amides.

Moreover, an amino group is protected by a protecting group, so that it may form a saturated or unsaturated heterocyclyl group, such as a phthalic acid imide group, a succinic acid imide group, a glutaric acid imide group, or a 1-pyrrolyl group.

When a carboxy group is converted to an ester group or an amide group, which may be substituted, examples of such an ester group may include a $C_{1-6}$ alkyl ester, an aryl ester, a heteroaryl ester, an aryl $C_{1-6}$ alkyl ester, a heteroaryl $C_{1-6}$ alkyl ester, a $C_{1-6}$ alkoxy $C_{1-6}$ alkyl ester, an aryloxy $C_{1-6}$ alkyl ester, an aryl $C_{1-6}$ alkoxy $C_{1-6}$ alkyl ester, a hydroxy $C_{1-6}$ alkyl ester, an amino $C_{1-6}$ alkyl ester, a $C_{1-6}$ alkylamino $C_{1-6}$ alkyl ester, and a di($C_{1-6}$ alkyl)amino $C_{1-6}$ alkyl ester. Preferred ester groups include a methyl ester group, an ethyl ester group, a 2-hydroxyethyl ester group, and a 2-(dimethylamino)ethyl ester group.

The amide group is an amide group represented by —$CONR^{71}R^{72}$, for example. Each of $R^{71}$ and $R^{72}$ may be independently selected from a hydrogen atom, a $C_{1-6}$ alkyl group, an aryl group, a heteroaryl group, an aryl $C_{1-6}$ alkyl group, a heteroaryl $C_{1-6}$ alkyl group, a $C_{1-6}$ alkoxy $C_{1-6}$ alkyl group, an aryloxy $C_{1-6}$ alkyl group, an aryl $C_{1-6}$ alkoxy $C_{1-6}$ alkyl group, a hydroxyl $C_{1-6}$ alkyl group, an amino $C_{1-6}$ alkyl group, a $C_{1-6}$ alkylamino $C_{1-6}$ alkyl group, a di($C_{1-6}$ alkyl) amino $C_{1-6}$ alkyl group, a hydroxyl group, and an alkoxy group. Each of $R^{71}$ and $R^{72}$ is preferably a hydrogen atom, a methyl group, an ethyl group, a 2-hydroxyethyl group, or a 2-(dimethylamino)ethyl group.

Specific examples of —$(OCHR^{74}CH_2)_l$—$OR^{73}$ (wherein l, $R^{73}$, and $R^{74}$ are the same as those defined as above) may include —$(OCH_2CH_2)_2$—OH, —$OCH_2CH_2$—$OCH_3$, —$(OCH_2CH_2)_2$—$OCH_3$, —$(OCH_2CH_2)_5$—$OCH_3$, —$(OCH_2CH_2)_3$—$OCH_3$, —$(OCH_2CH_2)_4$—$OCH_3$, —$(OCH_2CH_2)_6$—$OCH_3$, —$(OCH_2CH_2)_3$—OH, —$(OCH_2CH_2)_5$—OH, —$(OCH_2CH_2)_6$—OH, —$(OCH_2CH_2)_{10}$—$OCH_3$, —$(OCH_2CH_2)_7$—$OCH_3$, —$(OCH_2CH_2)_8$—$OCH_3$, —$(OCH_2CH_2)_9$—$OCH_3$, —$(OCH_2CH_2)_1$—$OCH_3$, —$(OCH_2CH_2)_{12}$—$OCH_3$, —$(OCH_2CH_2)_7$—OH, —$(OCH_2CH_2)$—OH, —$(OCH_2CH_2)_9$—OH, —$(OCH_2CH_2)_{10}$—OH, —$(OCH_2CH_2)_1$—OH, and —$(OCH_2CH_2)_{12}$—OH. In addition, an acetyl group is particularly preferable as a $C_{1-6}$ alkylcarbonyl group in a $C_{1-6}$ alkylcarbonyl group, which is substituted with —$(OCHR^{74}CH_2)_l$—$OR^{73}$.

Specific examples of —$CO(OCHR^{76}CH_2)_k$—$OR^{75}$ (wherein k, $R^{75}$, and $R^{76}$ are the same as those defined above) may include —$CO(OCH_2CH_2)_2$—OH, —$CO(OCH_2CH_2)_3$—OH, —$CO(OCH_2CH_2)_4$—OH, —$CO(OCH_2CH_2)_6$—OH, —$CO(OCH_2CH_2)_7$—OH, —$CO(OCH_2CH_2)_8$—OH, —$CO(OCH_2CH_2)_9$—OH, —$COOCH_2CH_2$—$OCH(CH_2OH)CH_2OH$, —$CO(OCH_2CH_2)_2$—$OCH(CH_2OH)CH_2OH$, —$CO(OCH_2CH_2)_{10}$—OH, —$CO(OCH_2CH_2)_{10}$—$OCH_3$, —$COOCH(CH_2 (OCH_2CH_2)_2$—OH)$CH_2 (OCH_2CH_2)_2$—OH, —$COOCH(CH_2OCH(CH_2 (OCH_2CH_2)_2$—OH)$CH_2 (OCH_2CH_2)_2$—OH)$CH_2 (OCH_2CH_2)_2$—OH, —$COOCH (CH_2OCH_2CH_2OH)CH_2OCH_2CH_2OH$, —$COOCH(CH_2 (OCH_2CH_2)_3$—OH)$CH_2 (OCH_2CH_2)_3$—OH, —$COOCH_2CH_2$—$OCH_3$, —$CO(OCH_2CH_2)_2$—$OCH_3$, —$CO(OCH_2CH_2)_3$—$OCH_3$, —$CO(OCH_2CH_2)_4$—$OCH_3$, —$CO(OCH_2CH_2)_5$—$OCH_3$, —$CO(OCH_2CH_2)_6$—$OCH_3$, —$CO(OCH_2CH_2)_7$—$OCH_3$, —$CO(OCH_2CH_2)$—$OCH_3$, —$CO(OCH_2CH_2)_9$—$OCH_3$, —$CO(OCH_2CH_2)_1$, —$OCH_3$, —$CO(OCH_2CH_2)_{12}$—$OCH_3$, —$CO(OCH_2CH_2)_1$, —OH, and —$CO(OCH_2CH_2)_{12}$—OH.

Each of k, l, i, m, and j represents an integer from 1 to 20. Each of them is preferably an integer from 1 to 12 in view of commercial availability of corresponding reagent.

Preferably, each of $R^{51}$ and $R^{52}$ is independently selected from a hydrogen atom, a methyl group, and a vinyl group. In addition, $R^{51}$ and $R^{52}$ are preferably identical to each other. Moreover, particularly preferably, $R^{51}$ and $R^{52}$ are simultaneously a hydrogen atom and a methyl group.

$R^{53}$ is preferably selected from a hydrogen atom, a $C_{1-6}$ alkylcarbonyl group (wherein the $C_{1-6}$ alkylcarbonyl group may be substituted with 1 to 3 substituents selected from a hydroxyl group, —(OCH$_2$CH$_2$)$_l$—OR$^{73}$ (wherein R$^{73}$ and l are the same as those defined above)), and —CO(OCHR$^{76}$CH$_2$)$_k$—OR$^{75}$ (wherein R$^{75}$, R$^{76}$, and k are the same as those defined above).

Preferred examples of a C$_{1-6}$ alkylcarbonyl group in R$^{53}$, which may be substituted with a hydroxyl group, may include a 2,3-dihydroxypropionyl group, a 2,2-bis(hydroxymethyl)propionyl group, and a 3-hydroxy-2,2-bis(hydroxymethyl)propionyl group.

Preferred examples of a propionyl group, which is substituted with 1 or 2 hydroxyl groups, in a propionyloxy group substituted with 1 or 2 hydroxyl groups, may include a 2,3-dihydroxypropionyl group and a 2,2-bis(hydroxymethyl)propionyl group.

Specific examples of the present invention include the compound represented by the following formula and compounds shown in the following table:

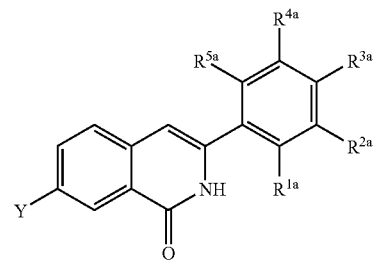

[Formula 7]

However, the present invention is not limited to such examples.

TABLE 1

| Compound No. | R$^{1a}$ | R$^{2a}$ | R$^{3a}$ | R$^{4a}$ | R$^{5a}$ | Y | Example |
|---|---|---|---|---|---|---|---|
| 1 | CF$_3$ | H | H | H | H | β-lactam (azetidinone) | Example 1-1 |
| 2 | CF$_3$ | H | H | H | H | 2-oxopiperidinyl | Example 1-2 |
| 3 | CF$_3$ | H | H | H | H | 2-oxo-2H-pyridinyl | Example 1-3 |
| 4 | CF$_3$ | H | H | H | H | (4S)-4-hydroxy-2-oxopyrrolidinyl | Example 1-4 |
| 5 | CF$_3$ | H | H | H | H | (4R)-4-hydroxy-2-oxopyrrolidinyl | Example 1-5 |
| 6 | CF$_3$ | H | H | H | H | 4-methoxy-3-pyrrolin-2-one | Example 1-6 |

TABLE 1-continued

| Compound No. | $R^{1a}$ | $R^{2a}$ | $R^{3a}$ | $R^{4a}$ | $R^{5a}$ | Y | Example |
|---|---|---|---|---|---|---|---|
| 7 | $CF_3$ | H | H | H | H | (5-hydroxymethyl-2-oxopyrrolidin-1-yl) | Example 1-7 |
| 8 | $CF_3$ | H | H | H | H | (4-benzyloxy-2-oxo-2,5-dihydropyrrol-1-yl) | Example 1-8 |
| 9 | $CF_3$ | H | H | H | H | (3-(2-hydroxyethyl)-2-oxoimidazolidin-1-yl) | Example 1-9 |
| 10 | $CF_3$ | H | H | H | H | (4-hydroxymethyl-2-oxooxazolidin-3-yl) | Example 1-10 |
| 11 | $CF_3$ | H | H | H | H | (4-((1-phenylvinyloxy)methyl)-2-oxooxazolidin-3-yl) | Example 1-11 |
| 12 | $CF_3$ | H | H | H | H | (5-chloromethyl-2-oxooxazolidin-3-yl) | Example 1-12 |
| 13 | $CF_3$ | H | H | H | H | (5-hydroxymethyl-2-oxooxazolidin-3-yl) | Example 1-13 |

TABLE 1-continued

| Compound No. | $R^{1a}$ | $R^{2a}$ | $R^{3a}$ | $R^{4a}$ | $R^{5a}$ | Y | Example |
|---|---|---|---|---|---|---|---|
| 14 | $CF_3$ | H | H | H | H | (S)-5-(hydroxymethyl)oxazolidin-2-one-N-yl | Example 1-14 |
| 15 | $CF_3$ | H | H | H | H | 2-oxopyrrolidin-1-yl | Example 1-15 |
| 16 | $CF_3$ | H | H | H | H | (R)-4-(hydroxymethyl)oxazolidin-2-one-N-yl | Example 1-16 |
| 17 | $CF_3$ | H | H | H | H | oxazolidin-2-one-N-yl | Example 1-17 |
| 18 | $CF_3$ | H | H | H | H | 3-methyl-2-oxo-2,3-dihydro-1H-imidazol-1-yl | Example 1-18 |
| 19 | morpholin-4-yl | H | H | H | H | (S)-5-(hydroxymethyl)oxazolidin-2-one-N-yl | Example 1-19 |
| 20 | OMe | H | H | H | H | (S)-5-(hydroxymethyl)oxazolidin-2-one-N-yl | Example 1-20 |
| 21 | Me | H | H | H | H | (S)-5-(hydroxymethyl)oxazolidin-2-one-N-yl | Example 1-21 |
| 22 | $OCF_3$ | H | H | H | H | (S)-5-(hydroxymethyl)oxazolidin-2-one-N-yl | Example 1-22 |

TABLE 1-continued

| Compound No. | $R^{1a}$ | $R^{2a}$ | $R^{3a}$ | $R^{4a}$ | $R^{5a}$ | Y | Example |
|---|---|---|---|---|---|---|---|
| 23 | phenyl* | H | H | H | H | 5-(hydroxymethyl)-2-oxo-oxazolidin-3-yl* | Example 1-23 |
| 24 | Et | H | H | H | H | 5-(hydroxymethyl)-2-oxo-oxazolidin-3-yl* | Example 1-24 |
| 25 | OMe | H | H | H | OMe | 5-(hydroxymethyl)-2-oxo-oxazolidin-3-yl* | Example 1-25 |
| 26 | F | H | H | H | H | 5-(hydroxymethyl)-2-oxo-oxazolidin-3-yl* | Example 1-26 |
| 27 | OCF$_3$ | H | H | H | H | 5-(hydroxymethyl)-2-oxo-oxazolidin-3-yl* | Example 1-27 |
| 28 | morpholin-4-yl* | H | H | H | H | 5-(hydroxymethyl)-2-oxo-oxazolidin-3-yl* | Example 1-28 |
| 29 | CF$_3$ | H | H | H | H | 5-(2-hydroxyethyl)-2-oxo-oxazolidin-3-yl* | Example 1-29 |
| 30 | CF$_3$ | H | H | H | H | 5-(azidomethyl)-2-oxo-oxazolidin-3-yl* | Example 1-30 |

TABLE 1-continued

| Compound No. | $R^{1a}$ | $R^{2a}$ | $R^{3a}$ | $R^{4a}$ | $R^{5a}$ | Y | Example |
|---|---|---|---|---|---|---|---|
| 31 | $CF_3$ | H | H | H | H | 5-(aminomethyl)-2-oxo-oxazolidin-3-yl | Example 1-31 |
| 32 | $CF_3$ | H | H | H | H | 5-((acetimidamido)methyl)-2-oxo-oxazolidin-3-yl | Example 1-32 |
| 33 | $CF_3$ | H | H | H | H | 5-(morpholinomethyl)-2-oxo-oxazolidin-3-yl | Example 1-33 |
| 34 | $CF_3$ | H | H | H | H | 5-((4-hydroxypiperidin-1-yl)methyl)-2-oxo-oxazolidin-3-yl | Example 1-34 |
| 35 | $CF_3$ | H | H | H | H | 4-((benzyloxy)methyl)-1-methyl-2-oxo-imidazolidin-3-yl | Example 1-35 |

TABLE 1-continued
| Compound No. | R$^{1a}$ | R$^{2a}$ | R$^{3a}$ | R$^{4a}$ | R$^{5a}$ | Y | Example |
|---|---|---|---|---|---|---|---|
| 36 | CF$_3$ | H | H | H | H | 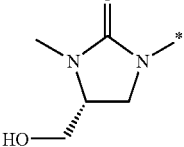 | Example 1-36 |
| 37 | Et | H | H | H | H | 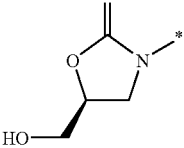 | Example 1-37 |
| 38 | CF$_3$ | H | H | H | H | 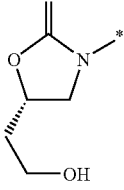 | Example 1-38 |
| 39 | CF$_3$ | H | H | H | H | 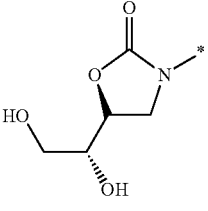 | Example 1-39 |
| 40 | 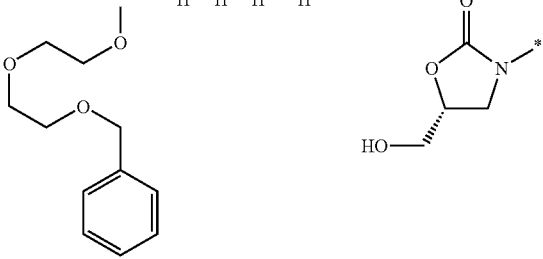 | H | H | H | H | | Example 1-40 |
| 41 | 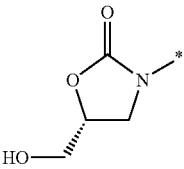 | H | H | H | H | | Example 1-41 |

TABLE 1-continued

| Compound No. | R¹ᵃ | R²ᵃ | R³ᵃ | R⁴ᵃ | R⁵ᵃ | Y | Example |
|---|---|---|---|---|---|---|---|
| 42 | (CH₂CH₂O)₂CH₂CH₂OH | H | H | H | H | 5-(hydroxymethyl)-oxazolidin-2-on-3-yl | Example 1-42 |
| 43 | CF₃ | H | H | H | CF₃ | 5-(hydroxymethyl)-oxazolidin-2-on-3-yl | Example 1-43 |
| 44 | CF₃ | H | H | H | H | 5-[1,3-dihydroxyprop-2-yl]-oxazolidin-2-on-3-yl | Example 1-44 |
| 45 | CF₃ | H | H | H | H | 3-(ethoxycarbonyl)-2-oxopyrrolidin-1-yl | Example 1-45 |
| 46 | CF₃ | H | H | H | H | 3-(hydroxymethyl)-2-oxopyrrolidin-1-yl | Example 1-46 |
| 47 | isobutyl | H | H | H | H | 5-(hydroxymethyl)-oxazolidin-2-on-3-yl | Example 1-47 |
| 48 | allyl(but-3-enyl) | H | H | H | H | 5-(hydroxymethyl)-oxazolidin-2-on-3-yl | Example 1-48 |
| 49 | CF₃ | H | H | H | H | 2-oxo-1,3-oxazinan-3-yl | Example 1-49 |

TABLE 1-continued

| Compound No. | $R^{1a}$ | $R^{2a}$ | $R^{3a}$ | $R^{4a}$ | $R^{5a}$ | Y | Example |
|---|---|---|---|---|---|---|---|
| 50 | $CF_3$ | H | H | H | H | 3-hydroxy-2,5-dihydro-1H-pyrrol-1-yl (2,5-dihydro-4-hydroxy-2-oxo-1H-pyrrol-1-yl) | Example 1-50 |
| 51 | $CF_3$ | H | H | H | H | 2,5-dioxopyrrolidin-1-yl | Example 1-51 |

Hereinafter, compound names corresponding to the aforementioned compound numbers are shown.

(1): 7-(2-oxoazetidin-1-yl)-3-(2-trifluoromethylphenyl)-2H-isoquinolin-1-one,
(2): 7-(2-oxopiperidin-1-yl)-3-(2-trifluoromethylphenyl)-2H-isoquinolin-1-one,
(3): 7-(2-oxo-2H-pyridin-1-yl)-3-(2-trifluoromethylphenyl)-2H-isoquinolin-1-one,
(4): 7-((R)-4-hydroxy-2-oxopyrrolidin-1-yl)-3-(2-trifluoromethylphenyl)-2H-isoquinolin-1-one,
(5): 7-((S)-4-hydroxy-2-oxopyrrolidin-1-yl)-3-(2-trifluoromethylphenyl)-2H-isoquinolin-1-one,
(6): 7-(4-methoxy-2-oxo-2,5-dihydropyrrol-1-yl)-3-(2-trifluoromethylphenyl)-2H-isoquinolin-1-one,
(7): 7-((S)-2-hydroxymethyl-5-oxopyrrolidin-1-yl)-3-(2-trifluoromethylphenyl)-2H-isoquinolin-1-one,
(8): 7-(4-benzyloxy-2-oxo-2,5-dihydropyrrol-1-yl)-3-(2-trifluoromethylphenyl)-2H-isoquinolin-1-one,
(9): 7-[3-(2-hydroxyethyl)-2-oxoimidazolidin-1-yl]-3-(2-trifluoromethylphenyl)-2H-isoquinolin-1-one,
(10): 7-((R)-4-hydroxymethyl-2-oxazolidin-3-yl)-3-(2-trifluoromethylphenyl)-2H-isoquinolin-1-one,
(11): (R)-2-oxo-3-[1-oxo-3-(2-trifluoromethylphenyl)-1,2-dihydroisoquinolin-7-yl]oxazolidin-4-ylmethyl benzoate,
(12): 7-(5-chloromethyl-2-oxooxazolidin-3-yl)-3-(2-trifluoromethylphenyl)-2H-isoquinolin-1-one,
(13): 7-((S)-5-hydroxymethyl-2-oxooxazolidin-3-yl)-3-(2-trifluoromethylphenyl)-2H-isoquinolin-1-one,
(14): 7-((R)-5-hydroxymethyl-2-oxooxazolidin-3-yl)-3-(2-trifluoromethylphenyl)-2H-isoquinolin-1-one,
(15): 7-(2-oxopyrrolidin-1-yl)-3-(2-trifluoromethylphenyl)-2H-isoquinolin-1-one,
(16): 7-((R)-2-hydroxymethyl-5-oxopyrrolidin-1-yl)-3-(2-trifluoromethylphenyl)-2H-isoquinolin-1-one,
(17): 7-(2-oxooxazolidin-3-yl)-3-(2-trifluoromethylphenyl)-2H-isoquinolin-1-one,
(18): 7-(3-methyl-2-oxo-2,3-dihydroimidazol-1-yl)-3-(2-trifluoromethylphenyl)-2H-isoquinolin-1-one,
(19): 7-((R)-5-hydroxymethyl-2-oxooxazolidin-3-yl)-3-(2-morpholin-4-ylphenyl)-2H-isoquinolin-1-one,
(20): 7-((R)-5-hydroxymethyl-2-oxooxazolidin-3-yl)-3-(2-methoxyphenyl)-2H-isoquinolin-1-one,
(21): 7-((R)-5-hydroxymethyl-2-oxooxazolidin-3-yl)-3-o-tolyl-2H-isoquinolin-1-one,
(22): 7-((R)-5-hydroxymethyl-2-oxooxazolidin-3-yl)-3-(2-trifluoromethoxyphenyl)-2H-isoquinolin-1-one,
(23): 3-biphenyl-2-yl-7-((R)-5-hydroxymethyl-2-oxooxazolidin-3-yl)-2H-isoquinolin-1-one,
(24): 3-(2-ethylphenyl)-7-((R)-5-hydroxymethyl-2-oxooxazolidin-3-yl)-2H-isoquinolin-1-one,
(25): 3-(2,6-dimethoxyphenyl)-7-((R)-5-hydroxymethyl-2-oxooxazolidin-3-yl)-2H-isoquinolin-1-one,
(26): 3-(2-fluorophenyl)-7-((S)-5-hydroxymethyl-2-oxooxazolidin-3-yl)-2H-isoquinolin-1-one,
(27): 7-((S)-5-hydroxymethyl-2-oxooxazolidin-3-yl)-3-(2-trifluoromethoxyphenyl)-2H-isoquinolin-1-one,
(28): 7-((S)-5-hydroxymethyl-2-oxooxazolidin-3-yl)-3-(2-morpholin-4-ylphenyl)-2H-isoquinolin-1-one,
(29): 7-[5-(2-hydroxyethyl)-2-oxooxazolidin-3-yl]-3-(2-trifluoromethylphenyl)-2H-isoquinolin-1-one,
(30): 7-(5-azidomethyl-2-oxooxazolidin-3-yl)-3-(2-trifluoromethylphenyl)-2H-isoquinolin-1-one,
(31): 7-(5-aminomethyl-2-oxooxazolidin-3-yl)-3-(2-trifluoromethylphenyl)-2H-isoquinolin-1-one,
(32): N-{2-oxo-3-[1-oxo-3-(2-trifluoromethylphenyl)-1,2-dihydroisoquinolin-7-yl]oxazolidin-5-ylmethyl}acetamide,
(33): 7-(5-morpholin-4-ylmethyl-2-oxooxazolidin-3-yl)-3-(2-trifluoromethylphenyl)-2H-isoquinolin-1-one,
(34): 7-[5-(4-hydroxypiperidin-1-ylmethyl)-2-oxooxazolidin-3-yl]-3-(2-trifluoromethylphenyl)-2H-isoquinolin-1-one,
(35): 7-((R)-4-benzyloxymethyl-3-methyl-2-oxoimidazolidin-1-yl)-3-(2-trifluoromethylphenyl)-2H-isoquinolin-1-one,
(36): 7-((R)-4-hydroxymethyl-3-methyl-2-oxoimidazolidin-1-yl)-3-(2-trifluoromethylphenyl)-2H-isoquinolin-1-one,
(37): 3-(2-ethylphenyl)-7-((S)-5-hydroxymethyl-2-oxooxazolidin-3-yl)-2H-isoquinolin-1-one,
(38): 7-[(S)-5-(2-hydroxyethyl)-2-oxooxazolidin-3-yl]-3-(2-trifluoromethylphenyl)-2H-isoquinolin-1-one,
(39): 7-[(S)-5-((R)-1,2-dihydroxyethyl)-2-oxooxazolidin-3-yl]-3-(2-trifluoromethylphenyl)-2H-isoquinolin-1-one,
(40): 3-{2-[2-(2-benzyloxyethoxy)ethoxy]phenyl}-7-((R)-5-hydroxymethyl-2-oxooxazolidin-3-yl)-2H-isoquinolin-1-one,
(41): 3-{2-[2-(2-hydroxyethoxy)ethoxy]phenyl}-7-((R)-5-hydroxymethyl-2-oxooxazolidin-3-yl)-2H-isoquinolin-1-one,
(42): 3-{2-[2-(2-hydroxyethoxy)ethoxy]phenyl}-7-((S)-5-hydroxymethyl-2-oxooxazolidin-3-yl)-2H-isoquinolin-1-one,
(43): 3-(2,6-bistrifluoromethylphenyl)-7-((R)-5-hydroxymethyl-2-oxooxazolidin-3-yl)-2H-isoquinolin-1-one, (44): 7-[5-(2-hydroxy-1-hydroxymethylethyl)-2-oxooxazolidin-3-yl]-3-(2-trifluoromethylphenyl)-2H-isoquinolin-1-one, (45): ethyl 2-oxo-1-[1-oxo-3-(2-trifluoromethylphenyl)-1,2-dihydroisoquinolin-7-yl]pyrrolidine-3-carboxylate, (46): 7-(3-hydroxymethyl-2-oxopyrrolidin-1-yl)-3-(2-trifluoromethylphenyl)-2H-isoquinolin-1-one, (47): 7-((R)-5-hydroxymethyl-2-oxooxazolidin-3-yl)-3-(2-isobutylphenyl)-2H-isoquinolin-1-one, (48): 3-(2-allylphenyl)-7-((R)-5-hydroxymethyl-2-oxooxazolidin-3-yl)-2H-isoquinolin-1-one, (49): 7-(2-oxo-[1,3]oxazinan-3-yl)-3-(2-trifluoromethylphenyl)-2H-isoquinolin-1-one, (50): 7-(4-hydroxy-2-oxo-2,5-dihydropyrrol-1-yl)-3-(2-trifluoromethylphenyl)-2H-isoquinolin-1-one, and (51): 1-[1-oxo-3-(2-trifluoromethylphenyl)-1,2-dihydroisoquinolin-7-yl]pyrrolidine-2,5-dione.

Specific examples of the present invention include the compound represented by the following formula and compounds shown in the following table:

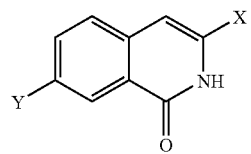

[Formula 8]

However, the present invention is not limited to such examples.

TABLE 2

| Compound No. | Y | X | Example |
|---|---|---|---|
| A1 | ethyl ester oxazolidinone | 2-CF3-phenyl | Example 2-1 |
| A2 | methyl ester oxazolidinone | 2-CF3-phenyl | Example 2-2 |
| A3 | HO-C(CH3)2-oxazolidinone | 2-CF3-phenyl | Example 2-3 |
| A4 | HOOC-oxazolidinone | 2-CF3-phenyl | Example 2-4 |
| A5 | H2NCO-oxazolidinone | 2-CF3-phenyl | Example 2-5 |

TABLE 2-continued

| Compound No. | Y | X | Example |
|---|---|---|---|
| A6 | (5-methylcarbamoyl-oxazolidin-2-one, N-*) | 2-CF₃-phenyl-* | Example 2-6 |
| A7 | (5-dimethylcarbamoyl-oxazolidin-2-one, N-*) | 2-CF₃-phenyl-* | Example 2-7 |
| A8 | (5-(2-hydroxyethyl)carbamoyl-oxazolidin-2-one, N-*) | 2-CF₃-phenyl-* | Example 2-8 |
| A9 | (5-(morpholin-4-ylcarbonyl)-oxazolidin-2-one, N-*) | 2-CF₃-phenyl-* | Example 2-9 |
| A10 | (5-(4-hydroxypiperidin-1-ylcarbonyl)-oxazolidin-2-one, N-*) | 2-CF₃-phenyl-* | Example 2-10 |
| A11 | (5-(2-hydroxypropan-2-yl)-oxazolidin-2-one, N-*) | 2-CF₃-phenyl-* | Example 2-11 |
| A12 | (5-(2-hydroxypropan-2-yl)-oxazolidin-2-one, N-*) | 2-CF₃-phenyl-* | Example 2-12 |

TABLE 2-continued

| Compound No. | Y | X | Example |
|---|---|---|---|
| A13 | (S)-2-oxo-1,3-oxazolidine-5-carboxamide (H₂N-C(=O)- at 5-position) attached via N | 2-(trifluoromethyl)phenyl | Example 2-13 |
| A14 | (R)-2-oxo-1,3-oxazolidine-5-carboxamide attached via N | 2-(trifluoromethyl)phenyl | Example 2-14 |
| A15 | (S)-5-[(4-hydroxypiperidin-1-yl)carbonyl]-2-oxo-1,3-oxazolidin-3-yl | 2-(trifluoromethyl)phenyl | Example 2-15 |
| A16 | (R)-5-[(4-hydroxypiperidin-1-yl)carbonyl]-2-oxo-1,3-oxazolidin-3-yl | 2-(trifluoromethyl)phenyl | Example 2-16 |
| A17 | (R)-5-[(2-methoxyethoxy)methyl]-2-oxo-1,3-oxazolidin-3-yl | 2-(trifluoromethyl)phenyl | Example 2-17 |
| A18 | (R)-5-(methoxymethyl)-2-oxo-1,3-oxazolidin-3-yl | 2-(trifluoromethyl)phenyl | Example 2-18 |
| A19 | (R)-5-{[2-(2-methoxyethoxy)ethoxy]methyl}-2-oxo-1,3-oxazolidin-3-yl | 2-(trifluoromethyl)phenyl | Example 2-19 |

TABLE 2-continued

| Compound No. | Y | X | Example |
|---|---|---|---|
| A20 | morpholine-CH₂CH₂-O-CH₂-(oxazolidinone) | 2-CF₃-phenyl | Example 2-20 |
| A21 | benzyl-O-CH₂-(oxazolidinone) | 2-CF₃-phenyl | Example 2-21 |
| A22 | piperidine-CH₂-(oxazolidinone) | 2-CF₃-phenyl | Example 2-22 |
| A23 | (2-hydroxymethyl-pyrrolidine)-CH₂-(oxazolidinone) | 2-CF₃-phenyl | Example 2-23 |
| A24 | (3-hydroxy-piperidine)-CH₂-(oxazolidinone) | 2-CF₃-phenyl | Example 2-24 |
| A25 | (3-hydroxy-piperidine)-CH₂-(oxazolidinone) | 2-CF₃-phenyl | Example 2-25 |
| A26 | (2-hydroxymethyl-pyrrolidine)-CH₂-(oxazolidinone) | 2-CF₃-phenyl | Example 2-26 |

TABLE 2-continued

| Compound No. | Y | X | Example |
|---|---|---|---|
| A27 | 4-(hydroxymethyl)piperidin-1-yl-methyl-oxazolidinone | 2-CF₃-phenyl | Example 2-27 |
| A28 | 4-methoxypiperidin-1-yl-methyl-oxazolidinone | 2-CF₃-phenyl | Example 2-28 |
| A29 | morpholin-4-yl-methyl-oxazolidinone | 2-CF₃-phenyl | Example 2-29 |
| A30 | 4-hydroxypiperidin-1-yl-methyl-oxazolidinone | 2-CF₃-phenyl | Example 2-30 |
| A31 | methanesulfonylamino-methyl-oxazolidinone | 2-CF₃-phenyl | Example 2-31 |
| A32 | ethanesulfonylamino-methyl-oxazolidinone | 2-CF₃-phenyl | Example 2-32 |
| A33 | propanesulfonylamino-methyl-oxazolidinone | 2-CF₃-phenyl | Example 2-33 |

TABLE 2-continued

| Compound No. | Y | X | Example |
|---|---|---|---|
| A34 | isopropyl-SO2-NH-CH2-(oxazolidinone)-* | *-C6H4-CF3 (ortho) | Example 2-34 |
| A35 | n-butyl-SO2-NH-CH2-(oxazolidinone)-* | *-C6H4-CF3 (ortho) | Example 2-35 |
| A36 | phenyl-SO2-NH-CH2-(oxazolidinone)-* | *-C6H4-CF3 (ortho) | Example 2-36 |
| A37 | vinyl-SO2-NH-CH2-(oxazolidinone)-* | *-C6H4-CF3 (ortho) | Example 2-37 |
| A38 | HO-CH2CH2-SO2-NH-CH2-(oxazolidinone)-* | *-C6H4-CF3 (ortho) | Example 2-38 |
| A39 | HO-CH2-(oxazolidinone)-* | *-C6H4-CH2CH2CH3 (ortho) | Example 2-39 |
| A40 | HO-CH2-(oxazolidinone)-* | *-C6H4-CH2-C(=CH2)-CH3 (ortho) | Example 2-40 |

TABLE 2-continued

| Compound No. | Y | X | Example |
|---|---|---|---|
| A41 | (S)-5-(hydroxymethyl)oxazolidin-2-one, N-linked | 2-propoxyphenyl | Example 2-41 |
| A42 | (S)-5-(hydroxymethyl)oxazolidin-2-one, N-linked | 2-(2-methoxyethoxy)phenyl | Example 2-42 |
| A43 | (S)-5-(hydroxymethyl)oxazolidin-2-one, N-linked | 2-ethoxyphenyl | Example 2-43 |
| A44 | (S)-5-(hydroxymethyl)oxazolidin-2-one, N-linked | 2-(3-hydroxy-2-(hydroxymethyl)-2-methylpropyl)phenyl | Example 2-44 |
| A45 | (S)-5-(hydroxymethyl)oxazolidin-2-one, N-linked | 2-(2-hydroxypropyl)phenyl | Example 2-45 |
| A46 | (S)-5-(hydroxymethyl)oxazolidin-2-one, N-linked | 1-ethyl-1H-benzimidazol-2-yl | Example 2-46 |
| A47 | (S)-5-(hydroxymethyl)oxazolidin-2-one, N-linked | 2-(methylthio)phenyl | Example 2-47 |
| A48 | (S)-5-(hydroxymethyl)oxazolidin-2-one, N-linked | 2-(methylsulfonyl)phenyl | Example 2-48 |

TABLE 2-continued

| Compound No. | Y | X | Example |
|---|---|---|---|
| A49 | (S)-4-hydroxy-5-(hydroxymethyl)oxazolidin-2-yl (N-attached) | 2-(trifluoromethyl)phenyl | Example 2-49 |
| A50 | (S)-5-(1,2-dihydroxyethyl)oxazolidin-2-on-3-yl | 2-(trifluoromethyl)phenyl | Example 2-50 |
| A51 | (S)-5-((cyclopropanesulfonamido)methyl)oxazolidin-2-on-3-yl | 2-(trifluoromethyl)phenyl | Example 2-51 |
| A52 | 5-(hydroxymethyl)oxazolidin-2-on-3-yl | 2-(trifluoromethyl)phenyl | Example 2-52 |
| A53 | (S)-3-hydroxy-2-oxopyrrolidin-1-yl | 2-(trifluoromethyl)phenyl | Example 2-53 |
| A54 | 3-(N,N-dimethylcarbamoyl)-2-oxopyrrolidin-1-yl | 2-(trifluoromethyl)phenyl | Example 2-54 |
| A55 | 3-(morpholinomethyl)-2-oxopyrrolidin-1-yl | 2-(trifluoromethyl)phenyl | Example 2-55 |
| A56 | 3-(piperidin-1-ylmethyl)-2-oxopyrrolidin-1-yl | 2-(trifluoromethyl)phenyl | Example 2-56 |

TABLE 2-continued

| Compound No. | Y | X | Example |
|---|---|---|---|
| A57 | 4-hydroxypiperidin-1-ylmethyl pyrrolidin-2-one (N-*) | 2-(trifluoromethyl)phenyl (*) | Example 2-57 |
| A58 | (3,4-dihydroxy)pyrrolidin-2-one (N-*) | 2-(trifluoromethyl)phenyl (*) | Example 2-58 |
| A59 | 1-methyl-4-(hydroxymethyl)imidazolidin-2-one (N-*) | 2-(trifluoromethyl)phenyl (*) | Example 2-59 |
| A60 | 4-(benzyloxymethyl)imidazolidin-2-one (N-*) | 2-(trifluoromethyl)phenyl (*) | Example 2-60 |
| A61 | 4-(hydroxymethyl)imidazolidin-2-one (N-*) | 2-(trifluoromethyl)phenyl (*) | Example 2-61 |
| A62 | 1-methyltetrahydropyrimidin-2(1H)-one (N-*) | 2-(trifluoromethyl)phenyl (*) | Example 2-62 |
| A63 | 4-(benzyloxycarbonyl)piperazin-2-one (N-*) | 2-(trifluoromethyl)phenyl (*) | Example 2-63 |
| A64 | piperazin-2-one (N-*) | 2-(trifluoromethyl)phenyl (*) | Example 2-64 |

TABLE 2-continued

| Compound No. | Y | X | Example |
|---|---|---|---|
| A65 | (S)-5-[(R)-1,2-dihydroxyethyl]-oxazolidin-2-one, N-* | 2-(trifluoromethyl)phenyl-* | Example 2-65 |
| A66 | (R)-5-[(S)-1,2-dihydroxyethyl]-oxazolidin-2-one, N-* | 2-(trifluoromethyl)phenyl-* | Example 2-66 |
| A67 | 5,5-bis(hydroxymethyl)-oxazolidin-2-one, N-* | 2-(trifluoromethyl)phenyl-* | Example 2-67 |
| A68 | 1-(2-hydroxyethyl)-imidazolidin-4-one, N-* | 2-(trifluoromethyl)phenyl-* | Example 2-68 |
| A69 | 5-(hydroxymethyl)-oxazolidin-2-one, N-* | 3-(trifluoromethyl)phenyl-* | Example 2-69 |
| A70 | 5-(hydroxymethyl)-oxazolidin-2-one, N-* | naphthalen-1-yl-* | Example 2-70 |
| A71 | 5-(hydroxymethyl)-oxazolidin-2-one, N-* | furan-2-yl-* | Example 2-71 |

TABLE 2-continued

| Compound No. | Y | X | Example |
|---|---|---|---|
| A72 | 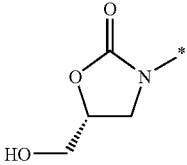 |  | Example 2-72 |
| A73 | 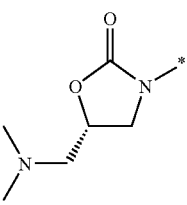 | 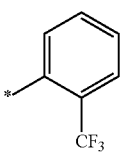 | Example 2-73 |
| A74 | 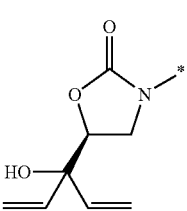 | 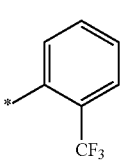 | Example 2-74 |
| A75 | 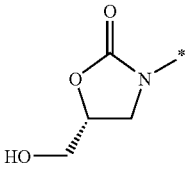 | 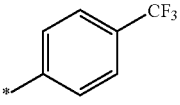 | Example 2-75 |
| A76 | 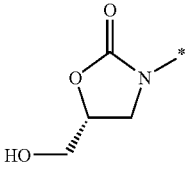 | 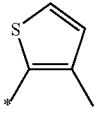 | Example 2-76 |
| A77 | 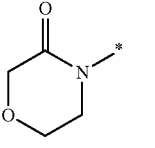 | 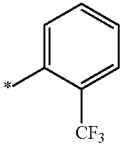 | Example 2-77 |

Hereinafter, compound names corresponding to the aforementioned compound numbers are shown.

(A1): ethyl 2-oxo-3-[1-oxo-3-(2-trifluoromethylphenyl)-1,2-dihydroisoquinolin-7-yl]oxazolidine-5-carboxylate, (A2): methyl 2-oxo-3-[1-oxo-3-(2-trifluoromethylphenyl)-1,2-dihydroisoquinolin-7-yl]oxazolidine-5-carboxylate, (A3): 7-[5-(1-hydroxy-1-methylethyl)-2-oxooxazolidin-3-yl]-3-(2-trifluoromethylphenyl)-2H-isoquinolin-1-one, (A4): 2-oxo-3-[1-oxo-3-(2-trifluoromethylphenyl)-1,2-dihydroisoquinolin-7-yl]oxazolidine-5-carboxylic acid, (A5): 2-oxo-3-[1-oxo-3-(2-trifluoromethylphenyl)-1,2-dihydroisoquinolin-7-yl]oxazolidine-5-carboxylic acid amide, (A6): 2-oxo-3-[1-oxo-3-(2-trifluoromethylphenyl)-1,2-dihydroisoquinolin-7-yl]oxazolidine-5-carboxylic acid methylamide, (A7): 2-oxo-3-[1-oxo-3-(2-trifluoromethylphenyl)-1,2-dihydroisoquinolin-7-yl]oxazolidine-5-carboxylic acid dimethylamide, (A8): 2-oxo-3-[1-oxo-3-(2-trifluoromethylphenyl)-1,2-dihydroisoquinolin-7-yl]oxazolidine-5-carboxylic acid (2-hydroxyethyl)amide, (A9): 7-[5-(morpholine-4-carbonyl)-2-oxooxazolidin-3-yl]-3-(2-trifluoromethylphenyl)-2H-isoquinolin-1-one, (A10): 7-[5-(4-hydroxypiperidine-1-carbonyl)-2-oxooxazolidin-3-yl]-3-(2-trifluoromethylphenyl)-2H-isoquinolin-1-one, (A11): 7-[(S)-5-(1-hydroxy-1-methylethyl)-2-oxooxazolidin-3-yl]-3-(2-trifluoromethylphenyl)-2H-isoquinolin-1-one, (A12): 7-[(R)-5-(1-hydroxy-1-methylethyl)-2-oxooxazolidin-3-yl]-3-(2-trifluoromethylphenyl)-2H-isoquinolin-1-one,
(A13): (S)-2-oxo-3-[1-oxo-3-(2-trifluoromethylphenyl)-1,2-dihydroisoquinolin-7-yl]oxazolidine-5-carboxylic acid amide,
(A14): (R)-2-oxo-3-[1-oxo-3-(2-trifluoromethylphenyl)-1,2-dihydroisoquinolin-7-yl]oxazolidine-5-carboxylic acid amide,
(A15): 7-[(S)-5-(4-hydroxypiperidine-1-carbonyl)-2-oxooxazolidin-3-yl]-3-(2-trifluoromethylphenyl)-2H-isoquinolin-1-one,
(A16): 7-[(R)-5-(4-hydroxypiperidine-1-carbonyl)-2-oxooxazolidin-3-yl]-3-(2-trifluoromethylphenyl)-2H-isoquinolin-1-one,
(A17): 7-[(R)-5-(2-methoxyethoxymethyl)-2-oxooxazolidin-3-yl]-3-(2-trifluoromethylphenyl)-2H-isoquinolin-1-one,
(A18): 7-((R)-5-methoxymethyl-2-oxooxazolidin-3-yl)-3-(2-trifluoromethylphenyl)-2H-isoquinolin-1-one,
(A19): 7-{(R)-5-[2-(2-methoxyethoxy)ethoxymethyl]-2-oxooxazolidin-3-yl}-3-(2-trifluoromethylphenyl)-2H-isoquinolin-1-one,
(A20): 7-[(R)-5-(2-morpholin-4-ylethoxymethyl)-2-oxooxazolidin-3-yl]-3-(2-trifluoromethylphenyl)-2H-isoquinolin-1-one,
(A21): 7-((R)-5-benzyloxymethyl-2-oxooxazolidin-3-yl)-3-(2-trifluoromethylphenyl)-2H-isoquinolin-1-one,
(A22): 7-((S)-2-oxo-5-piperidin-1-ylmethyloxazolidin-3-yl)-3-(2-trifluoromethylphenyl)-2H-isoquinolin-1-one,
(A23): 7-[(S)-5-((S)-2-hydroxymethylpyrrolidin-1-ylmethyl)-2-oxooxazolidin-3-yl]-3-(2-trifluoromethylphenyl)-2H-isoquinolin-1-one,
(A24): 7-[(S)-5-((S)-3-hydroxypiperidin-1-ylmethyl)-2-oxooxazolidin-3-yl]-3-(2-trifluoromethylphenyl)-2H-isoquinolin-1-one,
(A25): 7-[(S)-5-((R)-3-hydroxypiperidin-1-ylmethyl)-2-oxooxazolidin-3-yl]-3-(2-trifluoromethylphenyl)-2H-isoquinolin-1-one,
(A26): 7-[(S)-5-((R)-2-hydroxymethylpyrrolidin-1-ylmethyl)-2-oxooxazolidin-3-yl]-3-(2-trifluoromethylphenyl)-2H-isoquinolin-1-one,
(A27): 7-[(S)-5-(4-hydroxymethylpiperidin-1-ylmethyl)-2-oxooxazolidin-3-yl]-3-(2-trifluoromethylphenyl)-2H-isoquinolin-1-one,
(A28): 7-[(S)-5-(4-methoxypiperidin-1-ylmethyl)-2-oxooxazolidin-3-yl]-3-(2-trifluoromethylphenyl)-2H-isoquinolin-1-one,
(A29): 7-((S)-5-morpholin-4-ylmethyl-2-oxooxazolidin-3-yl)-3-(2-trifluoromethylphenyl)-2H-isoquinolin-1-one,
(A30): 7-[(S)-(4-hydroxypiperidin-1-ylmethyl)-2-oxooxazolidin-3-yl]-3-(2-trifluoromethylphenyl)-2H-isoquinolin-1-one,
(A31): N-{(R)-2-oxo-3-[1-oxo-3-(2-trifluoromethylphenyl)-1,2-dihydroisoquinolin-7-yl]oxazolidin-5-ylmethyl}methanesulfonamide,
(A32): ethanesulfonic acid {(R)-2-oxo-3-[1-oxo-3-(2-trifluoromethylphenyl)-1,2-dihydroisoquinolin-7-yl]oxazolidin-5-ylmethyl}amide,
(A33): propane-1-sulfonic acid {(R)-2-oxo-3-[1-oxo-3-(2-trifluoromethylphenyl)-1,2-dihydroisoquinolin-7-yl]oxazolidin-5-ylmethyl}amide,
(A34): propane-2-sulfonic acid {(R)-2-oxo-3-[1-oxo-3-(2-trifluoromethylphenyl)-1,2-dihydroisoquinolin-7-yl]oxazolidin-5-ylmethyl}amide,
(A35): pentane-1-sulfonic acid {(R)-2-oxo-3-[1-oxo-3-(2-trifluoromethylphenyl)-1,2-dihydroisoquinolin-7-yl]oxazolidin-5-ylmethyl}amide,
(A36): N-{(R)-2-oxo-3-[1-oxo-3-(2-trifluoromethylphenyl)-1,2-dihydroisoquinolin-7-yl]oxazolidin-5-ylmethyl}benzenesulfonamide,
(A37): ethenesulfonic acid {(R)-2-oxo-3-[1-oxo-3-(2-trifluoromethylphenyl)-1,2-dihydroisoquinolin-7-yl]oxazolidin-5-ylmethyl}amide,
(A38): 2-hydroxyethanesulfonic acid {(R)-2-oxo-3-[1-oxo-3-(2-trifluoromethylphenyl)-1,2-dihydroisoquinolin-7-yl]oxazolidin-5-ylmethyl}amide,
(A39): 7-((R)-5-hydroxymethyl-2-oxooxazolidin-3-yl)-3-(2-propylphenyl)-2H-isoquinolin-1-one,
(A40): 7-((R)-5-hydroxymethyl-2-oxooxazolidin-3-yl)-3-[2-(2-methylallyl)phenyl]-2H-isoquinolin-1-one,
(A41): 7-((R)-5-hydroxymethyl-2-oxooxazolidin-3-yl)-3-(2-propoxyphenyl)-2H-isoquinolin-1-one,
(A42): 7-((R)-5-hydroxymethyl-2-oxooxazolidin-3-yl)-3-[2-(2-methoxyethoxy)phenyl]-2H-isoquinolin-1-one,
(A43): 3-(2-ethoxyphenyl)-7-((R)-5-hydroxymethyl-2-oxooxazolidin-3-yl)-2H-isoquinolin-1-one,
(A44): 3-[2-(2,3-dihydroxy-2-methylpropyl)phenyl]-7-((R)-5-hydroxymethyl-2-oxooxazolidin-3-yl)-2H-isoquinolin-1-one,
(A45): 7-((R)-5-hydroxymethyl-2-oxooxazolidin-3-yl)-3-[2-(2-hydroxypropyl)phenyl]-2H-isoquinolin-1-one,
(A46): 3-(1-ethyl-1H-benzimidazol-2-yl)-7-((R)-5-hydroxymethyl-2-oxooxazolidin-3-yl)-2H-isoquinolin-1-one,
(A47): 7-((R)-5-hydroxymethyl-2-oxooxazolidin-3-yl)-3-(2-methylsulfanylphenyl)-2H-isoquinolin-1-one,
(A48): 7-((R)-5-hydroxymethyl-2-oxooxazolidin-3-yl)-3-(2-methanesulfonylphenyl)-2H-isoquinolin-1-one,
(A49): 7-(4-hydroxy-5-hydroxymethyl-2-oxooxazolidin-3-yl)-3-(2-trifluoromethylphenyl)-2H-isoquinolin-1-one,
(A50): 7-[(S)-5-((S)-1,2-dihydroxyethyl)-2-oxooxazolidin-3-yl]-3-(2-trifluoromethylphenyl)-2H-isoquinolin-1-one,
(A51): cyclopropanesulfonic acid {(R)-2-oxo-3-[1-oxo-3-(2-trifluoromethylphenyl)-1,2-dihydroisoquinolin-7-yl]oxazolidin-5-ylmethyl}amide,
(A52): 7-(4-hydroxymethyl-2-oxopyrrolidin-1-yl)-3-(2-trifluoromethylphenyl)-2H-isoquinolin-1-one,
(A53): 7-((S)-3-hydroxy-2-oxopyrrolidin-1-yl)-3-(2-trifluoromethylphenyl)-2H-isoquinolin-1-one,
(A54): 2-oxo-1-[1-oxo-3-(2-trifluoromethylphenyl)-1,2-dihydroisoquinolin-7-yl]pyrrolidine-3-carboxylic acid dimethylamide,
(A55): 7-(3-morpholin-4-ylmethyl-2-oxopyrrolidin-1-yl)-3-(2-trifluoromethylphenyl)-2H-isoquinolin-1-one,
(A56): 7-(2-oxo-3-piperidin-1-ylmethylpyrrolidin-1-yl)-3-(2-trifluoromethylphenyl)-2H-isoquinolin-1-one,
(A57): 7-[3-(4-hydroxypiperidin-1-ylmethyl)-2-oxopyrrolidin-1-yl]-3-(2-trifluoromethylphenyl)-2H-isoquinolin-1-one,
(A58): 7-((3R,4R)-3,4-dihydroxy-2-oxopyrrolidin-1-yl)-3-(2-trifluoromethylphenyl)-2H-isoquinolin-1-one,
(A59): 7-(5-hydroxymethyl)-3-methyl-2-oxoimidazolidin-1-yl)-3-(2-trifluoromethylphenyl)-2H-isoquinolin-1-one,
(A60): 7-((R)-4-benzyloxymethyl-2-oxoimidazolidin-1-yl)-3-(2-trifluoromethylphenyl)-2H-isoquinolin-1-one,
(A61): 7-((R)-4-hydroxymethyl-2-oxoimidazolidin-1-yl)-3-(2-trifluoromethylphenyl)-2H-isoquinolin-1-one,
(A62): 7-(3-methyl-2-oxotetrahydropyrimidin-1-yl)-3-(2-trifluoromethylphenyl)-2H-isoquinolin-1-one,
(A63): benzyl 3-oxo-4-[1-oxo-3-(2-trifluoromethylphenyl)-1,2-dihydroisoquinolin-7-yl]piperazine-1-carboxylate, (A64): 7-(2-oxopiperazin-1-yl)-3-(2-trifluoromethylphenyl)-2H-isoquinolin-1-one,
(A65): 7-[(R)-5-((S)-1,2-dihydroxyethyl)-2-oxooxazolidin-3-yl]-3-(2-trifluoromethylphenyl)-2H-isoquinolin-1-one,
(A66): 7-[(R)-5-((R)-1,2-dihydroxyethyl)-2-oxooxazolidin-3-yl]-3-(2-trifluoromethylphenyl)-2H-isoquinolin-1-one,
(A67): 7-(5,5-bishydroxymethyl-2-oxooxazolidin-3-yl)-3-(2-trifluoromethylphenyl)-2H-isoquinolin-1-one,
(A68): 7-[3-(2-hydroxyethyl)-5-oxoimidazolidin-1-yl]-3-(2-trifluoromethylphenyl)-2H-isoquinolin-1-one,
(A69): 7-((R)-5-hydroxymethyl-2-oxooxazolidin-3-yl)-3-(3-trifluoromethylphenyl)-2H-isoquinolin-1-one,
(A70): 7-((R)-5-hydroxymethyl-2-oxooxazolidin-3-yl)-3-naphthalen-1-yl-2H-isoquinolin-1-one,
(A71): 3-furan-2-yl-7-((R)-5-hydroxymethyl-2-oxooxazolidin-3-yl)-2H-isoquinolin-1-one,
(A72): 7-((R)-5-hydroxymethyl-2-oxooxazolidin-3-yl)-3-thiophen-2-yl-2H-isoquinolin-1-one,
(A73): 7-((S)-5-dimethylaminomethyl-2-oxooxazolidin-3-yl)-3-(2-trifluoromethylphenyl)-2H-isoquinolin-1-one,
(A74): 7-[(S)-5-(1-hydroxy-1-vinylallyl)-2-oxooxazolidin-3-yl]-3-(2-trifluoromethylphenyl)-2H-isoquinolin-1-one,
(A75): 7-((R)-5-hydroxymethyl-2-oxooxazolidin-3-yl)-3-(4-trifluoromethylphenyl)-2H-isoquinolin-1-one, and
(A76): 7-((R)-5-hydroxymethyl-2-oxooxazolidin-3-yl)-3-(3-methylthiophen-2-yl)-2H-isoquinolin-1-one.
(A77): 7-(3-oxomorpholin-4-yl)-3-(2-trifluoromethylphenyl)-2H-isoquinolin-1-one.

Moreover, specific examples of the present invention include the compound represented by the following formula and compounds shown in the following table:

[Formula 9]

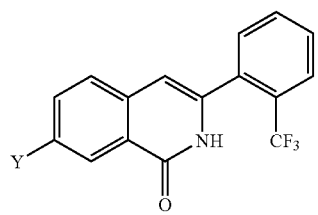

However, the present invention is not limited to such examples.

TABLE 3-1

| Compound No. | Y | Example |
|---|---|---|
| B1 | 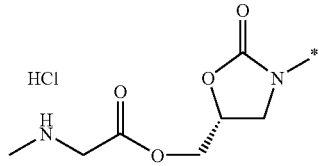 | Example 3-1 |
| B2 | 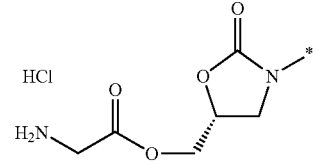 | Example 3-2 |
| B3 | 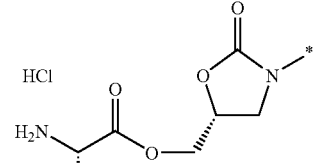 | Example 3-3 |
| B4 | 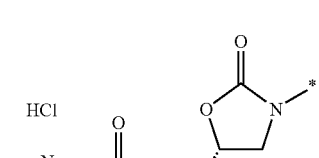 | Example 3-4 |

TABLE 3-1-continued

| Compound No. | Y | Example |
|---|---|---|
| B5 | (structure: L-2-aminobutanoyloxymethyl-oxazolidinone, HCl salt) | Example 3-5 |
| B6 | (structure: L-norvaloyloxymethyl-oxazolidinone, HCl salt) | Example 3-6 |
| B7 | (structure: L-leucyloxymethyl-oxazolidinone, HCl salt) | Example 3-7 |
| B8 | (structure: L-isoleucyloxymethyl-oxazolidinone, HCl salt) | Example 3-8 |
| B9 | (structure: L-valyloxymethyl-oxazolidinone, HCl salt) | Example 3-9 |
| B10 | (structure: L-norleucyloxymethyl-oxazolidinone, HCl salt) | Example 3-10 |

TABLE 3-1-continued
| Compound No. | Y | Example |
|---|---|---|
| B11 | 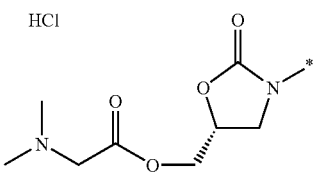 HCl | Example 3-11 |
| B12 | 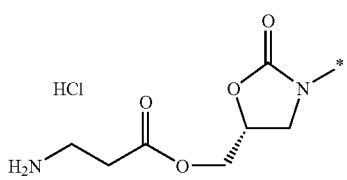 HCl | Example 3-12 |
| B13 | 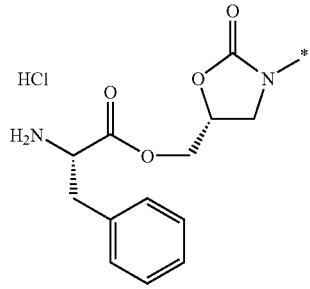 HCl | Example 3-13 |
| B14 | 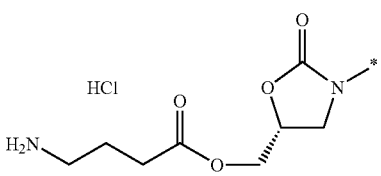 HCl | Example 3-14 |
| B15 | 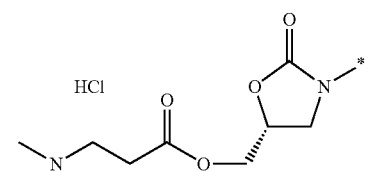 HCl | Example 3-15 |
| B16 | 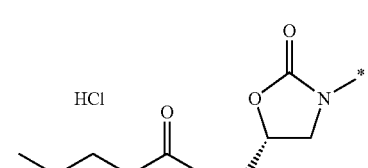 HCl | Example 3-16 |

TABLE 3-1-continued

| Compound No. | Y | Example |
|---|---|---|
| B17 | [structure: Na⁺ ⁻O-CO-CH₂-CH₂-C(O)O-CH₂-oxazolidinone-N*] | Example 3-17 |
| B18 | [structure: Na⁺ phthalate monoester linked to CH₂-oxazolidinone-N*] | Example 3-18 |
| B19 | [structure: HCl·H₂N-CH₂CH₂-NH-C(O)-CH₂CH₂-C(O)O-CH₂-oxazolidinone-N*] | Example 3-19 |
| B20 | [structure: HCl·CH₃NH-CH₂-C(O)O-CH₂-oxazolidinone-N*] | Example 3-20 |
| B21 | [structure: HCl·(CH₃)₂N-CH₂-C(O)O-CH₂-oxazolidinone-N*] | Example 3-21 |
| B22 | [structure: HCl·H₂N-CH(iPr)-C(O)O-CH₂-oxazolidinone-N*] (valine ester) | Example 3-22 |
| B23 | [structure: HCl·H₂N-C(CH₃)₂-C(O)O-CH₂-oxazolidinone-N*] | Example 3-23 |

TABLE 3-1-continued

| Compound No. | Y | Example |
|---|---|---|
| B24 | 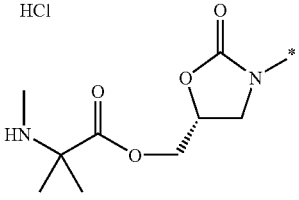 HCl | Example 3-24 |
| B25 | 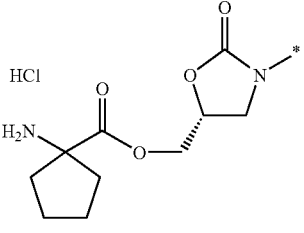 HCl | Example 3-25 |
| B26 | 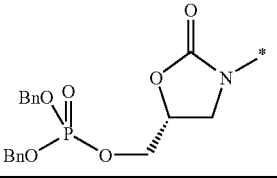 | Example 3-26 |

Hereinafter, compound names corresponding to the aforementioned compound numbers are shown.

(B1): (R)-2-oxo-3-[1-oxo-3-(2-trifluoromethylphenyl)-1,2-dihydroisoquinolin-7-yl]oxazolidin-5-ylmethyl methylaminoacetate hydrochloride, (B2): (R)-2-oxo-3-[1-oxo-3-(2-trifluoromethylphenyl)-1,2-dihydroisoquinolin-7-yl]oxazolidin-5-ylmethyl aminoacetate hydrochloride, (B3): (R)-2-oxo-3-[1-oxo-3-(2-trifluoromethylphenyl)-1,2-dihydroisoquinolin-7-yl]oxazolidin-5-ylmethyl(S)-2-aminopropionate hydrochloride, (B4): (R)-2-oxo-3-[1-oxo-3-(2-trifluoromethylphenyl)-1,2-dihydroisoquinolin-7-yl]oxazolidin-5-ylmethyl(S)-pyrrolidine-2-carboxylate hydrochloride, (B5): (R)-2-oxo-3-[1-oxo-3-(2-trifluoromethylphenyl)-1,2-dihydroisoquinolin-7-yl]oxazolidin-5-ylmethyl(S)-2-aminobutanoate hydrochloride, (B6): (R)-2-oxo-3-[1-oxo-3-(2-trifluoromethylphenyl)-1,2-dihydroisoquinolin-7-yl]oxazolidin-5-ylmethyl(S)-2-aminopentanoate hydrochloride, (B7): (R)-2-oxo-3-[1-oxo-3-(2-trifluoromethylphenyl)-1,2-dihydroisoquinolin-7-yl]oxazolidin-5-ylmethyl(S)-2-amino-4-methyl-pentanoate hydrochloride, (B8): (R)-2-oxo-3-[1-oxo-3-(2-trifluoromethylphenyl)-1,2-dihydroisoquinolin-7-yl]oxazolidin-5-ylmethyl(2S,3S)-2-amino-3-methylpentanoate hydrochloride, (B9): (R)-2-oxo-3-[1-oxo-3-(2-trifluoromethylphenyl)-1,2-dihydroisoquinolin-7-yl]oxazolidin-5-ylmethyl(S)-2-amino-3-methyl-butanoate hydrochloride, (B10): (R)-2-oxo-3-[1-oxo-3-(2-trifluoromethylphenyl)-1,2-dihydroisoquinolin-7-yl]oxazolidin-5-ylmethyl(S)-2-aminohexanoate hydrochloride, (B11): (R)-2-oxo-3-[1-oxo-3-(2-trifluoromethylphenyl)-1,2-dihydroisoquinolin-7-yl]oxazolidin-5-ylmethyl dimethylaminoacetate hydrochloride, (B12): (R)-2-oxo-3-[1-oxo-3-(2-trifluoromethylphenyl)-1,2-dihydroisoquinolin-7-yl]oxazolidin-5-ylmethyl 3-aminopropionate hydrochloride, (B13): (R)-2-oxo-3-[1-oxo-3-(2-trifluoromethylphenyl)-1,2-dihydroisoquinolin-7-yl]oxazolidin-5-ylmethyl(S)-2-amino-3-phenylpropionate hydrochloride, (B14): (R)-2-oxo-3-[1-oxo-3-(2-trifluoromethylphenyl)-1,2-dihydroisoquinolin-7-yl]oxazolidin-5-ylmethyl 4-aminobutanoate hydrochloride, (B15): (R)-2-oxo-3-[1-oxo-3-(2-trifluoromethylphenyl)-1,2-dihydroisoquinolin-7-yl]oxazolidin-5-ylmethyl 3-methylaminopropionate hydrochloride, (B16): (R)-2-oxo-3-[1-oxo-3-(2-trifluoromethylphenyl)-1,2-dihydroisoquinolin-7-yl]oxazolidin-5-ylmethyl 3-dimethylaminopropionate hydrochloride, (B17): sodium 3-{(R)-2-oxo-3-[1-oxo-3-(2-trifluoromethylphenyl)-1,2-dihydroisoquinolin-7-yl]oxazolidin-5-ylmethoxycarbonyl}propionate, (B18): sodium 2-{(R)-2-oxo-3-[1-oxo-3-(2-trifluoromethylphenyl)-1,2-dihydroisoquinolin-7-yl]oxazolidin-5-ylmethoxycarbonyl}benzoate, (B19): (R)-2-oxo-3-[1-oxo-3-(2-trifluoromethylphenyl)-1,2-dihydroisoquinolin-7-yl]oxazolidin-5-ylmethyl 2-aminoethylsuccinamate hydrochloride, (B20): (S)-2-oxo-3-[1-oxo-3-(2-trifluoromethylphenyl)-1,2-dihydroisoquinolin-7-yl]oxazolidin-5-ylmethyl methylaminoacetate hydrochloride, (B21): (S)-2-oxo-3-[1-oxo-3-(2-trifluoromethylphenyl)-1,2-dihydroisoquinolin-7-yl]oxazolidin-5-ylmethyl dimethylaminoacetate hydrochloride, (B22): (S)-2-oxo-3-[1-oxo-3-(2-trifluoromethylphenyl)-1,2-dihydroisoquinolin-7-yl]oxazolidin-5-ylmethyl(S)-2-amino-3-methylbutyrate hydrochloride, (B23): (R)-2-oxo-3-[1-oxo-3-trifluoromethylphenyl]-1,2-dihydroisoquinolin-7-yl]-oxazolidin-5-ylmethyl 2-amino-2-methylpropionate hydrochloride,
(B24): (R)-2-oxo-3-[1-oxo-3-(2-trifluoromethylphenyl)-1,2-dihydroisoquinolin-7-yl]oxazolidin-5-ylmethyl 2-methyl-2-(methylamino)propionate hydrochloride,
(B25): (R)-2-oxo-3-[1-oxo-3-(2-trifluoromethylphenyl)-1,2-dihydroisoquinolin-7-yl]oxazolidin-5-ylmethyl 1-aminocyclopentanecarboxylate hydrochloride, and
(B26): dibenzyl phosphoate (R)-2-oxo-3-[1-oxo-3-(2-trifluoromethylphenyl)-1,2-dihydroisoquinolin-7-yl]-oxazolidin-5-ylmethyl ester.

Furthermore, the present invention includes the compound represented by the following formula and compounds shown in the following table:

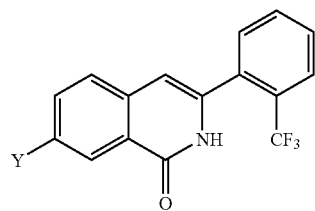

[Formula 10]

However, the present invention is not limited to such examples.

TABLE 4-1

| Compound No. | Y | Example |
|---|---|---|
| C1 | (Na⁺ succinate ester of oxazolidinone-methyl) | Example 4-1 |
| C2 | (Na⁺ phthalate ester of oxazolidinone-methyl) | Example 4-2 |
| C3 | (Na⁺ glutarate ester of oxazolidinone-methyl) | Example 4-3 |
| C4 | (Na⁺ maleate ester of oxazolidinone-methyl) | Example 4-4 |
| C5 | (Na⁺ succinate ester of oxazolidinone-dimethylmethyl) | Example 4-5 |

TABLE 4-1-continued

| Compound No. | Y | Example |
|---|---|---|
| C6 | (Na⁺ phthalate ester linked via C(CH₃)₂ to oxazolidinone-2-one N*) | Example 4-6 |
| C7 | (H₂N-CH(CH₂COOH)-C(O)O-CH₂- linked to oxazolidin-2-one N*) | Example 4-7 |
| C8 | TFA; (H₂N-CH(CH₂OH)-C(O)O-CH₂- linked to oxazolidin-2-one N*) | Example 4-8 |
| C9 | TFA; (HO-CH(CH₃)-CH(NH₂)-C(O)O-CH₂- linked to oxazolidin-2-one N*) | Example 4-9 |
| C10 | (Na⁺ maleate ester linked via CH₂ to oxazolidin-2-one N*) | Example 4-10 |

TABLE 4-1-continued

| Compound No. | Y | Example |
|---|---|---|
| C11 | (structure: sodium glutarate ester linked to oxazolidinone CH₂) | Example 4-11 |
| C12 | (structure: sodium glutarate ester linked to oxazolidinone via C(CH₃)₂) | Example 4-12 |
| C13 | Na⁺ (structure: sodium malate ester linked to oxazolidinone CH₂) | Example 4-13 |
| C14 | Na⁺ (structure: sodium malonate ester linked to oxazolidinone CH₂) | Example 4-14 |
| C15 | (structure: 2,3-dihydroxypropanoate ester linked to oxazolidinone CH₂) | Example 4-15 |
| C16 | (structure: 3-hydroxy-2-(hydroxymethyl)-2-methylpropanoate ester linked to oxazolidinone CH₂) | Example 4-16 |

TABLE 4-1-continued
| Compound No. | Y | Example |
|---|---|---|
| C17 | 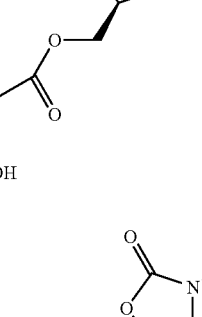 | Example 4-17 |
| C18 | 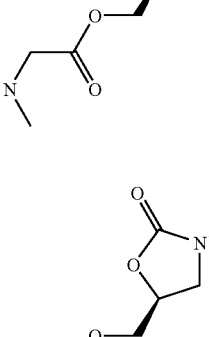 | Example 4-18 |
| C19 | 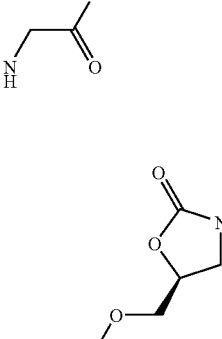 | Example 4-19 |
| C20 | 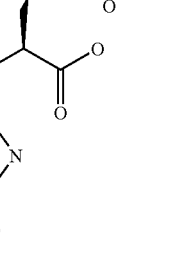 | Example 4-20 |

TABLE 4-1-continued

| Compound No. | Y | Example |
|---|---|---|
| C21 | (structure) | Example 4-21 |
| C22 | (structure) | Example 4-22 |
| C23 | (structure) | Example 4-23 |
| C24 | (structure) | Example 4-24 |
| C25 | (structure) | Example 4-25 |
| C26 | (structure) | Example 4-26 |

TABLE 4-1-continued

| Compound No. | Y | Example |
|---|---|---|
| C27 | (structure: ethyl ester-CH2-NH-C(=O)-O-CH2-[(5S)-oxazolidin-2-one-3-yl*]) | Example 4-27 |
| C28 | (structure: ethyl-O-C(=O)-O-CH2-[(5S)-oxazolidin-2-one-3-yl*]) | Example 4-28 |
| C29 | (structure: nicotinoyl-O-CH2-[(5S)-oxazolidin-2-one-3-yl*]) · HCl | Example 4-29 |
| C30 | (structure: CH3-C(=O)-O-CH2-C(=O)-O-CH2-[(5S)-oxazolidin-2-one-3-yl*]) | Example 4-30 |
| C31 | (structure: CH3-O-CH2CH2-O-CH2-C(=O)-O-CH2-[(5S)-oxazolidin-2-one-3-yl*]) | Example 4-31 |

TABLE 4-1-continued

| Compound No. | Y | Example |
|---|---|---|
| C32 | | Example 4-32 |
| C33 | | Example 4-33 |
| C34 | | Example 4-34 |
| C35 | | Example 4-35 |
| C36 | | Example 4-36 |

TABLE 4-1-continued

| Compound No. | Y | Example |
|---|---|---|
| C37 | (structure: HO-CH₂CH₂-O-CH₂CH₂-O-CH₂-C(=O)-O-CH₂-[oxazolidinone-N*]) | Example 4-37 |
| C38 | (structure: HO-CH₂CH₂-O-CH₂CH₂-O-CH₂CH₂-O-CH₂-C(=O)-O-CH₂-[oxazolidinone-N*]) | Example 4-38 |
| C39 | (structure: HO-CH₂CH₂-O-CH₂CH₂-O-CH₂CH₂-O-CH₂CH₂-O-CH₂-C(=O)-O-CH₂-[oxazolidinone-N*]) | Example 4-39 |
| C40 | (structure: HO-CH₂-O-CH₂CH₂-O-CH₂CH₂-O-CH₂CH₂-O-CH₂CH₂-O-CH₂-C(=O)-O-CH₂-[oxazolidinone-N*]) | Example 4-40 |

TABLE 4-1-continued

| Compound No. | Y | Example |
|---|---|---|
| C41 | (structure: methoxy-terminated tri(propylene glycol) carbonate linked to oxazolidinone methylene) | Example 4-41 |
| C42 | (structure: HO-CH₂CH₂-O-CH₂CH₂-O-C(=O)-O-CH₂-oxazolidinone) | Example 4-42 |
| C43 | (structure: cyclic/branched PEG-OH carbonate linked to oxazolidinone methylene) | Example 4-43 |
| C44 | (structure: HO-terminated tetra(ethylene glycol) carbonate linked to oxazolidinone methylene) | Example 4-44 |

TABLE 4-1-continued

| Compound No. | Y | Example |
|---|---|---|
| C45 | | Example 4-45 |
| C46 | | Example 4-46 |
| C47 | | Example 4-47 |
| C48 | | Example 4-48 |

TABLE 4-1-continued
| Compound No. | Y | Example |
|---|---|---|
| C49 | 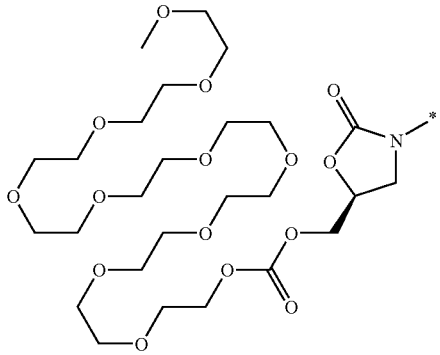 | Example 4-49 |
| C50 | 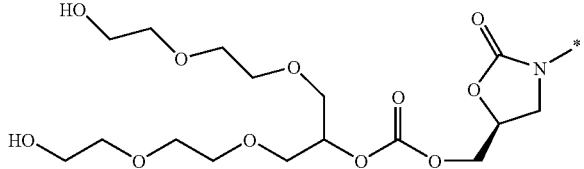 | Example 4-50 |
| C51 | 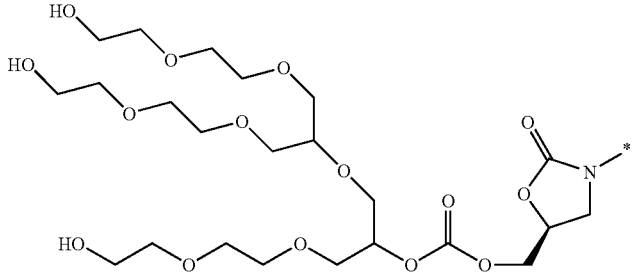 | Example 4-51 |
| C53 | 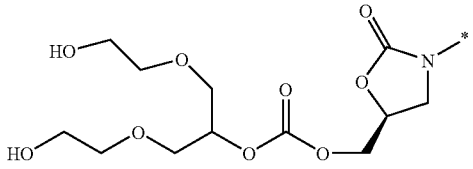 | Example 4-52 |
| C54 | 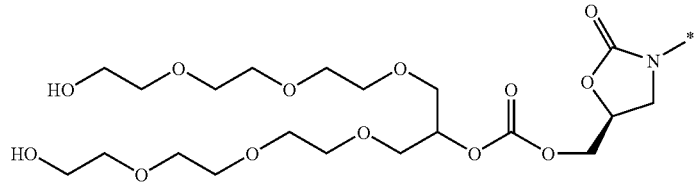 | Example 4-53 |
| C55 | 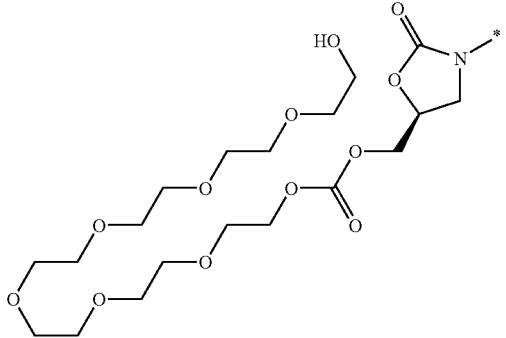 | Example 4-54 |

TABLE 4-1-continued

| Compound No. | Y | Example |
|---|---|---|
| C56 | | Example 4-55 |
| C57 | | Example 4-56 |
| C58 | | Example 4-57 |

(C1): sodium 3-{(S)-2-oxo-3-[1-oxo-3-(2-trifluoromethylphenyl)-1,2-dihydroisoquinolin-7-yl]oxazolidin-5-ylmethoxycarbonyl}propionate, (C2): sodium 2-{(S)-2-oxo-3-[1-oxo-3-(2-trifluoromethylphenyl)-1,2-dihydroisoquinolin-7-yl]oxazolidin-5-ylmethoxycarbonyl}benzoate, (C3): sodium 3-{(R)-2-oxo-3-[1-oxo-3-(2-trifluoromethylphenyl)-1,2-dihydroisoquinolin-7-yl]oxazolidin-5-ylmethoxycarbonyl}butanoate, (C4): sodium (Z)-3-{(R)-2-oxo-3-[1-oxo-3-(2-trifluoromethylphenyl)-1,2-dihydroisoquinolin-7-yl]oxazolidin-5-ylmethoxycarbonyl}acrylate, (C5): sodium 2-(1-methyl-1-{(S)-2-oxo-3-[1-oxo-3-(2-trifluoromethylphenyl)-1,2-dihydroisoquinolin-7-yl]oxazolidin-5-ylethoxycarbonyl}propionate, (C6): sodium 2-(1-methyl-1-{(S)-2-oxo-3-[1-oxo-3-(2-trifluoromethylphenyl)-1,2-dihydroisoquinolin-7-yl]oxazolidin-5-ylethoxycarbonyl}benzoate, (C7): 1-{(R)-2-oxo-3-[1-oxo-3-(2-trifluoromethylphenyl)-1,2-dihydroisoquinolin-7-yl]-oxazolidin-5-ylmethyl} (S)-2-aminosuccinate, (C8): (R)-2-oxo-3-[1-oxo-3-(2-trifluoromethylphenyl)-1,2-dihydroisoquinolin-7-yl]oxazolidin-5-ylmethyl(S)-2-amino-3-hydroxypropionate trifluoroacetic acid, (C9): (R)-2-oxo-3-[1-oxo-3-(2-trifluoromethylphenyl)-1,2-dihydroisoquinolin-7-yl]oxazolidin-5-ylmethyl(2S,3R)-2-amino-3-hydroxybutanoate trifluoroacetate, (C10): sodium (Z)-3-{(S)-2-oxo-3-[1-oxo-3-(2-trifluoromethylphenyl)-1,2-dihydroisoquinolin-7-yl]oxazolidin-5-ylmethoxycarbonyl}acrylate, (C11): sodium 3-{(S)-2-oxo-3-[1-oxo-3-(2-trifluoromethylphenyl)-1,2-dihydroisoquinolin-7-yl]oxazolidin-5-ylmethoxycarbonyl}butanoate, (C12): sodium 2-(1-methyl-1-{(S)-2-oxo-3-[1-oxo-3-(2-trifluoromethylphenyl)-1,2-dihydroisoquinolin-7-yl]oxazolidin-5-ylethoxycarbonyl}butanoate, (C13): sodium 3-{(S)-2-oxo-3-[1-oxo-3-(2-trifluoromethylphenyl)-1,2-dihydroisoquinolin-7-yl]oxazolidin-5-ylmethoxycarbonyl}-(S)-2-hydroxypropionate, (C14): sodium 3-{(S)-2-oxo-3-[1-oxo-3-(2-trifluoromethylphenyl)-1,2-dihydroisoquinolin-7-yl]oxazolidin-5-ylmethoxycarbonyl}ethanoate, (C15): (S)-2-oxo-3-[1-oxo-3-(2-trifluoromethylphenyl)-1,2-dihydroisoquinolin-7-yl]oxazolidin-5-ylmethyl(R)-2,3-dihydroxypropionate, (C16): (S)-2-oxo-3-[1-oxo-3-(2-trifluoromethylphenyl)-1,2-dihydroisoquinolin-7-yl]oxazolidin-5-ylmethyl 3-hydroxy-2-hydroxymethyl-2-methylpropionate, (C17): (S)-2-oxo-3-[1-oxo-3-(2-trifluoromethylphenyl)-1,2-dihydroisoquinolin-7-yl]oxazolidin-5-ylmethyl 3-hydroxy-2,2-bishydroxymethylpropionate, (C18): (S)-2-oxo-3-[1-oxo-3-(2-trifluoromethylphenyl)-1,2-dihydroisoquinolin-7-yl]oxazolidin-5-ylmethyl(2-aminoacetyl)methylaminoacetate hydrochloride, (C19): (S)-2-oxo-3-[1-oxo-3-(2-trifluoromethylphenyl)-1,2-dihydroisoquinolin-7-yl]oxazolidin-5-ylmethyl 2-aminoacetylaminoacetate hydrochloride, (C20): 5-{(S)-2-oxo-3-[1-oxo-3-(2-trifluoromethylphenyl)-1,2-dihydroisoquinolin-7-yl]oxazolidin-5-ylmethyl} (S)-2-[(S)-2-amino-3-(1H-indol-3-yl)-propionylamino]-pentanedioate, (C21): (S)-2-oxo-3-[1-oxo-3-(2-trifluoromethylphenyl)-1,2-dihydroisoquinolin-7-yl]oxazolidin-5-ylmethyl[2-(2-hydroxyethoxy)ethyl]carbamate, (C22): (R)-2-oxo-3-[1-oxo-3-(2-trifluoromethylphenyl)-1,2-dihydroisoquinolin-7-yl]oxazolidin-5-ylmethyl(2,3-dihydroxypropyl)carbamate, (C23): (S)-2-oxo-3-[1-oxo-3-(2-trifluoromethylphenyl)-1,2-dihydroisoquinolin-7-yl]oxazolidin-5-ylmethyl(2,3-dihydroxypropyl)carbamate, (C24): (S)-2-oxo-3-[1-oxo-3-(2-trifluoromethylphenyl)-1,2-dihydroisoquinolin-7-yl]oxazolidin-5-ylmethyl(2-hydroxy-1-hydroxymethylethyl)carbamate, (C25): (S)-2-oxo-3-[1-oxo-3-(2-trifluoromethylphenyl)-1,2-dihydroisoquinolin-7-yl]oxazolidin-5-ylmethyl[(2R,3S)-2,3,4-trihydroxybutyl]carbamate, (C26): (S)-2-oxo-3-[1-oxo-3-(2-trifluoromethylphenyl)-1,2-dihydroisoquinolin-7-yl]oxazolidin-5-ylmethyl[(2S,3R,4R,5R)-2,3,4,5,6-pentahydroxyhexyl]carbamate, (C27): ethyl {(R)-2-oxo-3-[1-oxo-3-(2-trifluoromethylphenyl)-1,2-dihydroisoquinolin-7-yl]oxazolidin-5-ylmethoxycarbonylamino}acetate, (C28): ethyl carbonate (R)-2-oxo-3-[1-oxo-3-(2-trifluoromethylphenyl)-1,2-dihydroisoquinolin-7-yl]oxazolidin-5-ylmethyl ester, (C29): (S)-2-oxo-3-[1-oxo-3-(2-trifluoromethylphenyl)-1,2-dihydroisoquinolin-7-yl]oxazolidin-5-ylmethyl nicotinate hydrochloride, (C30): (S)-2-oxo-3-[1-oxo-3-(2-trifluoromethylphenyl)-1,2-dihydroisoquinolin-7-yl]oxazolidin-5-ylmethyl acetoxyacetate, (C31): (S)-2-oxo-3-[1-oxo-3-(2-trifluoromethylphenyl)-1,2-dihydroisoquinolin-7-yl]oxazolidin-5-ylmethyl(2-methoxyethoxy)acetate, (C32): (S)-2-oxo-3-[1-oxo-3-(2-trifluoromethylphenyl)-1,2-dihydroisoquinolin-7-yl]oxazolidin-5-ylmethyl[2-(2-methoxyethoxy)ethoxy]acetate, (C33): (S)-2-oxo-3-[1-oxo-3-(2-trifluoromethylphenyl)-1,2-dihydroisoquinolin-7-yl]oxazolidin-5-ylmethyl[2-(2-{2-[2-(2-methoxyethoxy)ethoxy]ethoxy}ethoxy)ethoxy]acetate, (C34): (S)-2-oxo-3-[1-oxo-3-(2-trifluoromethylphenyl)-1,2-dihydroisoquinolin-7-yl]oxazolidin-5-ylmethyl {2-[2-(2-methoxyethoxy)ethoxy]ethoxy}acetate, (C35): (S)-2-oxo-3-[1-oxo-3-(2-trifluoromethylphenyl)-1,2-dihydroisoquinolin-7-yl]oxazolidin-5-ylmethyl(2-{2-[2-(2-methoxyethoxy)ethoxy]ethoxy}ethoxy)acetate, (C36): (S)-2-oxo-3-[1-oxo-3-(2-trifluoromethylphenyl)-1,2-dihydroisoquinolin-7-yl]oxazolidin-5-ylmethyl {2-[2-(2-{2-[2-(2-methoxyethoxy)ethoxy]ethoxy}ethoxy)ethoxy]ethoxy}acetate, (C37): (S)-2-oxo-3-[1-oxo-3-(2-trifluoromethylphenyl)-1,2-dihydroisoquinolin-7-yl]oxazolidin-5-ylmethyl[2-(2-hydroxyethoxy)ethoxy]acetate, (C38): (S)-2-oxo-3-[1-oxo-3-(2-trifluoromethylphenyl)-1,2-dihydroisoquinolin-7-yl]oxazolidin-5-ylmethyl {2-[2-(2-hydroxyethoxy)ethoxy]ethoxy}acetate, (C39): (S)-2-oxo-3-[1-oxo-3-(2-trifluoromethylphenyl)-1,2-dihydroisoquinolin-7-yl]oxazolidin-5-ylmethyl[2-(2-{2-[2-(2-hydroxyethoxy)ethoxy]ethoxy}ethoxy)ethoxy]acetate, (C40): (S)-2-oxo-3-[1-oxo-3-(2-trifluoromethylphenyl)-1,2-dihydroisoquinolin-7-yl]oxazolidin-5-ylmethyl {2-[2-(2-{2-[2-(2-hydroxyethoxy)ethoxy]ethoxy}ethoxy)ethoxy]ethoxy}acetate, (C41): 2-[2-(2-methoxy-1-methylethoxy)-1-methylethoxy]-1-methylethyl carbonate (S)-2-oxo-3-[1-oxo-3-(2-trifluoromethylphenyl)-1,2-dihydroisoquinolin-7-yl]oxazolidin-5-ylmethyl ester, (C42): 2-(2-hydroxyethoxy)ethyl carbonate (S)-2-oxo-3-[1-oxo-3-(2-trifluoromethylphenyl)-1,2-dihydroisoquinolin-7-yl]oxazolidin-5-ylmethyl ester, (C43): 2-[2-(2-hydroxyethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester, (C44): 2-{2-[2-(2-hydroxyethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester, (C45): 2-[2-(2-{2-[2-(2-hydroxyethoxy)ethoxy]ethoxy}ethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester, (C46): (S)-2-oxo-3-[1-oxo-3-(2-trifluoromethylphenyl)-1,2-dihydroisoquinolin-7-yl]oxazolidin-5-ylmethyl carbonate 1,4,7,10-tetraoxacyclododec-2-ylmethyl ester, (C47): 2-(2-hydroxy-1-hydroxymethylethoxy)ethyl carbonate (S)-2-oxo-3-[1-oxo-3-(2-trifluoromethylphenyl)-1,2-dihydroisoquinolin-7-yl]oxazolidin-5-ylmethyl ester, (C48): 2-{2-[2-(2-{2-[2-(2-{2-[2-(2-hydroxyethoxy)ethoxy]ethoxy}ethoxy)ethoxy]ethoxy}ethoxy)-ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester, (C49): 2-{2-[2-(2-{2-[2-(2-{2-[2-(2-methoxyethoxy)ethoxy]ethoxy}ethoxy)ethoxy]ethoxy}ethoxy)-ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester, (C50): 2-[2-(2-hydroxyethoxy)ethoxy]-1-[2-(2-hydroxyethoxy)ethoxymethyl]ethyl carbonate (S)-2-oxo-3-[1-oxo-3-(2-trifluoromethylphenyl)-1,2-dihydroisoquinolin-7-yl]oxazolidin-5-ylmethyl ester, (C51): 2-[2-(2-hydroxyethoxy)ethoxy]-1-{2-[2-(2-hydroxyethoxy)ethoxy]-1-[2-(2-hydroxyethoxy)ethoxymethyl]ethoxymethyl}ethyl carbonate (S)-2-oxo-3-[1-oxo-3-(2-trifluoromethylphenyl)-1,2-dihydroisoquinolin-7-yl]oxazolidin-5-ylmethyl ester, (C53): 2-(2-hydroxyethoxy)-1-(2-hydroxyethoxymethyl) ethyl carbonate (S)-2-oxo-3-[1-oxo-3-(2-trifluoromethylphenyl)-1,2-dihydroisoquinolin-7-yl]oxazolidin-5-ylmethyl ester, (C54): 2-{2-[2-(2-hydroxyethoxy)ethoxy]ethoxy}-1-{2-[2-(2-hydroxyethoxy)ethoxy]ethoxymethyl}ethyl carbonate (S)-2-oxo-3-[1-oxo-3-(2-trifluoromethylphenyl)-1,2-dihydroisoquinolin-7-yl]oxazolidin-5-ylmethyl ester, (C55): 2-{2-[2-(2-{2-[2-(2-hydroxyethoxy)ethoxy]ethoxy}ethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester, (C56): 2-(2-{2-[2-(2-{2-[2-(2-hydroxyethoxy)ethoxy]ethoxy}ethoxy)ethoxy]ethoxy}ethoxy)-ethyl carbonate (S)-2-oxo-3-[1-oxo-3-(2-trifluoromethylphenyl)-1,2-dihydroisoquinolin-7-yl]oxazolidin-5-ylmethyl ester, (C57): 2-[2-(2-{2-[2-(2-{2-[2-(2-hydroxyethoxy)ethoxy]ethoxy}ethoxy)ethoxy]ethoxy}ethoxy)-ethoxy]ethyl carbonate (S)-2-oxo-3-[1-oxo-3-(2-trifluoromethylphenyl)-1,2-dihydroisoquinolin-7-yl]oxazolidin-5-ylmethyl ester, and (C58): (2-{2-[2-(2-{2-[2-(2-{2-[2-(2-Methoxy-ethoxy)-ethoxy]-ethoxy}-ethoxy)-ethoxy]-ethoxy}-ethoxy)-ethoxy]-ethoxy}-ethoxy)-acetic acid (S)-2-oxo-3-[1-oxo-3-(2-trifluoromethylphenyl)-1,2-dihydro-isoquinolin-7-yl]-oxazolidin-5-ylmethyl ester.

Furthermore, the present invention includes the compound represented by the following formula and compound shown in the following table:

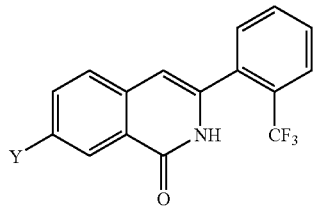

[Formula 11]

However, the present invention is not limited to such examples.

TABLE 5-1

| Compound No. | Y |
|---|---|
| D1 | HCl · H₂N-CH₂-C(=O)-O-C(CH₃)₂-[oxazolidinone]-* |
| D2 | HCl · CH₃-NH-CH₂-C(=O)-O-C(CH₃)₂-[oxazolidinone]-* |
| D3 | HCl · (CH₃)₂N-CH₂-C(=O)-O-C(CH₃)₂-[oxazolidinone]-* |
| D4 | HCl · H₂N-(CH₂)₃-C(=O)-O-C(CH₃)₂-[oxazolidinone]-* |

TABLE 5-1-continued

| Compound No. | Y |
|---|---|
| D5 | HCl, [structure: H2N-CH(CH3)-C(=O)-O-C(CH3)2-oxazolidin-2-one-N*] |
| D6 | HCl, [structure: H2N-CH(iPr)-C(=O)-O-C(CH3)2-oxazolidin-2-one-N*] |
| D7 | HCl, [structure: pyrrolidine-2-C(=O)-O-C(CH3)2-oxazolidin-2-one-N*] |
| D8 | HCl, [structure: H2N-CH2-C(=O)-N(CH3)-CH2-C(=O)-O-C(CH3)2-oxazolidin-2-one-N*] |
| D9 | HCl, [structure: H2N-CH2-C(=O)-N-pyrrolidine-2-C(=O)-O-C(CH3)2-oxazolidin-2-one-N*] |
| D10 | Na$^+$, [structure: $^-$O-C(=O)-CH=CH-C(=O)-O-CH2-oxazolidin-2-one-N*] |

TABLE 5-1-continued

| Compound No. | Y |
|---|---|
| D11 | (structure: L-glutamic acid esterified via α-carboxyl to CH2 of (5R)-oxazolidin-2-one, N attached to *) |
| D12 | (structure: hexose (pyranose with 4 OH) C1-carboxylate ester to CH2-oxazolidinone-N-*) |
| D13 | (structure: CH3O-(CH2CH2O)7-CH2-C(=O)-O-CH2-oxazolidinone-N-*) |
| D14 | (structure: CH3O-(CH2CH2O)7-CH2-C(=O)-O-CH2-oxazolidinone-N-*) |
| D15 | (structure: CH3O-(CH2CH2O)8-CH2-C(=O)-O-CH2-oxazolidinone-N-*) |

TABLE 5-1-continued

| Compound No. | Y |
| --- | --- |
| D16 | (structure) |
| D17 | (structure) |
| D18 | (structure) |
| D19 | (structure) |

TABLE 5-1-continued

| Compound No. | Y |
| --- | --- |
| D20 | |
| D21 | |
| D22 | |
| D23 | |
| D24 | |

TABLE 5-1-continued
| Compound No. | Y |
|---|---|
| D25 | 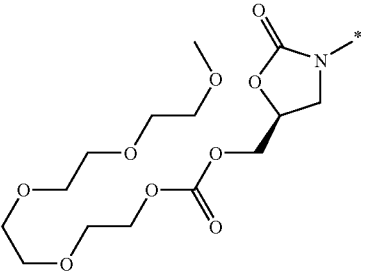 |
| D26 | 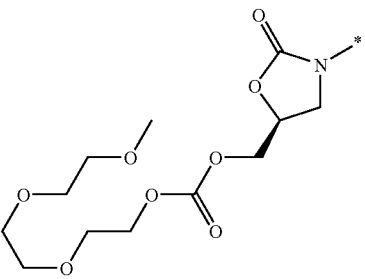 |
| D27 | 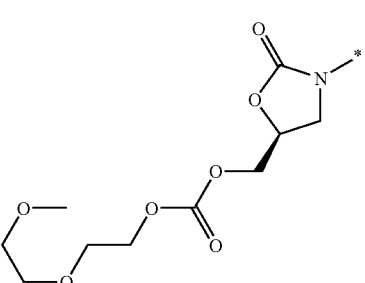 |
| D28 | 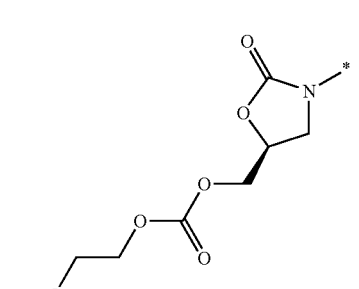 |
| D29 | 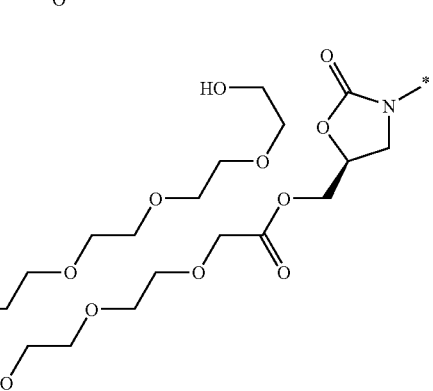 |

TABLE 5-1-continued

| Compound No. | Y |
| --- | --- |
| D30 | |
| D31 | |
| D32 | |
| D33 | |

TABLE 5-1-continued

| Compound No. | Y |
|---|---|
| D34 | 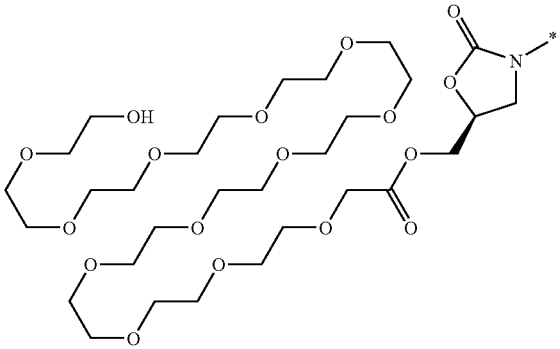 |
| D35 | 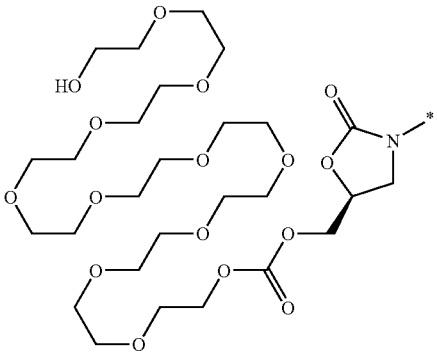 |
| D36 | 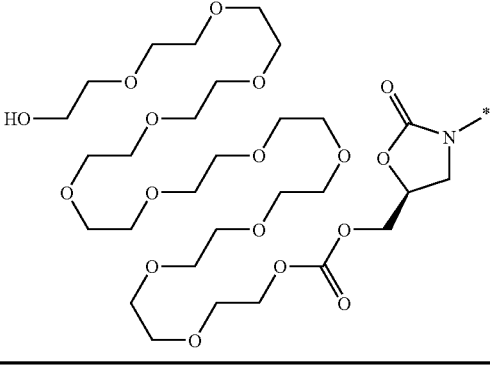 |

(D1): 1-methyl-1-{(S)-2-oxo-3-[1-oxo-3-(2-trifluoromethylphenyl)-1,2-dihydroisoquinolin-7-yl]oxazolidin-5-yl}ethyl aminoacetate hydrochloride, (D2): 1-methyl-1-{(S)-2-oxo-3-[1-oxo-3-(2-trifluoromethylphenyl)-1,2-dihydroisoquinolin-7-yl]oxazolidin-5-yl}ethyl methylaminoacetate hydrochloride, (D3): 1-methyl-1-{(S)-2-oxo-3-[1-oxo-3-(2-trifluoromethylphenyl)-1,2-dihydroisoquinolin-7-yl]oxazolidin-5-yl}ethyl dimethylaminoacetate hydrochloride, (D4): 1-methyl-1-{(S)-2-oxo-3-[1-oxo-3-(2-trifluoromethylphenyl)-1,2-dihydroisoquinolin-7-yl]oxazolidin-5-yl}ethyl 4-aminobutanoate hydrochloride, (D5): 1-methyl-1-{(S)-2-oxo-3-[1-oxo-3-(2-trifluoromethylphenyl)-1,2-dihydroisoquinolin-7-yl]oxazolidin-5-yl}ethyl(S)-2-aminopropionate hydrochloride, (D6): 1-methyl-1-{(S)-2-oxo-3-[1-oxo-3-(2-trifluoromethylphenyl)-1,2-dihydroisoquinolin-7-yl]oxazolidin-5-yl}ethyl(S)-2-amino-3-methylbutanoate hydrochloride, (D7): 1-methyl-1-{(S)-2-oxo-3-[1-oxo-3-(2-trifluoromethylphenyl)-1,2-dihydroisoquinolin-7-yl]oxazolidin-5-yl}ethyl(S)-pyrrolidine-2-carboxylate hydrochloride, (D8): 1-methyl-1-{(S)-2-oxo-3-[1-oxo-3-(2-trifluoromethylphenyl)-1,2-dihydroisoquinolin-7-yl]oxazolidin-5-yl}ethyl [(2-aminoacetyl)methylamino]acetate hydrochloride, and (D9): 1-methyl-1-{(S)-2-oxo-3-[1-oxo-3-(2-trifluoromethylphenyl)-1,2-dihydroisoquinolin-7-yl]oxazolidin-5-yl}ethyl(S)-1-(2-aminoacetyl)pyrrolidine-2-carboxylate hydrochloride.

(D10): sodium (E)-3-{(R)-2-oxo-3-[1-oxo-3-(2-trifluoromethylphenyl)-1,2-dihydroisoquinolin-7-yl]oxazolidin-5-ylmethoxycarbonyl}acrylate, (D11): 1-{(R)-2-oxo-3-[1-oxo-3-(2-trifluoromethylphenyl)-1,2-dihydroisoquinolin-7-yl]oxazolidin-5-ylmethyl} (S)-2-aminopentanedionate, and (D12): (S)-2-oxo-3-[1-oxo-3-(2-trifluoromethylphenyl)-1,2-dihydroisoquinolin-7-yl]oxazolidin-5-ylmethyl(2S,3R,4S,5R)-3,4,5,6-tetrahydroxytetrahydropyrane-2-carboxylate.

The following compounds (D13-D17) are synthesized by a method similar to that of Example 4-36.

(D13): (2-{2-[2-(2-{2-[2-(2-Methoxyethoxy)ethoxy]ethoxy}ethoxy)ethoxy]ethoxy}ethoxy)acetic acid (S)-2-oxo-3-[1-oxo-3-(2-trifluoromethylphenyl)-1,2-dihydroisoquinolin-7-yl]oxazolidin-5-ylmethyl ester, (D14): [2-(2-{2-[2-(2-{2-[2-(2-Methoxyethoxy)ethoxy]ethoxy}ethoxy)ethoxy]ethoxy}ethoxy)-ethoxy]acetic acid (S)-2-oxo-3-[1-oxo-3-(2-trifluoromethylphenyl)-1,2-dihydroisoquinolin-7-yl]oxazolidin-5-ylmethyl ester, (D15): {2-[2-(2-{2-[2-(2-{2-[2-(2-Methoxyethoxy)ethoxy]ethoxy)ethoxy]ethoxy}ethoxy)-ethoxy]ethoxy}acetic acid (S)-2-oxo-3-[1-oxo-3-(2-trifluoromethylphenyl)-1,2-dihydroisoquinolin-7-yl]oxazolidin-5-ylmethyl ester, (D16): [2-(2-{2-[2-(2-{2-[2-(2-{2-[2-(2-Methoxyethoxy)ethoxy]ethoxy}ethoxy)ethoxy]ethoxy}ethoxy)-ethoxy]ethoxy}ethoxy)ethoxy]acetic acid (S)-2-oxo-3-[1-oxo-3-(2-trifluoromethylphenyl)-1,2-dihydroisoquinolin-7-yl]oxazolidin-5-ylmethyl ester, and (D17): {2-[2-(2-{2-[2-(2-{2-[2-(2-{2-[2-(2-Methoxyethoxy)ethoxy]ethoxy}ethoxy)ethoxy]ethoxy}ethoxy)-ethoxy]ethoxy}ethoxy)ethoxy]ethoxy}acetic acid (S)-2-oxo-3-[1-oxo-3-(2-trifluoromethylphenyl)-1,2-dihydroisoquinolin-7-yl]oxazolidin-5-ylmethyl ester.

The following compounds (D18-D28) are synthesized by a method similar to that of Example 4-49.

(D18): 2-[2-(2-{2-[2-(2-{2-[2-(2-{2-[2-(2-methoxyethoxy)ethoxy]ethoxy}ethoxy)ethoxy]ethoxy}ethoxy)-ethoxy]ethoxy}ethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester, (D19): 2-(2-{2-[2-(2-{2-[2-(2-{2-[2-(2-methoxyethoxy)ethoxy]ethoxy}ethoxy)ethoxy]ethoxy}ethoxy)-ethoxy]ethoxy}ethoxy)ethyl carbonate (S)-2-oxo-3-[1-oxo-3-(2-trifluoromethylphenyl)-1,2-dihydroisoquinolin-7-yl]oxazolidin-5-ylmethyl ester, (D20): 2-[2-(2-{2-[2-(2-{2-[2-(2-methoxyethoxy)ethoxy]ethoxy}ethoxy)ethoxy]ethoxy}ethoxy)-ethoxy]ethyl carbonate (S)-2-oxo-3-[1-oxo-3-(2-trifluoromethylphenyl)-1,2-dihydroisoquinolin-7-yl]oxazolidin-5-ylmethyl ester, (D21): 2-(2-{2-[2-(2-{2-[2-(2-methoxyethoxy)ethoxy]ethoxy}ethoxy)ethoxy]ethoxy}ethoxy)-ethyl carbonate (S)-2-oxo-3-[1-oxo-3-(2-trifluoromethylphenyl)-1,2-dihydroisoquinolin-7-yl]oxazolidin-5-ylmethyl ester, (D22): 2-{2-[2-(2-{2-[2-(2-methoxyethoxy)ethoxy]ethoxy}ethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester, (D23): 2-[2-(2-{2-[2-(2-methoxyethoxy)ethoxy]ethoxy}ethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester, (D24): 2-(2-{2-[2-(2-methoxyethoxy)ethoxy]ethoxy}ethoxy)ethyl carbonate (S)-2-oxo-3-[1-oxo-3-(2-trifluoromethylphenyl)-1,2-dihydroisoquinolin-7-yl]oxazolidin-5-ylmethyl ester, (D25): 2-{2-[2-(2-methoxyethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester, (D26): 2-[2-(2-methoxyethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester, (D27): 2-(2-methoxyethoxy)ethyl carbonate (S)-2-oxo-3-[1-oxo-3-(2-trifluoromethylphenyl)-1,2-dihydroisoquinolin-7-yl]oxazolidin-5-ylmethyl ester, and (D28): 2-methoxyethyl carbonate (S)-2-oxo-3-[1-oxo-3-(2-trifluoromethylphenyl)-1,2-dihydroisoquinolin-7-yl]oxazolidin-5-ylmethyl ester.

The following compounds (D29-D34) are synthesized by a method similar to that of Example 4-39.

(D29): (S)-2-oxo-3-[1-oxo-3-(2-trifluoromethylphenyl)-1,2-dihydroisoquinolin-7-yl]oxazolidin-5-ylmethyl(2-{2-[2-(2-{2-[2-(2-hydroxyethoxy)ethoxy]ethoxy}ethoxy)ethoxy]ethoxy}ethoxy)acetate, (D30): (S)-2-oxo-3-[1-oxo-3-(2-trifluoromethylphenyl)-1,2-dihydroisoquinolin-7-yl]oxazolidin-5-ylmethyl[2-(2-{2-[2-(2-{2-[2-(2-hydroxyethoxy)ethoxy]ethoxy}ethoxy)ethoxy]ethoxy}ethoxy)-ethoxy]acetate, (D31): (S)-2-oxo-3-[1-oxo-3-(2-trifluoromethylphenyl)-1,2-dihydroisoquinolin-7-yl]oxazolidin-5-ylmethyl {2-[2-(2-{2-[2-(2-{2-[2-(2-hydroxyethoxy)ethoxy]ethoxy}ethoxy)ethoxy]ethoxy}ethoxy)-ethoxy]ethoxy}acetate, (D32): (S)-2-oxo-3-[1-oxo-3-(2-trifluoromethylphenyl)-1,2-dihydroisoquinolin-7-yl]oxazolidin-5-ylmethyl(2-{2-[2-(2-{2-[2-(2-{2-[2-(2-hydroxyethoxy)ethoxy]ethoxy}ethoxy)ethoxy]ethoxy}ethoxy)-ethoxy]ethoxy}ethoxy)acetate, (D33): (S)-2-oxo-3-[1-oxo-3-(2-trifluoromethylphenyl)-1,2-dihydroisoquinolin-7-yl]oxazolidin-5-ylmethyl[2-(2-{2-[2-(2-{2-[2-(2-{2-[2-(2-hydroxyethoxy)ethoxy]ethoxy}ethoxy)ethoxy]ethoxy}ethoxy)-ethoxy]ethoxy}ethoxy)ethoxy]acetate, (D34): (S)-2-oxo-3-[1-oxo-3-(2-trifluoromethylphenyl)-1,2-dihydroisoquinolin-7-yl]oxazolidin-5-ylmethyl {2-[2-(2-{2-[2-(2-{2-[2-(2-hydroxyethoxy)ethoxy]ethoxy}ethoxy)ethoxy]ethoxy}ethoxy)-ethoxy]ethoxy}ethoxy}acetate.

The following compounds (D35-D36) are synthesized by a method similar to that of Example 4-48.

(D35): 2-(2-{2-[2-(2-{2-[2-(2-{2-[2-(2-hydroxyethoxy)ethoxy]ethoxy}ethoxy)ethoxy]ethoxy}ethoxy)-ethoxy]ethoxy}ethoxy)ethyl carbonate (S)-2-oxo-3-[1-oxo-3-(2-trifluoromethylphenyl)-1,2-dihydroisoquinolin-7-yl]oxazolidin-5-ylmethyl ester, (D36): 2-[2-(2-{2-[2-(2-{2-[2-(2-{2-[2-(2-hydroxyethoxy)ethoxy]ethoxy}ethoxy)ethoxy]ethoxy}ethoxy)-ethoxy]ethoxy}ethoxy)ethyl carbonate (S)-2-oxo-3-[1-oxo-3-(2-trifluoromethylphenyl)-1,2-dihydroisoquinolin-7-yl]oxazolidin-5-ylmethyl ester.

Next, a method for producing the compound of the present invention will be described.

Further, when the defined groups undergo an undesirable chemical conversion under the conditions for carrying out the method in the preparation method as shown below, for example, by using means to protect and deprotect the functional groups, the preparation can be performed. Herein, as the selection of a protective group and the operation of deprotection, for example, the method as described in Greene and Wuts, "Protective Groups in Organic Synthesis" (Second Edition, John Wiley & Sons, 1991)" can be mentioned, and this may be suitably used in accordance with reaction conditions. Further, if necessary or required, the order of the reaction step for introducing a substituent and the like may be changed. As the method for preparing the compound represented by formula (1), various methods can be thought and the compound can be synthesized by using the conventional organic synthesis means and, for example, the compound can be prepared by the following method as a representative method.

Representative Production Methods

The compound represented by the formula (1) of the present invention can be produced by the following method, for example. However, the method for producing the compound of the present invention is not limited thereto. The compounds of the present invention are all novel compounds, which have not been described in any publications. The compounds can be produced by known chemical techniques. As a raw material compound used in production, a commercially available compound can be used. Otherwise, such a compound can also be produced by conventional methods, as necessary. In the following reaction processes 1 to 8 and the relevant descriptions, X, Cy, and Ra have the same definitions as those described in the formula (1). Moreover, codes used in the following reaction formulas have common means, which can be understood by persons skilled in the art in the present technical field. Furthermore, L represents Cl or Br, LG represents a leaving group such as a halogen atom, a nitro group, a methanesulfonyloxy group, a trifluoromethanesulfonyloxy group, or a p-toluenesulfonyloxy group; G represents a hydrogen atom or a $C_{1-6}$ alkyl group such as a methyl group; Rc represents a $C_{1-6}$ alkyl group; Rd represents an acyl group included in the definitions of $R^{32}$ (for example, —S(O)$_2$R$^{39}$, a $C_{1-6}$ alkylcarbonyl group, which may be substituted (wherein when a substituent is an amino group or a $C_{1-6}$ alkylamino group, the group is protected by a protecting group), etc.); J represents an azido group, —OR$^3$, or —NR$^{32}$R$^{33}$; Rf and Rg have the same definitions as those of the aforementioned R$^{21}$ and R$^{22}$; Rh represents a $C_{1-5}$ alkyl group or a $C_{2-7}$ alkenyl group; Y represents O or S; and PG represents a protecting group (for example, acetyl, t-butoxycarbonyl, benzyloxycarbonyl, t-butyldimethylsilyl, etc.) or a hydrogen atom; wherein R$^{21}$, R$^{22}$, R$^{31}$, R$^{32}$, and R$^{39}$ are the same as those defined above.

1. General Synthesis Method of Compound (1a) Represented by the Formula (1)

Reaction Process 1

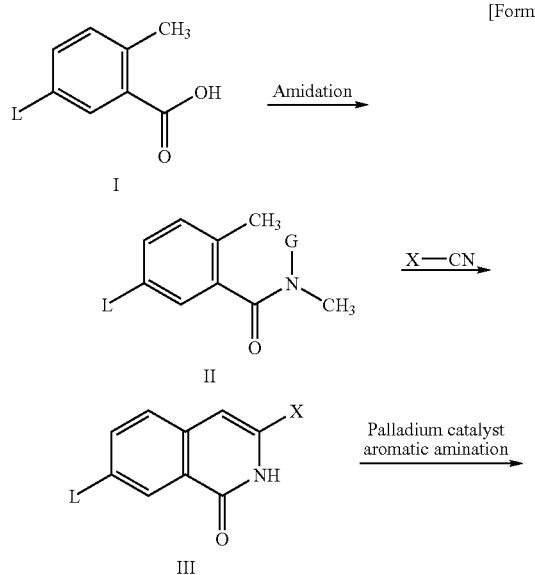

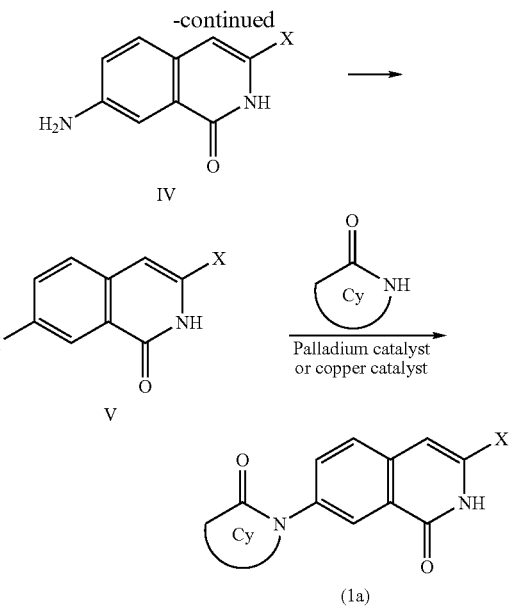

[wherein L represents Cl or Br; G represents a hydrogen atom or a methyl group; and X and Cy are the same as those defined above].

A 2-methylbenzamide derivative II can be easily prepared by applying a conventional amidation method to a known 2-methylbenzoic acid derivative I. A compound represented by the formula (III) can be produced from the obtained compound represented by the formula II according to known methods (U.S. Pat. No. 4,942,163; Arch. Pharm. Res., vol. 20, pp. 264-268 (1997); Bioorg. Med. Chem. Lett. vol. 8, pp. 41-46 (1998); Arch. Pharm. Res., vol. 24, pp. 276-280 (2001); Bioorg. Med. Chem. vol. 10, pp. 2953-2961 (2002)). Thus, the compound represented by the formula (III) can be obtained by subjecting the compound represented by the formula II to lithiation with a suitable base (for example, LDA, t-BuLi, s-BuLi, or BuLi) in a suitable solvent (for example, THF or Et$_2$O) at a suitable temperature (for example, between −78° C. and the boiling point of the solvent), and then allowing the resulting intermediate to react with a commercially available reagent, or with an aromatic or hetero aromatic nitrile derivative, which has been prepared by a known method, at a suitable temperature (for example, between −78° C. and the boiling point of the solvent)

A compound represented by the formula (IV) can be produced from the compound represented by the formula (III) according to known methods (Aromatic amination reaction: Wolfe, J. P., J. Org. Chem., vol. 65, pp. 1158-1174 (2000), Harris, M. C., Org. Lett., vol. 4, pp. 2885-2888 (2002), Huang, X., Org. Lett., vol. 3, pp. 3417-3419 (2001)). Thus, the compound represented by the formula IV can be produced by allowing the compound represented by the formula (III) to react in a suitable solvent (toluene, THF, 1,4-dioxane, xylene, dimethoxyethane, etc.) in the presence of a suitable palladium catalyst (for example, Pd(OAc)$_2$, Pd$_2$dba$_3$, PdCl$_2$[P(o-tol)$_3$]$_2$, Pd(O$_2$CCF$_3$)$_2$, etc.), a suitable ligand (for example, P(o-tol)$_3$, BINAP, DPPF, P(t-Bu)$_3$, 2-dicyclohexylphosphino-2'-(N,N-dimethylamino)biphenyl, 2-(di-t-butylphosphino)biphenyl, 2-(dicyclohexylphosphino)biphenyl, etc.), and LiHMDS, at a suitable temperature (between a room temperature and the boiling point of the solvent).

A compound represented by the formula (V) can be produced from the compound represented by the formula (IV) according to known methods (Sandmeyer's reaction: J. L. Hartwell, Org. Synth., III, p. 185 (1955); P. J. Harrington, and L. S. Hegedus, J. Org. Chem., vol. 49, p. 2657 (1984)).

A compound represented by the formula (1a) can be produced from the compound represented by the formula (V) according to known methods (Palladium catalyst aromatic amidation: Org. Lett., vol. 2, pp. 1101-1104 (2000); Tetrahedron Lett., vol. 42, pp. 7155-7157 (2001)). Thus, the compound represented by the formula (1a) can be produced by allowing the compound represented by the formula (V) to react with a commercially available reagent or a cyclic amide prepared by a known method, a suitable solvent (toluene, THF, 1,4-dioxane, xylene, dimethoxyethane, etc.), a suitable palladium catalyst (for example, $Pd(OAc)_2$, $Pd_2 dba_3$, $PdCl_2[P(O-tol)_3]_2$, $Pd(O_2CCF_3)_2$, etc.), a suitable ligand (for example, $P(o-tol)_3$, BINAP, DPPF, $P(t-Bu)_3$, 2-dicyclohexylphosphino-2'-(N,N-dimethylamino)biphenyl, 2-(di-t-butylphosphino)biphenyl, 2-(dicyclohexylphosphino)biphenyl, 2',6'-dimethoxy-2-(dicyclohexylphosphino)biphenyl, 2',4',6'-triisopropyl-2-(dicyclohexylphosphino)biphenyl, 4,5-bis-diphenylphosphanyl-9,9-dimethyl-9H-xanthene, 4,5-bis[bis(3,5-bistrifluoromethylphenyl)phosphanyl]-9,9-dimethyl-9H-xanthene, 1,3-diallyldihydroimidazolium salt, etc.), and a suitable base (t-BuONa, $Cs_2CO_3$, $K_3PO_4$, etc.), at a suitable temperature (between a room temperature and the boiling point of the solvent).

Moreover, the compound represented by the formula (1a) can also be produced from the compound represented by the formula (V) according to known methods (Copper catalyst aromatic amidation reaction: Buchwald, S. L., J. Am. Chem. Soc., vol. 123, pp. 7727-7729 (2001), Buchwald, S. L., J. Am. Chem. Soc., vol. 124, pp. 7421-7428 (2002)). Thus, the compound represented by the formula (1a) can be produced by allowing the compound represented by the formula (V) to react with a commercially available reagent or a suitable amide compound prepared by a known method in the presence of a suitable solvent (1,4-dioxane, tetrahydrofuran, diethyl ether, toluene, etc.), a suitable copper catalyst (metal copper (powders), copper (I) chloride, copper (I) oxide, copper (II) oxide, copper (II) chloride, copper (II) sulfate, copper (II) acetate, copper (II) acetoacetate, copper (I) iodide, copper (I) trifluoromethanesulfonate, etc.), a suitable ligand (1,2-cyclohexanediamine, N,N'-dimethylethylenediamine, N,N'-dimethyl-1,2-cyclohexanediamine, 1,10-phenanthroline, etc.), and a suitable base (potassium phosphate, potassium carbonate, cesium carbonate, sodium t-butoxide, potassium hexamethyldisilazane, sodium hexamethyldisilazane, phosphazene, etc.), at a suitable temperature (between a room temperature and the boiling point of the solvent).

2. General Synthesis Method of Compound (1b) Represented by the Formula (1)

Reaction Process 2

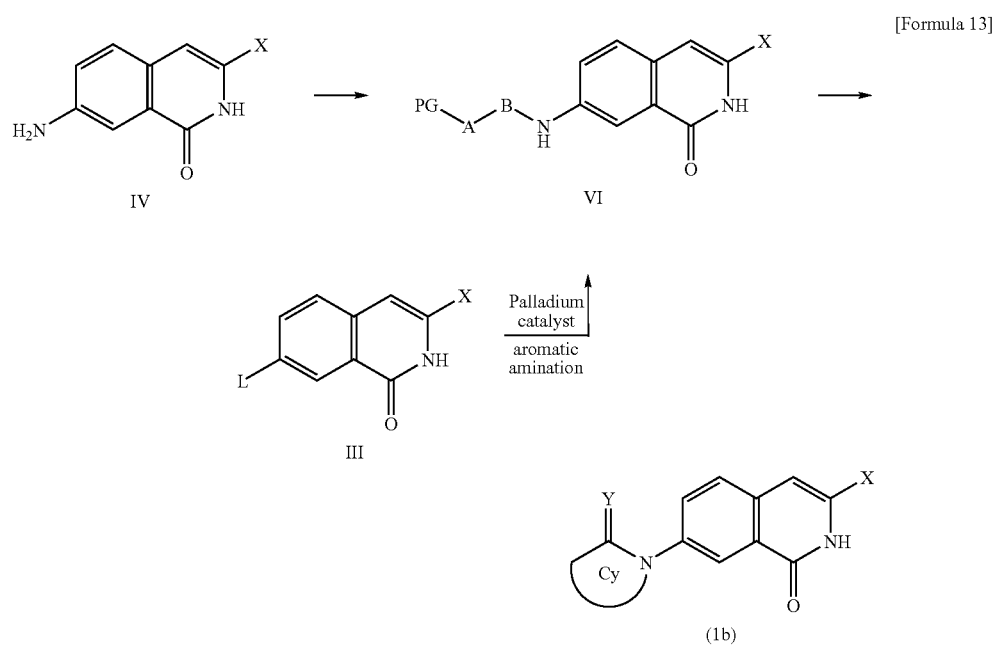

[Formula 13]

[wherein A represents —O—C(=O)— (wherein PG binds to an oxygen atom, and B binds to a carbonyl group), O, or N—$Rb^1$; $Rb^1$ represents a substituents selected from Group Q2, which has already been defined above; B represents a linking group having, as a main chain, 1 to 5 atoms selected from an oxygen atom, a sulfur atom, a nitrogen atom, and a carbon atom (wherein the main chain terminal atom of B that binds to —$NH_2$ of the compound represented by the formula (IV) is a carbon atom), wherein the linking group may contain a double bond, and wherein the carbon atom(s) of the linking group may be substituted with one or more substituents selected from the defined Group Q1, and the nitrogen atom thereof may be substituted with one or more substituents selected from the defined Group Q2; PG represents a protecting group (for example, acetyl, t-butoxycarbonyl, benzyloxycarbonyl, t-butyldimethylsilyl, etc.) or a hydrogen atom; and Cy, Y, X, and L are the same as those defined above].

A compound represented by the formula (VI) can be obtained by subjecting the compound represented by the formula (IV) used in reaction process 1 to a known method (for example, an N-alkylation reaction with an alkyl halide, which can be purchased as a reagent, or is prepared by a known method; a reductive alkylation reaction with aldehyde or ketone, which can be purchased as a reagent, or is prepared by a known method; a reaction with a commercially available reagent such as glycidol or with epoxide prepared by a known method; the methods disclosed in EP50827 and U.S. Pat. No. 4,461,773, etc.).

Moreover, the compound represented by the formula (VI) can also be produced from the compound represented by the formula (III) used in reaction process 1 according to known methods (Aromatic amination: Org. Lett., vol. 2, pp. 1101-1104 (2000); Tetrahedron Lett., vol. 42, pp. 7155-7157 (2001)). A compound represented by the formula (1b) can be produced by deprotecting the compound represented by the formula (VI) according to a known method, as necessary, and then subjecting the resulting compound to known methods (when A is O or N—$Rb^1$, a carbonylation reaction or thiocarbonylation reaction using phosgene, $CS_2$, etc.; Journal of Organic Chemistry, vol. 60(20), pp. 6604-6607 (1995), Journal of Organic Chemistry, vol. 66(11), pp. 3940-3947 (2001); a cyclization reaction using a halogenated acetyl halide: Heterocycles, vol. 38(5), pp. 1033-1040 (1994); when A is CO(=O), a condensation reaction using DCC, WSCI (N-ethyl-N'-(3-dimethylaminopropyl)carbodiimide hydrochloride) or a BOP reagent).

3. General Synthesis Method of Compound (1c) Represented by the Formula (1)

Reaction Process 3

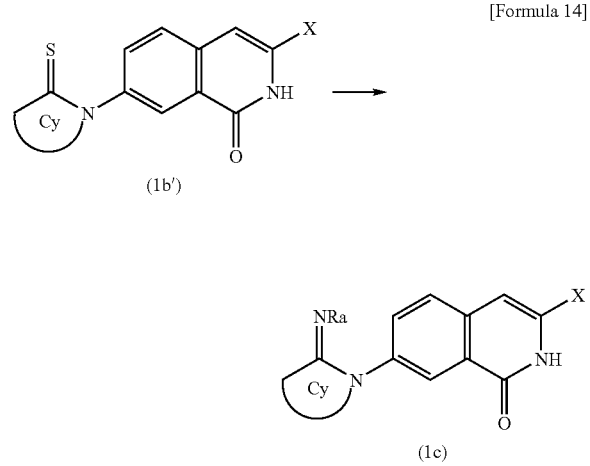

[wherein Ra, Cy, and X are the same as those defined above].

A compound represented by the formula (1c) can be produced by subjecting the compound represented by the formula (1b'), which can be produced by reaction process 2, to a known method (for example, a reaction of ammonia, or alkylamine or alkoxyamine which is commercially available or can be prepared by a known method, with a condensing agent such as WSC or DCC: Bioorganic & Medicinal Chemistry Letters, vol. 12, pp. 2931-2934 (2002)).

4. General Synthesis Method of Compound (1d) Represented by the Formula (1)

Reaction Process 4

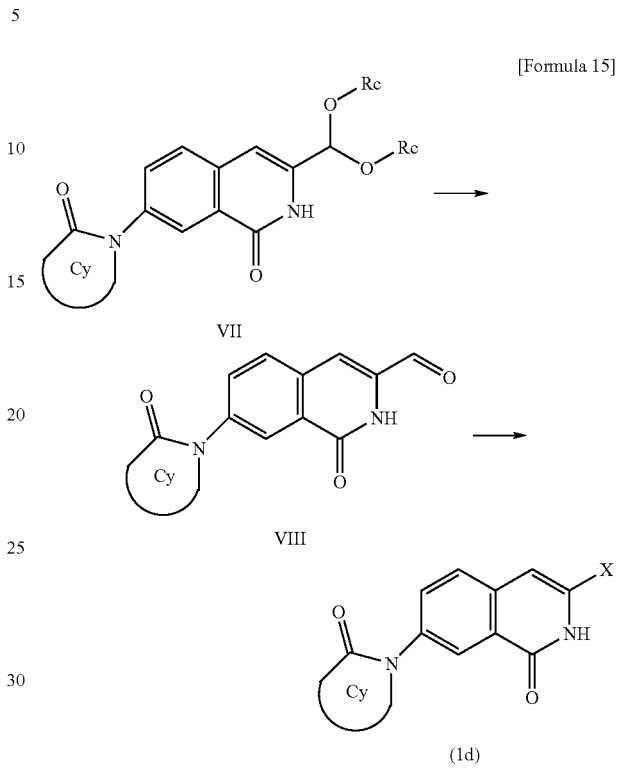

[wherein Rc, Cy, and X are the same as those defined above].

A compound represented by the formula (1d) can be produced by deprotecting the compound represented by the formula (VII), which can be produced by reaction process 2, by known methods (for example, a reaction under acidic conditions such as TFA, etc.), and then subjecting the obtained compound represented by the formula (VIII) to a known method (for example, a condensation reaction with a diamine derivative, which can be purchased as a reagent or prepared by a known method; Tetrahedron Letters, vol. 46, pp. 2197-2199 (2005), Bioorganic & Medicinal Chemistry Letters, vol. 8, pp. 361-364 (1998), Journal of Medicinal Chemistry, vol. 29, pp. 1065-1080 (1986), Bioorganic & Medicinal Chemistry Letters, vol. 13, pp. 1989-1992 (2003)).

5. General Synthesis Method of Compound (1e) Represented by the Formula (1)

Reaction Process 5

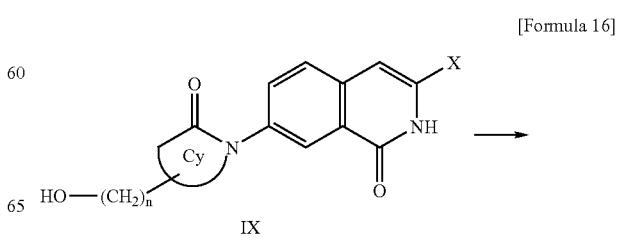

-continued

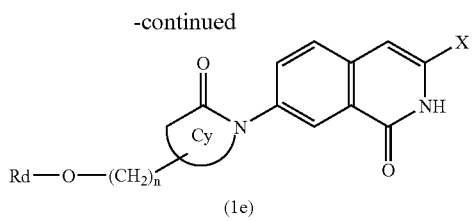

(1e)

[wherein Rd, Cy, and X are the same as those defined above, and n represents an integer between 0 and 8].

With regard to the synthesis of an ester derivative, a compound represented by the formula (1e) can be produced by subjecting the compound represented by the formula (IX), which can be produced by reaction process 1 or 2, to a known method (for example, a condensation reaction of a DCC, WSCI reagent, or the like, with DMAP, or an acylation reaction using an acid anhydride or an acid halide: *Jikken Kagaku Koza*, 4th edition, (Maruzen), vol. 22, pp. 43-82), using carboxylic acid, an acid anhydride, amino acid, or the like, which is commercially available or can be synthesized by a known method.

With regard to the synthesis of a carbonate derivative, a compound represented by the formula (1e) can be produced by activating alcohol, which is commercially available or can be synthesized by a known method, according to a known method (a reaction using phosgene or the like: Organic Synthesis Collective Volume 6, p. 715, (1988), a reaction using 4-nitrophenyl chloroformate; WO2005-018568), and then condensing the resultant compound with the compound represented by the formula (IX). As an alternative synthesis method, such a compound represented by the formula (1e) can be produced by activating the compound represented by the formula (IX) according to a known method (a reaction using phosgene or the like: Organic Synthesis Collective Volume 6, p. 715, (1988), a reaction using 4-nitrophenyl chloroformate; WO2005-018568), and then condensing the resultant compound with alcohol, which is commercially available or can be synthesized by a known method.

With regard to the synthesis of a carbamate derivative, a compound represented by the formula (1e) can be produced by activating the compound represented by the formula (IX) according to a known method (a reaction using phosgene or the like: Organic Synthesis Collective Volume 6, p. 715, (1988), a reaction using 4-nitrophenyl chloroformate; WO2005-018568), and then condensing the resultant compound with amine, which is commercially available or can be synthesized by a known method. Further, as an alternative synthesis method, such a derivative can be produced by subjecting the compound represented by the formula (IX) to a known method (*Jikken Kagaku Koza*, vol. 20, p. 358 (4th edition)), using isocyanate, which is commercially available or can be synthesized by a known method.

6. General Synthesis Method of Compound (1f, 1g, 1k, 1l) Represented by the Formula (1)

Reaction Process 6

[Formula 17]

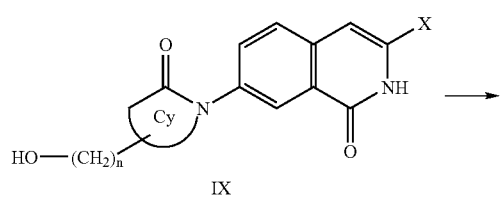

IX

-continued

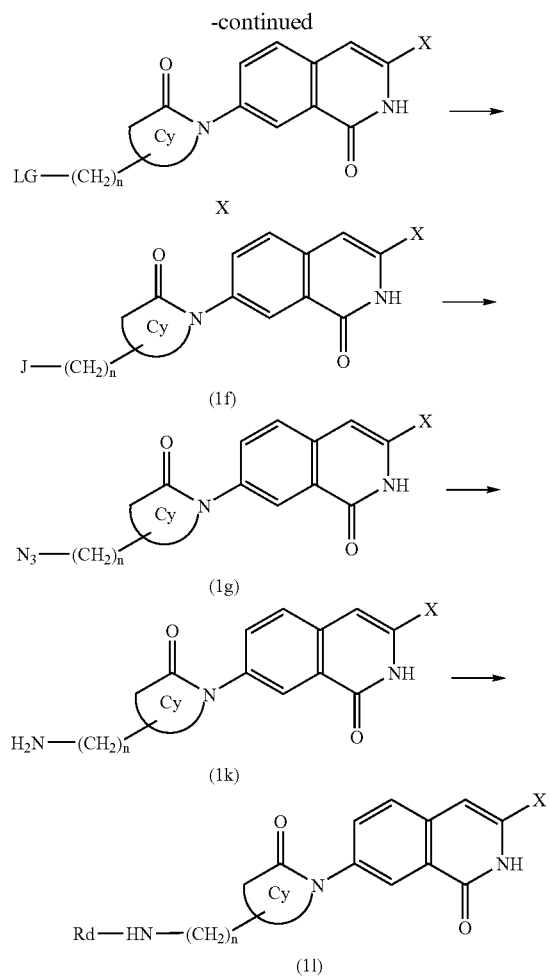

[wherein LG, J, Rd, Cy, and X are the same as those defined above, and n represents an integer between 0 and 8].

A compound represented by the formula (1f) can be produced by converting a hydroxyl group of the compound represented by the formula (IX), which can be produced by reaction process 1 or 2, to a leaving group according to the known method, and then subjecting the obtained compound to a known method (for example, a reaction with oxygen nucleophilic species (for example, sodium alkoxide, etc.): Tetrahedron, vol. 43, pp. 3803-3816 (1987), nitrogen nucleophilic species (for example, morpholine, piperidine, pyrrolidine, etc.): J. Med. Chem. vol. 23, pp. 1380-1386 (1980), Bioorg. Med. Chem. Lett. vol. 13, pp. 4169-4172 (2003), or sulfur nucleophilic species (for example, NaSMe etc.): Bioorganic Med. Chem. Lett. vol. 15, pp. 699-703 (2005), Bioorganic Med. Chem. vol. 12, pp. 4393-4401 (2004)). A compound represented by the formula (1k) can be synthesized by allowing the compound represented by the formula (X) to react with sodium azide acting as nucleophilic species according to the known method, and then reducing the obtained compound. A compound represented by the formula (1l) can be produced by subjecting the obtained compound represented by the formula (1k) to an acylation reaction (for example, a condensation reaction of carboxylic acid or the like with a DCC, WSCI reagent, or the like, an acylation reaction using an acid anhydride or an acid halide: *Jikken*

Kagaku Koza, 4th edition (Maruzen), vol. 22, pp. 137-173, Tetrahedron, vol. 57, pp. 1551-1558 (2001)).

7. General Synthesis Method of Compound (1m) Represented by the Formula (1)

Reaction Process 7

[Formula 18]

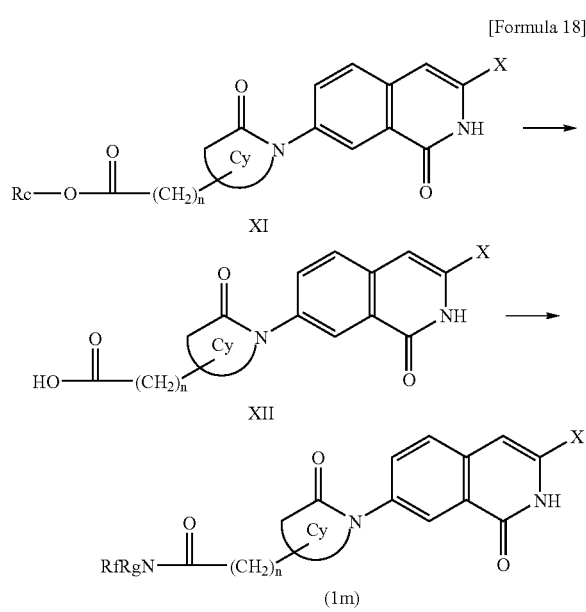

[wherein Rc, Rf, Rg, Cy, and X are the same as those defined above, and n represents an integer between 0 and 6].

A compound represented by the formula (1m) can be produced by hydrolyzing according to the known method the compound represented by the formula (XI), which can be produced by reaction process 1 or reaction process 2, and then subjecting the resulting compound to the same acylation reaction as performed in reaction process 6, using amine, which is commercially available or can be synthesized by a known method.

8. General Synthesis Method of Compound (1n) Represented by the Formula (1)

Reaction Process 8

[Formula 19]

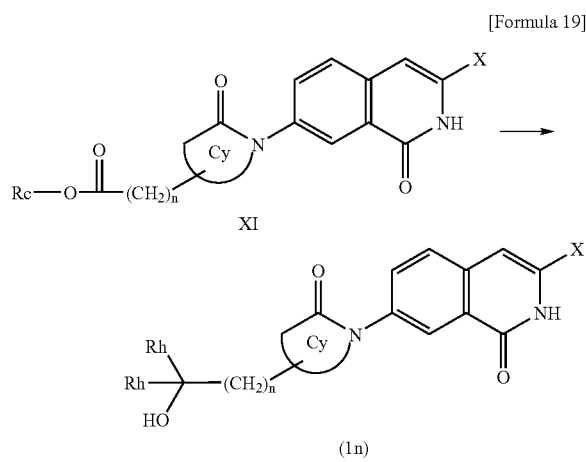

[wherein Rc, Rh, Cy, and X are the same as those defined above, and n represents an integer between 0 and 6].

A compound represented by the formula (1n) can be produced by subjecting the compound represented by the formula (XI), which can be produced by reaction process 1 or reaction process 2, to a known method (for example, a reaction with an organic metal reagent such as MeMgBr: J. Org. Chem. vol. 70, pp. 261-267 (2005)).

Some of starting material compounds for the compound of the present invention are novel compounds. Such novel compounds can be easily synthesized in the same manner as for known raw material compounds, or by applying methods known to persons skilled in the art.

Examples of a method for producing the compound represented by the formula (1) of the present invention have been given above. Isolation and purification of the compounds of interest shown in the aforementioned reaction processes can be carried out by applying common chemical operations such as extraction, concentration, distillation, crystallization, filtration, recrystallization, or various types of chromatography.

The compound of the present invention and a pharmaceutically acceptable salt thereof include all stereoisomers of the compound represented by the formula (1) (for example, an enantiomer and a diastereomer (including cis- and trans-geometric isomers)), racemate of the aforementioned isomers, and other mixtures.

In addition, the compound of the present invention and a pharmaceutically acceptable salt thereof can be present in several tautomeric forms, such as enol and imine forms, keto and enamine forms, and mixtures thereof. Such tautomeric isomers are present in a solution in the form of a mixture of tautomeric sets. In a solid form, either one tautomeric isomer is generally dominant. There are cases where only either one tautomeric isomer is described, but the present invention includes all tautomeric isomers of the compound of the present invention.

When the compound of the present invention is obtained in the free form, it can be converted into a salt, which the compound may form, a hydrate thereof, or a solvate thereof, according to a common method.

In addition, when the compound of the present invention is obtained in the form of such a salt, hydrate, or solvate of the compound, they can be converted to a free form of the compound according to a common method.

The compound of the present invention or a pharmaceutically acceptable salt thereof has excellent antitumor action. It is excellent in terms of stability in vivo and solubility in water, and is useful as a preventive or therapeutic agent (particularly as a therapeutic agent) used for proliferative diseases such as cancer. Excellent water solubility results in excellent absorbing properties of the compound, a prodrug thereof, and a salt thereof, in vivo. Further, an increase in beneficial effect can be anticipated. Moreover, the compound of the present invention or a pharmaceutically acceptable salt is useful as a preventive or therapeutic agent (particularly as a therapeutic agent) used for various types of cancers such as breast cancer, colon cancer, ovarian cancer, lung cancer, pancreatic cancer, liver cancer, uterine cancer, brain tumor, prostatic cancer, blood cancer (acute leukemia, malignant lymphoma, etc.), bladder cancer, esophageal cancer, skin cancer, testicular cancer, thyroid cancer, and stomach cancer, and in particular, solid cancers such as breast cancer, colon cancer, ovarian cancer, lung cancer, pancreatic cancer, liver cancer, uterine cancer, brain tumor, prostatic cancer, and stomach cancer. Furthermore, since the compound of the present invention is characterized in that it causes few effects (enzyme inhibition, etc.) on drug metabolizing enzymes such as CYP3A4, it has preferred effects as a pharmaceutical in terms of safety.

The aforementioned methods include a step of administering to patients, who need such treatment or who suffer from the aforementioned diseases or symptoms, a pharmaceutical composition comprising the compound disclosed in the present invention or a pharmaceutically acceptable salt thereof, at a pharmaceutically effective dosage.

When the pharmaceutical composition of the present invention is used as a therapeutic or preventive agent for proliferative diseases such as cancer, examples of an administration method may include oral, intrarectal, parenteral (intravenous, intramuscular, or subcutaneous), intracisternal, intravaginal, intraperitoneal, intravesical, and local (administration of drop, powders, ointment, or cream) administrations, and inhalation (intraoral or nasal spray). Examples of such an administration form may include a tablet, a capsule, a granule, a powder, a pill, an aqueous or nonaqueous oral solution, a suspension, and a parenteral solution, which is filled in a container suitable for dividing the solution into individual dosages. In addition, such an administration form can also be adapted to various administration methods including controlled released preparations such as those used in subcutaneous transplantation.

The aforementioned pharmaceutical can be produced according to known methods using additives such as an excipient, a lubricant (coating agent), a binder, a disintegrator, a stabilizer, a flavoring agent, or a diluent.

Examples of an excipient may include starches such as starch, potato starch, or corn starch, lactose, crystalline cellulose, and calcium hydrogen phosphate.

Examples of a coating agent may include ethyl cellulose, hydroxypropylcellulose, hydroxypropylmethylcellulose, shellac, talc, carnauba wax, and paraffin.

Examples of a binder may include polyvinylpyrrolidone, macrogol, and the same compounds as those described in the excipient.

Examples of a disintegrator may include the same compounds as those described in the excipient, and chemically modified starches and celluloses, such as croscarmellose sodium, carboxymethyl starch sodium, or crosslinked polyvinylpyrrolidone.

Examples of a stabilizer may include: p-hydroxybenzoic esters such as methylparaben or propylparaben; alcohols such as chlorobutanol, benzyl alcohol, or phenylethyl alcohol; benzalkonium chloride; phenols such as phenol or cresol; thimerosal; dehydroacetic acid; and sorbic acid.

Examples of a flavoring agent may include commonly used sweeteners, acidulants, and aromatics.

Examples of a solvent used in production of a liquid agent may include ethanol, phenol, chlorocresol, purified water, and distilled water.

Examples of a surfactant or emulsifier may include polysorbate 80, polyoxyl 40 stearate, and lauromacrogol.

When the pharmaceutical composition of the present invention is used as a therapeutic or preventive agent for proliferative diseases, the amount used of the compound of the present invention or a pharmaceutically acceptable salt thereof is different depending on symptom, age, body weight, relative physical conditions, the use of other agents, an administration method, etc. For example, for a patient (a hematherm, and particularly a human), in the case of administering an active ingredient (the compound represented by the formula (1) of the present invention) as an oral agent, an effective amount is generally preferably 0.01 and 5,000 mg, and more preferably between 0.1 and 500 mg per kg of body weight per day. In the case of a parenteral agent, such an effective amount is preferably 0.01 and 5,000 mg, and more preferably between 0.1 and 500 mg per kg of body weight per day. It is desired that such an amount of pharmaceutical composition be administered depending on symptoms.

EXAMPLES

The present invention will be more specifically described in the following examples. However, these examples are not intended to limit the scope of the present invention. It is to be noted that NMR analysis was carried out using JNM-EX270 (270 MHz), JNMGSX400 (400 MHz) or JNM-A500 (500 MHz), which are manufactured by JEOL, or NMR (300 MHz) manufactured by Bruker. NMR data was indicated with ppm (parts per million). The deuterium lock signal from a sample solvent was referred. Mass spectrum data was obtained using JMS-DX303 or JMS-SX/SX102A manufactured by JEOL, or Quttromicro manufactured by Micromass. In addition, mass spectrum data including high performance liquid chromatography was obtained, using a micromass (ZMD manufactured by Micromass) equipped with a 996-600E gradient high performance liquid chromatography manufactured by Waters, or using a micromass (ZQ manufactured by Micromass) equipped with a 2525 gradient high performance liquid chromatography manufactured by Waters. Any of the following conditions were applied for such high performance liquid chromatography.

High Performance Liquid Chromatography Condition 1

Column: Combi ODS (ODS, 5 μm, 4.6 mm I.D.×50 mm, manufactured by Wako Pure Chemical Industries, Ltd.), COSMOSIL (ODS, 5 μm, 4.6 mm I.D.×50 mm, manufactured by Nacalai Tesque, Inc.), Inertsil C18 (ODS, 5 μm, 4.6 mm I.D.×50 mm, manufactured by GL Sciences, Inc), or SunFire C18 (ODS, 5 μm, 4.6 mm I.D.×50 mm, manufactured by Waters)

Mobile phase: Water (A) that contains 0.05% trifluoroacetic acid and acetonitrile (B) that contains 0.05% trifluoroacetic acid Elution method: A stepwise solvent gradient elution comprising eluting from 10% B to 95% B (3.5 minutes), eluting from 95% B to 10% B (1 minute), and then retaining at 10% B (0.5 minutes)

Flow rate: 4.0 ml/minute

High Performance Liquid Chromatography Condition 2

Column: Combi ODS (ODS, 5 μm, 4.6 mm I.D.×50 mm, manufactured by Wako Pure Chemical Industries, Ltd.), COSMOSIL (ODS, 5 μm, 4.6 mm I.D.×50 mm, manufactured by Nacalai Tesque, Inc.), Inertsil C18 (ODS, 5 μm, 4.6 mm I.D.×50 mm, manufactured by GL Sciences, Inc), or SunFire C18 (ODS, 5 μm, 4.6 mm I.D.×50 mm, manufactured by Waters)

Mobile phase: Water (A) that contains 0.05% trifluoroacetic acid and acetonitrile (B) that contains 0.05% trifluoroacetic acid Elution method: A stepwise solvent gradient elution comprising eluting from 30% B to 35% B (0.2 minutes), eluting from 35% B to 98% B (3.3 minutes), eluting from 98% B to 30% B (1 minute), and then retaining at 30% B (0.5 minutes)

Flow rate: 4.0 ml/minute

High Performance Liquid Chromatography Condition 3

Column: Combi ODS (ODS, 5 μm, 4.6 mm I.D.×50 mm, manufactured by Wako Pure Chemical Industries, Ltd.), or SunFire C18 (ODS, 5 μm, 4.6 mm I.D.×50 mm, manufactured by Waters)

Mobile phase: Water (A) that contains 0.05% trifluoroacetic acid and acetonitrile (B) that contains 0.05% trifluoroacetic acid Elution method: A stepwise solvent gradient elution comprising eluting from 10% B to 95% B (2 minutes), retaining at 95% B (1.5 minutes), eluting from 95% B to 10% B, and retaining at 10% B (0.5 minutes)

Flow rate: 4.0 ml/minute

An organic synthetic reaction was carried out using a commercially available reagent, which has not been further purified before use. The term "room temperature" is used herein to mean a temperature ranging from 20° C. to 25° C. All antiposic reactions were carried out in a nitrogen atmosphere. Concentration under reduced pressure or solvent distillation was carried out using a rotary evaporator, unless otherwise specified.

For preparation of compounds, a functional group is protected by a protecting group as necessary, a protector of a target molecule is prepared, and the protecting group is then removed. Operations to select such a protecting group and to remove it were carried out according to the method described in Greene and Wuts, "Protective Group in Organic Synthesis," 2nd edition, John Wiley & Sons, 1991, for example.

Example 1-1

7-(2-Oxoazetidin-1-yl)-3-(2-trifluoromethylphenyl)-2H-isoquinolin-1-one

Step A

5-Chloro-2,N-dimethylbenzamide

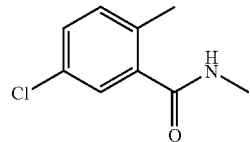

[Formula 20]

Thionyl chloride (42.8 ml, 586 mmol) was added to 5-chloro-2-methylbenzoic acid (25.0 g, 147 mmol). The mixture was stirred under heating to reflux for 1.5 hours. Thereafter, excessive thionyl chloride was distilled away under reduced pressure. The residue was dissolved in methylene chloride (140 ml), and a 40% methylamine aqueous solution (34.2 ml, 440 mmol) was then added dropwise thereto under cooling on ice. Thereafter, the obtained mixture was stirred at 0° C. for 1 day. Thereafter, the reaction solution was extracted with ethyl acetate, and the extract was then washed with a saturated saline solution. The resultant was then dried over anhydrous sodium sulfate, and the solvent was distilled away under reduced pressure. The obtained residue was purified by silica gel column chromatography (ethyl acetate:hexane=1:3 to 3:2), so as to obtain 5-chloro-2,N-dimethylbenzamide (24.2 g; yield: 90%) in the form of a colorless solid.

$^1$H-NMR (270 MHz, CDCl$_3$) δ (ppm): 2.40 (3H, s), 2.99 (3H, d, J=4.6 Hz), 5.77 (1H, brs), 7.15 (1H, d, J=8.3 Hz), 7.27 (1H, dd, J=2.3, 8.3 Hz), 7.33 (1H, d, J=2.3 Hz)

ESI (LC-MS positive mode) m/z 184 (M+H).

Step B

7-Chloro-3-(2-trifluoromethylphenyl)-2H-isoquinolin-1-one

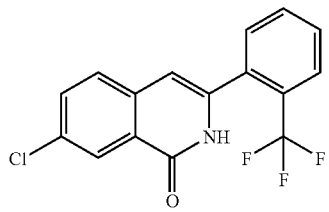

[Formula 21]

A 1.8 M lithium diisopropylamide THF solution (45.3 ml, 81.6 mmol) was diluted with THF (68 ml). Thereafter, a solution obtained by dissolving the 5-chloro-2,N-dimethylbenzamide (5.0 g, 27.2 mmol) prepared in step A in THF (28 ml) was added dropwise to the diluted solution at -78° C. Thereafter, a solution obtained by dissolving 2-trifluoromethylbenzonitrile (4.65 g, 27.2 mmol) in THF (28 ml) was further added thereto, and the obtained mixture was then stirred at -78° C. for 2.5 hours. The temperature of the reaction solution was increased to a room temperature, and a saturated ammonium chloride aqueous solution was added thereto, followed by extraction with ethyl acetate. The extract was washed with a saturated saline solution, and was then dried over anhydrous sodium sulfate. Thereafter, a solid generated as a result of vacuum concentration was filtrated, so as to obtain 7-chloro-3-(2-trifluoromethylphenyl)-2H-isoquinolin-1-one (6.87 g; yield: 78%) in the form of a colorless solid.

$^1$H-NMR (270 MHz, CDCl$_3$) δ (ppm): 6.49 (1H, s), 7.33-7.72 (5H, m), 7.81-7.84 (1H, d, J=7.26 Hz), 8.32-8.33 (1H, d, J=1.65 Hz), 9.18 (1H, brs)

ESI (LC-MS positive mode) m/z 324 (M+H).

Step C

7-Amino-3-(2-trifluoromethylphenyl)-2H-isoquinolin-1-one

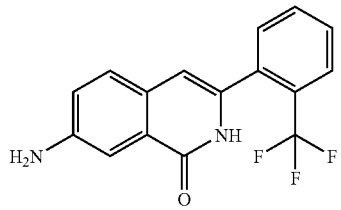

[Formula 22]

A 1 M lithium bis(trimethylsilyl)amide THF solution (21 mL, 21 mmol) was added to a mixture of the 7-chloro-3-(2-trifluoromethylphenyl)-2H-isoquinolin-1-one (2.50 g, 7.72 mmol) prepared in step B, 2-(dicyclohexylphosphino)biphenyl (64.9 mg, 0.185 mmol), and tris(dibenzylideneacetone)dipalladium (70.7 mg, 0.0772 mmol), and the obtained mixture was stirred under heating to reflux for 1 day. Thereafter, the reaction solution was cooled to a room temperature, and 1 N hydrochloric acid (63 ml) was then added thereto, followed by stirring for 5 minutes. Thereafter, the reaction solution was neutralized with a 5 N sodium hydroxide aqueous solution (8 ml), and then extracted with methylene chloride. The extract was washed with a saturated saline solution, and was then dried over anhydrous sodium sulfate, followed by concentration. The obtained residue was purified by silica gel column chromatography (ethyl acetate hexane=3:1 to 6:1), so as to obtain 7-amino-3-(2-trifluoromethylphenyl)-2H-isoquinolin-1-one (2.14 g; yield: 91%) in the form of a brown solid.

$^1$H-NMR (270 MHz, CDCl$_3$) δ (ppm): 4.00 (2H, brs), 6.43 (1H, s), 7.07 (1H, dd, J=2.5, 8.3 Hz), 7.40 (1H, d, J=8.3 Hz), 7.50-7.69 (4H, m), 7.76-7.83 (1H, m), 8.63 (1H, brs)

ESI (LC-MS positive mode) m/z 305 (M+H).

Step D

7-Iodo-3-(2-trifluoromethylphenyl)-2H-isoquinolin-1-one

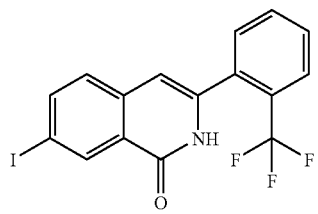

[Formula 23]

A 1 N sulfuric acid aqueous solution (30 ml) and sodium nitrite (862.5 mg, 12.5 mmol) were added at 0° C. to an acetic acid solution (15 ml) that contained the 7-amino-3-(2-trifluoromethylphenyl)-2H-isoquinolin-1-one (1.52 g, 5.0 mmol) obtained in step C, and the obtained mixture was stirred for 30 minutes. Thereafter, sodium iodide (2.62 g, 17.5 mmol) and copper iodide (I) (952.3 mg, 5.0 mmol) were added to the reaction solution, and the obtained mixture was stirred at 80° C. for 1 hour. The reaction solution was cooled, and a saturated sodium bicarbonate aqueous solution was added thereto, followed by extraction with ethyl acetate. The extract was washed with a saturated saline solution, and was then dried over anhydrous sodium sulfate, followed by concentration. The obtained residue was purified by silica gel column chromatography (ethyl acetate:hexane=1:4 to 1:2). The resultant was washed with a sodium thiosulfate aqueous solution, so as to obtain 7-iodo-3-(2-trifluoromethylphenyl)-2H-isoquinolin-1-one (1.87 g; yield: 90%) in the form of a pale yellow solid.

$^1$H-NMR (270 MHz, CDCl$_3$) δ (ppm): 6.47 (1H, s), 7.31 (1H, d, J=8.6 Hz), 7.55 (1H, dd, J=1.7, 7.3 Hz), 7.59-7.73 (2H, m), 7.83 (1H, dd, J=2.0, 6.9 Hz), 7.96 (1H, dd, J=1.8, 8.4 Hz), 8.72 (1H, d, J=1.6 Hz), 9.06 (1H, brs)

ESI (LC-MS positive mode) m/z 416 (M+H).

Step E 7-(2-Oxoazetidin-1-yl)-3-(2-trifluoromethylphenyl)-2H-isoquinolin-1-one

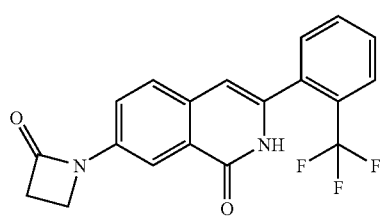

[Formula 24]

The 7-iodo-3-(2-trifluoromethylphenyl)-2H-isoquinolin-1-one (10.0 mg, 0.024 mmol) prepared in step D, copper iodide (I) (0.48 mg, 0.0025 mmol), 2-azetidinone (2.13 mg, 0.03 mmol), and potassium phosphate (11.1 mg, 0.0525 mmol) were suspended in 1,4-dioxane (0.25 ml). Thereafter, N,N'-dimethylethylenediamine (2.6 µl) was added to the suspension, and the obtained mixture was stirred under heating to reflux overnight. Thereafter, the reaction solution was cooled to a room temperature, and a saturated ammonium chloride aqueous solution was then added thereto, followed by extraction with ethyl acetate. The extract was dried over anhydrous sodium sulfate, and the solvent was then distilled away under reduced pressure. The obtained residue was purified by silica gel column chromatography (ethyl acetate hexane=3:1 to 6:1), so as to obtain 7-(2-oxoazetidin-1-yl)-3-(2-trifluoromethylphenyl)-2H-isoquinolin-1-one (3.8 mg; yield: 44%) in the form of a colorless solid.

$^1$H-NMR (270 MHz, CDCl$_3$) δ (ppm): 3.20 (2H, t, J=4.6 Hz), 3.77 (2H, t, J=4.6 Hz), 6.51 (1H, s), 7.50-7.71 (4H, m), 7.80-7.87 (2H, m), 8.27 (1H, dd, J=2.3, 8.6 Hz), 8.65 (1H, brs)

ESI (LC-MS positive mode) m/z 359 (M+H).

The following compounds (Examples 1-2 to 1-12) were synthesized by a reaction similar to step E of Example 1-1, using the 7-iodo-3-(2-trifluoromethylphenyl)-2H-isoquinolin-1-one obtained in step D of Example 1-1 as a raw material.

Example 1-2

7-(2-Oxopiperidin-1-yl)-3-(2-trifluoromethylphenyl)-2H-isoquinolin-1-one

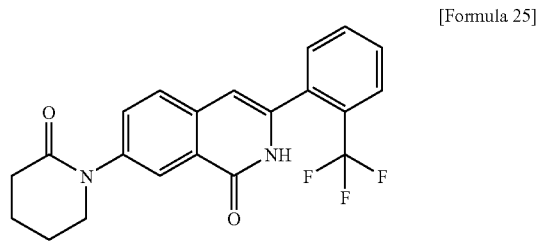

[Formula 25]

$^1$H-NMR (270 MHz, CDCl$_3$) δ (ppm): 1.95-2.00 (4H, m), 2.61 (2H, t, J=5.9 Hz), 3.78 (2H, t, J=6.1 Hz), 6.52 (1H, s), 7.52-7.69 (4H, m), 7.73 (1H, dd, J=2.3, 8.6 Hz), 7.83 (1H, dd, J=1.7, 7.6 Hz), 8.24 (1H, d, J=2.3 Hz), 8.44 (1H, brs)

ESI (LC-MS positive mode) m/z 387 (M+H).

Example 1-3

7-(2-Oxo-2H-pyridin-1-yl)-3-(2-trifluoromethylphenyl)-2H-isoquinolin-1-one

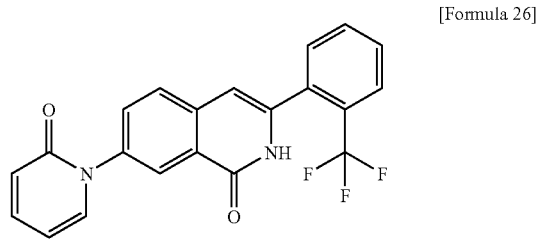

[Formula 26]

¹H-NMR (270 MHz, CDCl₃) δ (ppm): 6.31 (1H, dt, J=1.3, 6.8 Hz), 6.57 (1H, s), 6.70 (1H, dd, J=1.2, 9.7 Hz), 7.40-7.49 (2H, m), 7.52-7.63 (4H, m), 7.80-7.89 (2H, m), 8.34 (1H, d, J=2.3 Hz), 8.67 (1H, brs)

ESI (LC-MS positive mode) m/z 383 (M+H).

Example 1-4

7-((R)-4-Hydroxy-2-oxopyrrolidin-1-yl)-3-(2-trifluoromethylphenyl)-2H-isoquinolin-1-one

[Formula 27]

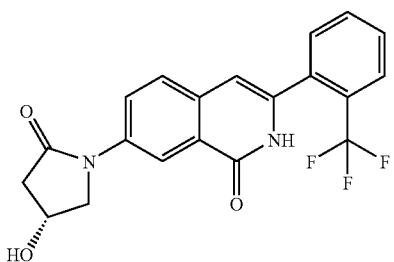

¹H-NMR (270 MHz, DMSO-d₆) δ (ppm): 2.37 (1H, d, J=17.9 Hz), 2.90 (1H, dd, J=17.9, 6.3 Hz), 3.70 (1H, d, J=10.6 Hz), 4.19 (1H, dd, J=10.6, 5.2 Hz), 4.45 (1H, brs), 5.43 (1H, d, J=3.6 Hz), 6.49 (1H, s), 7.63-7.81 (4H, m), 7.88 (1H, d, J=7.8 Hz), 8.14 (1H, dd, J=7.8, 2.3 Hz), 8.36 (1H, d, J=2.3 Hz), 11.60 (1H, s)

ESI (LC-MS positive mode) m/z 389 (M+H).

Example 1-5

7-((S)-4-Hydroxy-2-oxopyrrolidin-1-yl)-3-(2-trifluoromethylphenyl)-2H-isoquinolin-1-one

[Formula 28]

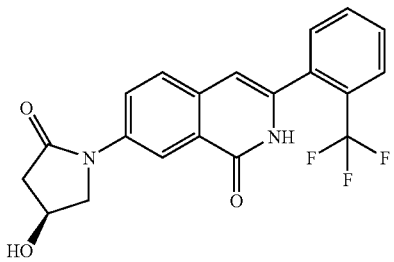

¹H-NMR (270 MHz, DMSO-d₆) δ (ppm): 2.37 (1H, d, J=17.2 Hz), 2.90 (1H, dd, J=17.2, 6.2 Hz), 3.70 (1H, d, J=10.1 Hz), 4.19 (1H, dd, J=10.1, 5.1 Hz), 4.45 (1H, brs), 5.44 (1H, brs), 6.49 (1H, s), 7.66-7.82 (4H, m), 7.88 (1H, d, J=7.7 Hz), 8.14 (1H, dd, J=7.7, 2.4 Hz), 8.37 (1H, d, J=2.4 Hz), 11.61 (1H, s)

ESI (LC-MS positive mode) m/z 389 (M+H).

Example 1-6

7-(4-Methoxy-2-oxo-2,5-dihydropyrrol-1-yl)-3-(2-trifluoromethylphenyl)-2H-isoquinolin-1-one

[Formula 29]

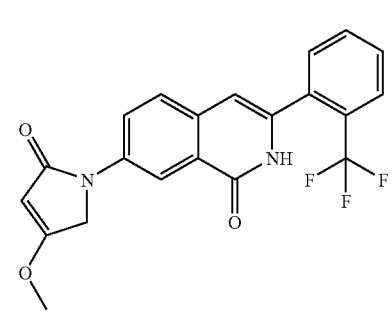

¹H-NMR (270 MHz, DMSO-d₆) δ (ppm): 3.89 (3H, s), 4.62 (2H, s), 5.39 (1H, s), 6.45 (1H, s), 7.61-7.88 (5H, m), 8.16 (1H, dd, J=8.7, 2.5 Hz), 8.42 (1H, d, J=2.5 Hz), 11.53 (1H, brs)

ESI (LC-MS positive mode) m/z 401 (M+H).

Example 1-7

7-((S)-2-Hydroxymethyl-5-oxopyrrolidin-1-yl)-3-(2-trifluoromethylphenyl)-2H-isoquinolin-1-one

[Formula 30]

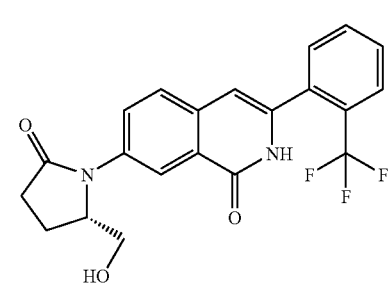

¹H-NMR (270 MHz, DMSO-d₆) δ (ppm): 2.00-2.70 (4H, m), 3.43-3.52 (2H, m), 4.47 (1H, dd, J=7.9, 3.6 Hz), 6.49 (1H, s), 7.62-7.93 (6H, m), 8.34 (1H, d, J=2.0 Hz), 11.60 (1H, s)

ESI (LC-MS positive mode) m/z 403 (M+H).

Example 1-8

7-(4-Benzyloxy-2-oxo-2,5-dihydropyrrol-1-yl)-3-(2-trifluoromethylphenyl)-2H-isoquinolin-1-one

[Formula 31]

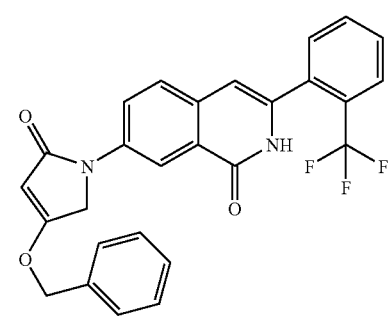

¹H-NMR (270 MHz, DMSO-d₆) δ (ppm): 4.68 (2H, s), 5.14 (2H, s), 5.50 (1H, s), 6.45 (1H, s), 7.31-7.81 (9H, m), 7.87 (1H, d, J=7.3 Hz), 8.13 (1H, dd, J=8.0, 2.3 Hz), 8.46 (1H, d, J=2.3 Hz), 11.55 (1H, s)

ESI (LC-MS positive mode) m/z 477 (M+H).

Example 1-9

7-[3-(2-Hydroxyethyl)-2-oxoimidazolidin-1-yl]-3-(2-trifluoromethylphenyl)-2H-isoquinolin-1-one

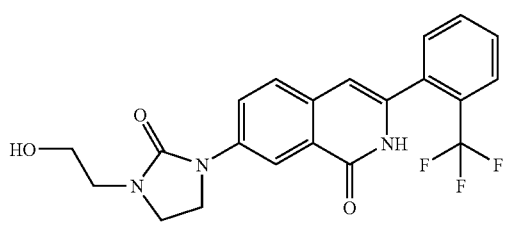

[Formula 32]

¹H-NMR (270 MHz, CDCl₃) δ (ppm): 2.75-2.83 (1H, m), 3.50 (2H, t, J=5.0 Hz), 3.62-3.72 (2H, m), 3.80-3.90 (2H, m), 3.96-4.03 (2H, m), 6.51 (1H, s), 7.52-7.73 (4H, m), 7.78-7.85 (2H, m), 8.46 (1H, brs), 8.69 (1H, dd, J=2.6, 8.8 Hz)

ESI (LC-MS positive mode) m/z 418 (M+H).

Example 1-10

7-((R)-4-Hydroxymethyl-2-oxazolidin-3-yl)-3-(2-trifluoromethylphenyl)-2H-isoquinolin-1-one

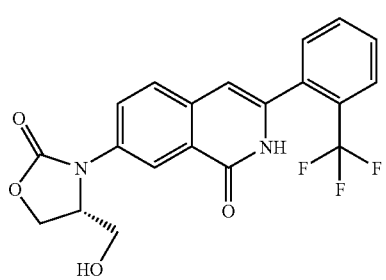

[Formula 33]

¹H-NMR (270 MHz, DMSO-d₆) δ (ppm): 3.41-3.65 (2H, m), 4.36 (1H, dd, J=4.3, 8.3 Hz), 4.54 (1H, t, J=8.6 Hz), 4.71-4.81 (1H, m), 5.12 (1H, t, J=5.3 Hz), 6.49 (1H, s), 7.64 (1H, d, J=6.9 Hz), 7.66-7.82 (3H, m), 7.88 (1H, d, J=7.9 Hz), 7.95 (1H, dd, J=2.3, 8.6 Hz), 8.34 (1H, d, J=2.3 Hz), 11.63 (1H, s)

ESI (LC-MS positive mode) m/z 405 (M+H).

Example 1-11

(R)-2-Oxo-3-[1-oxo-3-(2-trifluoromethylphenyl)-1,2-dihydroisoquinolin-7-yl]oxazolidin-4-ylmethyl benzoate

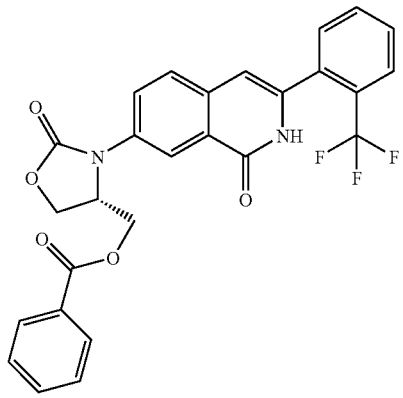

[Formula 34]

¹H-NMR (270 MHz, CDCl₃) δ (ppm): 4.45-4.60 (3H, m), 4.72 (1H, t, J=8.9 Hz), 5.00-5.10 (1H, m), 6.51 (1H, s), 7.43 (2H, t, J=7.9 Hz), 7.52-7.75 (5H, m), 7.83 (1H, d, J=7.4 Hz), 7.90-7.98 (2H, m), 8.20-8.28 (2H, m), 8.57 (1H, brs)

ESI (LC-MS positive mode) m/z 509 (M+H).

Example 1-12

7-(5-Chloromethyl-2-oxooxazolidin-3-yl)-3-(2-trifluoromethylphenyl)-2H-isoquinolin-1-one

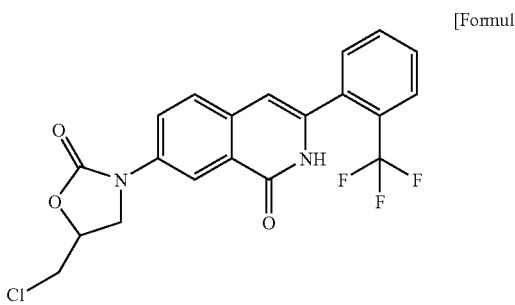

[Formula 35]

¹H-NMR (270 MHz, CDCl₃) δ (ppm): 3.77-3.90 (2H, m), 4.10-4.20 (1H, m), 4.32 (1H, t, J=9.1 Hz), 4.90-5.03 (1H, m), 6.54 (1H, s), 7.53-7.72 (4H, m), 7.83 (1H, d, J=7.6 Hz), 7.95 (1H, d, J=2.3 Hz), 8.58 (1H, dd, J=2.6, 8.9 Hz), 8.75 (1H, brs)

ESI (LC-MS positive mode) m/z 423 (M+H).

Example 1-13

7-((S)-5-Hydroxymethyl-2-oxooxazolidin-3-yl)-3-(2-trifluoromethylphenyl)-2H-isoquinolin-1-one Step A 7-((S)-2,3-Dihydroxypropylamino)-3-(2-trifluoromethylphenyl)-2H-isoquinolin-1-one

[Formula 36]

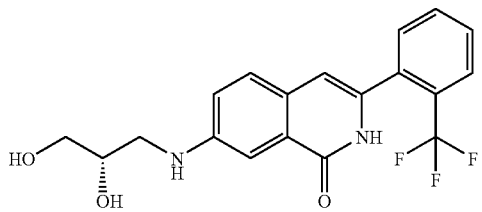

(R)-Glycidol (78.3 µl, 1.18 mmol) was added to an ethanol solution (4 ml) that contained the 7-amino-3-(2-trifluoromethylphenyl)-2H-isoquinolin-1-one obtained in step C of Example 1-1, and the obtained mixture was stirred under heating to reflux for 3 days. Thereafter, the reaction solution was concentrated under reduced pressure, and the obtained residue was purified by silica gel column chromatography (methylene chloride:methanol=20:1), so as to obtain 7-((S)-2,3-dihydroxypropylamino)-3-(2-trifluoromethylphenyl)-2H-isoquinolin-1-one (281.9 mg; yield: 63%) in the form of a pale yellow amorphous substance.

$^1$H-NMR (270 MHz, DMSO-$d_6$) δ (ppm): 2.95-3.05 (1H, m), 3.23-3.46 (3H, m), 3.64-3.73 (1H, m), 4.66 (1H, t, J=5.3 Hz), 4.84 (1H, d, J=5.0 Hz), 6.03 (1H, t, J=5.4 Hz), 6.29 (1H, s), 7.13 (1H, dd, J=2.0, 8.8 Hz), 7.24 (1H, d, J=2.0 Hz), 7.40 (1H, d, J=8.8 Hz), 7.58 (1H, d, J=7.5 Hz), 7.66 (1H, t, J=7.5 Hz), 7.75 (1H, t, J=7.5 Hz), 7.84 (1H, d, J=7.5 Hz), 11.24 (1H, brs)

ESI (LC-MS positive mode) m/z 379 (M+H).

Step B 7-((S)-5-Hydroxymethyl-2-oxooxazolidin-3-yl)-3-(2-trifluoromethylphenyl)-2H-isoquinolin-1-one

[Formula 37]

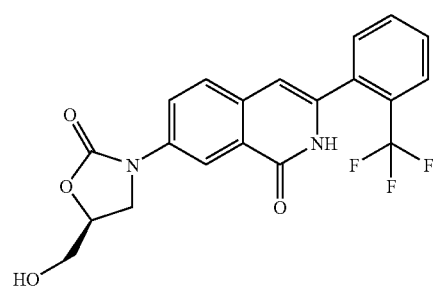

The 7-((S)-2,3-dihydroxypropylamino)-3-(2-trifluoromethylphenyl)-2H-isoquinolin-1-one (281.9 mg, 0.745 mmol) obtained in step A was suspended in diethyl carbonate (2.93 ml), and thereafter, a 28% sodium methoxide-methanol solution (117 µl) was added thereto. The obtained mixture was stirred at 105° C. for 13 hours. Thereafter, diethyl carbonate was distilled away under reduced pressure. The obtained residue was dissolved in methanol (15 ml), and the obtained solution was stirred under heating to reflux for 10 minutes. Thereafter, the reaction solution was concentrated, and a saturated ammonium chloride aqueous solution was then added to the residue, followed by extraction with ethyl acetate. The extract was dried over anhydrous sodium sulfate, and was then concentrated. The obtained residue was purified by silica gel column chromatography (methylene chloride:methanol=40:1 to 20:1), so as to obtain 7-((S)-5-hydroxymethyl-2-oxooxazolidin-3-yl)-3-(2-trifluoromethylphenyl)-2H-isoquinolin-1-one (233.8 mg; yield: 78%).

$^1$H-NMR (270 MHz, DMSO-$d_6$) δ (ppm): 3.55-3.79 (2H, m) 3.90-4.00 (1H, m), 4.22 (1H, t, J=8.9 Hz), 4.70-4.83 (1H, m), 5.25 (1H, t, J=5.6 Hz), 6.49 (1H, s), 7.60-7.90 (5H, m), 8.09 (1H, dd, J=2.3, 8.6 Hz), 8.25 (1H, d, J=2.3 Hz), 11.62 (1H, brs)

ESI (LC-MS positive mode) m/z 405 (M+H).

Example 1-14

7-((R)-5-Hydroxymethyl-2-oxooxazolidin-3-yl)-3-(2-trifluoromethylphenyl)-2H-isoquinolin-1-one Step A 7-((R)-2,3-Dihydroxypropylamino)-3-(2-trifluoromethylphenyl)-2H-isoquinolin-1-one

[Formula 38]

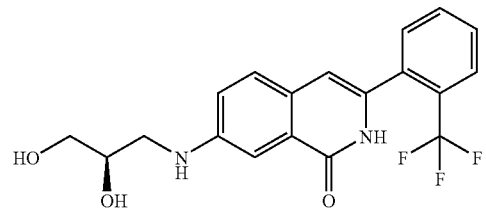

The captioned compound was prepared by a reaction similar to step A of Example 1-13.

$^1$H-NMR (270 MHz, DMSO-$d_6$) δ (ppm): 2.95-3.05 (1H, m), 3.20-3.46 (3H, m), 3.64-3.73 (1H, m), 4.60-4.70 (1H, m), 4.85 (1H, d, J=4.6 Hz), 6.00-6.08 (1H, m), 6.29 (1H, s), 7.13 (1H, dd, J=2.0, 8.3 Hz), 7.24 (1H, s), 7.40 (1H, d, J=8.3 Hz), 7.58 (1H, d, J=7.3 Hz), 7.66 (1H, t, J=7.3 Hz), 7.75 (1H, t, J=7.3 Hz), 7.84 (1H, d, J=7.3 Hz), 11.24 (1H, brs)

ESI (LC-MS positive mode) m/z 379 (M+H).

Step B 7-((R)-5-Hydroxymethyl-2-oxooxazolidin-3-yl)-3-(2-trifluoromethylphenyl)-2H-isoquinolin-1-one

[Formula 39]

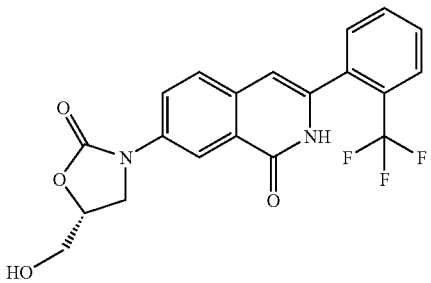

The captioned compound was prepared by a reaction similar to step B of Example 1-13.

$^1$H-NMR (270 MHz, DMSO-d$_6$) δ (ppm): 3.55-3.79 (2H, m) 3.90-4.00 (1H, m), 4.21 (1H, t, J=8.7 Hz), 4.70-4.83 (1H, m), 5.25 (1H, t, J=5.4 Hz), 6.49 (1H, s), 7.60-7.90 (5H, m), 8.09 (1H, dd, J=2.3, 8.9 Hz), 8.25 (1H, d, J=2.3 Hz), 11.62 (1H, brs)

ESI (LC-MS positive mode) m/z 405 (M+H).

Example 1-15

7-(2-Oxopyrrolidin-1-yl)-3-(2-trifluoromethylphenyl)-2H-isoquinolin-1-one

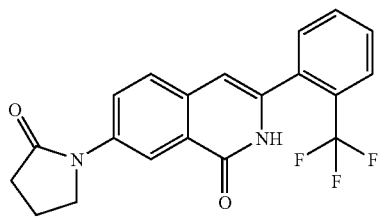

[Formula 40]

The 7-iodo-3-(2-trifluoromethylphenyl)-2H-isoquinolin-1-one (20.8 mg, 0.05 mmol) prepared in step D of Example 1-1, tris(dibenzylideneacetone)dipalladium (2.2 mg, 0.0025 mmol), 9,9-dimethyl-4,5-bis(diphenylphosphino)xanthene (4.2 mg, 0.0075 mmol), cesium carbonate (22.8 mg, 0.07 mmol), and 2-pyrrolidone (4.6 µl) were suspended in 1,4-dioxane (0.5 ml), and the suspension was then stirred under heating to reflux overnight. Thereafter, the reaction solution was cooled to a room temperature, and a saturated ammonium chloride aqueous solution was then added thereto, followed by extraction with ethyl acetate. The extract was dried over anhydrous sodium sulfate, and the solvent was then distilled away under reduced pressure. The obtained residue was purified by silica gel column chromatography (ethyl acetate hexane=2:1 to 5:1), so as to obtain 7-(2-oxopyrrolidin-1-yl)-3-(2-trifluoromethylphenyl)-2H-isoquinolin-1-one (15.3 mg; yield: 82%) in the form of a colorless solid.

$^1$H-NMR (270 MHz, CDCl$_3$) δ (ppm): 2.23 (2H, quintet, J=7.5 Hz), 2.68 (2H, t, J=7.5 Hz), 4.01 (2H, t, J=7.5 Hz), 6.52 (1H, s), 7.53-7.71 (4H, m), 7.82 (1H, d, J=7.3 Hz), 8.05 (1H, d, J=2.3 Hz), 8.65 (1H, dd, J=2.3, 8.6 Hz), 8.76 (1H, brs)

ESI (LC-MS positive mode) m/z 373 (M+H).

The following compounds (Examples 1-16 and 1-17) were synthesized by a reaction similar to that of Example 1-15.

Example 1-16

7-((R)-2-Hydroxymethyl-5-oxopyrrolidin-1-yl)-3-(2-trifluoromethylphenyl)-2H-isoquinolin-1-one

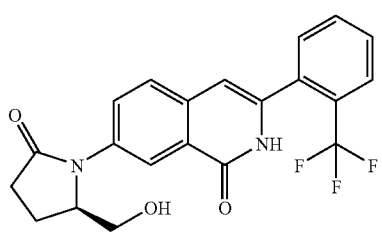

[Formula 41]

$^1$H-NMR (270 MHz, CDCl$_3$) δ (ppm): 2.20-2.41 (2H, m), 2.52-2.64 (1H, m), 2.73-2.86 (1H, m), 3.70-3.90 (2H, m), 4.49-4.53 (1H, m), 6.53 (1H, s), 7.53-7.70 (4H, m), 7.80-7.83 (1H, m), 8.21 (1H, s), 8.25 (1H, d, J=2.31 Hz), 8.72 (1H, brs)

EI-MS m/z 402 (M+).

Example 1-17

7-(2-Oxooxazolidin-3-yl)-3-(2-trifluoromethylphenyl)-2H-isoquinolin-1-one

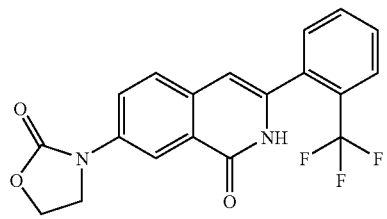

[Formula 42]

$^1$H-NMR (270 MHz, CDCl$_3$) δ (ppm): 4.21 (2H, t, J=8.0 Hz), 4.57 (2H, t, J=8.0 Hz), 6.54 (1H, s), 7.55-7.75 (4H, m), 7.83 (1H, d, J=7.3 Hz), 7.90-8.00 (1H, m), 8.60 (1H, dd, J=2.5, 8.7 Hz), 8.73 (1H, brs)

ESI (LC-MS positive mode) m/z 375 (M+H).

Example 1-18

7-(3-Methyl-2-oxo-2,3-dihydroimidazol-1-yl)-3-(2-trifluoromethylphenyl)-2H-isoquinolin-1-one Step A 1-(2,2-Dimethoxyethyl)-1-methyl-3-[1-oxo-3-(2-trifluoromethylphenyl)-1,2-dihydroisoquinolin-7-yl] urea

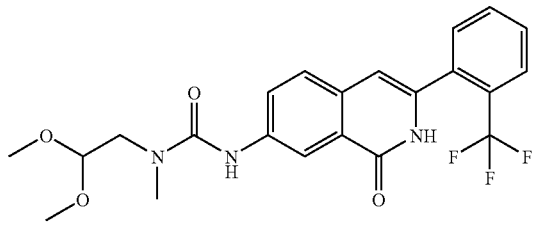

[Formula 43]

The 7-amino-3-(2-trifluoromethylphenyl)-2H-isoquinolin-1-one (30.4 mg, 0.1 mmol) obtained in step C of Example 1-1 was dissolved in a mixed solvent (0.5 ml) of methylene chloride and DMF (1:1). Thereafter, pyridine (16.2 µl, 0.2 mmol) and 4-nitrophenyl chloroformate (24.2 mg, 0.12 mmol) were added thereto under cooling on ice. The obtained mixture was then stirred at a room temperature for 2 hours. Thereafter, 2,2-dimethoxy-N-methylethylamine (15.4 µl, 0.12 mmol) was added to the reaction solution, and the obtained mixture was then stirred at a room temperature overnight. Thereafter, water was added to the reaction solution, followed by extraction with ethyl acetate. The extract was washed with a saturated saline solution, and then dried over anhydrous sodium sulfate, followed by concentration. The obtained residue was purified by silica gel column chromatography (ethyl acetate:hexane=5:1), so as to obtain 1-(2,2-dimethoxyethyl)-1-methyl-3-[1-oxo-3-(2-trifluoromethylphenyl)-1,2-dihydroisoquinolin-7-yl]urea (17.5 mg; yield: 39%) in the form of a colorless amorphous substance.

$^1$H-NMR (270 MHz, DMSO-$d_6$) δ (ppm): 3.08 (3H, s), 3.45-3.54 (8H, m), 4.55 (1H, t, J=5.1 Hz), 6.48 (1H, s), 7.50-7.70 (4H, m), 7.78-7.83 (1H, m), 7.98-8.02 (1H, m), 8.11 (1H, brs), 8.22 (1H, dd, J=2.3, 8.6 Hz), 8.71 (1H, brs)

ESI (LC-MS positive mode) m/z 450 (M+H).

Step B 7-(3-Methyl-2-oxo-2,3-dihydroimidazol-1-yl)-3-(2-trifluoromethylphenyl)-2H-isoquinolin-1-one

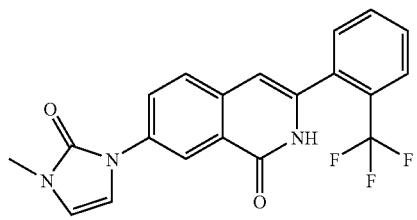

[Formula 44]

The 1-(2,2-dimethoxyethyl)-1-methyl-3-[1-oxo-3-(2-trifluoromethylphenyl)-1,2-dihydroisoquinolin-7-yl]urea (17.5 mg, 0.0389 mmol) obtained in step A was dissolved in formic acid (0.2 ml). The obtained solution was stirred at a room temperature overnight. Thereafter, formic acid was distilled away under reduced pressure, and the obtained residue was then dissolved in methylene chloride. The obtained solution was washed with a saturated sodium bicarbonate aqueous solution, and was then dried over anhydrous sodium sulfate, followed by concentration. The obtained residue was purified by silica gel column chromatography (ethyl acetate:hexane=4:1 to 1:0), so as to obtain 7-(3-methyl-2-oxo-2,3-dihydroimidazol-1-yl)-3-(2-trifluoromethylphenyl)-2H-isoquinolin-1-one (10.9 mg; yield: 73%) in the form of a colorless solid.

$^1$H-NMR (270 MHz, DMSO-$d_6$) δ (ppm): 3.23 (3H, s) 6.52 (1H, s), 6.80 (1H, d, J=3.3 Hz), 7.20 (1H, d, J=3.3 Hz), 7.61-7.84 (4H, m), 7.85-7.93 (1H, m), 8.09 (1H, dd, J=2.6, 8.6 Hz), 8.56 (1H, d, J=2.3 Hz), 11.66 (1H, brs)

ESI (LC-MS positive mode) m/z 386 (M+H).

Example 1-19

7-((R)-5-Hydroxymethyl-2-oxooxazolidin-3-yl)-3-(2-morpholin-4-ylphenyl)-2H-isoquinolin-1-one Step A 5-Chloro-2,N,N-trimethylbenzamide

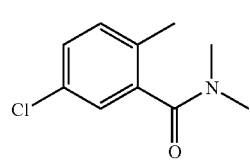

[Formula 45]

Using 5-chloro-2-methylbenzoic acid as a staring material, the captioned compound was synthesized by a method similar to step A of Example 1-1.

$^1$H-NMR (270 MHz, CDCl$_3$) δ (ppm): 2.25 (3H, s), 2.85 (3H, s), 3.12 (3H, s), 7.15 (1H, d, J=8.4 Hz) 7.16 (1H, d, J=2.3 Hz), 7.24 (1H, dd, J=2.3, 8.4 Hz)

ESI (LC-MS positive mode) m/z 198 (M+H).

Step B

7-Chloro-3-(2-morpholin-4-ylphenyl)-2H-isoquinolin-1-one

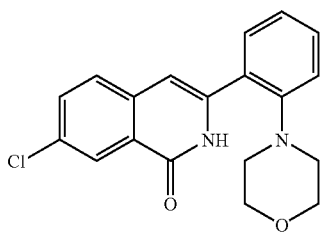

[Formula 46]

A 1.8 M lithium diisopropylamide THF solution (5.39 ml, 9.69 mmol) was diluted with THF (10 ml). To the diluted solution, a solution obtained by dissolving the 5-chloro-2,N,N-trimethylbenzamide (383 mg, 1.94 mmol) prepared in step A in THF (5 ml) was added dropwise at −78° C. A solution obtained by dissolving 2-(4-morpholino)benzonitrile (438 mg, 2.33 mmol) in THF (5 ml) was further added to the mixture. The obtained mixture was stirred at −78° C. for 30 minutes. Thereafter, a saturated ammonium chloride aqueous solution was added to the reaction solution, followed by extraction with ethyl acetate. The extract was washed with a saturated saline solution, and was then dried over anhydrous sodium sulfate, followed by concentration under reduced pressure. The obtained yellow oil product was crystallized from hexane/ethyl acetate (3:1), so as to obtain 7-chloro-3-(2-morpholin-4-ylphenyl)-2H-isoquinolin-1-one (575 mg; yield: 87%) in the form of a colorless crystal.

$^1$H-NMR (400 MHz, CDCl$_3$) δ (ppm): 2.97-3.00 (4H, m), 3.87-3.90 (4H, m), 6.71 (1H, s), 7.19 (2H, m), 7.43 (1H, dt, J=1.2, 7.6 Hz), 7.53 (1H, d, J=8.4 Hz), 7.59-7.62 (2H, m), 8.39 (1H, s), 11.10 (1H, brs)

ESI (LC-MS positive mode) m/z 341 (M+H).

Step C

7-Amino-3-(2-morpholin-4-ylphenyl)-2H-isoquinolin-1-one

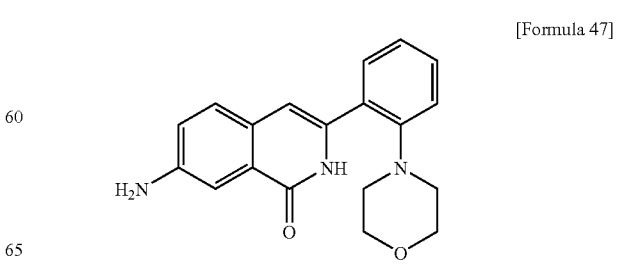

[Formula 47]

Using the 7-chloro-3-(2-morpholin-4-ylphenyl)-2H-isoquinolin-1-one obtained in step B as a starting material, the captioned compound was prepared by a method similar to step C of Example 1-1.

¹H-NMR (400 MHz, CDCl₃) δ (ppm): 2.95-2.99 (4H, m), 3.84-3.90 (4H, m), 4.00 (2H, brs), 6.67 (1H, s), 7.05 (1H, dd, J=2.0, 7.1 Hz), 7.10-7.20 (2H, m), 7.35-7.45 (2H, m), 7.55-7.59 (1H, m), 7.64 (1H, d, J=2.4 Hz), 10.86 (1H, brs)

ESI (LC-MS positive mode) m/z 322 (M+H).

Step D 7-((R)-2,3-Dihydroxypropylamino)-3-(2-morpholin-4-ylphenyl)-2H-isoquinolin-1-one

[Formula 48]

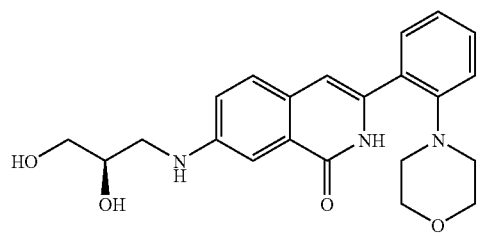

Using the 7-amino-3-(2-morpholin-4-ylphenyl)-2H-isoquinolin-1-one obtained in step C as a starting material, the captioned compound was prepared by a reaction similar to step A of Example 1-13.

¹H-NMR (270 MHz, CDCl₃) δ (ppm): 2.96-2.99 (4H, m), 3.34 (1H, dd, J=13.0, 7.5 Hz), 3.48 (1H, dd, J=13.0, 5.0 Hz), 3.71 (1H, dd, J=11.5, 6.0 Hz), 3.81-3.90 (5H, m), 4.07-4.13 (1H, m), 6.69 (1H, d, J=1.5 Hz), 7.06 (1H, dd, J=8.5, 2.5 Hz), 7.12-7.20 (2H, m), 7.37 (1H, ddd, J=8.0, 8.0, 1.5 Hz), 7.43 (1H, d, J=8.5 Hz), 7.55-7.59 (2H, m), 10.97 (1H, brs)

ESI (LC-MS positive mode) m/z 396 (M+H).

Step E 7-((R)-5-Hydroxymethyl-2-oxooxazolidin-3-yl)-3-(2-morpholin-4-ylphenyl)-2H-isoquinolin-1-one

[Formula 49]

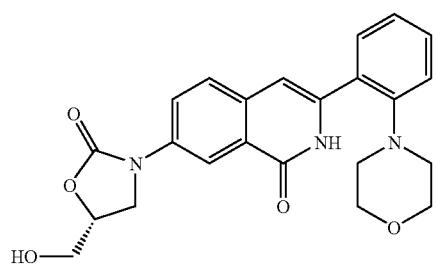

Using the 7-((R)-2,3-dihydroxypropylamino)-3-(2-morpholin-4-ylphenyl)-2H-isoquinolin-1-one obtained in step D as a starting material, the captioned compound was prepared by a reaction similar to step B of Example 1-13.

¹H-NMR (270 MHz, DMSO-d₆) δ (ppm): 2.81-2.89 (4H, m), (6H, m), 3.96 (1H, dd, J=8.5, 6.0 Hz), 4.22 (1H, t, J=8.5 Hz), 4.70-4.79 (1H, m), 5.25 (1H, t, J=5.5 Hz), 6.82 (1H, s), 7.12-7.17 (2H, m), 7.42 (1H, ddd, J=8.0, 8.0, 2.0 Hz), 7.52 (1H, dd, J=8.0, 2.0 Hz), 7.75 (1H, d, J=9.0 Hz), 8.08 (1H, dd, J=9.0, 2.5 Hz), 8.22 (1H, d, J=2.5 Hz), 11.49 (1H, s)

ESI (LC-MS positive mode) m/z 422 (M+H).

The following compounds (Examples 1-20 to 1-28) were synthesized by a method similar to that of Example 1-19.

Example 1-20

7-((R)-5-Hydroxymethyl-2-oxooxazolidin-3-yl)-3-(2-methoxyphenyl)-2H-isoquinolin-1-one

[Formula 50]

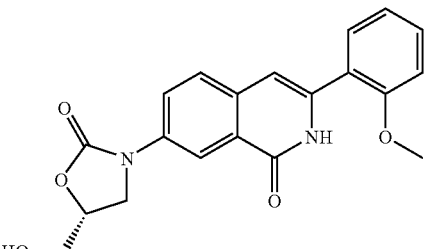

¹H-NMR (270 MHz, DMSO-d₆) δ (ppm): 3.57-3.76 (2H, m) 3.82 (3H, s), 3.95 (1H, dd, J=9.0, 6.0 Hz), 4.21 (1H, t, J=9.0 Hz), 4.71-4.79 (1H, m), 5.25 (1H, t, J=5.5 Hz), 6.62 (1H, s), 7.05 (1H, t, J=7.5 Hz), 7.14 (1H, d, J=8.0 Hz), 7.42-7.48 (2H, m), 7.72 (1H, d, J=9.0 Hz), 8.07 (1H, dd, J=9.0, 2.5 Hz), 8.22 (1H, d, J=2.5 Hz), 11.26 (1H, brs)

ESI (LC-MS positive mode) m/z 367 (M+H).

Example 1-21

7-((R)-5-Hydroxymethyl-2-oxooxazolidin-3-yl)-3-o-tolyl-2H-isoquinolin-1-one

[Formula 51]

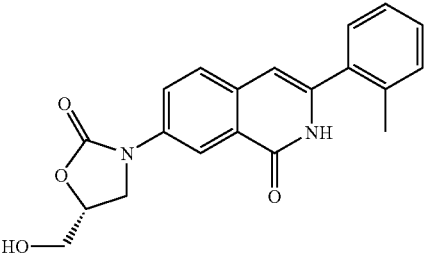

¹H-NMR (270 MHz, DMSO-d₆) δ (ppm): 2.31 (3H, s), 3.57-3.76 (2H, m), 3.96 (1H, dd, J=9.0, 6.5 Hz), 4.21 (1H, t, J=9.0 Hz), 4.71-4.79 (1H, m), 5.25 (1H, t, J=5.5 Hz), 6.49 (1H, s), 7.26-7.40 (4H, m), 7.72 (1H, d, J=9.0 Hz), 8.08 (1H, dd, J=9.0, 2.5 Hz), 8.23 (1H, d, J=2.5 Hz), 11.45 (1H, s)

ESI (LC-MS positive mode) m/z 351 (M+H).

Example 1-22

7-((R)-5-Hydroxymethyl-2-oxooxazolidin-3-yl)-3-(2-trifluoromethoxyphenyl)-2H-isoquinolin-1-one

[Formula 52]

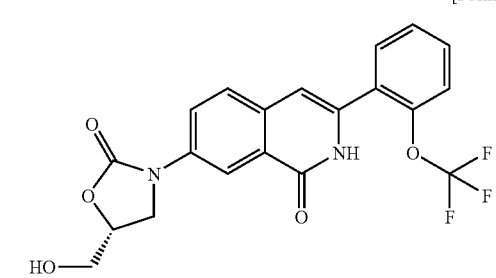

¹H-NMR (270 MHz, DMSO-d₆) δ (ppm): 3.57-3.76 (2H, m) 3.96 (1H, dd, J=9.0, 6.5 Hz), 4.22 (1H, t, J=9.0 Hz), 4.71-4.80 (1H, m), 5.26 (1H, t, J=5.5 Hz), 6.66 (1H, s), 7.50-7.70 (4H, m), 7.76 (1H, d, J=9.0 Hz), 8.09 (1H, dd, J=9.0, 2.5 Hz), 8.25 (1H, d, J=2.5 Hz), 11.61 (1H, brs)

ESI (LC-MS positive mode) m/z 421 (M+H).

Moreover, an intermediate of the present compound, 7-((R)-2,3-hydroxypropylamino)-3-(2-trifluoromethoxyphenyl)-2H-isoquinolin-1-one can also be synthesized by the method described below, using the 7-chloro-3-(2-trifluoromethoxyphenyl)-2H-isoquinolin-1-one obtained by a method similar to step D of Example 1-19 as a raw material.

7-((R)-2,3-Hydroxypropylamino)-3-(2-trifluoromethoxyphenyl)-2H-isoquinolin-1-one

[Formula 53]

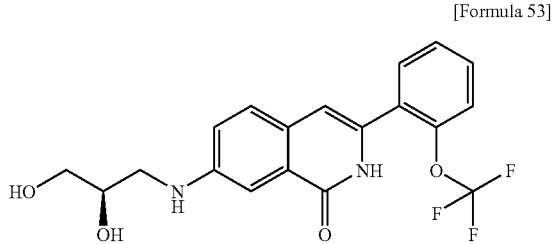

7-Chloro-3-(2-trifluoromethoxyphenyl)-2H-isoquinolin-1-one (340 mg, 1.00 mmol), (R)-(+)-3-amino-1,2-propanediol (273 mg, 3.00 mmol), 2-dicyclohexylphosphino-2'-(N,N-dimethylamino)biphenyl (47.2 mg, 0.12 mmol), and tris(dibenzylideneacetone)dipalladium (45.8 mg, 0.05 mmol) were dissolved in THF (5 ml). Thereafter, to the obtained solution, a 1 M lithium bis(trimethylsilyl)amide THF solution (7 ml, 7.00 mmol) was added. The obtained mixture was stirred under heating to reflux for 14 hours. The reaction solution was cooled to a room temperature, and a saturated ammonium chloride aqueous solution was then added thereto, followed by extraction with ethyl acetate. The extract was washed with a saturated saline solution, and was then dried over anhydrous sodium sulfate. The residue obtained by concentration of the extract was purified by silica gel column chromatography (dichloromethane:methanol=50:1 to 20:1), so as to obtain 7-((R)-2,3-hydroxypropylamino)-3-(2-trifluoromethoxyphenyl)-2H-isoquinolin-1-one (83.4 mg, 21%) in the form of a Mars yellow solid.

¹H-NMR (270 MHz, CDCl₃) δ (ppm): 3.30 (1H, dd, J=13.0, 7.5 Hz), 3.45 (1H, dd, J=13.0, 4.0 Hz), 3.69 (1H, dd, J=11.0, 6.0 Hz), 3.81 (1H, dd, J=11.0, 3.5 Hz), 4.03-4.12 (1H, m), 6.61 (1H, s), 7.03 (1H, dd, J=8.5, 2.5 Hz), 7.34-7.45 (4H, m), 7.52 (1H, d, J=2.0 Hz), 7.55 (1H, dd, J=7.5, 2.0 Hz), 9.03 (1H, brs)

ESI (LC-MS positive mode) m/z 395 (M+H).

Example 1-23

3-Biphenyl-2-yl-7-((R)-5-hydroxymethyl-2-oxooxazolidin-3-yl)-2H-isoquinolin-1-one

[Formula 54]

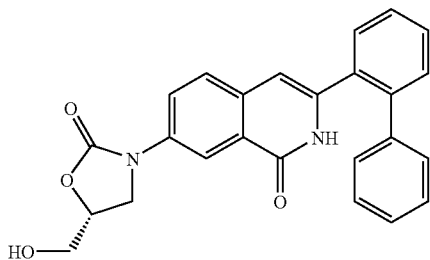

¹H-NMR (270 MHz, DMSO-d₆) δ (ppm): 3.54-3.72 (2H, m) 3.92 (1H, dd, J=9.0, 6.5 Hz), 4.17 (1H, t, J=9.0 Hz), 4.68-4.78 (1H, m), 5.23 (1H, t, J=5.5 Hz), 6.31 (1H, s), 7.23-7.30 (5H, m), 7.45-7.60 (5H, m), 8.01 (1H, dd, J=8.5, 2.0 Hz), 8.13 (1H, d, J=2.0 Hz), 11.26 (1H, s)

ESI (LC-MS positive mode) m/z 413 (M+H).

Example 1-24

3-(2-Ethylphenyl)-7-((R)-5-hydroxymethyl-2-oxooxazolidin-3-yl)-2H-isoquinolin-1-one

[Formula 55]

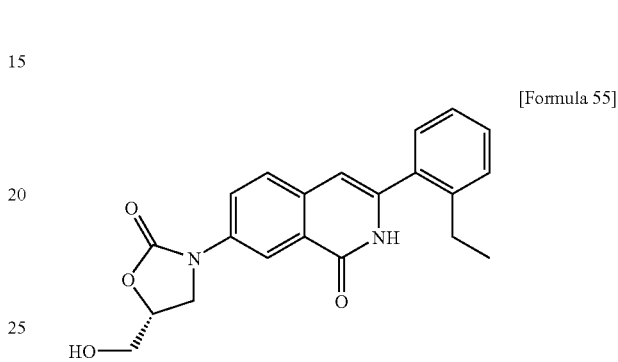

¹H-NMR (270 MHz, CD₃OD) δ (ppm): 1.15 (3H, t, J=7.5 Hz), 2.70 (2H, q, J=7.5 Hz), 3.74 (1H, dd, J=12.5, 4.0 Hz), 3.90 (1H, dd, J=12.5, 3.0 Hz), 4.08 (1H, dd, J=9.0, 6.5 Hz), 4.27 (1H, t, J=9.0 Hz), 4.77-4.84 (1H, m), 6.59 (1H, s), 7.26-7.45 (4H, m), 7.72 (1H, d, J=9.0 Hz), 8.25 (1H, d, J=2.5 Hz), 8.29 (1H, dd, J=9.0, 2.5 Hz)

ESI (LC-MS positive mode) m/z 365 (M+H).

Example 1-25

3-(2,6-Dimethoxyphenyl)-7-((R)-5-hydroxymethyl-2-oxooxazolidin-3-yl)-2H-isoquinolin-1-one

[Formula 56]

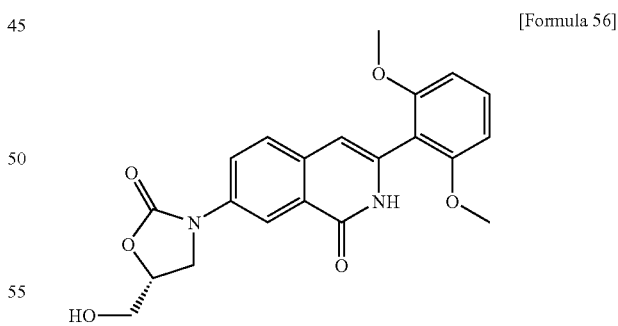

¹H-NMR (270 MHz, DMSO-d₆) δ (ppm): 3.57-3.77 (2H, m) 3.72 (6H, s), 3.95 (1H, dd, J=9.0, 6.5 Hz), 4.21 (1H, t, J=9.0 Hz), 4.70-4.79 (1H, m), 5.26 (1H, t, J=5.5 Hz), 6.39 (1H, s), 6.75 (2H, d, J=8.5 Hz), 7.39 (1H, t, J=8.5 Hz), 7.66 (1H, d, J=8.5 Hz), 8.06 (1H, dd, J=8.5, 2.5 Hz), 8.20 (1H, d, J=2.5 Hz), 11.20 (1H, s)

ESI (LC-MS positive mode) m/z 397 (M+H).

Example 1-26

3-(2-Fluorophenyl)-7-((S)-5-hydroxymethyl-2-oxooxazolidin-3-yl)-2H-isoquinolin-1-one

[Formula 57]

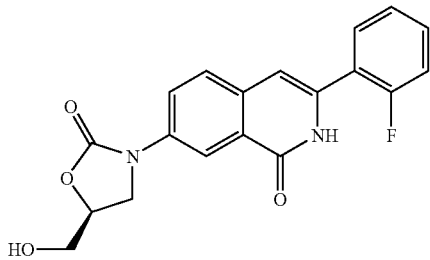

¹H-NMR (270 MHz, DMSO-d₆) δ (ppm): 3.57-3.75 (2H, m) 3.96 (1H, dd, J=9.0, 6.5 Hz), 4.22 (1H, t, J=9.0 Hz), 4.70-4.80 (1H, m), 6.75 (1H, s), 7.30-7.39 (2H, m), 7.48-7.56 (1H, m), 7.66 (1H, t, J=8.0 Hz), 7.76 (1H, d, J=9.0 Hz), 8.09 (1H, d, J=9.0 Hz), 8.25 (1H, s)

ESI (LC-MS positive mode) m/z 355 (M+H).

Example 1-27

7-((S)-5-Hydroxymethyl-2-oxooxazolidin-3-yl)-3-(2-trifluoromethoxyphenyl)-2H-isoquinolin-1-one

[Formula 58]

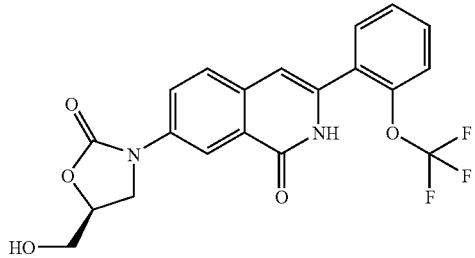

¹H-NMR (270 MHz, DMSO-d₆) δ (ppm): 3.57-3.76 (2H, m) 3.96 (1H, dd, J=9.0, 6.5 Hz), 4.22 (1H, t, J=9.0 Hz), 4.72-4.80 (1H, m), 5.24 (1H, t, J=5.5 Hz), 6.66 (1H, s), 7.50-7.70 (4H, m), 7.77 (1H, d, J=9.0 Hz), 8.10 (1H, dd, J=9.0, 2.5 Hz), 8.26 (1H, d, J=2.5 Hz), 11.60 (1H, s)

ESI (LC-MS positive mode) m/z 421 (M+H).

Example 1-28

7-((S)-5-Hydroxymethyl-2-oxooxazolidin-3-yl)-3-(2-morpholin-4-ylphenyl)-2H-isoquinolin-1-one

[Formula 59]

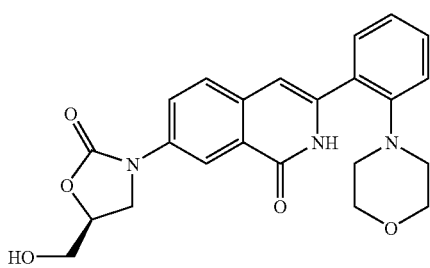

¹H-NMR (270 MHz, DMSO-d₆) δ (ppm): 2.82-2.88 (4H, m), 3.59-3.76 (6H, m), 3.96 (1H, dd, J=6.1, 8.8 Hz), 4.22 (1H, t, J=9.0 Hz), 4.70-4.79 (1H, m), 5.25 (1H, t, J=5.7 Hz), 6.82 (1H, s), 7.12-7.18 (2H, m), 7.42 (1H, t, J=7.7 Hz), 7.51 (1H, dd, J=1.7, 7.7 Hz), 7.75 (1H, d, J=8.9 Hz), 8.07 (1H, dd, J=2.5, 8.9 Hz), 8.22 (1H, d, J=2.5 Hz), 11.49 (1H, brs)

ESI (LC-MS positive mode) m/z 422 (M+H).

Example 1-29

7-[5-(2-Hydroxyethyl)-2-oxooxazolidin-3-yl]-3-(2-trifluoromethylphenyl)-2H-isoquinolin-1-one Step A 7-(2,4-Dihydroxybutylamino)-3-(2-trifluoromethylphenyl)-2H-isoquinolin-1-one

[Formula 60]

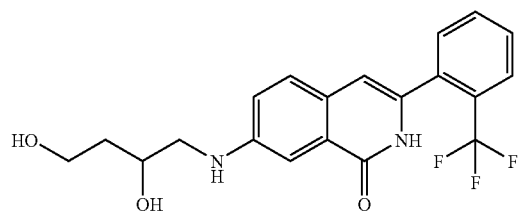

The captioned compound was prepared by a reaction similar to step A of Example 1-13, using 3,4-epoxy-1-butanol prepared in accordance with a known method described in publications (for example, Journal of Organic Chemistry (1981), 46(5), pp. 930-9).

¹H-NMR (270 MHz, DMSO-d₆) δ (ppm): 1.45-1.60 (1H, m), (1H, m), 3.00-3.18 (2H, m), 3.49-3.61 (2H, m), 3.73-3.83 (1H, m), 4.40 (1H, t, J=5.0 Hz), 4.72 (1H, d, J=5.3 Hz), (1H, m), 6.29 (1H, s), 7.12 (1H, dd, J=2.5, 8.6 Hz), 7.23 (1H, d, J=2.1 Hz), 7.40 (1H, d, J=8.9 Hz), 7.53-7.86 (4H, m), 11.24 (1H, brs)

ESI (LC-MS positive mode) m/z 393 (M+H).

Step B

7-[5-(2-Hydroxyethyl)-2-oxooxazolidin-3-yl]-3-(2-trifluoromethylphenyl)-2H-isoquinolin-1-one

[Formula 61]

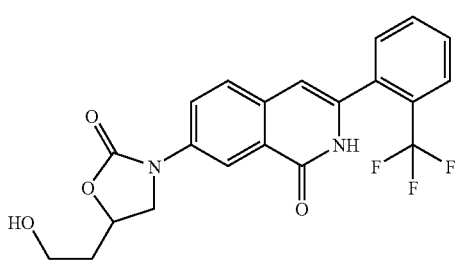

Using the 7-(2,4-dihydroxybutylamino)-3-(2-trifluoromethylphenyl)-2H-isoquinolin-1-one obtained in step A as a starting material, the captioned compound was synthesized by a reaction similar to step B of Example 1-13.

$^1$H-NMR (270 MHz, DMSO-d$_6$) δ (ppm): 1.80-2.06 (2H, m), 3.53-3.65 (2H, m), 3.92 (1H, dd, J=7.3, 8.9 Hz), 4.29 (1H, t, J=8.7 Hz), 4.73 (1H, t, J=5.0 Hz), 4.80-4.95 (1H, m), 6.49 (1H, s), 6.60-7.93 (5H, m), 8.09 (1H, dd, J=2.6, 8.7 Hz), 8.23 (1H, d, J=2.6 Hz), 11.62 (1H, brs)

ESI (LC-MS positive mode) m/z 419 (M+H).

Example 1-30

7-(5-Azidomethyl-2-oxooxazolidin-3-yl)-3-(2-trifluoromethylphenyl)-2H-isoquinolin-1-one Step A 7-(2,3-Dihydroxypropylamino)-3-(2-trifluoromethylphenyl)-2H-isoquinolin-1-one

[Formula 62]

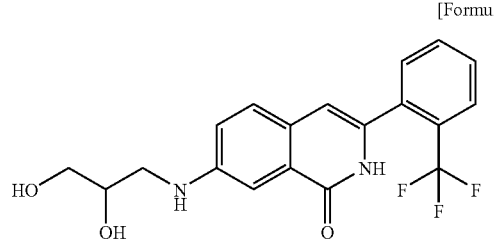

Using the 7-amino-3-(2-trifluoromethylphenyl)-2H-isoquinolin-1-one obtained in step C of Example 1-1 as a raw material, the captioned compound was synthesized by a method similar to step A of Example 1-13.

$^1$H-NMR (270 MHz, DMSO-d$_6$) δ (ppm): 2.95-3.05 (1H, m), 3.20-3.46 (3H, m), 3.64-3.73 (1H, m), 4.65 (1H, t, J=5.6 Hz), 4.84 (1H, d, J=4.9 Hz), 6.00-6.08 (1H, m), 6.30 (1H, s), 7.13 (1H, dd, J=2.5, 8.6 Hz), 7.24 (1H, d, J=2.5 Hz), 7.40 (1H, d, J=8.6 Hz), 7.58 (1H, d, J=7.4 Hz), 7.60-7.80 (2H, m), 7.84 (1H, d, J=7.9 Hz), 11.24 (1H, brs)

ESI (LC-MS positive mode) m/z 379 (M+H).

Step B 7-(5-Hydroxymethyl-2-oxooxazolidin-3-yl)-3-(2-trifluoromethylphenyl)-2H-isoquinolin-1-one

[Formula 63]

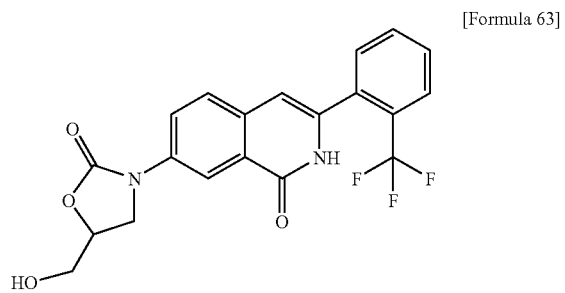

Using the 7-(2,3-dihydroxypropylamino)-3-(2-trifluoromethylphenyl)-2H-isoquinolin-1-one obtained in step A as a raw material, the captioned compound was synthesized by a method similar to step B of Example 1-13.

$^1$H-NMR (270 MHz, CDCl$_3$) δ (ppm): 2.65 (1H, t, J=6.4 Hz), 3.76-3.87 (1H, m), 3.98-4.01 (1H, m), 4.12-4.24 (2H, m), 5.78-5.90 (1H, m), 6.52 (1H, s), 7.52-7.73 (4H, m), 7.78-7.85 (1H, m), 7.96 (1H, d, J=2.5 Hz), 8.55 (1H, dd, J=2.6, 8.8 Hz), 8.64 (1H, brs)

ESI (LC-MS positive mode) m/z 405 (M+H).

Step C

2-Oxo-3-[1-oxo-3-(2-trifluoromethylphenyl)-1,2-dihydroisoquinolin-7-yl]oxazolidin-5-ylmethyl methanesulfonate

[Formula 64]

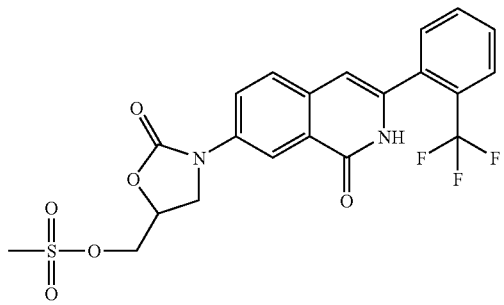

Triethylamine (128 μl) and methanesulfonyl chloride (71 μl) were added to a solution obtained by dissolving the 7-(5-hydroxymethyl-2-oxooxazolidin-3-yl)-3-(2-trifluoromethylphenyl)-2H-isoquinolin-1-one (186.7 mg, 0.462 mmol) obtained in step B in methylene chloride (2.3 ml), under cooling on ice. The obtained mixture was stirred for 30 minutes. Thereafter, a saturated ammonium chloride aqueous solution was added to the reaction solution, followed by extraction with ethyl acetate. The extract was dried over anhydrous sodium sulfate, and was then concentrated. The obtained residue was purified by silica gel column chromatography (ethyl acetate:hexane=2:1, and then methylene chloride:methanol=30:1), so as to obtain 2-oxo-3-[1-oxo-3-(2-trifluoromethylphenyl)-1,2-dihydroisoquinolin-7-yl]oxazolidin-5-ylmethyl methanesulfonate (169.1 mg; yield: 76%) in the form of a colorless foaming substance.

$^1$H-NMR (270 MHz, CDCl$_3$) δ (ppm): 3.13 (3H, s), 4.11 (1H, dd, J=6.1, 9.4 Hz), 4.33 (1H, t, J=9.2 Hz), 4.48 (1H, dd, J=4.4, 11.6 Hz), 4.55 (1H, dd, J=3.8, 11.6 Hz), 4.96-5.07 (1H, m), 6.53 (1H, s), 7.53-7.72 (4H, m), 7.80-7.86 (1H, m), 7.98 (1H, d, J=2.3 Hz), 8.53 (1H, dd, J=2.4, 8.8 Hz), 8.60 (1H, brs)

ESI (LC-MS positive mode) m/z 483 (M+H).

Step D 7-(5-Azidomethyl-2-oxooxazolidin-3-yl)-3-(2-trifluoromethylphenyl)-2H-isoquinolin-1-one

[Formula 65]

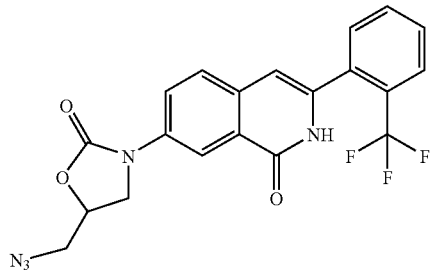

The 2-oxo-3-[1-oxo-3-(2-trifluoromethylphenyl)-1,2-dihydroisoquinolin-7-yl]oxazolidin-5-ylmethyl methanesulfonate (169.1 mg, 0.351 mmol) obtained in step C was dissolved in N,N-dimethylformamide (1.3 ml). Thereafter, sodium azide (96.2 mg, 1.33 mmol) was added to the obtained solution, and the mixture was then stirred at 65° C. for 4 hours. Thereafter, water was added to the reaction solution, followed by extraction with ethyl acetate. The extract was washed with a saturated saline solution, and was then dried over anhydrous sodium sulfate, followed by concentration under reduced pressure. The obtained residue was purified by silica gel column chromatography (ethyl acetate:hexane=2:1 to 3:1), so as to obtain 7-(5-azidomethyl-2-oxooxazolidin-3-yl)-3-(2-trifluoromethylphenyl)-2H-isoquinolin-1-one (139.6 mg; yield: 93%) in the form of a colorless solid.

$^1$H-NMR (270 MHz, CDCl$_3$) δ (ppm): 3.64 (1H, dd, J=4.5, 13.3 Hz), 3.76 (1H, dd, J=4.4, 13.3 Hz), 4.03 (1H, dd, J=6.3, 9.2 Hz), 4.25 (1H, t, J=9.1 Hz), 4.82-4.93 (1H, m), 6.53 (1H, s), 7.52-7.72 (4H, m), 7.83 (1H, dd, J=1.5, 7.4 Hz), 7.94 (1H, d, J=2.6 Hz), 8.59 (1H, dd, J=2.6, 8.9 Hz), 8.64 (1H, brs)

ESI (LC-MS positive mode) m/z 430 (M+H).

Example 1-31

7-(5-Aminomethyl-2-oxooxazolidin-3-yl)-3-(2-trifluoromethylphenyl)-2H-isoquinolin-1-one

[Formula 66]

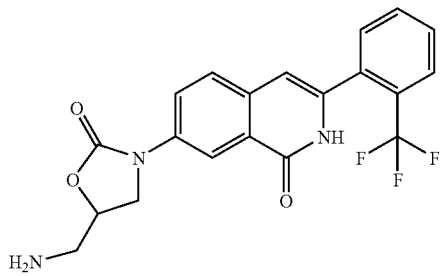

The 7-(5-azidomethyl-2-oxooxazolidin-3-yl)-3-(2-trifluoromethylphenyl)-2H-isoquinolin-1-one (50.0 mg, 0.116 mmol) obtained in Example 1-30 was dissolved in tetrahydrofuran (387 μl). Thereafter, triphenylphosphine (33.6 mg, 0.128 mmol) and water (20.9 μl) were added to the obtained solution, and the obtained mixture was then stirred at 40° C. for 14 hours. Thereafter, 1 N hydrochloric acid (0.5 ml) was added to the reaction solution, followed by washing with ethyl acetate. A 1 N sodium hydroxide aqueous solution (1.0 ml) was added to the residual water layer, followed by extraction with ethyl acetate. The extract was washed with a saturated saline solution, and was then dried over anhydrous sodium sulfate, followed by concentration under reduced pressure. The obtained residue was purified by column chromatography using Bond Elut (registered trademark) NH2 (Varian; 1g), so as to obtain 7-(5-aminomethyl-2-oxooxazolidin-3-yl)-3-(2-trifluoromethylphenyl)-2H-isoquinolin-1-one (45.8 mg; yield: 98%) in the form of a colorless foaming substance.

$^1$H-NMR (270 MHz, CDCl$_3$) δ (ppm): 1.59 (3H, brs), 3.01 (1H, dd, J=5.6, 13.7 Hz), 3.16 (1H, dd, J=4.0, 13.7 Hz), 4.04 (1H, dd, J=6.8, 8.9 Hz), 4.19 (1H, t, J=8.9 Hz), 4.69-4.80 (1H, m), 6.49 (1H, s), 7.52-7.72 (4H, m), 7.77-7.82 (1H, m), 7.90-7.92 (1H, m), 8.56 (1H, dd, J=2.5, 8.9 Hz)

ESI (LC-MS positive mode) m/z 404 (M+H).

Example 1-32

N-{2-Oxo-3-[1-oxo-3-(2-trifluoromethylphenyl)-1,2-dihydroisoquinolin-7-yl]oxazolidin-5-ylmethyl}acetamide

[Formula 67]

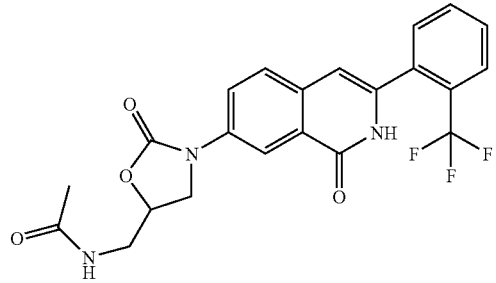

The 7-(5-aminomethyl-2-oxooxazolidin-3-yl)-3-(2-trifluoromethylphenyl)-2H-isoquinolin-1-one (15.3 mg, 0.038 mmol) obtained in Example 1-31 was dissolved in pyridine (380 μl). Thereafter, acetyl chloride (3.2 μl) was added to the obtained solution, and the obtained mixture was stirred at a room temperature for 2 hours. Thereafter, 1 N hydrochloric acid was added to the reaction solution under cooling on ice, followed by extraction with ethyl acetate. The extract was dried over anhydrous sodium sulfate, and the solvent was then distilled away under reduced pressure. The obtained residue was purified by silica gel column chromatography (methylene chloride:methanol=20:1), so as to obtain N-{2-oxo-3-[1-oxo-3-(2-trifluoromethylphenyl)-1,2-dihydroisoquinolin-7-yl]oxazolidin-5-ylmethyl}acetamide (12.1 mg; yield: 71%) in the form of a colorless amorphous substance.

$^1$H-NMR (270 MHz, DMSO-d$_6$) δ (ppm): 1.85 (3H, s), 3.43-3.52 (2H, m), 3.89 (1H, dd, J=6.5, 9.1 Hz), 4.24 (1H, t, J=9.0 Hz), 4.71-4.82 (1H, m), 6.49 (1H, s), 7.60-7.90 (5H, m), 8.08 (1H, dd, J=2.5, 8.7 Hz), 8.20 (1H, d, J=2.5 Hz), 8.23-8.32 (1H, m), 11.62 (1H, brs)

ESI (LC-MS positive mode) m/z 446 (M+H).

Example 1-33

7-(5-Morpholin-4-ylmethyl-2-oxooxazolidin-3-yl)-3-(2-trifluoromethylphenyl)-2H-isoquinolin-1-one

[Formula 68]

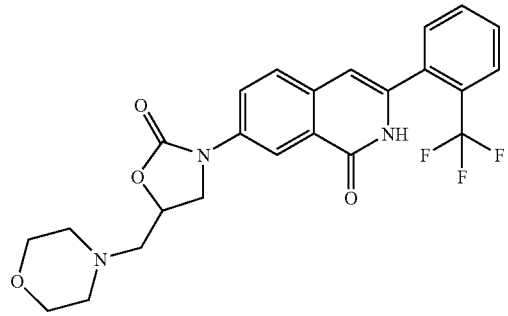

The 2-oxo-3-[1-oxo-3-(2-trifluoromethylphenyl)-1,2-dihydroisoquinolin-7-yl]oxazolidin-5-ylmethyl methanesulfonate (20.0 mg, 0.0415 mmol) obtained in step C of Example 1-30 was dissolved in acetonitrile (0.1 ml). Thereafter, morpholine (3.6 μl) was added to the obtained solution, and the obtained mixture was stirred under heating to reflux for 22 hours. Thereafter, the reaction solution was cooled to a room temperature, and it was then concentrated under reduced pressure. The obtained residue was purified by silica gel column chromatography (methylene chloride: methanol=40:1), so as to obtain 7-(5-morpholin-4-ylmethyl-2-oxooxazolidin-3-yl)-3-(2-trifluoromethylphenyl)-2H-isoquinolin-1-one (9.7 mg; yield: 49%) in the form of a colorless amorphous substance.

$^1$H-NMR (270 MHz, CD$_3$OD) δ (ppm): 2.55-2.70 (4H, m), 2.80 (2H, d, J=5.6 Hz), 3.70 (4H, t, J=4.6 Hz), 3.99 (1H, dd, J=7.0, 8.9 Hz), 4.30 (1H, t, J=8.9 Hz), 4.89-5.01 (1H, m), 6.61 (1H, s), 7.59-7.79 (4H, m), 7.83-7.89 (1H, m), 8.24 (1H, d, J=2.5 Hz), 8.29 (1H, dd, J=2.5, 8.7 Hz)

ESI (LC-MS positive mode) m/z 474 (M+H).

Example 1-34

7-[5-(4-Hydroxypiperidin-1-ylmethyl)-2-oxooxazolidin-3-yl]-3-(2-trifluoromethylphenyl)-2H-isoquinolin-1-one

[Formula 69]

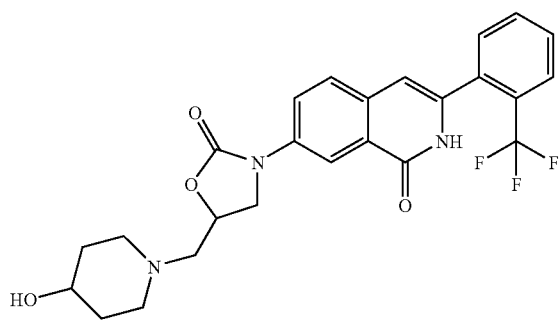

Using the 2-oxo-3-[1-oxo-3-(2-trifluoromethylphenyl)-1,2-dihydroisoquinolin-7-yl]oxazolidin-5-ylmethyl methanesulfonate obtained in step C of Example 1-30 as a raw material, the captioned compound was synthesized by a method similar to that of Example 1-33.

$^1$H-NMR (270 MHz, CD$_3$OD) δ (ppm): 1.50-1.65 (2H, m), 1.81-1.92 (2H, m), 2.30-2.45 (2H, m), 2.78-2.82 (2H, m), 2.87-3.00 (2H, m), 3.57-3.67 (1H, m), 3.95 (1H, dd, J=7.2, 8.9 Hz), 4.30 (1H, t, J=8.9 Hz), 4.85-5.00 (1H, m), 6.61 (1H, s), 7.60-7.80 (4H, m), 7.85-7.90 (1H, m), 8.24 (1H, d, J=2.4 Hz), 8.29 (1H, dd, J=2.4, 8.7 Hz)

ESI (LC-MS positive mode) m/z 488 (M+H).

Example 1-35

7-((R)-4-Benzyloxymethyl-3-methyl-2-oxoimidazolidin-1-yl)-3-(2-trifluoromethylphenyl)-2H-isoquinolin-1-one Step A 7-((R)-3-Benzyloxy-2-methylaminopropylamino)-3-(2-trifluoromethylphenyl)-2H-isoquinolin-1-one

[Formula 70]

Chiral

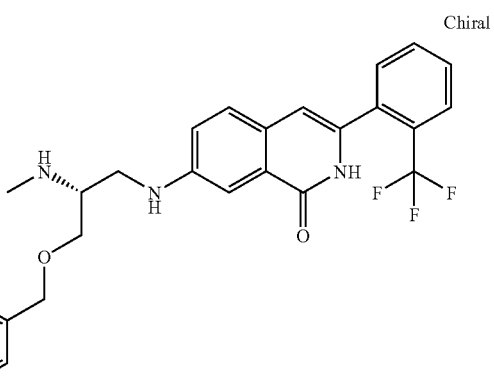

BOP Reagent (1.2 g, 2.8 mmol), N,N-diisopropylethylamine (0.5 ml, 3 mmol), and N,O-dimethylhydroxyamine hydrochloride (273 mg, 2.8 mmol) were added to a dichloromethane solution that contained Fmoc-MeSer(Bzl)-OH (1 g, 2.3 mmol). The obtained mixture was stirred at a room temperature for 1 day. Thereafter, the reaction solution was successively washed with 1 N hydrochloric acid, with a saturated sodium bicarbonate aqueous solution, and with a saturated saline solution. Thereafter, the resultant was dried over anhydrous sodium sulfate, and the solvent was distilled away under reduced pressure. The obtained residue was purified by silica gel column chromatography (ethyl acetate:hexane=1:2). 238 mg out of the obtained oil product (850 mg) was dissolved in THF (2 ml), and the obtained solution was added dropwise at −78° C. to a THF solution (8 ml) that contained lithium aluminum hydride (10 mg, 0.25 mmol). The obtained mixture was stirred at −78° C. for 1.5 hours. Thereafter, lithium aluminum hydride (10 mg, 0.25 mmol) was further added thereto, and the obtained mixture was stirred at −78° C. for 30 minutes. Thereafter, a saturated ammonium chloride aqueous solution was added to the reaction solution at −78° C., and the temperature of the obtained mixture was then increased to a room temperature. The mixture was filtered through celite, and the filtrate was then extracted with dichloromethane. The extract was washed with a saturated saline solution, and was dried over anhydrous sodium sulfate, followed by concentration under reduced pressure. The generated oil product was dissolved in 5 ml of methanol without being purified. Thereafter, 7-amino-3-(2-trifluoromethylphenyl)-2H-isoquinolin-1-one (100 mg, 0.33 mmol) and 1 ml of acetic acid were added thereto. Thereafter, sodium cyanoborohydride (135 mg, 2.1 mmol) was added to the mixture under cooling on ice, and the temperature of the obtained mixture was increased to a room temperature, followed by stirring for 3 hours. Thereafter, a saturated sodium bicarbonate aqueous solution was added to the reaction solution, and the mixture was then extracted with dichloromethane. The extract was dried over anhydrous sodium sulfate, and was then concentrated. The obtained residue was purified by silica gel column chromatography (ethyl acetate hexane=1:2 to 2:1), so as to obtain a yellow foaming substance. This yellow foaming substance was dissolved in dichloromethane (5 ml), and piperidine (1 ml) was then added to the solution. The obtained mixture was stirred at a room temperature. Four hours later, the reaction solution was concentrated, and 1 N hydrochloric acid (2 ml) and methanol (2 ml) were then added thereto, followed by stirring at 40° C. Six hours later, the reaction solution was neutralized with a 1 N sodium hydroxide aqueous solution under cooling on ice. A saturated sodium bicarbonate aqueous solution was added to the resultant, and the mixture was then extracted with dichloromethane. The extract was dried over anhydrous sodium sulfate, and was then concentrated. The obtained residue was purified by amino TLC used for preparative separation (Fuji Silysia Chemical Ltd., PLC05; dichloromethane:methanol=20:1), so as to obtain 7-((R)-3-benzyloxy-2-methylaminopropylamino)-3-(2-trifluoromethylphenyl)-2H-isoquinolin-1-one (48 mg; yield: 31%) in the form of a yellow foaming substance.

$^1$H-NMR (270 MHz, CDCl$_3$) δ (ppm): 2.43 (3H, s), 2.99-3.04 (1H, m), 3.18-3.27 (1H, m), 3.34-3.42 (1H, m), 3.54-3.66 (2H, m), 4.55 (2H, s), 4.73 (1H, brt), 6.42 (1H, s), 7.01 (1H, dd, J=2.31, 8.24 Hz), 7.31-7.39 (6H, m), 7.48 (1H, d, J=2.47 Hz), 7.52-7.67 (3H, m), 7.80 (1H, d, J=6.76 Hz)

ESI (LC-MS positive mode) m/z 482 (M+H).

Step B 7-((R)-4-Benzyloxymethyl-3-methyl-2-oxoimidazolidin-1-yl)-3-(2-trifluoromethylphenyl)-2H-isoquinolin-1-one

[Formula 71]

Chiral

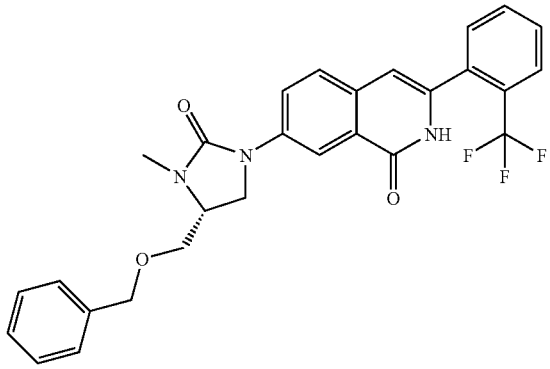

Bis(trichloromethyl)carbonate (4.5 mg, 0.015 mmol) was dissolved in dichloromethane (4 ml). Thereafter, to the thus obtained solution, a solution obtained by dissolving the 7-((R)-3-benzyloxy-2-methylaminopropylamino)-3-(2-trifluoromethylphenyl)-2H-isoquinolin-1-one (20 mg, 0.04 mmol) prepared in step A and N,N-diisopropylethylamine (16 µl, 0.09 mmol) in dichloromethane (1 ml) was added dropwise under cooling on ice. After completion of the addition, the obtained mixture was stirred for 1 hour. Thereafter, water was added to the reaction solution, and the mixture was then extracted with dichloromethane. The extract was dried over anhydrous sodium sulfate, and was then concentrated. The obtained residue was purified by silica gel TLC used for preparative separation (dichloromethane:methanol=20:1), so as to obtain 7-((R)-4-benzyloxymethyl-3-methyl-2-oxoimidazolidin-1-yl)-3-(2-trifluoromethylphenyl)-2H-isoquinolin-1-one (16 mg; yield: 77%) in the form of a white foaming substance.

$^1$H-NMR (270 MHz, CDCl$_3$) δ (ppm): 2.95 (3H, s), 3.58-3.68 (2H, m), 3.70-3.77 (1H, m), 3.81-3.90 (1H, m), 4.01-4.08 (1H, m), 4.59 (2H, s), 6.50 (1H, s), 7.31-7.40 (5H, m), 7.54-7.69 (4H, m), 7.77-7.83 (2H, m), 8.50 (1H, brs), 8.80 (1H, dd, J=2.31, 8.90 Hz)

ESI (LC-MS positive mode) m/z 508 (M+H).

Example 1-36

7-((R)-4-Hydroxymethyl-3-methyl-2-oxoimidazolidin-1-yl)-3-(2-trifluoromethylphenyl)-2H-isoquinolin-1-one

[Formula 72]

Chiral

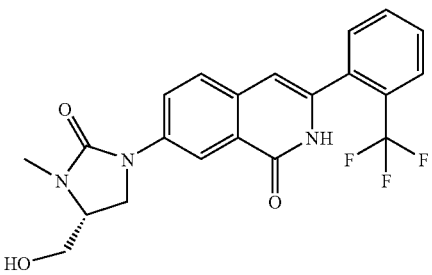

The 7-((R)-4-benzyloxymethyl-3-methyl-2-oxoimidazolidin-1-yl)-3-(2-trifluoromethylphenyl)-2H-isoquinolin-1-one (13 mg, 0.025 mmol) prepared in Example 1-35 was dissolved in methanol (5 ml). Thereafter, 10% Pd—C (3 mg) was added to the obtained solution, and the obtained mixture was then stirred in a hydrogen atmosphere for 3 hours. The reaction solution was filtered through celite, and the filtrate was then concentrated. The obtained residue was purified by silica gel TLC used for preparative separation (dichloromethane:methanol=20:1), so as to obtain 7-((R)-4-hydroxymethyl-3-methyl-2-oxoimidazolidin-1-yl)-3-(2-trifluoromethylphenyl)-2H-isoquinolin-1-one (10.9 mg, quantitative) in the form of a white solid.

$^1$H-NMR (270 MHz, CDCl$_3$) δ (ppm): 2.97 (3H, s), 3.49 (1H, brs), 3.74-3.81 (2H, m), 3.88-3.93 (2H, m), 4.01-4.08 (1H, m), 6.50 (1H, s), 7.52-7.70 (4H, m), 7.80-7.82 (2H, m), 8.44 (1H, brs), 8.76 (1H, dd, J=2.47, 8.90 Hz)

ESI (LC-MS positive mode) m/z 418 (M+H).

Example 1-37

3-(2-Ethylphenyl)-7-((S)-5-hydroxymethyl-2-oxooxazolidin-3-yl)-2H-isoquinolin-1-one

[Formula 73]

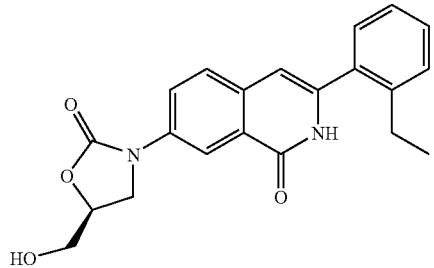

The captioned compound was synthesized by a method similar to that of Example 1-19.

$^1$H-NMR (270 MHz, DMSO-$d_6$) δ (ppm): 1.10 (3H, t, J=7.5 Hz), 2.65 (2H, q, J=7.5 Hz), 3.57-3.75 (2H, m), 3.96 (1H, dd, J=9.0, 6.5 Hz), 4.21 (1H, t, J=9.0 Hz), 4.70-4.80 (1H, m), 5.25 (1H, t, J=6.0 Hz), 6.48 (1H, s), 7.27-7.45 (4H, m), 7.72 (1H, d, J=8.5 Hz), 8.08 (1H, d, J=8.5 Hz), 8.24 (1H, brs), 11.47 (1H, brs)

ESI (LC-MS positive mode) m/z 365 (M+H).

Example 1-38

7-[(S)-5-(2-Hydroxyethyl)-2-oxooxazolidin-3-yl]-3-(2-trifluoromethylphenyl)-2H-isoquinolin-1-one Step A 7-((S)-2,4-Dihydroxybutylamino)-3-(2-trifluoromethylphenyl)-2H-isoquinolin-1-one

[Formula 74]

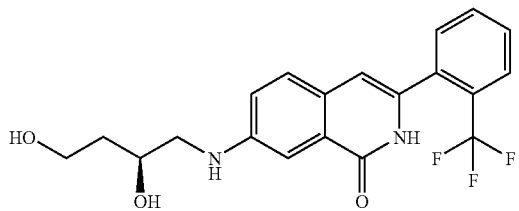

Using (S)-3,4-epoxy-1-butanol prepared in accordance with a known method described in publications (for example, Journal of Organic Chemistry, 1992, vol. 57, pp. 4352-4361), the captioned compound was prepared by a reaction similar to step A of Example 1-13.

$^1$H-NMR (270 MHz, DMSO-$d_6$) δ (ppm): 1.50-1.60 (1H, m), 1.66-1.74 (1H, m), 3.00-3.18 (2H, m), 3.50-3.59 (2H, m), 3.75-3.85 (1H, m), 4.40 (1H, t, J=5.1 Hz), 4.72 (1H, d, J=5.3 Hz), 6.06 (1H, t, J=5.5 Hz), 6.29 (1H, s), 7.11 (1H, dd, J=2.6, 8.7 Hz), 7.24 (1H, d, J=2.3 Hz), 7.40 (1H, d, J=8.6 Hz), 7.58 (1H, d, J=7.1 Hz), 7.63-7.77 (2H, m), 7.84 (1H, d, J=8.2 Hz), 11.24 (1H, brs)

ESI (LC-MS positive mode) m/z 393 (M+H).

Step B

7-[(S)-5-(2-Hydroxyethyl)-2-oxooxazolidin-3-yl]-3-(2-trifluoromethylphenyl)-2H-isoquinolin-1-one

[Formula 75]

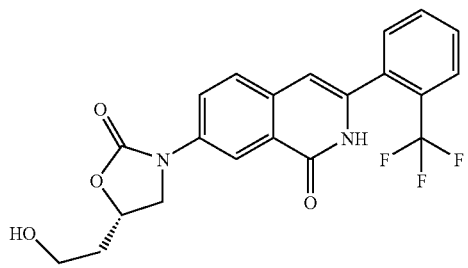

Using the 7-((S)-2,4-dihydroxybutylamino)-3-(2-trifluoromethylphenyl)-2H-isoquinolin-1-one obtained in step A as a starting material, the captioned compound was synthesized by a reaction similar to step B of Example 1-13.

$^1$H-NMR (270 MHz, DMSO-$d_6$) δ (ppm): 1.80-2.05 (2H, m), 3.54-3.63 (2H, m), 3.92 (1H, dd, J=7.4, 8.7 Hz), 4.29 (1H, t, J=8.7 Hz), 4.70 (1H, t, J=5.0 Hz), 4.85 (1H, quintet, J=7.1 Hz), 6.50 (1H, s), 7.60-7.90 (5H, m), 8.08 (1H, dd, J=2.5, 8.7 Hz), 8.23 (1H, d, J=2.5 Hz), 11.62 (1H, brs)

ESI (LC-MS positive mode) m/z 419 (M+H).

Example 1-39

7-[(S)-5-((R)-1,2-Dihydroxyethyl)-2-oxooxazolin-3-yl]-3-(2-trifluoromethylphenyl)-2H-isoquinolin-1-one Step A 3-(2-Trifluoromethylphenyl)-7-((2S,3R)-2,3,4-trihydroxybutylamino)-2H-isoquinolin-1-one

[Formula 76]

The 7-amino-3-(2-trifluoromethylphenyl)-2H-isoquinolin-1-one (2.04 g, 0.986 mmol) obtained in step C of Example 1-1 and D-(−)-erythrose (807 mg, 6.72 mmol) were dissolved in methanol (40 ml). Thereafter, acetic acid (2.31 ml, 40.3 mmol) and a 1 M sodium cyanoborohydride THF solution (20.2 ml, 20.2 mmol) were added at 0° C. to the obtained solution, and the obtained mixture was then stirred at a room temperature for 4 hours. Thereafter, the reaction mixture was concentrated under reduced pressure, and water was then added to the concentrate, followed by extraction with methylene chloride. The extract was washed with a saturated saline solution, and was then dried over sodium sulfate, followed by concentration under reduced pressure. The obtained residue was purified by silica gel chromatography (methylene chloride:methanol=15:1 to 10:1), so as to obtain 3-(2-trifluoromethylphenyl)-7-((2S,3R)-2,3,4-trihydroxybutylamino)-2H-isoquinolin-1-one (1.15 g, 42%).

$^1$H-NMR (300 MHz, DMSO-$d_6$) δ (ppm): 3.30-3.08 (1H, m), 3.43-3.45 (3H, m), 3.62 (2H, d, J=5.67 Hz), 4.41 (1H, s), 4.69 (1H, s), 4.79 (1H, s), 5.88 (1H, t, J=5.73 Hz), 6.29 (1H, s), 7.14 (1H, dd, J=2.26, 8.85 Hz), 7.26 (1H, d, J=2.25 Hz), 7.40 (1H, d, J=8.34 Hz), 7.58 (1H, d, J=7.71 Hz), 7.63-7.76 (2H, m), 7.84 (1H, d, J=8.11 Hz), 11.20 (1H, s)

ESI (positive mode) m/z 409 (M+H).

Step B

7-[(S)-5-((R)-1,2-Dihydroxyethyl)-2-oxooxazolin-3-yl]-3-(2-trifluoromethylphenyl)-2H-isoquinolin-1-one

[Formula 77]

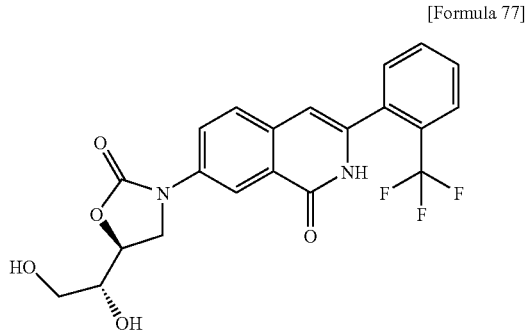

Using the 3-(2-trifluoromethylphenyl)-7-((2S,3R)-2,3,4-trihydroxybutylamino)-2H-isoquinolin-1-one obtained in step A as a raw material, the captioned compound was synthesized by a method similar to step B of Example 1-13.

$^1$H-NMR (300 MHz, DMSO-$d_6$) δ (ppm): 3.79-3.91 (1H, m), 4.17 (2H, d, J=9.15 Hz), 4.75-4.81 (2H, m), 5.39 (1H, s), 6.48 (1H, s), 7.64 (1H, d, J=7.62 Hz), 7.68-7.80 (3H, m), 7.87 (1H, d, J=7.31 Hz), 8.10 (1H, dd, J=2.40, 8.76 Hz), 8.26 (1H, d, J=2.61 Hz), 11.59 (1H, s)

ESI (positive mode) m/z 435 (M+H).

Example 1-40

3-{2-[2-(2-Benzyloxyethoxy)ethoxy]phenyl}-7-((R)-5-hydroxymethyl-2-oxooxazolidin-3-yl)-2H-isoquinolin-1-one Step A 2-[2-(2-Benzyloxyethoxy)ethoxy]benzonitrile

[Formula 78]

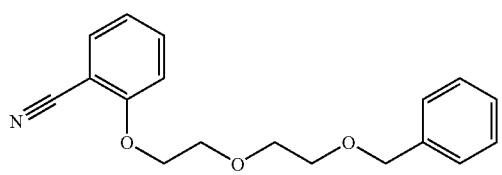

2-Hydroxybenzonitrile (300 mg, 2.52 mmol), di(ethylene glycol) benzyl ether (593 mg, 3.02 mmol), and 1,1'-azobis(N,N-dimethylformamide) (867 mg, 5.04 mmol) were dissolved in toluene (15 ml). Thereafter, tri-n-butylphosphine (1.26 ml, 5.04 mmol) was added at 20° C. to the obtained solution, and the obtained mixture was stirred at the same above temperature for 2 hours. The generated precipitate was filtrated, and the filtrate was then diluted with ethyl acetate (20 ml). The ethyl acetate solution was washed with water twice, and then with a saturated saline solution once. The resultant was dried over anhydrous sodium sulfate, and was then concentrated under reduced pressure. The obtained pale brown oil product was purified by silica gel column chromatography (dichloromethane), so as to obtain 2-[2-(2-benzyloxyethoxy)ethoxy]benzonitrile (529 mg, 71%) in the form of a colorless oil product.

$^1$H-NMR (400 MHz, CDCl$_3$) δ (ppm): 3.65-3.67 (2H, m), 3.79-3.81 (2H, m), 3.93 (2H, t, J=5.0 Hz), 4.24 (2H, t, J=5.0 Hz), 4.57 (2H, s), 6.88 (1H, d, J=7.5 Hz), 6.99 (1H, t, J=7.5 Hz), 7.26-7.35 (5H, m), 7.49 (1H, t, J=7.5 Hz), 7.54 (1H, d, J=7.5 Hz)

ESI (LC-MS positive mode) m/z 298 (M+H).

Step B

3-{2-[2-(2-Benzyloxyethoxy)ethoxy]phenyl}-7-((R)-5-hydroxymethyl-2-oxooxazolidin-3-yl)-2H-isoquinolin-1-one

[Formula 79]

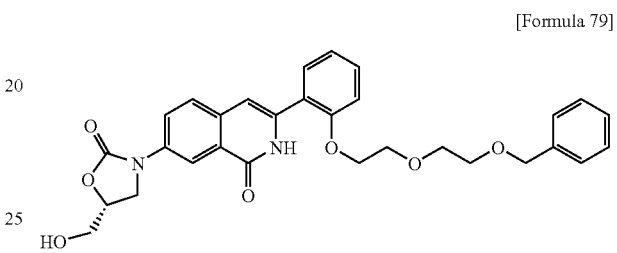

Using the 2-[2-(2-benzyloxyethoxy)ethoxy]benzonitrile prepared in step A as a raw material, the captioned compound was synthesized by a method similar to that of Example 1-19.

$^1$H-NMR (270 MHz, DMSO-$d_6$) δ: 3.40-3.85 (8H, m), (1H, m), 4.21-4.30 (3H, m), 4.64-4.83 (1H, m), 6.73 (1H, s), 7.0-7.30 (7H, m), 7.32-7.50 (2H, m), 7.69 (1H, d, J=8.6 Hz), 8.05 (1H, dd, J=2.4, 8.9 Hz), 8.21 (1H, d, J=2.4 Hz)

ESI (LC-MS positive mode) m/z 531 (M+H).

Example 1-41

3-{2-[2-(2-Hydroxyethoxy)ethoxy]phenyl}-7-((R)-5-hydroxymethyl-2-oxooxazolidin-3-yl)-2H-isoquinolin-1-one

[Formula 80]

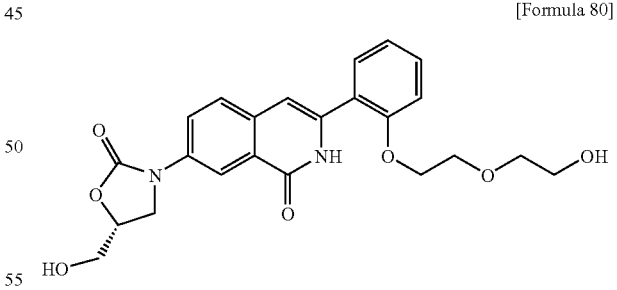

Using the 3-{2-[2-(2-benzyloxyethoxy)ethoxy]phenyl}-7-((R)-5-hydroxymethyl-2-oxooxazolidin-3-yl)-2H-isoquinolin-1-one obtained in Example 1-40 as a raw material, the captioned compound was synthesized by a method similar to that of Example 1-36.

$^1$H-NMR (270 MHz, DMSO-$d_6$) δ: 3.40-3.85 (8H, m), 3.87-4.0 (1H, m), 4.12-4.35 (3H, m), 4.64-4.83 (1H, m), 6.78 (1H, s), 7.0-7.26 (2H, m), 7.31-7.64 (2H, m), 7.73 (1H, d, J=8.9 Hz), 8.07 (1H, dd, J=2.5, 8.9 Hz), 8.22 (1H, d, J=2.5 Hz)

ESI (LC-MS positive mode) m/z 441 (M+H).

Example 1-42

3-{2-[2-(2-Hydroxyethoxy)ethoxy]phenyl}-7-((S)-5-hydroxymethyl-2-oxooxazolidin-3-yl)-2H-isoquinolin-1-one

[Formula 81]

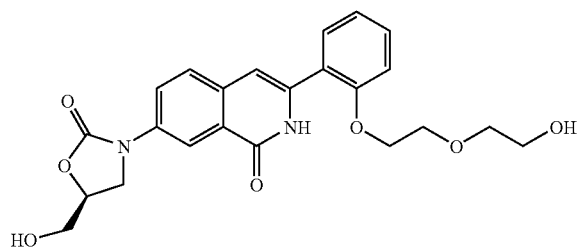

The captioned compound was synthesized by methods similar to those described in Examples 1-40 and 1-41.

Example 1-43

3-[2,6-Bis(trifluoromethyl)phenyl]-7-((R)-5-hydroxymethyl-2-oxooxazolidin-3-yl)-2H-isoquinolin-1-one

[Formula 82]

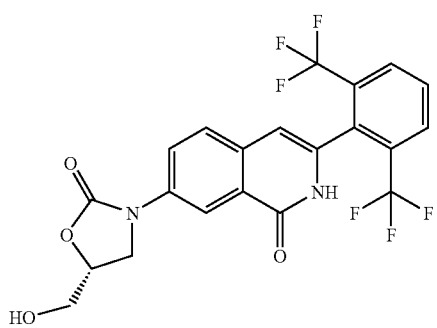

Using 2,6-bis(trifluoromethyl)benzonitrile as a raw material, the captioned compound was synthesized by a method similar to that of Example 1-19.

$^1$H-NMR (400 MHz, DMSO-$d_6$) δ: 3.52-3.80 (2H, m), 3.90-4.05 (1H, m), 4.22 (1H, t, J=9.2 Hz), 4.71-4.80 (1H, m), 5.28 (1H, brs), 6.55 (1H, s), 7.75 (1H, d, 8.6 Hz), 7.97 (1H, t, J=8.6 Hz), 8.10 (1H, d, J=8.6 Hz), 11.71 (1H, brs)

ESI (LC-MS positive mode) m/z 473 (M+H).

Example 1-44

7-[5-(2-Hydroxy-1-hydroxymethylethyl)-2-oxooxazolidin-3-yl]-3-(2-trifluoromethylphenyl)-2H-isoquinolin-1-one Step A 7-[5-(2,2-Dimethyl-[1,3]dioxan-5-yl)-2-oxooxazolidin-3-yl]-3-(2-trifluoromethylphenyl)-2H-isoquinolin-1-one

[Formula 83]

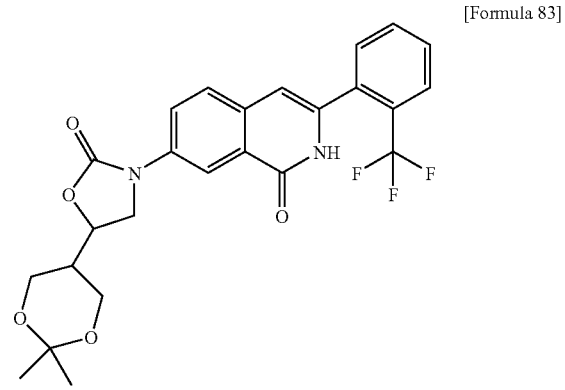

Using 2,2-dimethyl-5-oxilanyl[1,3]dioxane, which is a known compound described in a publication (J. Chem. Soc., Perkin Trans. I, pp. 1879-1883 (1985)), as a raw material, the captioned compound was synthesized by a method similar to that of Example 1-13.

$^1$H-NMR (300 MHz, CDCl$_3$) δ (ppm): 1.41 (3H, s), 1.48 (3H, s), 1.91 (1H, m), 3.83 (1H, m), 3.97-4.19 (4H, m), 4.31 (1H, t, J=8.8 Hz), 5.04 (1H, q, J=8.8 Hz), 6.55 (1H, s), 7.54-7.71 (4H, m), 7.82 (1H, d, J=7.6 Hz), 7.95 (1H, d, J=2.3 Hz), 8.59 (1H, dd, J=2, 3, 8.8 Hz), 9.29 (1H, brs)

Step B

7-[5-(2-Hydroxy-1-hydroxymethylethyl)-2-oxooxazolidin-3-yl]-3-(2-trifluoromethylphenyl)-2H-isoquinolin-1-one

[Formula 84]

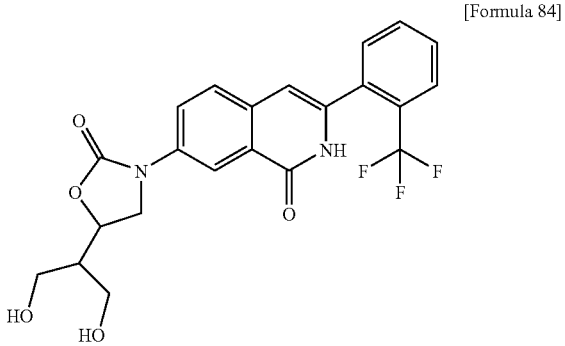

The 7-[5-(2,2-dimethyl-[1,3]dixane-5-yl)-2-oxooxazolidin-3-yl]-3-(2-trifluoromethylphenyl)-2H-isoquinolin-1-one (30 mg, 0.061 mmol) obtained in step A was dissolved in THF (2 ml). Thereafter, 3 N HCl (0.116 ml, 0.348 mmol) was added to the obtained solution, and the obtained mixture was then stirred at a room temperature for 1 hour. Thereafter, a saturated sodium bicarbonate solution was added to the reaction mixture, and the obtained mixture was then extracted with ethyl acetate. The extract was washed with a saturated saline solution, and was then dried over magnesium sulfate, followed by concentration under reduced pressure. The obtained residue was purified by silica gel chromatography (methylene chloride:methanol=15:1), so as to obtain 7-[5-(2-hydroxy-1-hydroxymethylethyl)-2-oxooxazolidin-3-yl]-3-(2-trifluoromethylphenyl)-2H-isoquinolin-1-one (20 mg, 73%).

$^1$H-NMR (300 MHz, CD$_3$OD) δ (ppm): 2.15 (1H, m), 3.78-3.93 (4H, m), 4.24-4.38 (2H, m), 4.94 (1H, q, J=8.1 Hz), 6.63 (1H, m), 7.63-7.81 (4H, m), 7.89 (1H, d, J=7.6 Hz), 8.27-8.31 (2H, m).

Example 1-45

Ethyl 2-oxo-1-[1-oxo-3-(2-trifluoromethylphenyl)-1,2-dihydroisoquinolin-7-yl]pyrrolidine-3-carboxylate Step A 1-tert-Butyl 2-oxopyrrolidine-1,3-dicarboxylate 3-ethyl ester

[Formula 85]

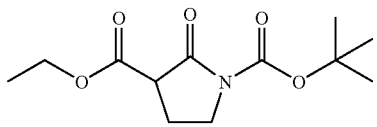

A mixture of 2-pyrrolidone (1.0 ml, 10.5 mmol), di-tert-butyl dicarbonate (4.6 g, 21.0 mmol), and 4-(dimethylamino)pyridine (5.1 g, 42.0 mmol) was dissolved in acetonitrile (50 ml), and the obtained solution was stirred at a room temperature for 2 hours. The reaction solution was poured into a saturated ammonium chloride aqueous solution, and the obtained solution was then extracted with ethyl acetate. The extract was washed with a saturated ammonium chloride aqueous solution and with a saturated saline solution. The resultant was dried over anhydrous sodium sulfate, and was then concentrated, so as to obtain a crude product of 2-oxopyrrolidin-1-carboxylic acid tert-butyl (1.7 g, 75%) in the form of a reddish brown substance.

A THF solution (10 ml) that contained the crude product of 2-oxopyrrolidin-1-carboxylic acid tert-butyl (500 mg, 2.70 mmol) was added dropwise at −78° C. to a 1 M lithium hexamethyldisilazane THF solution (5.4 ml, 5.4 mmol), and the obtained mixture was stirred for 50 minutes. A solution obtained by dissolving ethyl chloroformate (0.27 ml, 2.84 mmol) in THF (5 ml) was further added dropwise to the reaction solution at −78° C. The temperature of the mixture was increased to a room temperature, and the mixture was then stirred for 4 hours. Thereafter, the reaction solution was poured into a saturated ammonium chloride aqueous solution, followed by extraction with ethyl acetate. The extract was washed with a saturated saline solution, and was then dried over anhydrous sodium sulfate, followed by concentration. The obtained residue was purified by silica gel chromatography (hexane:ethyl acetate=5:1 to 2:1), so as to obtain 2-oxopyrrolidin-1,3-dicarboxylic acid 1-tert-butyl ester 3-ethyl ester (468 mg, 67%) in the form of a liver brown oil substance.

$^1$H-NMR (270 MHz, CDCl$_3$) δ (ppm): 1.31 (3H, t, J=7.1 Hz), 1.53 (9H, s), 2.16-2.46 (2H, m), 3.53 (1H, dd, J=7.4, 9.1 Hz), 3.66-3.75 (1H, m), 3.84-3.93 (1H, m), 4.24 (2H, dd, J=7.1, 14.3 Hz)

ESI (LC-MS positive mode) m/z 258 (M+H).

Step B

Ethyl 2-oxo-1-[1-oxo-3-(2-trifluoromethylphenyl)-1,2-dihydroisoquinolin-7-yl]pyrrolidine-3-carboxylate

[Formula 86]

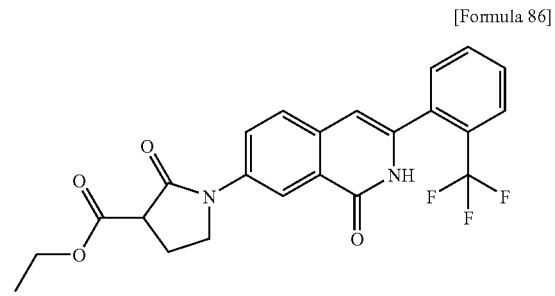

The 2-oxopyrrolidin-1,3-dicarboxylic acid 1-tert-butyl ester 3-ethyl ester (100 mg, 0.389 mmol) prepared in step A was suspended in dichloromethane (5 ml), and trifluoroacetic acid (0.5 mg, 6.490 mmol) was then added dropwise to the suspension under cooling on ice. The temperature of the mixture was increased to a room temperature, and the mixture was then stirred for 1 hour. Thereafter, the reaction solution was concentrated, so as to obtain a crude product of 2-oxopyrrolidin-3-carboxylic acid ethyl.

Using this crude product and the 7-iodo-3-(2-trifluoromethylphenyl)-2H-isoquinolin-1-one (161 mg, 0.389 mmol) obtained in step D of Example 1-1 as raw materials, 2-oxo-1-[1-oxo-3-(2-trifluoromethylphenyl)-1,2-dihydroisoquinolin-7-yl]pyrrolidin-3-carboxylic acid ethyl was synthesized by a reaction similar to step E of Example 1-1.

$^1$H-NMR (270 MHz, DMSO-d$_6$) δ (ppm): 1.24 (3H, t, J=7.1 Hz), 2.32-2.47 (2H, m), 3.81 (1H, t, J=8.7 Hz), 3.96-4.04 (2H, m), 4.18 (2H, ddd, J=14.1, 7.1, 1.3 Hz), 6.50 (1H, s), 7.63-7.81 (4H, m), 7.88 (1H, d, J=8.7 Hz), 8.10 (1H, dd, J=8.7, 2.3 Hz), 8.37 (1H, d, J=2.3 Hz) 11.64 (1H, brs)

ESI (LC-MS positive mode) m/z 445 (M+H).

Example 1-46

7-(3-Hydroxymethyl-2-oxopyrrolidin-1-yl)-3-(2-trifluoromethylphenyl)-2H-isoquinolin-1-one

[Formula 87]

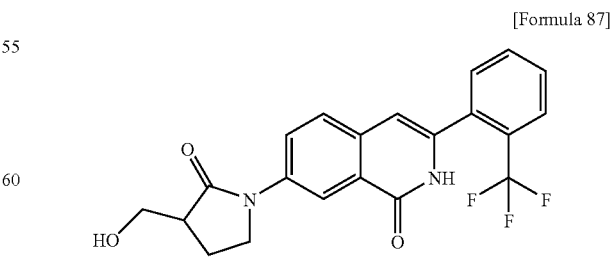

The 2-oxo-1-[1-oxo-3-(2-trifluoromethylphenyl)-1,2-dihydroisoquinolin-7-yl]pyrrolidin-3-carboxylic acid ethyl (11 mg, 0.025 mmol) prepared in step B of Example 1-45, sodium borohydride (9.5 mg, 0.25 mmol), and calcium chloride (27.7 mg, 0.25 mmol) were dissolved in methanol (5 ml), and the obtained solution was then stirred at a room temperature for 16 hours. Thereafter, the reaction solution was concentrated, and it was then purified using ODS cartridge 5 g (Mega Bond Elut (registered trademark) C18, manufactured by Varian; water methanol=1:0 to 0:1). The resultant was then preparatively separated by preparative HPLC (column: Combi ODS (φ: 28.0 mm×50 mm) manufactured by Wako; developing solvent: 0.05% trifluoroacetic acid-containing water: 0.05% trifluoroacetic acid-containing acetonitrile=90:10 to 5:95), so as to obtain 7-(3-hydroxymethyl-2-oxopyrrolidin-1-yl)-3-(2-trifluoromethylphenyl)-2H-isoquinolin-1-one (5 mg, 50%) in the form of a white amorphous substance.

$^1$H-NMR (270 MHz, DMSO-d$_6$) δ (ppm): 2.08-2.26 (2H, m), 2.71-2.79 (1H, m), 3.65 (1H, dd, J=3.6, 10.6 Hz), 3.76 (1H, dd, J=5.2, 10.6 Hz), 3.87-3.92 (2H, m), 4.85 (1H, brs), 6.48 (1H, s), 7.63-7.81 (4H, m), 7.87 (1H, d, J=6.7 Hz), 8.17 (1H, dd, J=2.5, 8.7 Hz), 8.36 (1H, d, J=2.5 Hz), 11.56 (1H, brs)

ESI (LC-MS positive mode) m/z 403 (M+H).

Example 1-47

7-((R)-5-Hydroxymethyl-2-oxooxazolidin-3-yl)-3-(2-isobutylphenyl)-2H-isoquinolin-1-one

[Formula 88]

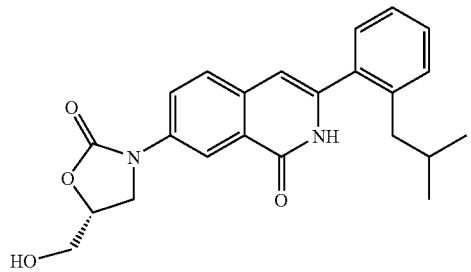

The captioned compound was synthesized by a method similar to that of Example 1-19.

$^1$H-NMR (270 MHz, CD$_3$OD) δ: 0.68 (6H, d, J=6.6 Hz), 1.68 (1H, sext, J=6.6 Hz), 2.50 (2H, d, J=6.6 Hz), 3.40-3.85 (8H, m), 3.59-3.87 (1H, m), 3.92-4.05 (1H, m), 4.10-4.26 (1H, m), 4.63-4.82 (1H, m), 6.50 (1H, s), 7.10-7.39 (4H, m), 7.63 (1H, d, J=8.6 Hz), 8.09-8.22 (1H, m)

ESI (LC-MS positive mode) m/z 393 (M+H).

Example 1-48

3-(2-Allylphenyl)-7-((R)-5-hydroxymethyl-2-oxooxazolidin-3-yl)-2H-isoquinolin-1-one

[Formula 89]

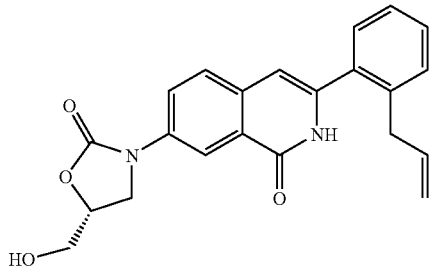

The captioned compound was synthesized by a method similar to that of Example 1-19.

$^1$H-NMR (270 MHz, CD$_3$OD) δ: 1.71 (2H, d, J=4.9 Hz), 3.59-3.86 (2H, m), 3.91-4.03 (1H, m), 4.11-4.25 (1H, m), 4.63-4.82 (1H, m), 6.1-6.35 (3H, m), 6.50 (1H, s), 7.16-7.39 (3H, m), 7.49-7.68 (2H, m), 8.11-8.26 (2H, m), 8.44 (1H, brs)

ESI (LC-MS positive mode) m/z 377 (M+H).

Example 1-49

7-(2-Oxo-[1,3]oxazinan-3-yl)-3-(2-trifluoromethylphenyl)-2H-isoquinolin-1-one

Step A

7-[3-(tert-Butyldimethylsilyloxy)propylamino]-3-(2-trifluoromethylphenyl)-2H-isoquinolin-1-one

[Formula 90]

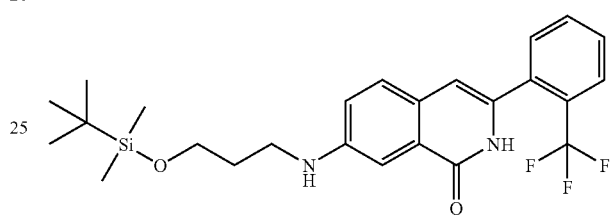

The 7-amino-3-(2-trifluoromethylphenyl)-2H-isoquinolin-1-one (300 mg, 0.986 mmol) obtained in step C of Example 1-1 was dissolved in methanol (10 ml). Thereafter, 3-[(tert-butyldimethylsilyl)oxy]-1-propanol (186 mg, 0.986 mmol), acetic acid (0.339 ml), and a 1 M sodium cyanoborohydride THF solution (2.96 ml, 2.96 mmol) were added at 0° C. to the obtained solution, and the obtained mixture was stirred at a room temperature for 1 hour. Thereafter, a saturated sodium bicarbonate solution was added to the reaction mixture, and the obtained mixture was then extracted with methylene chloride. The extract was dried over magnesium sulfate, and was then concentrated under reduced pressure. The obtained residue was purified by silica gel chromatography (ethyl acetate:hexane=1:3), so as to obtain 7-[3-(tert-butyldimethylsilyloxy)propylamino]-3-(2-trifluoromethylphenyl)-2H-isoquinolin-1-one (376 mg, 80%).

$^1$H-NMR (300 MHz, CDCl$_3$) δ (ppm): 0.09 (6H, s), 0.94 (9H, s), 1.85-1.95 (2H, m), 3.37 (2H, t, J=6.5 Hz), 3.81 (2H, t, J=5.3 Hz), 6.43 (1H, s), 6.98 (1H, dd, J=2.3, 8.4 Hz), 7.38 (1H, d, J=8.8 Hz), 7.45 (1H, d, J=2.7 Hz), 7.51-7.66 (3H, m), 7.79 (1H, d, J=7.5 Hz), 8.79 (1H, brs)

ESI (positive mode) m/z 477 (M+H).

Step B 7-(3-Hydroxypropylamino)-3-(2-trifluoromethylphenyl)-2H-isoquinolin-1-one

[Formula 91]

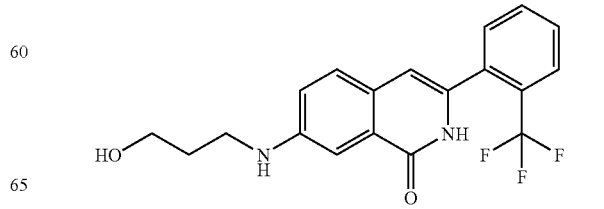

The 7-[3-(tert-butyldimethylsilyloxy)propylamino]-3-(2-trifluoromethylphenyl)-2H-isoquinolin-1-one (435 mg, 0.913 mmol) obtained in step A was dissolved in THF (9 ml). Thereafter, a 1 M tetrabutylammonium fluoride THF solution (1.1 ml, 1.1 mmol) was added to the obtained solution at a room temperature. The obtained mixture was stirred for 5 hours. Thereafter, methylene chloride was added to the reaction solution. An organic layer thereof was washed with a saturated saline solution, and was then dried over magnesium sulfate, followed by concentration under reduced pressure. The obtained residue was purified by silica gel chromatography (methylene chloride:methanol=30:1), so as to obtain 7-(3-hydroxypropylamino)-3-(2-trifluoromethylphenyl)-2H-isoquinolin-1-one (337 mg, 95%).

$^1$H-NMR (300 MHz, CDCl$_3$) δ (ppm): 1.90-1.99 (2H, m), (2H, t, J=6.9 Hz), 3.84 (2H, t, J=5.7 Hz), 6.43 (1H, s), (1H, dd, J=2.3, 8.0 Hz), 7.38 (1H, d, J=8.8 Hz), 7.51-7.66 (4H, m), 7.78 (1H, d, J=7.6 Hz), 8.65 (1H, brs)

ESI (positive mode) m/z 363 (M+H).

Step C 7-(2-Oxo-[1,3]oxazinan-3-yl)-3-(2-trifluoromethylphenyl)-2H-isoquinolin-1-one

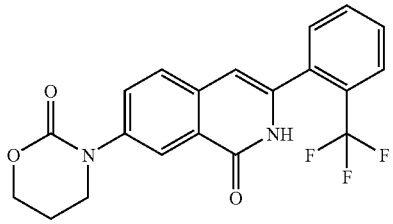

[Formula 92]

Using the 7-(3-hydroxypropylamino)-3-(2-trifluoromethylphenyl)-2H-isoquinolin-1-one obtained in step B as a raw material, the captioned compound was synthesized by a method similar to step B of Example 1-13.

$^1$H-NMR (300 MHz, CDCl$_3$) δ (ppm): 2.22-2.31 (2H, m), (2H, t, J=6.1 Hz), 4.47 (2H, t, J=5.3 Hz), 6.52 (1H, s), (4H, m), 7.80-7.84 (2H, m), 8.22 (1H, brs), 9.09 (1H, brs)

ESI (positive mode) m/z 389 (M+H).

Example 1-50

7-(4-Hydroxy-2-oxo-2,5-dihydropyrrol-1-yl)-3-(2-trifluoromethylphenyl)-2H-isoquinolin-1-one

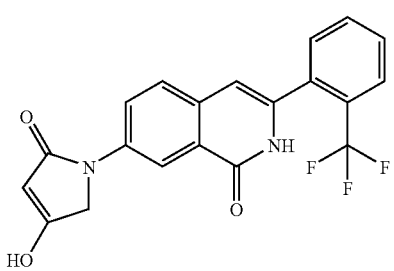

[Formula 93]

A mixture of the 7-(4-benzyloxy-2-oxo-2,5-dihydropyrrol-1-yl)-3-(2-trifluoromethylphenyl)-2H-isoquinolin-1-one (8 mg, 0.017 mmol) prepared in Example 1-8 and palladium hydroxide (2 mg) was dissolved in methanol. The obtained mixture was stirred in a hydrogen atmosphere for 1 hour. Thereafter, the reaction solution was filtered through celite, and the concentrated residue was then preparatively separated by preparative HPLC (column: Combi ODS (φ: 28.0 mm×50 mm), manufactured by Wako; developing solvent: 0.05% trifluoroacetic acid-containing water: 0.05% trifluoroacetic acid-containing acetonitrile=90:10 to 5:95), so as to obtain 7-(4-hydroxy-2-oxo-2,5-dihydropyrrol-1-yl)-3-(2-trifluoromethylphenyl)-2H-isoquinolin-1-one (1 mg, 15%) in the form of a colorless oil substance.

$^1$H-NMR (270 MHz, DMSO-d$_6$) δ (ppm): 4.48 (2H, s), 5.02 (1H, s), 6.41 (1H, s), 7.61-7.75 (4H, m), 7.84 (1H, d, J=7.6 Hz), 8.15 (1H, d, J=8.7 Hz), 8.35 (1H, s), 11.49 (1H, brs), 11.99 (1H, brs)

ESI (LC-MS positive mode) m/z 387 (M+H).

Example 1-51

1-[1-Oxo-3-(2-trifluoromethylphenyl)-1,2-dihydroisoquinolin-7-yl]pyrrolidine-2,5-dione

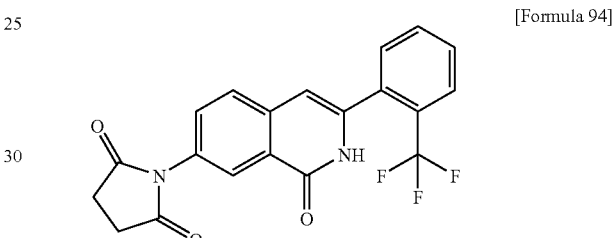

[Formula 94]

Using the 7-iodo-3-(2-trifluoromethylphenyl)-2H-isoquinolin-1-one (30 mg, 0.072 mmol) obtained in step D of Example 1-1 as a raw material, the captioned compound was synthesized by a reaction similar to step E of Example 1-1.

$^1$H-NMR (270 MHz, CDCl$_3$) δ (ppm): 2.97 (4H, s), 6.65 (1H, s), 7.26-7.84 (7H, m), 8.37 (1H, brs)

ESI (LC-MS positive mode) m/z 387 (M+H).

Example 2-1

Ethyl 2-oxo-3-[1-oxo-3-(2-trifluoromethylphenyl)-1,2-dihydroisoquinolin-7-yl]oxazolidine-5-carboxylate Step A Ethyl 2-hydroxy-3-[1-oxo-3-(2-trifluoromethylphenyl)-1,2-dihydroisoquinolin-7-ylamino]propanoate

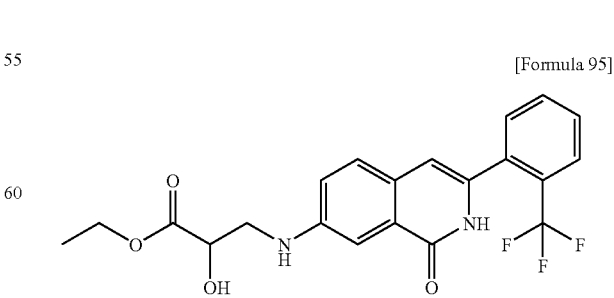

[Formula 95]

The 7-amino-3-(2-trifluoromethylphenyl)-2H-isoquinolin-1-one (820 mg, 2.69 mmol) obtained in step C of Example 1-1 was dissolved in ethanol (5.4 ml). Thereafter, methyl glycidate (313 mg, 2.69 mmol) was added to the obtained solution, and the obtained mixture was stirred under heating to reflux for 4 days. Thereafter, the reaction solution was concentrated, and the concentrate was then subjected to silica gel column chromatography (ethyl acetate:hexane=1:2 to 3:1), so as to obtain 2-hydroxy-3-[1-oxo-3-(2-trifluoromethylphenyl)-1,2-dihydroisoquinolin-7-ylamino]ethyl propanoate (795.5 mg, 70%) in the form of a yellow foaming substance.

$^1$H-NMR (270 MHz, CDCl$_3$) δ (ppm): 1.31 (3H, t, J=7.1 Hz), 3.28-3.33 (1H, m), 3.50-3.73 (2H, m), 4.08-4.31 (2H, m), 4.40-4.50 (2H, m), 6.44 (1H, s), 7.07 (1H, dd, J=2.6, 8.5 Hz), 7.40 (1H, d, J=8.5 Hz), 7.50-7.70 (4H, m), 7.78-7.83 (1H, m), 8.51 (1H, brs)

ESI (LC-MS positive mode) m/z 421 (M+H).

Step B

Ethyl 2-oxo-3-[1-oxo-3-(2-trifluoromethylphenyl)-1,2-dihydroisoquinolin-7-yl]oxazolidine-5-carboxylate

[Formula 96]

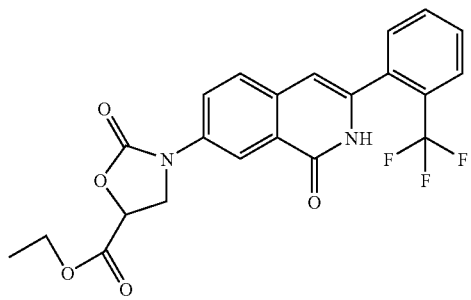

The 2-hydroxy-3-[1-oxo-3-(2-trifluoromethylphenyl)-1,2-dihydroisoquinolin-7-ylamino]propanoic acid methyl (203 mg, 0.5 mmol) obtained in step A was dissolved in THF (2.5 ml). Thereafter, carbonyldimidazole (81 mg, 0.5 mmol) was added to the obtained solution, and the obtained mixture was stirred at a room temperature for 5.5 hours. Thereafter, water was added to the reaction solution, followed by extraction with ethyl acetate. The extract was washed with a saturated saline solution, and was then dried over anhydrous sodium sulfate. Thereafter, the solvent was distilled away under reduced pressure. The obtained residue was purified by silica gel column chromatography (ethyl acetate:hexane=3:1 to 6:1), so as to obtain 2-oxo-3-[1-oxo-3-(2-trifluoromethylphenyl)-1,2-dihydroisoquinolin-7-yl]oxazolidin-5-carboxylic acid methyl mg, 70%) in the form of a colorless oil substance.

$^1$H-NMR (270 MHz, CDCl$_3$) δ (ppm): 1.37 (3H, t, J=7.2 Hz), 4.26-4.49 (4H, m), 5.12 (1H, dd, J=5.5, 9.6 Hz), 6.53 (1H, s), 7.54-7.72 (4H, m), 7.81-7.85 (1H, m), 7.94 (1H, d, J=2.4 Hz), 8.52 (1H, brs), 8.57 (1H, dd, J=2.4, 8.9 Hz)

ESI (LC-MS positive mode) m/z 447 (M+H).

Example 2-2

Methyl 2-oxo-3-[1-oxo-3-(2-trifluoromethylphenyl)-1,2-dihydroisoquinolin-7-yl]oxazolidine-5-carboxylate

[Formula 97]

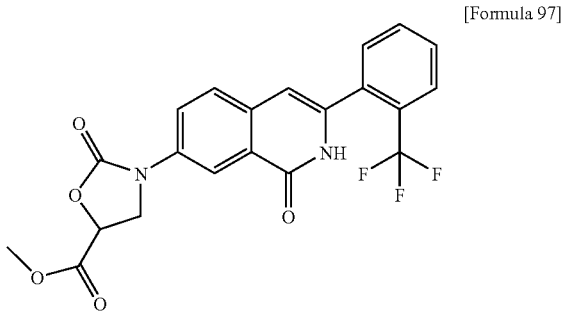

Using methyl glycidate, the captioned compound was synthesized by a method similar to that of Example 2-1.

$^1$H-NMR (270 MHz, DMSO-d$_6$) δ (ppm): 3.90 (3H, s), 4.30 (1H, dd, J=5.3, 9.6 Hz), 4.44 (1H, t, J=9.6 Hz), 5.15 (1H, dd, J=5.3, 9.6 Hz), 6.52 (1H, s), 7.53-7.73 (4H, m), 7.81 (1H, dd, J=1.0, 7.3 Hz), 7.91 (1H, d, J=2.5 Hz), 8.49 (1H, dd, J=2.5, 8.7 Hz), 9.28 (1H, brs)

ESI (LC-MS positive mode) m/z 433 (M+H).

Example 2-3

7-[5-(1-Hydroxy-1-methylethyl)-2-oxooxazolidin-3-yl]-3-(2-trifluoromethylphenyl)-2H-isoquinolin-1-one

[Formula 98]

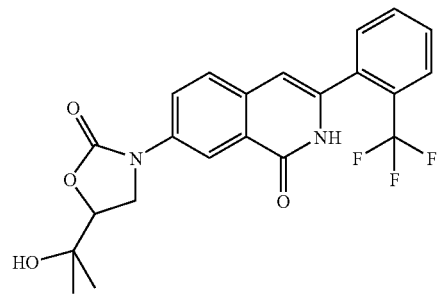

A THF solution that contained methylmagnesium chloride (0.6 M, 290 μl) was added to a THF solution (0.5 ml) that contained the 2-oxo-3-[1-oxo-3-(2-trifluoromethylphenyl)-1,2-dihydroisoquinolin-7-yl]oxazolidin-5-carboxylic acid methyl (15.5 mg, 0.0358 mmol) obtained in Example 2-1 under cooling on ice. The obtained mixture was stirred for 1 hour. Thereafter, a saturated ammonium chloride aqueous solution was added to the reaction solution, and the mixture was then extracted with ethyl acetate. The extract was dried over anhydrous sodium sulfate, and was then concentrated under reduced pressure. The obtained residue was purified by silica gel column chromatography (acetone:hexane=1:1), so as to obtain 7-[5-(1-hydroxy-1-methylethyl)-2-oxooxazolidin-3-yl]-3-(2-trifluoromethylphenyl)-2H-isoquinolin-1-one (12.6 mg, 81%) in the form of a colorless amorphous substance.

¹H-NMR (270 MHz, DMSO-d₆) δ (ppm): 1.30 (3H, s), 1.42 (3H, s), 2.76 (1H, s), 4.07 (1H, t, J=9.1 Hz), 4.25 (1H, dd, J=7.3, 9.1 Hz), 4.50 (1H, dd, J=7.3, 9.1 Hz), 6.51 (1H, s), 7.50-7.70 (4H, m), 7.78-7.83 (1H, m), 7.92 (1H, d, J=2.5 Hz), 8.51 (1H, dd, J=2.6, 8.8 Hz), 9.03 (1H, brs)

ESI (LC-MS positive mode) m/z 447 (M+H).

Example 2-4

2-Oxo-3-[1-oxo-3-(2-trifluoromethylphenyl)-1,2-dihydroisoquinolin-7-yl]oxazolidine-5-carboxylic acid

[Formula 99]

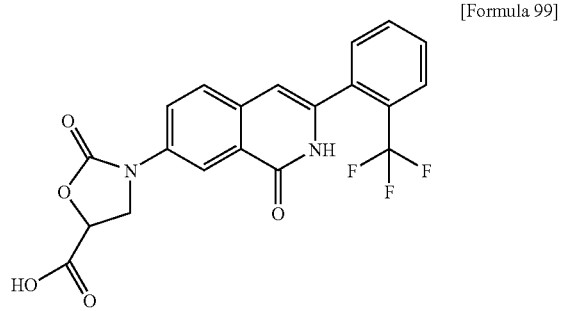

The 2-oxo-3-[1-oxo-3-(2-trifluoromethylphenyl)-1,2-dihydroisoquinolin-7-yl]oxazolidin-5-carboxylic acid methyl (24.3 mg, 0.0562 mmol) obtained in Example 2-1 was suspended in methanol (2 ml). Thereafter, lithium hydroxide monohydrate (11.8 mg, 0.281 mmol) was added to the suspension, and the obtained mixture was then stirred at a room temperature for 30 minutes. Thereafter, 1 N hydrochloric acid (300 μl) was added thereto, and the reaction solution was then concentrated under reduced pressure. Ethyl acetate was added to the obtained residue. The mixture was washed with water, and was then dried over anhydrous sodium sulfate, so as to obtain 2-oxo-3-[1-oxo-3-(2-trifluoromethylphenyl)-1,2-dihydroisoquinolin-7-yl]oxazolidin-5-carboxylic acid (23.2 mg, 99%) in the form of a colorless amorphous substance.

¹H-NMR (270 MHz, DMSO-d₆) δ (ppm): 4.23 (1H, dd, J=5.5, 9.0 Hz), 4.49 (1H, t, J=9.6 Hz), 5.23 (1H, dd, J=5.4, 9.7 Hz), 6.50 (1H, s), 7.62-7.88 (6H, m), 8.01 (1H, dd, J=2.4, 8.6 Hz), 8.30 (1H, d, J=2.4 Hz), 11.64 (1H, brs)

ESI (LC-MS positive mode) m/z 419 (M+H).

Example 2-5

2-Oxo-3-[1-oxo-3-(2-trifluoromethylphenyl)-1,2-dihydroisoquinolin-7-yl]oxazolidine-5-carboxylic acid amide

[Formula 100]

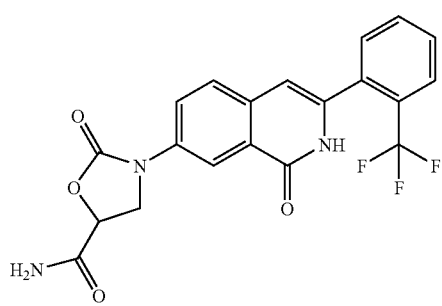

The 2-oxo-3-[1-oxo-3-(2-trifluoromethylphenyl)-1,2-dihydroisoquinolin-7-yl]oxazolidin-5-carboxylic acid (12.5 mg, 0.03 mmol) obtained in Example 2-4 and a 25% ammonia aqueous solution (3.06 μl, 0.045 mmol) were dissolved in isopropanol (0.3 ml). Thereafter, 4-(4,6-dimethoxy-1,3,5-triazin-2-yl)-4-methylmorpholinium chloride (13.3 mg, 0.045 mmol) was added to the solution, and the obtained mixture was then stirred at a room temperature for 3.5 hours. Thereafter, water was added to the reaction solution, and the mixture was then extracted with ethyl acetate. The extract was dried over anhydrous sodium sulfate, and the solvent was then distilled away under reduced pressure. The obtained residue was purified by silica gel column chromatography (methylene chloride:methanol=30:1), so as to obtain 2-oxo-3-[1-oxo-3-(2-trifluoromethylphenyl)-1,2-dihydroisoquinolin-7-yl]oxazolidin-5-carboxylic amide (9.8 mg, 78%) in the form of a colorless amorphous substance.

¹H-NMR (270 MHz, DMSO-d₆) δ (ppm): 4.12 (1H, dd, J=5.9, 8.9 Hz), 4.43 (1H, t, J=9.3 Hz), 5.09 (1H, dd, J=5.8, 9.6 Hz), 6.50 (1H, s), 7.63-7.92 (7H, m), 8.02 (1H, dd, J=2.7, 8.6 Hz), 8.32 (1H, d, J=2.4 Hz), 11.64 (1H, brs)

ESI (LC-MS positive mode) m/z 418 (M+H).

The following compounds (Examples 2-6 to 2-10) were synthesized by a method similar to that of Example 2-5.

Example 2-6

2-Oxo-3-[1-oxo-3-(2-trifluoromethylphenyl)-1,2-dihydroisoquinolin-7-yl]oxazolidine-5-carboxylic acid methylamide

[Formula 101]

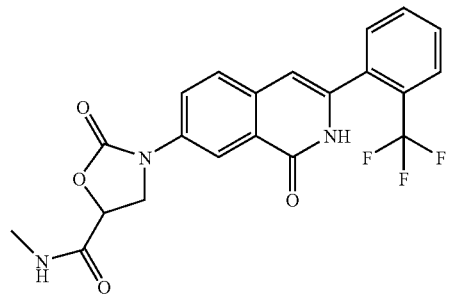

¹H-NMR (270 MHz, DMSO-d₆) δ (ppm): 2.68 (3H, d, J=4.9 Hz), 4.14 (1H, dd, J=5.9, 8.9 Hz), 4.43 (1H, t, J=9.2 Hz), 5.12 (1H, dd, J=5.8, 9.6 Hz), 6.50 (1H, s), 7.63-7.89 (5H, m), 8.00 (1H, dd, J=2.4, 8.6 Hz), 8.33 (1H, d, J=2.4 Hz), 8.41-8.45 (1H, m), 11.64 (1H, brs)

ESI (LC-MS positive mode) m/z 432 (M+H).

Example 2-7

2-Oxo-3-[1-oxo-3-(2-trifluoromethylphenyl)-1,2-dihydroisoquinolin-7-yl]oxazolidine-5-carboxylic acid dimethylamide

[Formula 102]

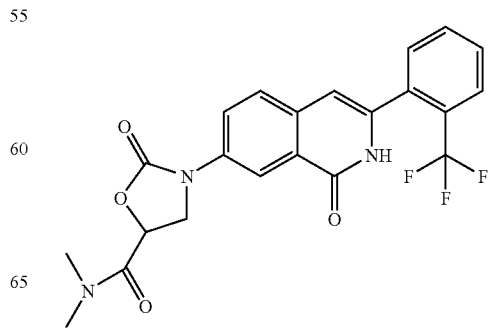

¹H-NMR (270 MHz, CDCl₃) δ (ppm): 3.03 (3H, s), 3.22 (3H, s), 4.23 (1H, t, J=9.2 Hz), 4.84 (1H, dd, J=5.9, 8.9 Hz), 5.34 (1H, dd, J=5.9, 8.9 Hz), 6.56 (1H, s), 7.54-7.71 (4H, m), 7.79-7.83 (1H, m), 8.07 (1H, d, J=2.7 Hz), 8.48 (1H, dd, J=2.6, 8.8 Hz), 9.98 (1H, brs)

ESI (LC-MS positive mode) m/z 446 (M+H).

Example 2-8

2-Oxo-3-[1-oxo-3-(2-trifluoromethylphenyl)-1,2-dihydroisoquinolin-7-yl]oxazolidine-5-carboxylic acid (2-hydroxyethyl)amide

[Formula 103]

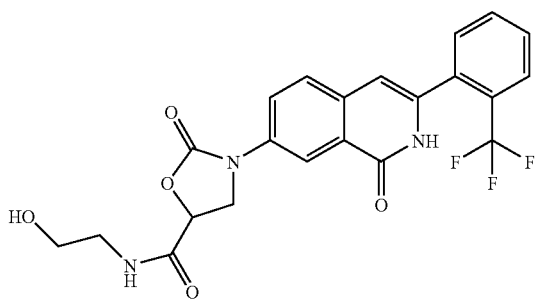

¹H-NMR (270 MHz, DMSO-d₆) δ (ppm): 3.15-3.26 (2H, m), 3.43-3.50 (2H, m), 4.12 (1H, dd, J=5.9, 8.9 Hz), 4.43 (1H, t, J=9.3 Hz), 4.77 (1H, t, J=5.3 Hz), 5.14 (1H, dd, J=5.9, 9.5 Hz), 6.50 (1H, s), 7.62-7.90 (5H, m), 8.02 (1H, dd, J=2.6, 8.8 Hz), 8.31 (1H, d, J=2.4 Hz), 8.44 (1H, t, J=5.7 Hz), 11.63 (1H, brs)

ESI (LC-MS positive mode) m/z 462 (M+H).

Example 2-9

7-[5-(Morpholine-4-carbonyl)-2-oxooxazolidin-3-yl]-3-(2-trifluoromethylphenyl)-2H-isoquinolin-1-one

[Formula 104]

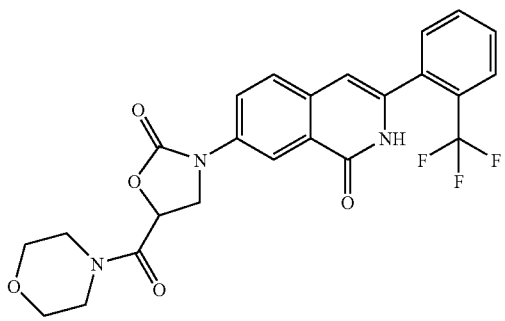

¹H-NMR (270 MHz, DMSO-d₆) δ (ppm): 3.48-4.05 (8H, m), (1H, dd, J=5.1, 9.2 Hz), 4.42 (1H, t, J=9.2 Hz), 5.70 (1H, dd, J=5.1, 9.2 Hz), 6.50 (1H, s), 7.62-7.90 (5H, m), 8.07 (1H, dd, J=2.4, 8.6 Hz), 8.27 (1H, d, J=2.4 Hz), 11.65 (1H, brs)

ESI (LC-MS positive mode) m/z 488 (M+H).

Example 2-10

7-[5-(4-Hydroxypiperidine-1-carbonyl)-2-oxooxazolidin-3-yl]-3-(2-trifluoromethylphenyl)-2H-isoquinolin-1-one

[Formula 105]

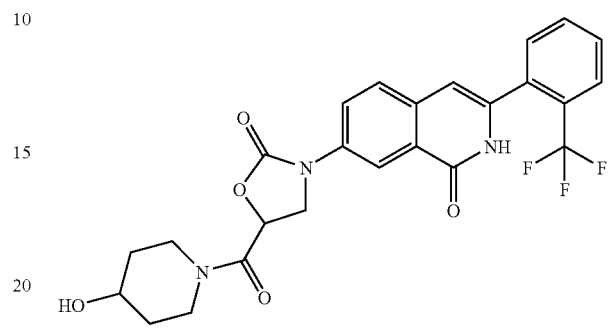

¹H-NMR (270 MHz, CDCl₃) δ (ppm): 1.56-1.70 (2H, m), 1.71-2.03 (3H, m), 3.18-3.40 (1H, m), 3.46-3.61 (1H, m), 3.79-4.16 (3H, m), 4.22 (1H, t, J=9.1 Hz), 4.89 (1H, dt, J=6.1, 8.8 Hz), 5.32 (1H, ddd, J=2.1, 5.7, 8.7 Hz), 6.51 (1H, s), 7.55-7.71 (4H, m), 7.78-7.83 (1H, m), 8.06-8.09 (1H, m), 8.47 (1H, dt, J=8.9, 2.6 Hz), 8.97 (1H, brs)

ESI (LC-MS positive mode) m/z 502 (M+H).

Example 2-11

7-[(S)-5-(1-Hydroxy-1-methylethyl)-2-oxooxazolidin-3-yl]-3-(2-trifluoromethylphenyl)-2H-isoquinolin-1-one Step A Methyl(S)-2-oxo-3-[1-oxo-3-(2-trifluoromethylphenyl)-1,2-dihydroisoquinolin-7-yl]oxazolidine-5-carboxylate

[Formula 106]

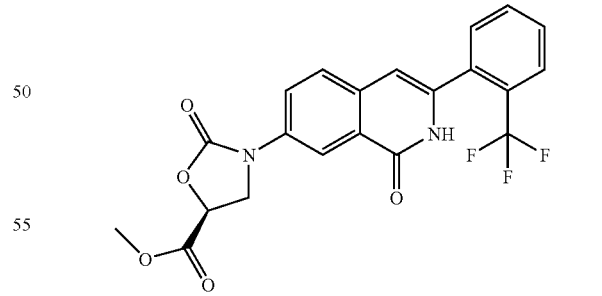

Using (S)-methyl glycidate, the captioned compound was synthesized by a method similar to that of Example 2-1.

¹H-NMR (270 MHz, CDCl₃) δ (ppm): 3.90 (3H, s), 4.31 (1H, dd, J=5.3, 9.6 Hz), 4.44 (1H, t, J=9.6 Hz), 5.14 (1H, dd, J=5.3, 9.6 Hz), 6.52 (1H, s), 7.25-7.72 (4H, m), 7.80-7.84 (1H, m), 7.93 (1H, d, J=2.5 Hz), 8.52 (1H, dd, J=2.5, 8.9 Hz), 8.81 (1H, brs)

ESI (LC-MS positive mode) m/z 433 (M+H).

Step B

7-[(S)-5-(1-Hydroxy-1-methylethyl)-2-oxooxazolidin-3-yl]-3-(2-trifluoromethylphenyl)-2H-isoquinolin-1-one

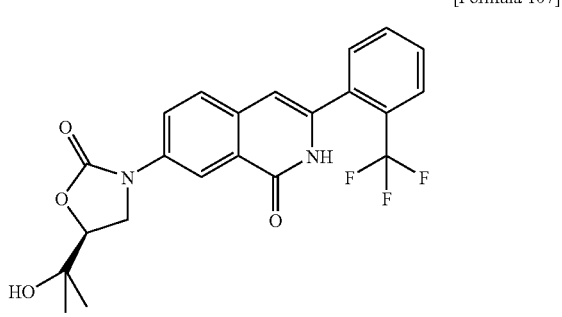

[Formula 107]

The (S)-2-oxo-3-[1-oxo-3-(2-trifluoromethylphenyl)-1,2-dihydroisoquinolin-7-yl]oxazolidin-5-carboxylic acid methyl (400 mg, 0.925 mmol) obtained in step A was dissolved in THF (4.6 ml). A 3 M methylmagnesium bromide THF solution (1.08 ml, 3.24 mmol) was added to the solution at −78° C., and the mixture was then stirred at 0° C. for 30 minutes. Thereafter, a saturated ammonium chloride aqueous solution was added to the reaction solution, and the mixture was then extracted with ethyl acetate. The extract was washed with a saturated saline solution, and was then dried over anhydrous sodium sulfate. Thereafter, the solvent was distilled away under reduced pressure. The obtained residue was purified by silica gel column chromatography (ethyl acetate:hexane=4:1), so as to obtain 7-[(S)-5-(1-hydroxy-1-methylethyl)-2-oxooxazolidin-3-yl]-3-(2-trifluoromethylphenyl)-2H-isoquinolin-1-one (205.1 mg, 51%) in the form of a colorless foaming substance.

$^1$H-NMR (270 MHz, CDCl$_3$) δ (ppm): 1.30 (3H, s), 1.43 (3H, s), 4.09 (1H, t, J=9.1 Hz), 4.23 (1H, dd, J=7.4, 8.9 Hz), 4.50 (1H, dd, J=7.4, 9.0 Hz), 6.52 (1H, s), 7.54-7.72 (5H, m), 7.80-7.85 (1H, m), 7.94 (1H, d, J=2.5 Hz), 8.57 (1H, dd, J=2.6, 8.8 Hz), 8.59 (1H, brs)

ESI (LC-MS positive mode) m/z 433 (M+H).

Example 2-12

7-[(R)-5-(1-Hydroxy-1-methylethyl)-2-oxooxazolidin-3-yl]-3-(2-trifluoromethylphenyl)-2H-isoquinolin-1-one Step A Methyl(R)-2-oxo-3-[1-oxo-3-(2-trifluoromethylphenyl)-1,2-dihydroisoquinolin-7-yl]oxazolidine-5-carboxylate

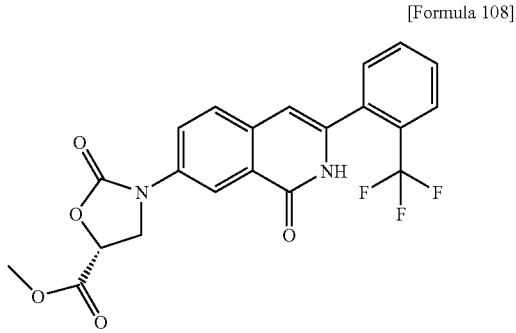

[Formula 108]

Using (R)-methyl glycidate, the captioned compound was synthesized by a method similar to that of Example 2-1.

ESI (LC-MS positive mode) m/z 433 (M+H).

Step B

7-[(R)-5-(1-Hydroxy-1-methylethyl)-2-oxooxazolidin-3-yl]-3-(2-trifluoromethylphenyl)-2H-isoquinolin-1-one

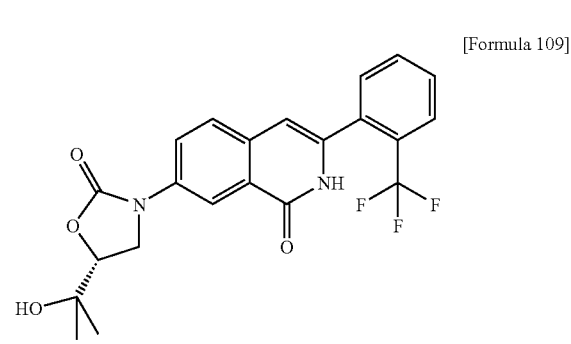

[Formula 109]

The captioned compound was synthesized by a method similar to step B of Example 2-11.

$^1$H-NMR (270 MHz, CDCl$_3$) δ (ppm): 1.29 (3H, s), 1.41 (3H, s), 3.61 (1H, brs), 4.03 (1H, t, J=9.1 Hz), 4.26 (1H, t, J=8.9 Hz), 4.49 (1H, t, J=8.4 Hz), 6.48 (1H, s), 7.43 (1H, d, J=8.9 Hz), 7.54-7.68 (3H, m), 7.76 (1H, d, J=7.7 Hz), 7.83 (1H, d, J=2.0), 8.40 (1H, dd, J=2.0, 8.8 Hz), 9.52 (1H, brs)

ESI (LC-MS positive mode) m/z 433 (M+H).

Example 2-13

(S)-2-Oxo-3-[1-oxo-3-(2-trifluoromethylphenyl)-1,2-dihydroisoquinolin-7-yl]oxazolidine-5-carboxylic acid amide Step A (S)-2-Oxo-3-[1-oxo-3-(2-trifluoromethylphenyl)-1,2-dihydroisoquinolin-7-yl]oxazolidine-5-carboxylic acid

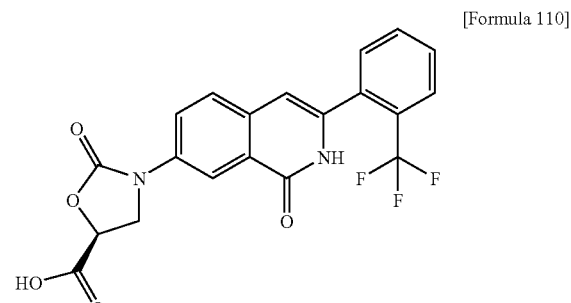

[Formula 110]

Using the (S)-2-oxo-3-[1-oxo-3-(2-trifluoromethylphenyl)-1,2-dihydroisoquinolin-7yl]oxazolidin-5-carboxylic acid methyl obtained in step A of Example 2-11 as a raw material, the captioned compound was prepared by a method similar to that of Example 2-4.

¹H-NMR (270 MHz, DMSO-d₆) δ (ppm): 4.24 (1H, dd, J=5.3, 9.8 Hz), 4.50 (1H, t, J=9.5 Hz), 5.26 (1H, dd, J=5.4, 9.2 Hz), 6.50 (1H, s), 7.62-7.90 (5H, m), 8.01 (1H, dd, J=2.5, 8.7 Hz), 8.30 (1H, d, J=2.5 Hz), 11.64 (1H, brs), 13.64 (1H, brs)
ESI (LC-MS positive mode) m/z 419 (M+H).

Step B (S)-2-Oxo-3-[1-oxo-3-(2-trifluoromethylphenyl)-1,2-dihydroisoquinolin-7-yl]oxazolidine-5-carboxylic acid amide

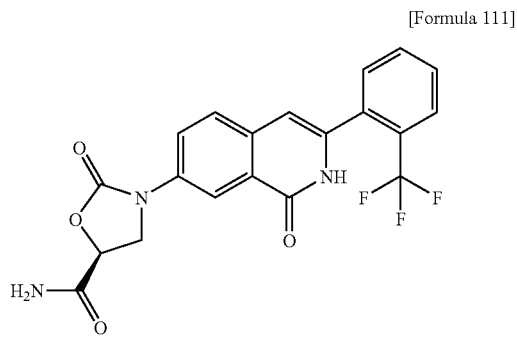

[Formula 111]

Using the (S)-2-oxo-3-[1-oxo-3-(2-trifluoromethylphenyl)-1,2-dihydroisoquinolin-7-yl]oxazolidin-5-carboxylic acid obtained in step A as a synthetic material, the captioned compound was synthesized by a method similar to that of Example 2-5.

¹H-NMR (270 MHz, DMSO-d₆) δ (ppm): 4.12 (1H, dd, J=5.8, 9.0 Hz), 4.42 (1H, t, J=9.3 Hz), 5.08 (1H, dd, J=5.8, 9.3 Hz), 6.50 (1H, s), 7.60-7.83 (6H, m), 7.84-7.94 (1H, m), 8.01 (1H, dd, J=2.5, 8.7 Hz), 8.32 (1H, d, J=2.6 Hz), 11.63 (1H, brs)
ESI (LC-MS positive mode) m/z 418 (M+H).

Example 2-14

(R)-2-Oxo-3-[1-oxo-3-(2-trifluoromethylphenyl)-1,2-dihydroisoquinolin-7-yl]oxazolidine-5-carboxylic acid amide Step A (R)-2-Oxo-3-[1-oxo-3-(2-trifluoromethylphenyl)-1,2-dihydroisoquinolin-7-yl]oxazolidine-5-carboxylic acid

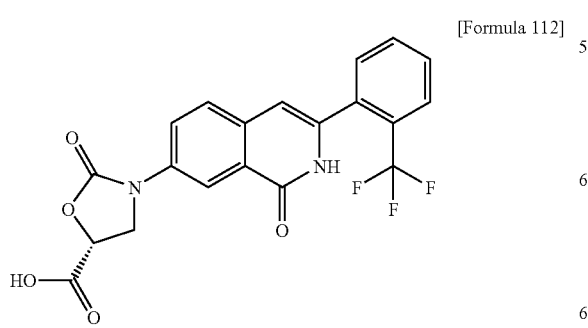

[Formula 112]

Using the (R)-2-oxo-3-[1-oxo-3-(2-trifluoromethylphenyl)-1,2-dihydroisoquinolin-7-yl]oxazolidin-5-carboxylic acid methyl obtained in step A of Example 2-12 as a raw material, the captioned compound was prepared by a method similar to that of Example 2-4.

¹H-NMR (270 MHz, DMSO-d₆) δ (ppm): 4.24 (1H, dd, J=5.4, 9.2 Hz), 4.50 (1H, t, J=9.5 Hz), 5.25 (1H, dd, J=5.4, 9.7 Hz), 6.50 (1H, s), 7.62-7.90 (5H, m), 8.01 (1H, dd, J=2.5, 8.8 Hz), 8.30 (1H, d, J=2.3 Hz), 11.63 (1H, brs), 13.64 (1H, brs)
ESI (LC-MS positive mode) m/z 419 (M+H).

Step B (R)-2-Oxo-3-[1-oxo-3-(2-trifluoromethylphenyl)-1,2-dihydroisoquinolin-7-yl]oxazolidine-5-carboxylic acid amide

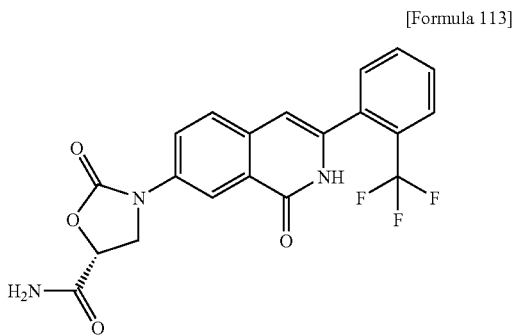

[Formula 113]

Using the (R)-2-oxo-3-[1-oxo-3-(2-trifluoromethylphenyl)-1,2-dihydroisoquinolin-7-yl]oxazolidin-5-carboxylic acid obtained in step A as a synthetic material, the captioned compound was synthesized by a method similar to that of Example 2-5.

¹H-NMR (270 MHz, DMSO-d₆) δ (ppm): 4.14 (1H, dd, J=6.0, 8.6 Hz), 4.44 (1H, t, J=9.3 Hz), 5.10 (1H, dd, J=6.0, 9.3 Hz), 6.50 (1H, s), 7.63-7.92 (5H, m), 8.02 (1H, dd, J=1.5, 8.7 Hz), 8.33 (1H, d, J=1.5 Hz), 11.65 (1H, brs)
ESI (LC-MS positive mode) m/z 418 (M+H).

Example 2-15

7-[(S)-5-(4-Hydroxypiperidine-1-carbonyl)-2-oxooxazolidin-3-yl]-3-(2-trifluoromethylphenyl)-2H-isoquinolin-1-one

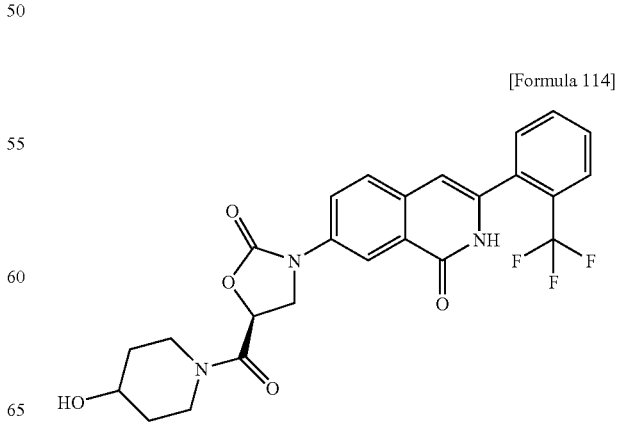

[Formula 114]

Using the (S)-2-oxo-3-[1-oxo-3-(2-trifluoromethylphenyl)-1,2-dihydroisoquinolin-7-yl]oxazolidin-5-carboxylic acid obtained in step A of Example 2-13 as a raw material, the captioned compound was synthesized by a method similar to that of Example 2-5.

$^{1}$H-NMR (270 MHz, DMSO-d$_{6}$) δ (ppm): 1.30-1.60 (2H, m), 1.70-1.90 (2H, m), 3.00-3.40 (2H, m), 3.70-4.00 (3H, m), 4.25-4.34 (1H, m), 4.35-4.45 (1H, m), 4.78 (1H, d, J=4.0 Hz), 5.62-5.75 (1H, m), 6.50 (1H, s), 7.60-7.83 (4H, m), 7.84-7.91 (1H, m), 8.00-8.10 (1H, m), 8.27 (1H, dd, J=2.3, 6.1 Hz), 11.63 (1H, brs)

ESI (LC-MS positive mode) m/z 502 (M+H).

Example 2-16

7-[(R)-5-(4-Hydroxypiperidine-1-carbonyl)-2-oxooxazolidin-3-yl]-3-(2-trifluoromethylphenyl)-2H-isoquinolin-1-one

[Formula 115]

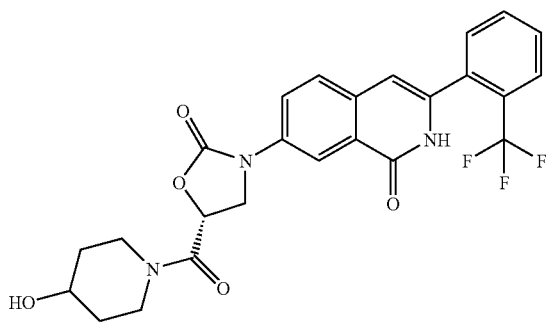

Using the (R)-2-oxo-3-[1-oxo-3-(2-trifluoromethylphenyl)-1,2-dihydroisoquinolin-7-yl]oxazolidin-5-carboxylic acid obtained in step A of Example 2-14 as a raw material, the captioned compound was synthesized by a method similar to that of Example 2-5.

$^{1}$H-NMR (270 MHz, DMSO-d$_{6}$) δ (ppm): 1.33-1.47 (2H, m), 1.75-1.87 (2H, m), 3.73-3.76 (1H, m), 4.11 (4H, dd, J=0.8, 5.3 Hz), 4.14-4.44 (2H, m), 4.83 (1H, d, J=3.8 Hz), 5.69 (1H, dd, J=5.3, 8.6 Hz), 6.50 (1H, s), 7.63-7.81 (4H, m), 7.87 (1H, d, J=7.6 Hz), 8.07 (1H, d, 8.7 Hz), 8.27 (1H, d, 4.0 Hz), 11.65 (1H, brs)

ESI (LC-MS positive mode) m/z 502 (M+H).

Example 2-17

7-[(R)-5-(2-Methoxyethoxymethyl)-2-oxooxazolidin-3-yl]-3-(2-trifluoromethylphenyl)-2H-isoquinolin-1-one

[Formula 116]

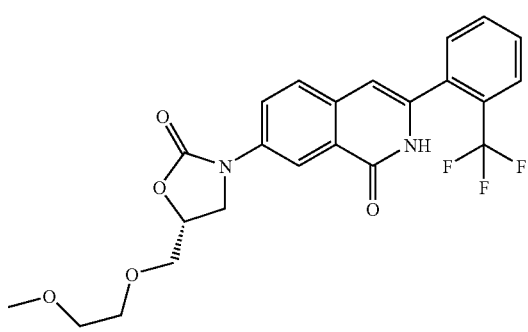

Sodium hydride (7.5 mg, 0.18 mmol) was added to a DMF solution (0.5 ml) that contained 2-methoxymethanol (14.2 mg, 0.18 mmol) under cooling on ice, and the obtained mixture was then stirred at 0° C. for 30 minutes. The methanesulfonic acid (R)-2-oxo-3-[1-oxo-3-(2-trifluoromethylphenyl)-1,2-dihydroisoquinolin-7-yl]oxazolidin-5-ylmethyl (30.0 mg, 0.06 mmol) obtained in step A of Example 2-22 was added to this reaction solution under cooling on ice, and the obtained mixture was then stirred at 0° C. for 30 minutes. Thereafter, water was added to the reaction solution, and the mixture was then extracted with methylene chloride. The extract was washed with water and a saturated saline solution, and was then dried over anhydrous magnesium sulfate. Thereafter, the solvent distilled away under reduced pressure. The obtained residue was purified by silica gel column chromatography (methylene chloride:methanol=40:1), so as to obtain 7-[(R)-5-(2-methoxyethoxymethyl)-2-oxooxazolidin-3-yl]-3-(2-trifluoromethylphenyl)-2H-isoquinolin-1-one (3.1 mg, 11%) in the form of a colorless solid.

$^{1}$H-NMR (300 MHz, DMSO-d$_{6}$) δ (ppm): 3.23 (3H, s) 3.45-3.55 (2H, m), 3.60-3.80 (4H, m), 3.90-4.00 (1H, m), 4.20-4.30 (1H, m), 4.80-5.00 (1H, m), 6.48 (1H, s), 7.60-7.90 (5H, m), 8.07 (1H, d, J=8.5 Hz), 8.23 (1H, s), 11.59 (1H, brs)

ESI (LC-MS positive mode) m/z 463 (M+H).

The following compounds (Examples 2-18 to 2-20) were synthesized by a reaction similar to that of Example 2-17.

Example 2-18

7-((R)-5-Methoxymethyl-2-oxooxazolidin-3-yl)-3-(2-trifluoromethylphenyl)-2H-isoquinolin-1-one

[Formula 117]

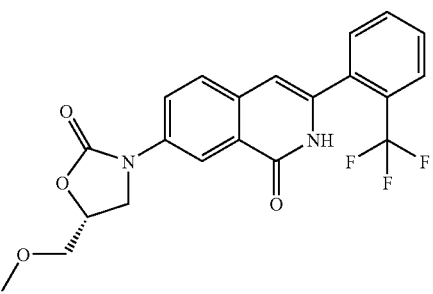

$^{1}$H-NMR (300 MHz, CDCl$_{3}$) δ (ppm): 3.45 (3H, s), 3.68-3.74 (2H, m), 4.10 (1H, t, J=6.0 Hz), 4.20 (1H, t, J=8.9 Hz), 4.75-4.90 (1H, m), 6.52 (1H, s), 7.5307.70 (4H, m), 7.82 (1H, d, J=7.5 Hz), 7.94 (1H, d, J=2.4 Hz), 8.60 (1H, brs), 8.62 (1H, dd, J=2.4, 8.8 Hz)

ESI (LC-MS positive mode) m/z 419 (M+H).

Example 2-19

7-{(R)-5-[2-(2-Methoxyethoxy)ethoxymethyl]-2-oxooxazolidin-3-yl}-3-(2-trifluoromethylphenyl)-2H-isoquinolin-1-one

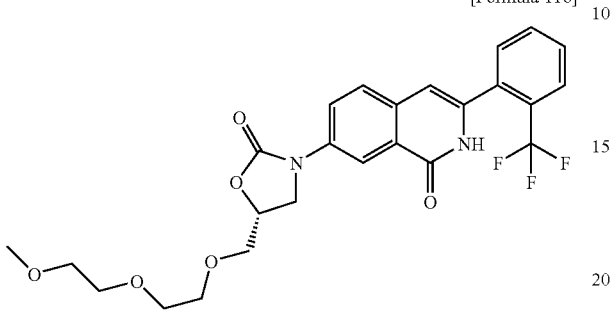

[Formula 118]

¹H-NMR (300 MHz, DMSO-d₆) δ (ppm): 2.52-2.56 (1H, m), 2.75 (1H, t, J=4.3 Hz), 3.19-3.25 (4H, m), 3.36-3.41 (2H, m), 3.46-3.50 (2H, m), 3.56-3.61 (2H, m), 3.63 (1H, dd, J=6.2, 15.2 Hz), 4.04 (1H, dd, J=3.6, 15.1 Hz), 4.17-4.22 (2H, m), 6.50 (1H, s), 7.60-7.89 (6H, m), 8.12 (1H, s), 11.63 (1H, brs)

ESI (LC-MS positive mode) m/z 507 (M+H).

Example 2-20

7-[(R)-5-(2-Morpholin-4-ylethoxymethyl)-2-oxooxazolidin-3-yl]-3-(2-trifluoromethylphenyl)-2H-isoquinolin-1-one

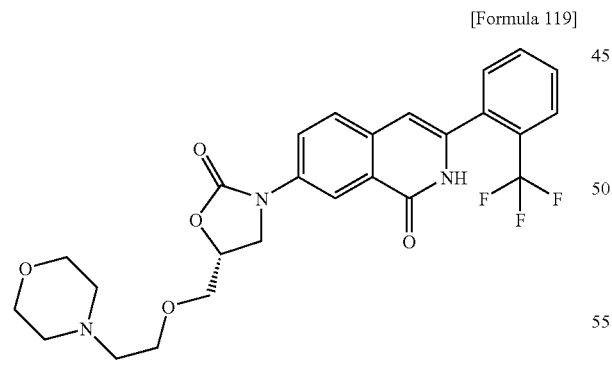

[Formula 119]

¹H-NMR (300 MHz, DMSO-d₆) δ (ppm): 2.32-2.37 (4H, m), 2.53-2.56 (3H, m), 2.75 (1H, t, J=4.6 Hz), 3.21-3.26 (1H, m), 3.48-3.53 (4H, m), 3.63 (1H, dd, J=6.1, 14.7 Hz), 4.03 (1H, dd, J=3.5, 15.0 Hz), 4.15-4.21 (2H, m), 6.50 (1H, s), 7.60-7.81 (5H, m), 7.88 (1H, d, J=8.7 Hz), 8.12 (1H, s), 11.62 (1H, brs)

ESI (LC-MS positive mode) m/z 518 (M+H).

Example 2-21

7-((R)-5-Benzyloxymethyl-2-oxooxazolidin-3-yl)-3-(2-trifluoromethylphenyl)-2H-isoquinolin-1-one

Step A 7-((R)-3-Benzyloxy-2-hydroxypropylamino)-3-(2-trifluoromethylphenyl)-2H-isoquinolin-1-one

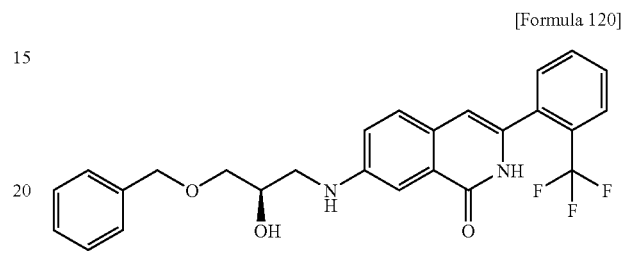

[Formula 120]

Using the 7-amino-3-(2-trifluoromethylphenyl)-2H-isoquinolin-1-one obtained in step C of Example 1-1 and (R)—benzyl glycidyl ether as raw materials, the captioned compound was synthesized by a reaction similar to step A of Example 2-1.

¹H-NMR (270 MHz, CDCl₃) δ (ppm): 2.55 (1H, brs), 3.29 (1H, dd, J=7.4, 12.8 Hz), 3.45 (1H, dd, J=4.0, 12.9 Hz), 3.56 (1H, dd, J=6.3, 9.6 Hz), 3.66 (1H, dd, J=3.7, 9.5 Hz), 4.08-4.18 (1H, m), 4.59 (2H, s), 6.43 (1H, s), 7.03 (1H, dd, J=2.6, 8.5 Hz), 7.27-7.41 (6H, m), 7.49-7.67 (4H, m), 7.77-7.82 (1H, m), 8.37 (1H, brs)

ESI (LC-MS positive mode) m/z 469 (M+H).

Step B 7-((R)-5-Benzyloxymethyl-2-oxooxazolidin-3-yl)-3-(2-trifluoromethylphenyl)-2H-isoquinolin-1-one

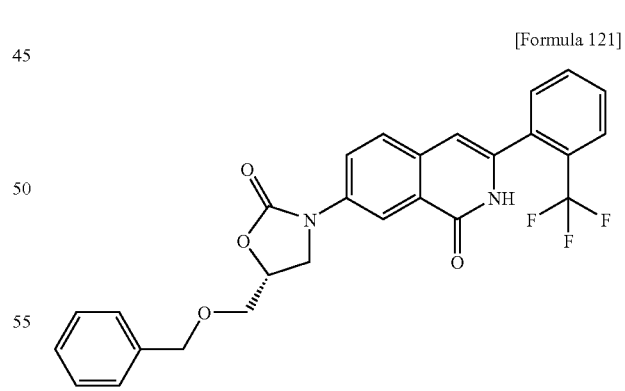

[Formula 121]

Using the 7-((R)-3-benzyloxy-2-hydroxypropylamino)-3-(2-trifluoromethylphenyl)-2H-isoquinolin-1-one obtained in step A as a raw material, the captioned compound was synthesized by a reaction similar to step B of Example 2-1.

¹H-NMR (270 MHz, CDCl₃) δ (ppm): 3.73 (1H, dd, J=4.3, 10.6 Hz), 3.78 (1H, dd, J=4.5, 10.6 Hz), 4.07 (1H, dd, J=6.3, 9.2 Hz), 4.19 (1H, t, J=8.9 Hz), 4.60 (1H, d, J=12.0 Hz), 4.66 (1H, d, J=12.0 Hz), 4.79-4.89 (1H, m), 6.52 (1H, s), 7.27-7.39

(5H, m), 7.54-7.69 (4H, m), 7.77-7.82 (1H, m), 7.90 (1H, d, J=2.5 Hz), 8.58 (1H, dd, J=2.5, 8.9 Hz), 9.08 (1H, brs)
ESI (LC-MS positive mode) m/z 495 (M+H).

Example 2-22

7-[(S)-2-Oxo-5-(piperidin-1-ylmethyl)oxazolidin-3-yl]-3-(2-trifluoromethylphenyl)-2H-isoquinolin-1-one Step A (R)-2-Oxo-3-[1-oxo-3-(2-trifluoromethylphenyl)-1,2-dihydroisoquinolin-7-yl]oxazolidin-5-ylmethyl methanesulfonate

[Formula 122]

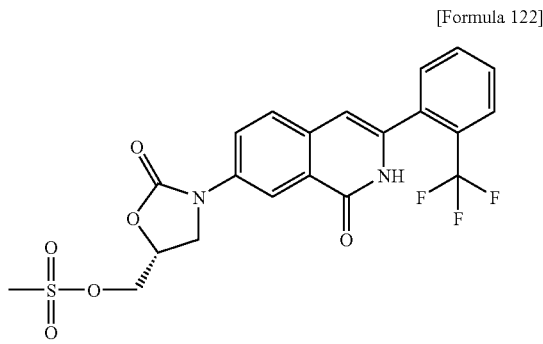

Using the 7-((R)-5-hydroxymethyl-2-oxooxazolidin-3-yl)-3-(2-trifluoromethylphenyl)-2H-isoquinolin-1-one obtained in step B of Example 1-14 as a raw material, the captioned compound was synthesized by a method similar to step C of Example 1-30.
$^1$H-NMR (270 MHz, CDCl$_3$) δ (ppm): 3.13 (3H, s), 4.11 (1H, dd, J=5.6, 8.9 Hz), 4.33 (1H, t, J=9.2 Hz), 4.47 (1H, dd, J=4.5, 11.5 Hz), 4.55 (1H, dd, J=3.9, 11.6 Hz), 4.92-5.08 (1H, m), 6.53 (1H, s), 7.54-7.74 (4H, m), 7.80-7.88 (1H, m), 7.98 (1H, d, J=2.6 Hz), 8.47 (1H, brs), 8.53 (1H, dd, J=2.5, 8.9 Hz)
ESI (LC-MS positive mode) m/z 483 (M+H).

Step B

7-[(S)-2-Oxo-5-(piperidin-1-ylmethyl)oxazolidin-3-yl]-3-(2-trifluoromethylphenyl)-2H-isoquinolin-1-one

[Formula 123]

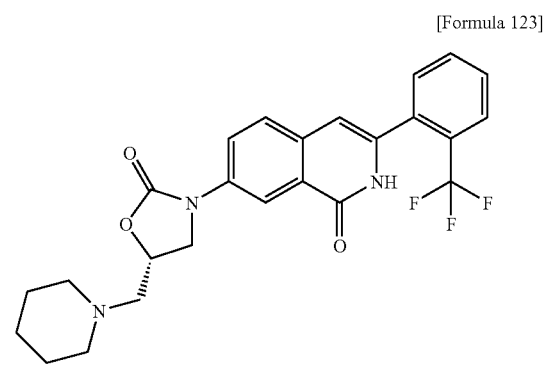

The methanesulfonic acid (R)-2-oxo-3-[1-oxo-3-(2-trifluoromethylphenyl)-1,2-dihydroisoquinolin-7-yl]oxazolidin-5-ylmethyl(20 mg, 0.0415 mmol) obtained in step A was dissolved in acetonitrile (0.1 ml). Thereafter, piperidine (8.2 μl) was added to the solution, and the obtained mixture was stirred under heating to reflux for 12 hours. Thereafter, the reaction solution was concentrated, and the obtained residue was then purified by silica gel column chromatography (methylene chloride:methanol=30:1), so as to obtain 7-((S)-2-oxo-5-piperidin-1-ylmethyloxazolidin-3-yl)-3-(2-trifluoromethylphenyl)-2H-isoquinolin-1-one (14.3 mg, 73%) in the form of a colorless amorphous substance.
$^1$H-NMR (270 MHz, CD$_3$OD) δ (ppm): 1.44-1.54 (2H, m), 1.56-1.69 (4H, m), 2.55-2.65 (4H, m), 2.70-2.80 (2H, m), 3.93 (1H, dd, J=7.3, 8.9 Hz), 4.30 (1H, t, J=8.9 Hz), 4.90-4.99 (1H, m), 6.60 (1H, s), 7.58-7.77 (4H, m), 7.82-7.88 (1H, m), 8.23 (1H, d, J=2.4 Hz), 8.27 (1H, dd, J=2.4, 8.6 Hz)
ESI (LC-MS positive mode) m/z 472 (M+H).

The following compounds (Examples 2-23 to 2-30) were synthesized by a method similar to that of Example 2-22.

Example 2-23

7-[(S)-5-((S)-2-Hydroxymethylpyrrolidin-1-ylmethyl)-2-oxooxazolidin-3-yl]-3-(2-trifluoromethylphenyl)-2H-isoquinolin-1-one

[Formula 124]

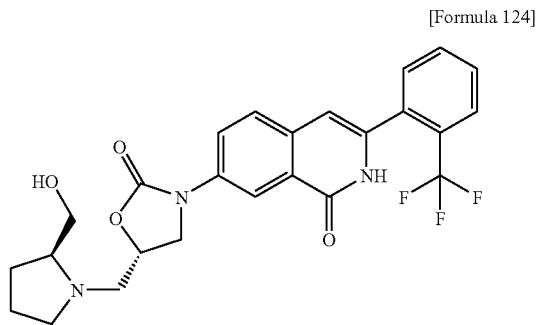

$^1$H-NMR (500 MHz, CDCl$_3$) δ (ppm): 1.66-1.91 (5H, m), (1H, q, J=8.4 Hz), 2.76-2.81 (1H, m), 2.83 (1H, dd, J=4.0, 13.8 Hz), 3.21 (1H, dd, J=6.5, 13.8 Hz), 3.24-3.28 (1H, m), 3.45 (1H, dd, J=3.8, 10.9 Hz), 3.65 (1H, dd, J=3.7, 10.9 Hz), 4.00 (1H, t, J=8.0 Hz), 4.16 (1H, t, J=8.8 Hz), 4.80-4.86 (1H, m), 6.49 (1H, s), 7.54-7.67 (4H, m), 7.78 (1H, d, J=8.2 Hz), 7.87 (1H, d, J=2.1 Hz), 8.52 (1H, dd, J=2.4, 8.8 Hz), 9.29 (1H, brs)
ESI (LC-MS positive mode) m/z 488 (M+H).

Example 2-24

7-[(S)-5-((S)-(3-Hydroxypiperidin-1-yl)methyl)-2-oxooxazolidin-3-yl]-3-(2-trifluoromethylphenyl)-2H-isoquinolin-1-one

[Formula 125]

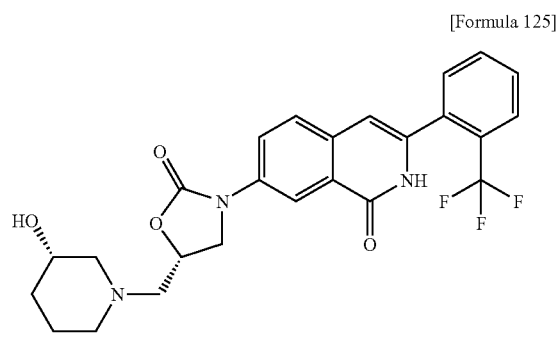

¹H-NMR (500 MHz, CDCl₃) δ (ppm): 1.48-1.59 (2H, m), 1.60-1.72 (1H, m), 1.76-1.83 (1H, m), 2.40-2.50 (4H, m), 2.58-2.83 (3H, m), 3.79-3.81 (1H, m), 3.92 (1H, dd, J=7.1, 8.9 Hz), 4.20 (1H, t, J=8.8 Hz), 4.80-4.87 (1H, m), 6.51 (1H, s), 7.55-7.68 (4H, m), 7.80 (1H, d, J=7.8 Hz), 7.90 (1H, d, J=2.3 Hz), 8.55 (1H, dd, J=2.5, 8.8 Hz), 9.08 (1H, brs)

ESI (LC-MS positive mode) m/z 488 (M+H).

Example 2-25

7-[(S)-5-((R)-3-Hydroxypiperidin-1-ylmethyl)-2-oxooxazolidin-3-yl]-3-(2-trifluoromethylphenyl)-2H-isoquinolin-1-one

[Formula 126]

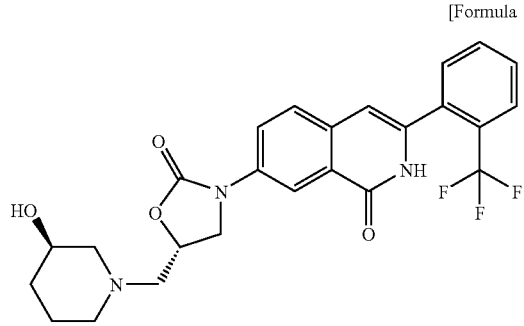

¹H-NMR (500 MHz, CDCl₃) δ (ppm): 1.50-1.61 (2H, m), 1.62-1.70 (1H, m), 1.78-1.86 (1H, m), 2.50-2.64 (4H, m), 2.65-2.70 (1H, m), 2.74 (1H, dd, J=5.8, 13.6 Hz), 2.83 (1H, dd, J=5.7, 13.6 Hz), 3.82-3.84 (1H, m), 3.96 (1H, dd, J=7.0, 8.8 Hz), 4.22 (1H, t, J=8.8 Hz), 4.78-4.86 (1H, m), 6.53 (1H, s), 7.54-7.70 (4H, m), 7.82 (1H, d, J=7.8 Hz), 7.93 (1H, s), 8.60-8.63 (2H, m)

ESI (LC-MS positive mode) m/z 488 (M+H).

Example 2-26

7-[(S)-5-((R)-(2-Hydroxymethylpyrrolidin-1-yl)methyl)-2-oxooxazolidin-3-yl]-3-(2-trifluoromethylphenyl)-2H-isoquinolin-1-one

[Formula 127]

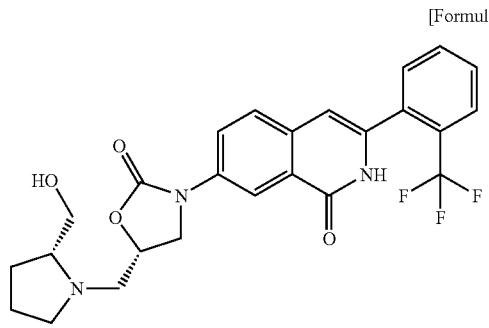

¹H-NMR (500 MHz, CDCl₃) δ (ppm): 1.68-1.91 (5H, m), (1H, q, J=8.4 Hz), 2.72-2.76 (1H, m), 2.83 (1H, dd, J=6.3, 13.0 Hz), 3.14 (1H, dd, J=6.2, 13.1 Hz), 3.24-3.28 (1H, m), 3.46 (1H, dd, J=3.1, 11.4 Hz), 3.65 (1H, dd, J=3.6, 11.0 Hz), 3.93 (1H, t, J=8.0 Hz), 4.23 (1H, t, J=8.9 Hz), 4.78-4.84 (1H, m), 6.49 (1H, s), 7.54-7.67 (4H, m), 7.79 (1H, d, J=7.8 Hz), 7.89 (1H, d, J=2.3 Hz), 8.51 (1H, dd, J=2.5, 8.8 Hz), 9.34 (1H, brs)

ESI (LC-MS positive mode) m/z 488 (M+H).

Example 2-27

7-[(S)-5-((4-Hydroxymethylpiperidin-1-yl)methyl)-2-oxooxazolidin-3-yl]-3-(2-trifluoromethylphenyl)-2H-isoquinolin-1-one

[Formula 128]

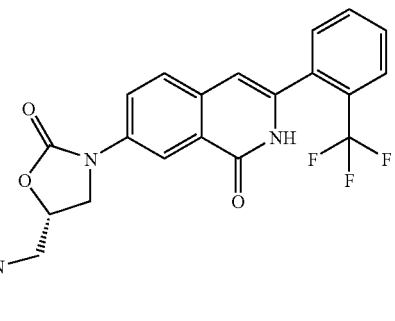

¹H-NMR (500 MHz, CDCl₃) δ (ppm): 1.20-1.40 (3H, m), 1.45-1.60 (1H, m), 1.65-1.80 (2H, m), 2.10-2.37 (2H, m), 2.70-2.90 (2H, m), 2.91-3.15 (2H, m), 3.51 (2H, d, J=6.3 Hz), 3.99 (1H, dd, J=7.1, 8.9 Hz), 4.21 (1H, t, J=8.9 Hz), 4.80-5.00 (1H, m), 6.53 (1H, s), 7.54-7.71 (4H, m), 7.83 (1H, d, J=7.4 Hz), 7.94 (1H, d, J=2.3 Hz), 8.63 (1H, dd, J=2.4, 8.8 Hz), 8.67 (1H, brs)

ESI (LC-MS positive mode) m/z 502 (M+H).

Example 2-28

7-[(S)-5-(4-Methoxypiperidin-1-ylmethyl)-2-oxooxazolidin-3-yl]-3-(2-trifluoromethylphenyl)-2H-isoquinolin-1-one

[Formula 129]

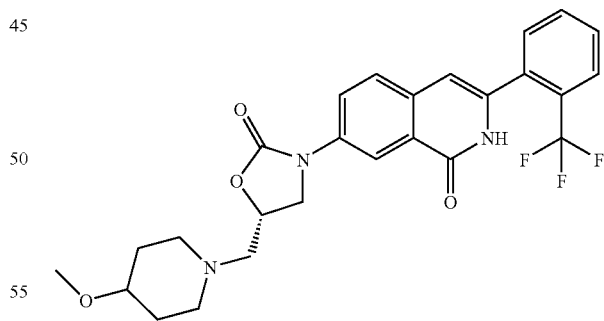

¹H-NMR (300 MHz, CDCl₃) δ (ppm): 1.50-1.70 (2H, m), 1.80-2.00 (2H, m), 2.33-2.40 (2H, m), 2.70-2.85 (4H, m), 3.20-3.30 (1H, m), 3.34 (3H, s), 2.98 (1H, dd, J=6.9, 9.1 Hz), 4.20 (1H, t, J=9.1 Hz), 4.75-4.90 (1H, m), 6.52 (1H, s), 7.50-7.70 (4H, m), 7.82 (1H, d, J=8.2 Hz), 7.92 (1H, d, J=2.5 Hz), 8.60 (1H, dd, J=2.6, 8.8 Hz), 8.86 (1H, brs)

ESI (LC-MS positive mode) m/z 502 (M+H).

Example 2-29

7-[(S)-(5-Morpholin-4-yl)methyl-2-oxooxazolidin-3-yl]-3-(2-trifluoromethylphenyl)-2H-isoquinolin-1-one

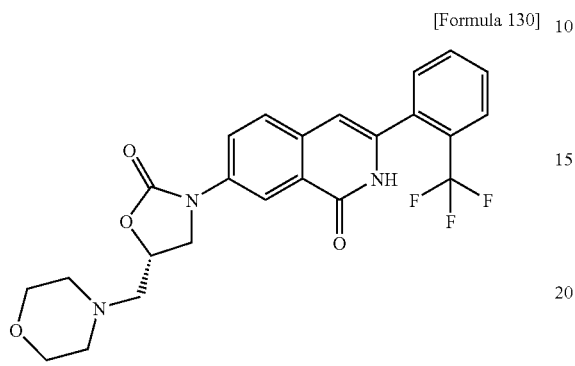

[Formula 130]

¹H-NMR (270 MHz, CD₃OD) δ (ppm): 2.60-2.69 (4H, m), 2.76-2.83 (2H, m), 3.65-3.75 (4H, m), 3.98 (1H, dd, J=7.0, 9.2 Hz), 4.30 (1H, t, J=8.8 Hz), 4.88-5.01 (1H, m), 6.60 (1H, s) 7.59-7.78 (4H, m), 7.83-7.87 (1H, m), 8.23 (1H, d, J=2.4 Hz), 8.28 (1H, dd, J=2.6, 8.8 Hz)

ESI (LC-MS positive mode) m/z 474 (M+H).

Example 2-30

7-{(S)-[(4-Hydroxypiperidin-1-yl)methyl]-2-oxooxazolidin-3-yl}-3-(2-trifluoromethylphenyl)-2H-isoquinolin-1-one

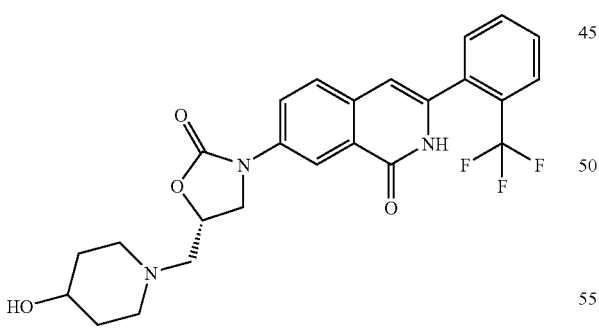

[Formula 131]

¹H-NMR (270 MHz, CD₃OD) δ (ppm): 1.54-1.66 (2H, m), 1.81-1.91 (2H, m), 2.31-2.43 (2H, m), 2.75-2.82 (2H, m), 2.83-3.00 (2H, m), 3.57-3.66 (1H, m), 3.94 (1H, dd, J=7.2, 9.0 Hz), 4.29 (1H, t, J=8.8 Hz), 4.86-4.99 (1H, m), 6.59 (1H, s), 7.58-7.76 (4H, m), 7.82-7.88 (1H, m), 8.23 (1H, d, J=2.7 Hz), 8.27 (1H, dd, J=2.4, 8.9 Hz)

ESI (LC-MS positive mode) m/z 488 (M+H).

Example 2-31

N-{(R)-2-Oxo-3-[1-oxo-3-(2-trifluoromethylphenyl)-1,2-dihydroisoquinolin-7-yl]oxazolidin-5-ylmethyl}methanesulfonamide Step A 7-((S)-5-Azidomethyl-2-oxooxazolidin-3-yl)-3-(2-trifluoromethylphenyl)-2H-isoquinolin-1-one

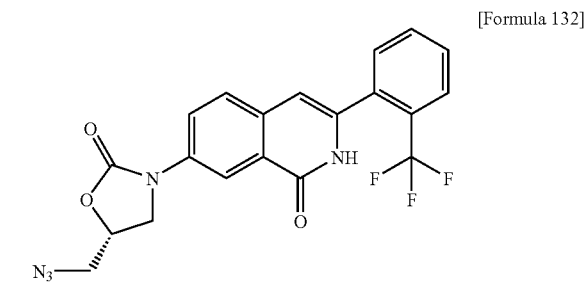

[Formula 132]

Using the methanesulfonic acid (R)-2-oxo-3-[1-oxo-3-(2-trifluoromethylphenyl)-1,2-dihydroisoquinolin-7-yl]oxazolidin-5-ylmethyl obtained in step A of Example 2-22 as a raw material, the captioned compound was synthesized by a reaction similar to step D of Example 1-30.

¹H-NMR (Bruker, 300 MHz, CDCl₃) δ: 3.64 (dd, J=4.21, 12.97 Hz, 1H), 3.75 (dd, J=4.25, 13.37 Hz, 1H), 4.02 (dd, J=6.21, 9.13 Hz, 1H), 4.23 (t, J=9.09 Hz, 1H), 4.81-4.89 (m, 1H), 6.52 (s, 1H), 7.53-7.69 (m, 4H), 7.81 (d, J=7.76 Hz, 1H), 7.93 (d, J=2.28 Hz, 1H), 8.56 (dd, J=2.38, 8.80 Hz, 1H), 9.09 (brs, 1H).

Step B 7-((S)-5-Aminomethyl-2-oxooxazolidin-3-yl)-3-(2-trifluoromethylphenyl)-2H-isoquinolin-1-one

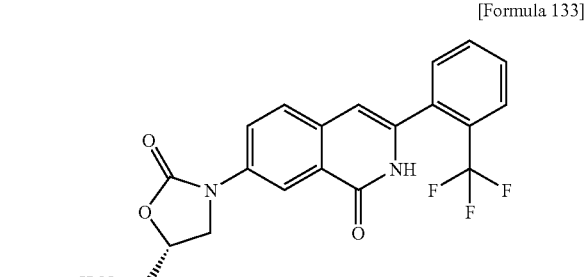

[Formula 133]

Using the 7-((S)-5-azidomethyl-2-oxooxazolidin-3-yl)-3-(2-trifluoromethylphenyl)-2H-isoquinolin-1-one prepared in step A as a raw material, the captioned compound was synthesized by a reaction similar to that of Example 1-31.

¹H-NMR (Bruker, 300 MHz, CDCl₃) δ: 1.51 (brs, 2H), 3.02 (dd, J=5.66, 13.68 Hz, 1H), 3.16 (dd, J=3.91, 13.90 Hz, 1H), 4.03 (dd, J=6.85, 8.79 Hz, 1H), 4.19 (t, J=9.24 Hz, 1H), 4.70-4.78 (m, 1H), 6.50 (s, 1H), 7.54-7.70 (m, 4H), 7.82 (d, J=7.21 Hz, 1H), 7.94 (d, J=2.34 Hz, 1H), 8.60 (dd, J=2.62, 9.14 Hz, 1H), 8.64 (brs, 1H).

Step C

N-{(R)-2-Oxo-3-[1-oxo-3-(2-trifluoromethylphenyl)-1,2-dihydroisoquinolin-7-yl]oxazolidin-5-ylmethyl}methanesulfonamide

[Formula 134]

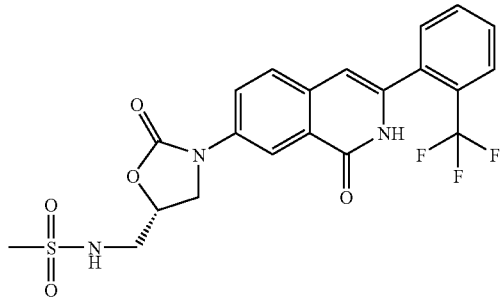

The 7-((S)-5-aminomethyl-2-oxooxazolidin-3-yl)-3-(2-trifluoromethylphenyl)-2H-isoquinolin-1-one (30 mg, 0.07 mmol) obtained in step B was dissolved in methylene chloride (0.3 ml). Thereafter, pyridine (30 μl, 0.37 mmol) and methanesulfonyl chloride (5.8 μl, 0.07 mmol) were added to the solution, and the obtained mixture was stirred at 0° C. for 30 minutes. Thereafter, water was added to the reaction solution, and the mixture was then extracted with methylene chloride. The extract was washed with water and a saturated saline solution, and was then dried over magnesium sulfate. Thereafter, the solvent was distilled away under reduced pressure. The obtained residue was purified by silica gel column chromatography (methylene chloride:methanol=20:1), so as to obtain N-{(R)-2-oxo-3-[1-oxo-3-(2-trifluoromethylphenyl)-1,2-dihydroisoquinolin-7-yl]oxazolidin-5-ylmethyl}methanesulfonamide (12.6 mg, 36%) in the form of a colorless solid.

$^1$H-NMR (300 MHz, DMSO-$d_6$) δ (ppm): 2.96 (3H, s), 3.30-3.45 (2H, m), 3.97 (1H, dd, J=6.2, 9.1 Hz), 4.27 (1H, t, J=9.1 Hz), 4.75-4.87 (1H, m), 6.49 (1H, s), 7.63 (1H, d, J=7.6 Hz), 7.68-7.80 (3H, m), 7.87 (1H, d, J=7.7 Hz), 8.09 (1H, dd, J=2.4, 8.4 Hz), 8.22 (1H, d, J=2.4 Hz)

ESI (LC-MS positive mode) m/z 482 (M+H).

The following compounds (Examples 2-32 to 2-36) were synthesized by a reaction similar to that of Example 2-31.

Example 2-32

Ethanesulfonic acid {(R)-2-oxo-3-[1-oxo-3-(2-trifluoromethylphenyl)-1,2-dihydroisoquinolin-7-yl]oxazolidin-5-ylmethyl}amide

[Formula 135]

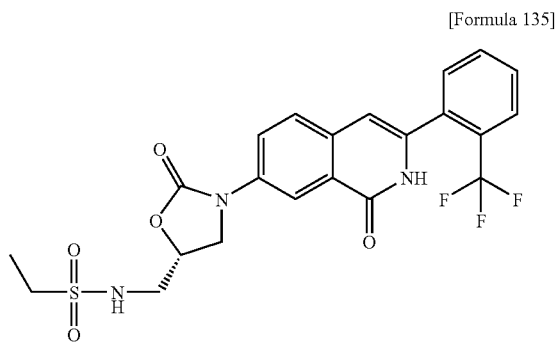

$^1$H-NMR (300 MHz, DMSO-$d_6$) δ (ppm): 1.20 (3H, t, J=7.4 Hz), 3.06 (2H, q, J=7.4 Hz), 3.30-3.50 (2H, m), 3.98 (1H, dd, J=6.4, 8.6 Hz), 4.26 (1H, t, J=8.6 Hz), 4.75-4.80 (1H, m), 6.48 (1H, s), 7.54 (1H, brs), 7.63 (1H, d, J=6.5 Hz), 7.64-7.80 (3H, m), 7.87 (1H, d, J=7.7 Hz), 8.07-8.11 (1H, m), 8.20 (1H, s), 11.60 (1H, brs)

ESI (LC-MS positive mode) m/z 496 (M+H).

Example 2-33

Propane-1-sulfonic acid {(R)-2-oxo-3-[1-oxo-3-(2-trifluoromethylphenyl)-1,2-dihydroisoquinolin-7-yl]oxazolidin-5-ylmethyl}amide

[Formula 136]

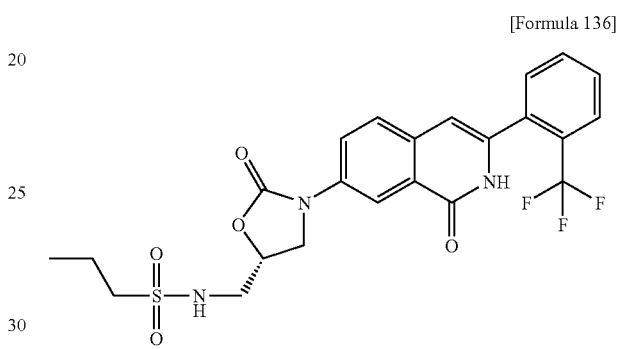

$^1$H-NMR (300 MHz, DMSO-$d_6$) δ (ppm): 0.97 (3H, t, J=7.5 Hz), 1.60-1.75 (2H, m), 3.00 (2H, t, J=7.6 Hz), 3.30-3.50 (2H, m), 3.98 (1H, dd, J=5.9, 9.0 Hz), 4.26 (1H, t, J=9.2 Hz), 4.70-4.90 (1H, m), 6.49 (1H, s), 7.54 (1H, brs), 7.63 (1H, d, J=7.2 Hz), 7.68-7.81 (3H, m), 7.87 (1H, d, J=7.6 Hz), 8.09 (1H, dd, J=2.5, 8.8 Hz), 8.21 (1H, d, J=1.9 Hz), 11.60 (1H, brs)

ESI (LC-MS positive mode) m/z 510 (M+H).

Example 2-34

Propane-2-sulfonic acid {(R)-2-oxo-3-[1-oxo-3-(2-trifluoromethylphenyl)-1,2-dihydroisoquinolin-7-yl]oxazolidin-5-ylmethyl}amide

[Formula 137]

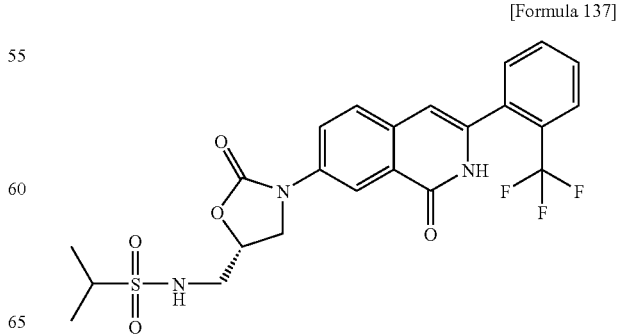

$^1$H-NMR (300 MHz, DMSO-d$_6$) δ (ppm): 1.21-1.25 (6H, m), 3.18-3.30 (1H, m), 3.31-3.50 (2H, m), 4.00 (1H, dd, J=5.9, 8.6 Hz), 4.25 (1H, t, J=9.2 Hz), 4.70-4.90 (1H, m), 6.49 (1H, s), 7.52 (1H, brs), 7.63 (1H, d, J=7.6 Hz), 7.67-7.81 (3H, m), 7.86 (1H, d, J=7.3 Hz), 8.09 (1H, dd, J=2.1, 9.0 Hz), 8.21 (1H, d, J=2.3 Hz), 11.60 (1H, brs)

ESI (LC-MS positive mode) m/z 510 (M+H).

Example 2-35

Pentane-1-sulfonic acid {(R)-2-oxo-3-[1-oxo-3-(2-trifluoromethylphenyl)-1,2-dihydroisoquinolin-7-yl]oxazolidin-5-ylmethyl}amide

[Formula 138]

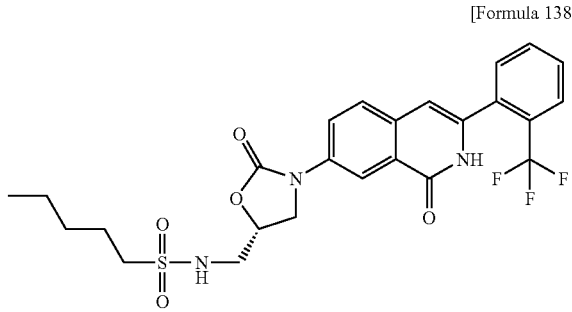

$^1$H-NMR (300 MHz, DMSO-d$_6$) δ (ppm): 0.84 (3H, t, J=7.1 Hz), 1.20-1.40 (4H, m), 1.60-1.70 (2H, m), 3.04 (2H, dd, J=6.5, 9.2 Hz), 3.30-3.50 (2H, m), 3.98 (1H, dd, J=6.4, 9.3 Hz), 4.25 (1H, t, J=8.8 Hz), 4.75-4.90 (1H, m), 6.49 (1H, s), 7.53 (1H, brs), 7.63 (1H, d, J=6.9 Hz), 7.68-7.81 (3H, m), 7.87 (1H, d, J=7.7 Hz), 8.09 (1H, dd, J=2.4, 8.7 Hz), 8.21 (1H, d, J=2.2 Hz), 11.60 (1H, brs)

ESI (LC-MS positive mode) m/z 538 (M+H).

Example 2-36

N-{(R)-2-Oxo-3-[1-oxo-3-(2-trifluoromethylphenyl)-1,2-dihydroisoquinolin-7-yl]oxazolidin-5-ylmethyl}benzenesulfonamide

[Formula 139]

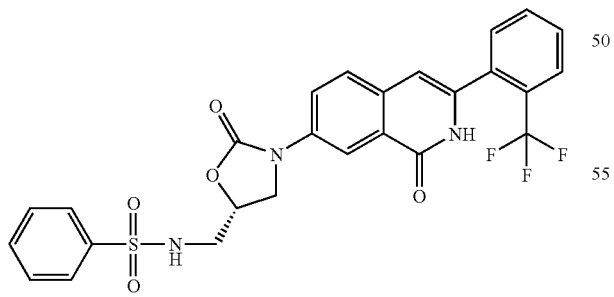

$^1$H-NMR (300 MHz, DMSO-d$_6$) δ (ppm): 3.13 (1H, dd, J=5.1, 14.4 Hz), 3.20 (1H, dd, J=4.9, 14.4 Hz), 3.93 (1H, dd, J=6.3, 7.9 Hz), 4.22 (1H, t, J=9.0 Hz), 4.70-4.81 (1H, m), 6.48 (1H, s), 7.58-7.90 (10H, m), 8.06 (1H, dd, J=2.7, 8.7 Hz), 8.18 (1H, d, J=2.3 Hz)

ESI (LC-MS positive mode) m/z 544 (M+H).

Example 2-37

Ethylenesulfonic acid {(R)-2-oxo-3-[1-oxo-3-(2-trifluoromethylphenyl)-1,2-dihydroisoquinolin-7-yl]oxazolidin-5-ylmethyl}amide

[Formula 140]

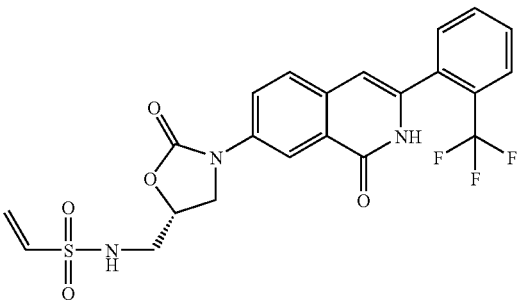

The 7-((S)-5-aminomethyl-2-oxooxazolidin-3-yl)-3-(2-trifluoromethylphenyl)-2H-isoquinolin-1-one (40 mg, 0.1 mmol) prepared in step B of Example 2-31 was dissolved in methylene chloride (0.4 ml). Thereafter, pyridine (40 μl, 0.5 mmol) and 2-chloroethanesulfonyl chloride (10.4 μl, 0.1 mmol) were added to the solution, and the obtained mixture was then stirred at 0° C. for 30 minutes. Thereafter, water was added to the reaction solution, and the obtained mixture was then extracted with methylene chloride. The extract was washed with water and a saturated saline solution, and was then dried over magnesium sulfate. Thereafter, the solvent was distilled away under reduced pressure. The obtained residue was purified by silica gel column chromatography (methylene chloride:methanol=20:1), so as to obtain ethylenesulfonic acid {(R)-2-oxo-3-[1-oxo-3-(2-trifluoromethylphenyl)-1,2-dihydroisoquinolin-7-yl]oxazolidin-5-ylmethyl}amide (2.7 mg, 10%) in the form of a colorless solid.

$^1$H-NMR (300 MHz, DMSO-d$_6$) δ (ppm): 3.20-3.35 (2H, m) 3.93-4.00 (1H, m), 4.26 (1H, t, J=9.0 Hz), 4.70-4.87 (1H, m), 6.00 (1H, d, J=10.3 Hz), 6.07 (1H, d, J=16.6 Hz), 6.49 (1H, s), 6.76 (1H, dd, J=10.3, 16.6 Hz), 7.63 (1H, d, J=7.2 Hz), 7.67-7.88 (4H, m), 8.05-8.10 (1H, m), 8.21 (1H, d, J=1.4 Hz) lacking 2H ESI (LC-MS positive mode) m/z 494 (M+H).

Example 2-38

2-Hydroxyethanesulfonic acid {(R)-2-oxo-3-[1-oxo-3-(2-trifluoromethylphenyl)-1,2-dihydroisoquinolin-7-yl]oxazolidin-5-ylmethyl}amide Step A Methyl Chlorosulfonylacetate

[Formula 141]

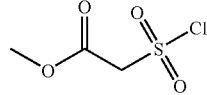

Chlorosulfonylacetyl chloride (900 mg, 5.08 mmol) was dissolved in diethyl ether (5 ml). Thereafter, methanol (206 μl, 5.08 mmol) was added to the solution at 0° C., and the obtained mixture was then stirred at 0° C. for 3 hours. Thereafter, the temperature of the reaction solution was returned to a room temperature, and the solvent was then distilled away under reduced pressure, so as to obtain methyl chlorosulfonyl acetate (850 mg, 97%) in the form of a colorless oil substance.

¹H-NMR (Bruker, 300 MHz, CDCl₃) δ: 3.91 (s, 3H), 4.61 (s, 2H).

Step B

2-Hydroxyethanesulfonic acid {(R)-2-oxo-3-[1-oxo-3-(2-trifluoromethylphenyl)-1,2-dihydroisoquinolin-7-yl]oxazolidin-5-ylmethyl}amide

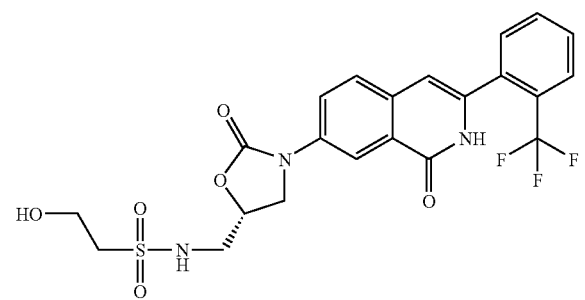

[Formula 142]

The 7-((S)-5-aminomethyl-2-oxooxazolidin-3-yl)-3-(2-trifluoromethylphenyl)-2H-isoquinolin-1-one (20 mg, 0.05 mmol) prepared in step B of Example 2-31 was dissolved in methylene chloride (0.2 ml). Thereafter, the methyl chlorosulfonyl acetate (10.5 μl, 0.05 mmol) obtained in step A was added to the solution under cooling on ice, and the obtained mixture was stirred at 0° C. for 30 minutes. Thereafter, water was added to the reaction solution, and the mixture was then extracted with methylene chloride. The extract was washed with water and a saline solution, and was then dried over anhydrous magnesium sulfate. Thereafter, the solvent was distilled away under reduced pressure. The obtained residue was purified by silica gel column chromatography (methylene chloride:methanol=20:1), so as to obtain a colorless solid (10 mg).

This colorless solid (10 mg, 0.02 mmol) was dissolved in THF (0.2 ml). Thereafter, lithium tetrahydroborate (2 mg, 0.10 mmol) was added to the solution, and the obtained mixture was stirred at a room temperature for 30 minutes. Thereafter, water was added to the reaction solution, and the mixture was then extracted with methylene chloride. The extract was washed with water and a saturated saline solution, and was then dried over anhydrous magnesium sulfate. Thereafter, the solvent was distilled away. The obtained residue was purified by silica gel column chromatography (methylene chloride:methanol=10:1), so as to obtain 2-hydroxyethanesulfonic acid {(R)-2-oxo-3-[1-oxo-3-(2-trifluoromethylphenyl)-1,2-dihydroisoquinolin-7-yl]oxazolidin-5-ylmethyl}amide (2.6 mg, 10%) in the form of a colorless solid.

¹H-NMR (300 MHz, DMSO-d₆) δ (ppm): 3.06 (2H, t, J=6.4 Hz), 3.23-3.35 (2H, m), 3.71 (2H, t, J=6.3 Hz), 3.98-4.03 (1H, m), 4.21 (1H, m), 4.72-4.78 (1H, m), 6.46 (1H, s), 7.60-7.87 (5H, m), 8.06 (1H, dd, J=2.0, 8.9 Hz), 8.20 (1H, d, J=1.8 Hz)

ESI (LC-MS positive mode) m/z 512 (M+H).

Example 2-39

7-((R)-5-Hydroxymethyl-2-oxooxazolidin-3-yl)-3-(2-propylphenyl)-2H-isoquinolin-1-one

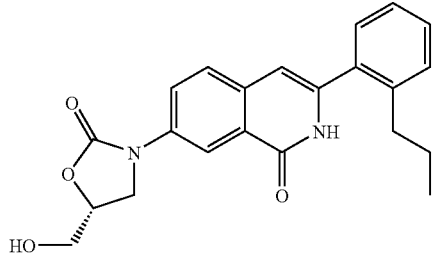

[Formula 143]

10 wt % Palladium carbon (10 mg) was added to a methanol solution (5 ml) that contained the 3-(2-allylphenyl)-7-((R)-5-hydroxymethyl-2- -oxazolidin-3-yl)-2H-isoquinolin-1-one (25 mg, 0.03 mmol) obtained in Example 1-48. The obtained mixture was stirred in a hydrogen atmosphere at a room temperature for 2 hours. Thereafter, the reaction mixture was filtrated, and the filtrate was then concentrated under reduced pressure, so as to obtain 7-((R)-5-hydroxymethyl-2-oxooxazolidin-3-yl)-3-(2-propylphenyl)-2H-isoquinolin-1-one (8.1 mg, 58%) in the form of white powders.

¹H-NMR (270 MHz, CD₃OD) δ: 0.83 (3H, t, J=7.6 Hz), 1.55 (2H, sext, J=7.6 Hz), 2.66 (2H, t, J=7.6 Hz), 3.69-3.94 (2H, m), 4.03-4.12 (1H, m), 4.21-4.32 (1H, m), 4.92-4.71 (1H, m), 6.58 (1H, s), 7.26-7.43 (4H, m), 7.71 (1H, d, J=8.6 Hz), 8.20-8.31 (2H, m)

ESI (LC-MS positive mode) m/z 379 (M+H).

The following compounds (Examples 2-40 to 2-43) were synthesized by a reaction similar to that of Example 1-19.

Example 2-40

7-((R)-5-Hydroxymethyl-2-oxooxazolidin-3-yl)-3-[2-(2-methylallyl)phenyl]-2H-isoquinolin-1-one

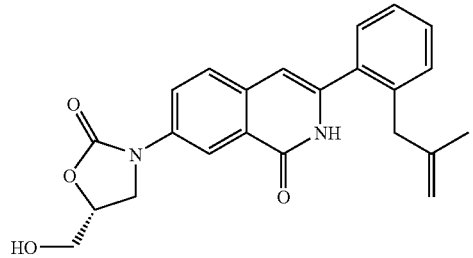

[Formula 144]

¹H-NMR (270 MHz, CDCl₃) δ: 1.79 (3H, s), 3.35 (3H, s), 3.76-3.87 (1H, m), 4.00-4.09 (1H, m), 4.11-4.26 (2H, m), 4.49 (1H, s), 4.74-4.86 (1H, m), 4.96 (1H, s), 6.49 (1H, s), 7.24-7.56 (5H, m), 7.90 (1H, d, J=2.5 Hz), 8.46 (1H, dd, J=8.9, 2.5 Hz), 8.89 (1H, s)

ESI (LC-MS positive mode) m/z 391 (M+H).

Example 2-41

7-((R)-5-Hydroxymethyl-2-oxooxazolidin-3-yl)-3-(2-propoxyphenyl)-2H-isoquinolin-1-one

[Formula 145]

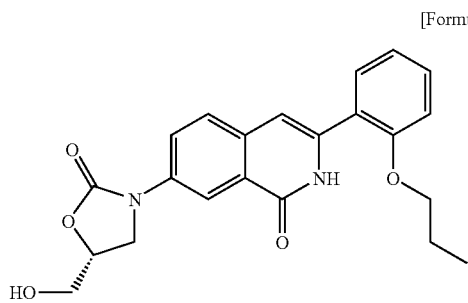

$^1$H-NMR (270 MHz, CDCl$_3$) δ: 1.06 (3H, t, J=7.3 Hz), 1.89 (2H, sext, J=7.3 Hz), 3.75-4.05 (2H, m), 4.05 (2H, t, J=7.3 Hz), 4.13-4.25 (2H, m), 4.74-4.87 (1H, m), 6.73 (1H, s), 6.92-7.13 (2H, m), 7.31-7.45 (1H, m), 7.50-7.64 (2H, m), 7.89 (1H, d, J=2.5 Hz), 8.49 (1H, dd, J=8.9, 2.5 Hz), 9.77 (1H, s)

ESI (LC-MS positive mode) m/z 395 (M+H).

Example 2-42

7-((R)-5-Hydroxymethyl-2-oxooxazolidin-3-yl)-3-[2-(2-methoxyethoxy)phenyl]-2H-isoquinolin-1-one

[Formula 146]

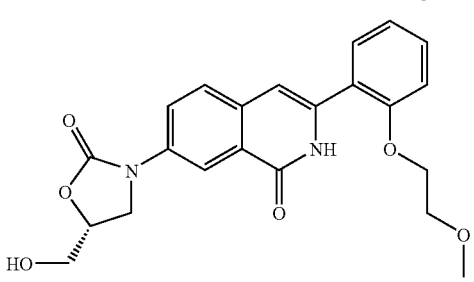

$^1$H-NMR (270 Hz, DMSO-d$_6$) δ: 3.29 (3H, s), 3.54-3.90 (3H, m), 3.90-4.03 (1H, m), 4.15-4.29 (2H, m), 4.70-4.80 (1H, m), 5.25 (1H, t, J=5.8 Hz), 6.74 (1H, s), 7.06 (1H, t, J=7.5 Hz) 7.17 (1H, d, J=7.9 Hz), 7.35-7.55 (2H, m), 7.71 (1H, d, J=8.7 Hz), 8.07 (1H, dd, J=8.7, 2.5 Hz), 8.23 (1H, d, J=2.5 Hz), 11.12 (1H, s)

ESI (LC-MS positive mode) m/z 411 (M+H).

Example 2-43

3-(2-Ethoxyphenyl)-7-((R)-5-hydroxymethyl-2-oxooxazolidin-3-yl)-2H-isoquinolin-1-one

[Formula 147]

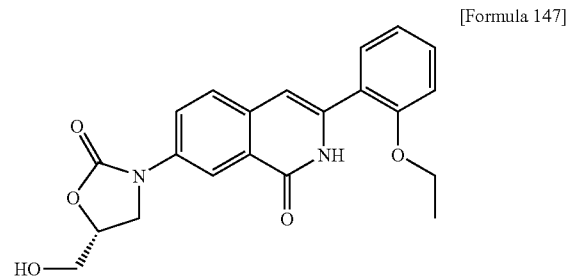

$^1$H-NMR (270 Hz, DMSO-d$_6$) δ: 1.31 (3H, t, J=6.8 Hz), 3.50-3.77 (1H, m), 4.09 (2H, q, 6.8 Hz), 4.15-4.27 (1H, m), 4.68-4.82 (1H, m), 6.65 (1H, s), 6.95-7.17 (2H, s), 7.33-7.50 (1H, m), 7.72 (1H, d, J=8.7 Hz), 8.07 (1H, dd, J=8.7, 2.5 Hz), 8.22 (1H, d, J=2.5 Hz), 11.23 (1H, s)

ESI (LC-MS positive mode) m/z 381 (M+H).

Example 2-44

3-[2-(2,3-Dihydroxy-2-methylpropyl)phenyl]-7-((R)-5-hydroxymethyl-2-oxooxazolidin-3-yl)-2H-isoquinolin-1-one

[Formula 148]

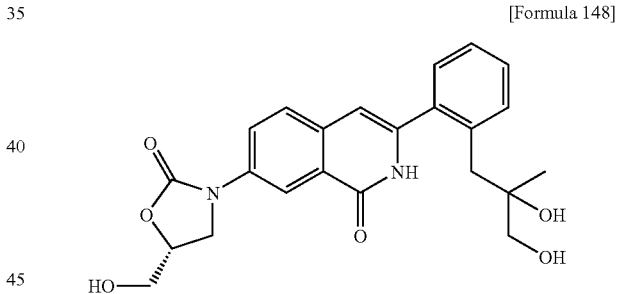

The 7-((R)-5-hydroxymethyl-2-oxooxazolidin-3-yl)-3-[2-(2-methylallyl)phenyl]-2H-isoquinolin-1-one (25 mg, 0.064 mmol) obtained in Example 2-40 was dissolved in THF (3 ml). Thereafter, an osmium oxide aqueous solution (0.1 mmol/ml, 0.032 ml, 0.0032 mmol) and a 3% hydrogen peroxide solution (0.218 ml, 0.19 mmol) were added to the solution, and the obtained mixture was then stirred at a room temperature for 9 hours. Thereafter, the reaction mixture was concentrated under reduced pressure, and the concentrate was then purified by preparative TLC (methylene chloride:methanol=10:1), so as to obtain 3-[2-(2,3-dihydroxy-2-methylpropyl)phenyl]-7-((R)-5-hydroxymethyl-2-oxooxazolidin-3-yl)-2H-isoquinolin-1-one (19.5 mg, 72%) in the form of white powders.

$^1$H-NMR (270 Hz, DMSO-d$_6$) δ: 1.06 (3H, s), 2.50-2.66 (1H, m), 2.92-3.09 (1H, m), 2.97 (1H, t, J=15.7 Hz), 3.17 (3H, s), 3.55-3.77 (2H, m), 3.89-4.00 (1H, m), 4.12-4.26 (1H, m), 4.64-4.82 (1H, m), 6.50 (1H, s), 7.22-7.50 (4H, m), 7.68 (1H, d, J=8.9 Hz), 8.04 (1H, dd, J=8.9, 2.2 Hz), 8.16 (1H, d, J=2.2 Hz)

ESI (LC-MS positive mode) m/z 425 (M+H).

Example 2-45

7-((R)-5-Hydroxymethyl-2-oxooxazolidin-3-yl)-3-[2-(2-hydroxypropyl)phenyl]-2H-isoquinolin-1-one

[Formula 149]

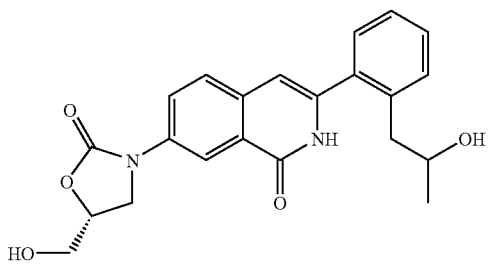

The 7-((R)-5-hydroxymethyl-2-oxooxazolidin-3-yl)-3-[2-(2-methylallyl)phenyl]-2H-isoquinolin-1-one (25 mg, 0.064 mmol) obtained in Example 2-40 was dissolved in THF-water (3 ml-1 ml). Thereafter, an osmium oxide aqueous solution (0.1 mmol/ml, 0.032 ml, 0.0032 mmol) and sodium periodate (55 mg, 0.26 mmol) were added to the solution, and the obtained mixture was then stirred at a room temperature for 15 hours. Thereafter, water was added to the reaction mixture, followed by extraction with methylene chloride. The extract was dried over magnesium sulfate, and was then concentrated under reduced pressure. The thus obtained ketone body (24 mg) that was a roughly purified product was dissolved in methanol (2 ml) without being further purified. Thereafter, sodium borohydride (7.3 mg, 0.19 mmol) was added to the obtained solution under cooling on ice. The obtained mixture was stirred at a room temperature for 2 hours. Thereafter, the reaction solution was concentrated, and was then purified by preparative TLC (methylene chloride:methanol=10:1), so as to obtain 7-((R)-5-hydroxymethyl-2-oxooxazolidin-3-yl)-3-[2-(2-hydroxypropyl)phenyl]-2H-isoquinolin-1-one (15.3 mg, 61%, two-stage) in the form of white powders.

$^1$H-NMR (270 MHz, DMSO-$d_6$) δ: 1.08 (3H, d, J=6.2 Hz), 2.71 (2H, d, J=5.8 Hz), 3.52-3.78 (2H, m), 3.82-4.03 (2H, m), 4.12-4.28 (1H, m), 4.68-4.83 (1H, m), 6.53 (1H, s), 7.23-7.48 (4H, m), 7.72 (1H, d, J=8.7 Hz), 8.07 (1H, dd, J=8.7, 2.5 Hz), 8.21 (1H, d, J=2.5 Hz)

ESI (LC-MS positive mode) m/z 395 (M+H).

Example 2-46

3-(1-Ethyl-1H-benzimidazol-2-yl)-7-((R)-5-hydroxymethyl-2-oxooxazolidin-3-yl)-2H-isoquinolin-1-one Step A 7-Chloro-3-diethoxymethyl-2H-isoquinolin-1-one {Formula 150}

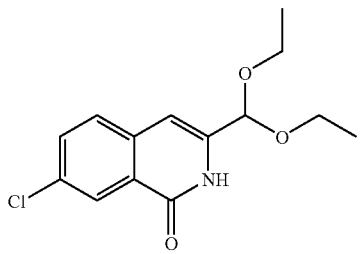

Using diethoxyacetonitrile as a raw material, the captioned compound was synthesized by a reaction similar to step B of Example 1-19.

$^1$H-NMR (DMSO-$d_6$) δ: 1.21-1.34 (6H, m), 3.50-3.76 (4H, m), 5.38 (1H, s), 6.55 (1H, s), 7.49 (1H, d, J=8.3 Hz), 7.60 (1H, dd, J=2.0, 8.3 Hz), 8.37 (1H, d, J=2.0 Hz), 8.83 (1H, brs)

ESI (LC-MS positive mode) m/z 208 (M+H—(C$_2$H$_5$)$_2$O).

Step B 7-((R)-2,3-Hydroxypropylamino)-3-diethoxymethyl-2H-isoquinolin-1-one

[Formula 151]

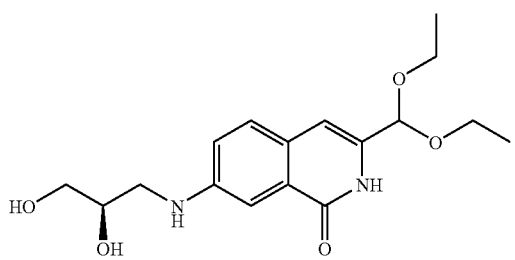

Using the 7-chloro-3-diethoxymethyl-2H-isoquinolin-1-one prepared in step A as a raw material, the captioned compound was synthesized by a reaction similar to that of Example 1-22.

$^1$H-NMR (400 MHz, CD$_3$OD) δ (ppm): 1.19-1.28 (6H, m), 3.19 (1H, dd, J=7.32, 13.18 Hz), 3.39 (1H, dd, J=4.88, 13.18 Hz), 3.56-3.72 (6H, m), 3.86-3.96 (1H, m), 5.36 (1H, s), 6.67 (1H, s), 7.15 (1H, dd, J=2.44, 8.79 Hz), 7.36 (1H, d, J=2.44 Hz), 7.45 (1H, d, J=8.79 Hz)

EI-MS m/z 336(M+).

Step C 7-((R)-5-Hydroxymethyl-2-oxooxazolidin-3-yl)-3-diethoxymethyl-2H-isoquinolin-1-one

[Formula 152]

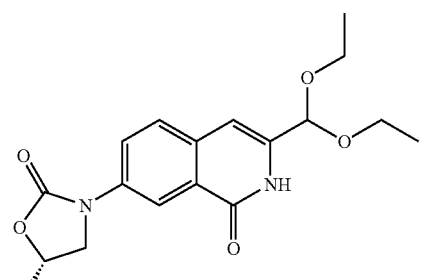

Using the 7-((R)-2,3-hydroxypropylamino)-3-diethoxymethyl-2H-isoquinolin-1-one prepared in step B as a raw material, the captioned compound was synthesized by a reaction similar to step B of Example 1-13.

$^1$H-NMR (400 MHz, DMSO-$d_6$) δ (ppm): 1.18 (6H, t, J=6.84 Hz), 3.51-3.65 (5H, m), 3.68-3.73 (1H, m), 3.93 (1H, dd, J=6.35, 8.79 Hz), 4.17-4.21 (1H, m), 4.71-4.76 (1H, m), 5.21-5.24 (0.5H, brt), 5.31 (1H, s), 6.63 (1H, s), 7.76 (1H, d, J=8.79 Hz), 8.05 (1H, dd, J=2.44, 8.79 Hz), 8.21 (1H, d, J=2.44 Hz) 11.1 (0.5H, brs)

EI-MS m/z 362 (M+).

Step D 3-(1-Ethyl-1H-benzimidazol-2-yl)-7-((R)-5-hydroxymethyl-2-oxooxazolidin-3-yl)-2H-isoquinolin-1-one

[Formula 153]

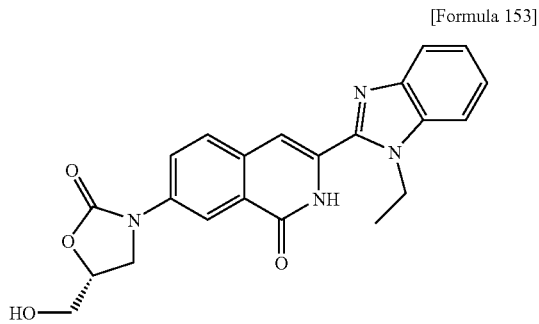

Purified water (0.01 ml) and TFA (0.01 ml) were added to a dichloromethane solution that contained the 7-((R)-5-hydroxymethyl-2-oxooxazolidin-3-yl)-3-diethoxymethyl-2H-isoquinolin-1-one (3.3 mg, 0.009 mmol) prepared in step C. The obtained mixture was left at a room temperature for 30 minutes, and the reaction solution was concentrated. The obtained yellow solid and an ethanol solution that contained N-ethyl-1,2-benzenediamine (1.2 mg, 0.009 mmol), which was a known compound described in a publication (Leicester Polytech; Synthetic Communications, vol. 19(7-8), p. 1381, (1989)), were heated to reflux for 17 hours. Thereafter, the reaction solution was concentrated. The obtained residue was purified by preparative silica gel TLC (dichloromethane:methanol=20:1), so as to obtain 3-(1-ethyl-1H-benzoimidazol-2-yl)-7-((R)-5-hydroxymethyl-2-oxooxazolidin-3-yl)-2H-isoquinolin-1-one (2.7 mg, yield: 74%) in the form of a yellow solid.

$^1$H-NMR (400 MHz, DMSO-$d_6$) δ (ppm): 1.37 (3H, t, J=6.84 Hz), 3.60-3.65 (1H, m), 3.70-3.75 (1H, m), 3.99 (1H, dd, J=5.86, 8.79 Hz), 4.22-4.26 (1H, m), 4.43-4.48 (2H, m), 4.74-4.79 (1H, m), 5.25 (1H, t, J=5.37 Hz), 7.07 (1H, s), 7.29-7.39 (2H, m), 7.72-7.75 (2H, m), 7.91 (1H, d, J=8.79 Hz), 8.15 (1H, dd, J=2.93, 8.79 Hz), 8.32 (1H, d, J=2.44 Hz), 11.36 (0.5H, brs)

FAB-MS m/z 405 (M+H).

Example 2-47

7-((R)-5-Hydroxymethyl-2-oxooxazolidin-3-yl)-3-(2-methylsulfanylphenyl)-2H-isoquinolin-1-one Step A 7-Bromo-3-(2-methylsulfanylphenyl)-2H-isoquinolin-1-one

[Formula 154]

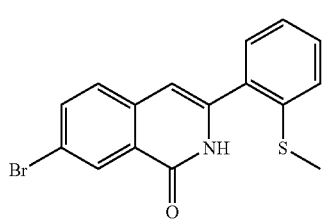

A crude product of 5-bromo-2,N,N-trimethylbenzamide was prepared from 2-bromo-5-methylbenzoic acid, which can be prepared by the method disclosed in WO2002/083066 or U.S. Pat. No. 4,282,365, according to a method similar to step A of Example 1, with the exception that purification was not carried out. The obtained compound was directly used for the next step.

Using the thus obtained 5-bromo-2,N,N-trimethylbenzamide as a raw material, 7-bromo-3-(2-methylsulfanylphenyl)-2H-isoquinolin-1-one was synthesized by a method similar to step B of Example 1.

$^1$H-NMR (270 MHz, DMSO-$d_6$) δ (ppm): 2.36 (3H, s), 6.56 (1H, s), 7.23-7.35 (4H, m), 7.64 (1H, d, J=8.5 Hz), 7.83 (1H, dd, J=2.3, 8.5 Hz), 8.27 (1H, d, J=2.3 Hz), 11.60 (1H, brs)

ESI (LC-MS positive mode) m/z 346 (M), 348 (M+2H).

Step B 7-((R)-5-Hydroxymethyl-2-oxooxazolidin-3-yl)-3-(2-methylsulfanylphenyl)-2H-isoquinolin-1-one

[Formula 155]

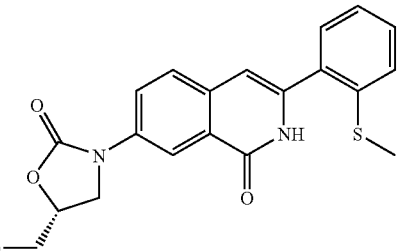

Using the 7-bromo-3-(2-methylsulfanylphenyl)-2H-isoquinolin-1-one prepared in step A as a raw material, the captioned compound was synthesized by a reaction similar to step E of Example 1-1.

$^1$H-NMR (270 MHz, DMSO-$d_6$) δ (ppm): 2.43 (3H, s), 3.61 (1H, dd, J=3.3, 12.0 Hz), 3.72 (1H, dd, J=3.3, 12.0 Hz), 3.96 (1H, dd, J=6.2, 8.8 Hz), 4.21 (1H, dd, J=8.8, 8.8 Hz), 4.71-4.78 (1H, m), 5.24 (1H, brs), 6.53 (1H, s), 7.26 (1H, ddd, J=1.5, 7.6, 7.6 Hz), 7.36-7.49 (3H, m), 7.72 (1H, d, J=8.7 Hz), 8.08 (1H, dd, J=2.4, 8.7 Hz), 8.24 (1H, d, J=2.4 Hz), 11.43 (1H, brs)

ESI (LC-MS positive mode) m/z 383 (M+H).

Example 2-48

7-((R)-5-Hydroxymethyl-2-oxooxazolidin-3-yl)-3-(2-methanesulfonylphenyl)-2H-isoquinolin-1-one Step A 7-Bromo-3-(2-methanesulfonylphenyl)-2H-isoquinolin-1-one

[Formula 156]

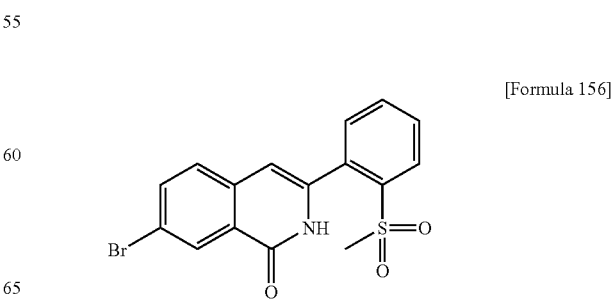

The 7-bromo-3-(2-methylsulfanylphenyl)-2H-isoquinolin-1-one (20.0 mg, 0.058 mmol) prepared in step B of Example 2-47, copper iodide (I) (11 mg, 0.058 mmol), (R)-5-hydroxymethyloxazolidin-2-one (6.8 mg, 0.058 mmol), and potassium carbonate (16.9 mg, 0.122 mmol) were suspended in 1,4-dioxane (1 ml). Thereafter, N,N'-dimethylethylenediamine ml, 0.29 mmol) was added to the suspension. The obtained mixture was stirred under heating to reflux overnight. Thereafter, the reaction solution was cooled to a room temperature. A saturated ammonium chloride aqueous solution was added to the reaction solution, and the mixture was extracted with ethyl acetate. The extract was dried over anhydrous sodium sulfate, and the solvent was distilled away under reduced pressure. The obtained residue was purified by silica gel column chromatography (methylene chloride:methanol=100:1->30:1), so as to obtain 7-bromo-3-(2-methanesulfonylphenyl)-2H-isoquinolin-1-one (7 mg, 32%) in the form of a colorless oil substance.

ESI (LC-MS positive mode) m/z 378 (M), 380 (M+2H).

Step B 7-((R)-5-Hydroxymethyl-2-oxooxazolidin-3-yl)-3-(2-methanesulfonylphenyl)-2H-isoquinolin-1-one

[Formula 157]

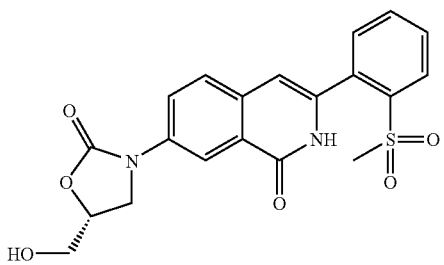

The 7-bromo-3-(2-methylsulfonylphenyl)-2H-isoquinolin-1-one (7 mg, 0.019 mmol) prepared in step A, copper iodide (I) (3.5 mg, 0.019 mmol), (R)-5-hydroxymethyloxazolidin-2-one (2.2 mg, 0.019 mmol), and potassium carbonate (5.3 mg, 0.039 mmol) were suspended in 1,4-dioxane (0.5 ml). Thereafter, N,N'-dimethylethylenediamine (0.01 ml, 0.093 mmol) was added to the suspension. The obtained mixture was stirred under heating to reflux overnight. The reaction solution was cooled to a room temperature. A saturated ammonium chloride aqueous solution was added to the reaction solution, and the mixture was extracted with ethyl acetate. The extract was dried over anhydrous sodium sulfate, and the solvent was distilled away under reduced pressure. The obtained residue was purified by silica gel column chromatography (methylene chloride:methanol=100:1->30:1), so as to obtain 7-((R)-5-hydroxymethyl-2-oxooxazolidin-3-yl)-3-(2-methanesulfonylphenyl)-2H-isoquinolin-1-one (2 mg, 26%) in the form of a colorless oil substance.

$^1$H-NMR (270 MHz, DMSO-$d_6$) δ (ppm): 3.15 (3H, s), 3.41-3.80 (2H, m), 3.93 (1H, dd, J=7.6, 7.6 Hz), 4.19 (1H, dd, J=9.0, 9.0 Hz), 4.69-4.80 (1H, m), 5.29 (1H, t, J=5.7 Hz), 6.57 (1H, s), 7.59 (1H, d, J=7.3 Hz), 7.69-7.83 (3H, m), 8.06 (1H, d, J=7.1 Hz), 8.22 (1H, s), 11.55 (1H, brs)

ESI (LC-MS positive mode) m/z 415 (M+H).

Example 2-49

7-(4-Hydroxy-5-hydroxymethyl-2-oxooxazolidin-3-yl)-3-(2-trifluoromethylphenyl)-2H-isoquinolin-1-one Step A 1-(tert-Butyldimethylsilyloxymethyl)-2,3-diethoxyethyl[1-oxo-3-(2-trifluoromethylphenyl)-1,2-dihydroisoquinolin-7-yl]carbamate

[Formula 158]

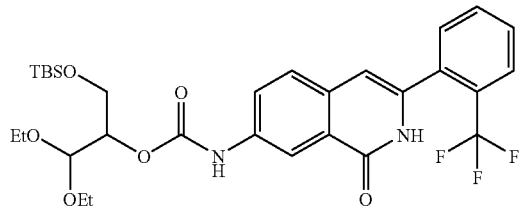

Triethylamine (18 μl, 0.10 mmol) and triphosgene (9.8 mg, 0.033 mmol) were added to a THF solution (0.5 ml) that contained the 7-amino-3-(2-trifluoromethylphenyl)-2H-isoquinolin-1-one (30.4 mg, 0.10 mmol) obtained in step C of Example 1-1. The obtained mixture was stirred at a room temperature for 1.5 hours. At the same time, a butyl lithium hexane solution (1.57 M, 70 μl) was added at −78° C. to a THF solution (0.5 ml) that contained 3-(tert-butyldimethylsilyloxy)-1,1-diethoxypropan-2-ol (27.8 mg, 0.10 mmol), which had been synthesized in accordance with Liebigs Ann. Chem. 1989, pp. 295-298. The obtained mixture was stirred at 0° C. for 10 minutes. Thereafter, the obtained reaction solution was added to the reaction solution, and the obtained mixture was stirred at 0° C. for 2.5 hours. Thereafter, a saturated ammonium chloride aqueous solution was added to the reaction solution, and the mixture was then extracted with ethyl acetate. Unnecessary products were removed by filtration, and the filtrate was then concentrated. The obtained residue was purified by silica gel column chromatography (ethyl acetate:hexane=1:2 to 1:1), so as to obtain [1-oxo-3-(2-trifluoromethylphenyl)-1,2-dihydroisoquinolin-7-yl]carbamic acid 1-(tert-butyldimethylsilyloxymethyl)-2,3-diethoxyethyl (12.6 mg, 21%) in the form of a colorless amorphous substance.

$^1$H-NMR (270 MHz, CDCl$_3$) δ (ppm): 0.06 (6H, s), 0.88 (9H, s), 1.17-1.26 (6H, m), 3.50-3.80 (4H, m), 3.87 (1H, dd, J=5.3, 11.2 Hz), 3.93 (1H, dd, J=3.6, 11.2 Hz), 4.71 (1H, d, J=5.6 Hz), 4.93-5.01 (1H, m), 6.50 (1H, s), 7.42 (1H, s), 7.50-7.72 (4H, m), 7.78-7.84 (1H, m), 8.11-8.20 (2H, m), 9.20 (1H, brs)

ESI (LC-MS positive mode) m/z 563 (M+H-EtOH).

Step B 7-(4-Hydroxy-5-hydroxymethyl-2-oxooxazolidin-3-yl)-3-(2-trifluoromethylphenyl)-2H-isoquinolin-1-one

[Formula 159]

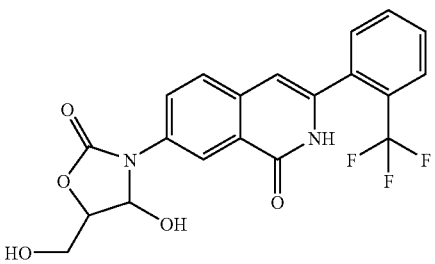

6 N Hydrochloric acid (0.3 ml) was added to an ethanol solution (0.1 ml) that contained the [1-oxo-3-(2-trifluoromethylphenyl)-1,2-dihydroisoquinolin-7-yl]carbamic acid 1-(tert-butyldimethylsilyloxymethyl)-2,3-diethoxyethyl (12.6 mg, 0.0207 mmol) obtained in step A. The obtained mixture was then stirred at a room temperature for 2 hours. Thereafter, the reaction solution was neutralized with a sodium hydroxide aqueous solution, and it was then extracted with ethyl acetate. The extract was dried over anhydrous sodium sulfate, and the solvent was distilled away under reduced pressure. The obtained residue was purified by silica gel column chromatography (methylene chloride:methanol=20:1 to 18:1), so as to obtain 7-(4-hydroxy-5-hydroxymethyl-2-oxooxazolidin-3-yl)-3-(2-trifluoromethylphenyl)-2H-isoquinolin-1-one (6.5 mg, 75%) in the form of a colorless amorphous substance.

$^1$H-NMR (270 MHz, DMSO-$d_6$) δ (ppm): 3.63-3.69 (2H, m), 4.31-4.35 (1H, m), 5.25 (1H, t, J=5.7 Hz), 5.66-5.70 (1H, m), 6.49 (1H, s), 7.05-7.10 (1H, m), 7.61-7.82 (4H, m), 7.85-7.90 (1H, m), 8.00 (1H, dd, J=2.3, 5.8 Hz), 8.43 (1H, d, J=2.4 Hz), 11.61 (1H, brs)

ESI (LC-MS positive mode) m/z 421 (M+H).

Example 2-50

7-[(S)-5-((S)-1,2-Dihydroxyethyl)-2-oxooxazolidin-3-yl]-3-(2-trifluoromethylphenyl)-2H-isoquinolin-1-one Step A (R)-2-Methanesulfonyloxy-2-{(S)-2-oxo-3-[1-oxo-3-(2-trifluoromethylphenyl)-1,2-dihydroisoquinolin-7-yl]oxazolidin-5-yl}ethyl methanesulfonate

[Formula 160]

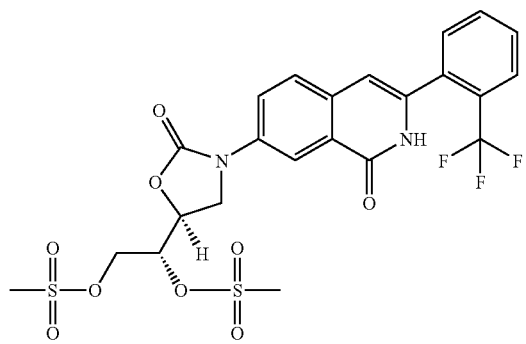

The 7-[(S)-5-((R)-1,2-dihydroxyethyl)-2-oxooxazolin-3-yl]-3-(2-trifluoromethylphenyl)-2H-isoquinolin-1-one (71 mg, 0.164 mmol) obtained in step B of Example 1-39 was dissolved in pyridine (1 ml). Thereafter, methanesulfonyl chloride (32 µl, 0.409 mmol) was added to the obtained solution. The obtained mixture was stirred at a room temperature for 2 hours. Thereafter, methanesulfonyl chloride (20 µl, 0.258 mmol) was added to the reaction solution, and the obtained mixture was stirred for 2 hours. Thereafter, the reaction solution was diluted with methylene chloride, and the diluted solution was washed with 1 N hydrochloric acid and a saturated saline solution, and was then dried over anhydrous sodium sulfate. Thereafter, the solvent was distilled away under reduced pressure. The obtained residue was purified by silica gel column chromatography (methylene chloride:methanol=30:1), so as to obtain (R)-2-methanesulfonyloxy-2-{(S)-2-oxo-3-[1-oxo-3-(2-trifluoromethylphenyl)-1,2-dihydroisoquinolin-7-yl]oxazolidin-5-yl}ethyl methanesulfonate (53 mg, 55%).

$^1$H-NMR (Bruker, 300 MHz, CDCl$_3$) δ: 3.14 (s, 3H), 3.21 (s, 3H), 4.24-4.38 (m, 2H), 4.55 (dd, J=12.00 Hz, 4.32 Hz, 1H), 4.69 (dd, J=12.05 Hz, 3.41 Hz, 1H), 4.93-5.00 (m, 1H), 5.10-5.15 (m, 1H), 6.51 (s, 1H), 7.55-7.69 (m, 4H), 7.82 (d, J=7.39 Hz, 1H), 8.06 (d, J=2.24 Hz, 1H), 8.38 (dd, J=8.73 Hz, 2.47 Hz, 1H), 8.64 (brs, 1H).

Step B (S)-2-Acetoxy-2-{(S)-2-oxo-3-[1-oxo-3-(2-trifluoromethylphenyl)-1,2-dihydroisoquinolin-7-yl]oxazolidin-5-yl}ethyl acetate

[Formula 161]

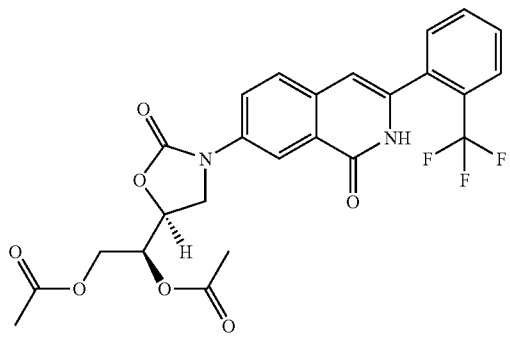

The (R)-2-methanesulfonyloxy-2-{(S)-2-oxo-3-[1-oxo-3-(2-trifluoromethylphenyl)-1,2-dihydroisoquinolin-7-yl]oxazolidin-5-yl}ethyl methanesulfonate (53 mg, 0.0897 mmol) obtained in step A was dissolved in acetic anhydride (1 ml). Thereafter, potassium acetate (44 mg, 0.449 mmol) was added to the solution, and the obtained mixture was then stirred at 120° C. for 6 hours. The reaction solution was cooled to a room temperature. A saturated sodium bicarbonate aqueous solution was added thereto, and the obtained mixture was then extracted with ethyl acetate. The extract was washed with water and a saturated saline solution, and was then dried over anhydrous sodium sulfate. Thereafter, the solvent was distilled away under reduced pressure. The obtained residue was purified by silica gel column chromatography (methylene chloride:methanol=50:1), so as to obtain (S)-2-acetoxy-2-{(S)-2-oxo-3-[1-oxo-3-(2-trifluoromethylphenyl)-1,2-dihydroisoquinolin-7-yl]oxazolidin-5-yl}ethyl acetate (25 mg, 54%).

$^1$H-NMR (Bruker, 300 MHz, CDCl$_3$) δ: 2.07 (s, 3H), 2.10 (s, 3H), 3.95-4.00 (m, 1H), 4.24-4.33 (m, 2H), 4.43-4.49 (m, 1H), 4.94-4.96 (m, 1H), 5.32-5.35 (m, 1H), 6.55 (s, 1H), 7.54-7.69 (m, 4H), 7.83 (d, J=7.39 Hz, 1H), 7.94 (d, J=2.09 Hz, 1H), 8.57 (dd, J=8.59 Hz, 2.23 Hz, 1H), 8.59 (brs, 1H).

Step C

7-[(S)-5-((S)-1,2-Dihydroxyethyl)-2-oxooxazolidin-3-yl]-3-(2-trifluoromethylphenyl)-2H-isoquinolin-1-one

[Formula 162]

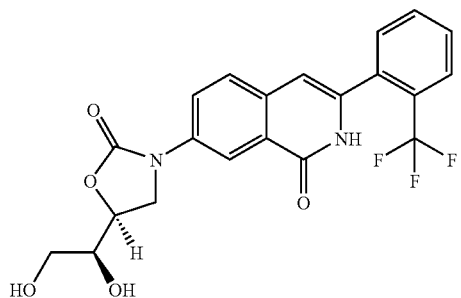

Potassium carbonate (17 mg, 0.121 mmol) was added to a methanol solution (2 ml) that contained the (S)-2-acetoxy-2-{(S)-2-oxo-3-[1-oxo-3-(2-trifluoromethylphenyl)-1,2-dihydroisoquinolin-7-yl]oxazolidin-5-yl}ethyl acetate (25 mg, mmol) obtained in step B. The obtained mixture was stirred at a room temperature for 1.5 hours. Thereafter, the reaction solution was neutralized with 1 N hydrochloric acid, and the resultant was then extracted with methylene chloride. The extract was washed with water and a saturated saline solution, and was then dried over anhydrous sodium sulfate. Thereafter, the solvent was distilled away under reduced pressure. The obtained residue was purified by silica gel column chromatography (methylene chloride:methanol=20:1) and preparative HPLC, so as to obtain 7-[(S)-5-((S)-1,2-dihydroxyethyl)-2-oxooxazolidin-3-yl]-3-(2-trifluoromethylphenyl)-2H-isoquinolin-1-one (6.7 mg, 32%).

$^1$H-NMR (Bruker, 300 MHz, CDCl$_3$) δ: 2.00-2.10 (m, 1H), 2.84-2.96 (m, 1H), 3.89 (s, 3H), 4.23 (d, J=7.96 Hz, 2H), 4.79-4.86 (m, 1H), 6.52 (s, 1H), 7.55-7.68 (m, 4H), 7.83 (d, J=8.08 Hz, 1H), 7.99 (d, J=1.93 Hz, 1H), 8.49 (brs, 1H), 8.56 (dd, J=9.03 Hz, 2.53 Hz, 1H)

Mass (Micromass, Quttromicro) (ESI+): m/z 457.25 (M+Na).

Example 2-51

Cyclopropanesulfonic acid {(R)-2-oxo-3-[1-oxo-3-(2-trifluoromethylphenyl)-1,2-dihydroisoquinolin-7-yl]oxazolidin-5-ylmethyl}amide

[Formula 163]

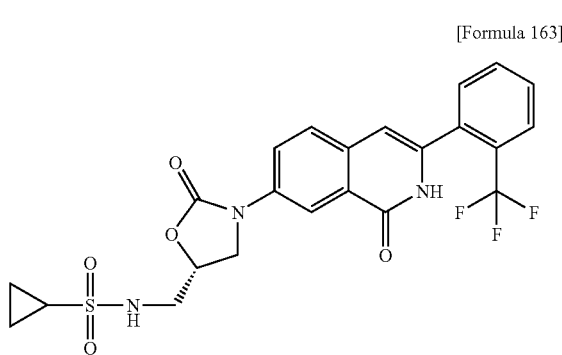

The captioned compound was synthesized by a reaction similar to that of Example 2-31.

$^1$H-NMR (300 MHz, DMSO-d$_6$) δ (ppm): 0.95 (4H, t, J=5.9 Hz), 2.55-2.66 (1H, m), 3.33-3.49 (2H, m), 3.99 (1H, dd, J=6.1, 9.1 Hz), 4.26 (1H, t, J=8.9 Hz), 4.79-4.85 (1H, m), 6.49 (1H, s), 7.54-7.81 (5H, m), 7.87 (1H, d, J=7.2 Hz), 8.09 (1H, dd, J=2.6, 8.6 Hz), 8.21 (1H, d, J=2.3 Hz), 11.60 (1H, brs)

ESI (LC-MS positive mode) m/z 508 (M+H).

Example 2-52

7-(4-Hydroxymethyl-2-oxopyrrolidin-1-yl)-3-(2-trifluoromethylphenyl)-2H-isoquinolin-1-one

[Formula 164]

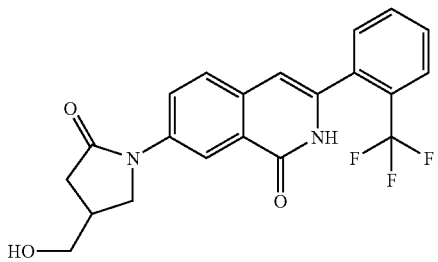

4-Hydroxymethylpyrrolidin-2-one, which is a known compound described in a publication (Journal of Chemical Research, Synopses, vol. 9, pp. 430-431, (1996)) and the 7-iodo-3-(2-trifluoromethylphenyl)-2H-isoquinolin-1-one obtained in step D of Example 1-1 were used as raw materials. Using such raw materials, the captioned compound was synthesized by a reaction similar to step E of Example 1-1.

$^1$H-NMR (270 MHz, DMSO-d$_6$) δ (ppm): 2.36 (1H, dd, J=4.9, 15.7 Hz), 2.61-2.72 (2H, m), 3.50 (2H, brs), 3.74 (1H, dd, J=4.9, 9.7 Hz), 4.01 (1H, dd, J=8.0, 9.7 Hz), 4.93 (1H, brs), 6.48 (1H, s), 7.62-7.81 (4H, m), 7.87 (1H, d, J=6.9 Hz), 8.18 (1H, dd, J=2.5, 8.7 Hz), 8.34 (1H, d, J=2.5 Hz), 11.60 (1H, brs)

ESI (LC-MS positive mode) m/z 403 (M+H).

Example 2-53

7-((S)-3-Hydroxy-2-oxopyrrolidin-1-yl)-3-(2-trifluoromethylphenyl)-2H-isoquinolin-1-one

[Formula 165]

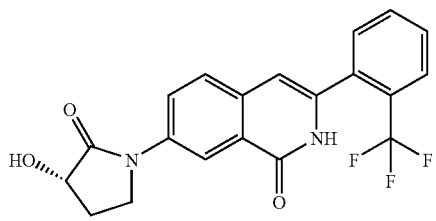

Using (S)-3-hydroxypyrrolidin-2-one, which is a known compound described in a publication (Heterocycles, 2003, vol. 60(8), pp. 1883-1841), as a raw material, the captioned compound was synthesized by a reaction similar to step E of Example 1-1.

$^1$H-NMR (300 MHz, DMSO-d$_6$) δ (ppm): 1.80-2.00 (1H, m), 2.40-2.60 (1H, m), 3.70-3.95 (2H, m), 4.36 (1H, t, J=8.2

Hz), 5.70-5.90 (1H, m), 6.48 (1H, s), 7.63 (1H, d, J=7.7 Hz), 7.66-7.80 (3H, m), 7.87 (1H, d, J=8.1 Hz), 8.17 (1H, dd, J=2.3, 8.5 Hz), 8.39 (1H, d, J=2.3 Hz), 11.58 (1H, brs)

ESI (LC-MS positive mode) m/z 389 (M+H).

Example 2-54

2-Oxo-1-[1-oxo-3-(2-trifluoromethylphenyl)-1,2-dihydroisoquinolin-7-yl]pyrrolidine-3-carboxylic acid dimethylamide

[Formula 166]

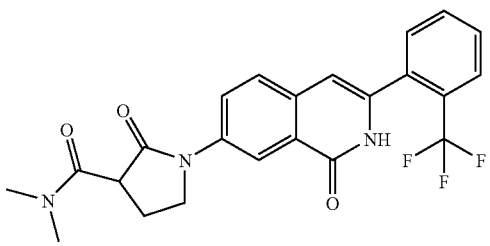

Dimethylamine (2.0 M-THF solution, 1.0 ml) was added to a THF solution (1 ml) that contained the 2-oxo-1-[1-oxo-3-(2-trifluoromethylphenyl)-1,2-dihydroisoquinolin-7-yl]pyrrolidin-3-carboxylic acid ethyl (10 mg, 0.023 mml) obtained in step B of Example 1-45. The obtained mixture was stirred at 130° C. for 3 days. Thereafter, the solvent was distilled away under reduced pressure. The obtained residue was purified by silica gel column chromatography (methylene chloride:methanol=100:1->30:1), so as to obtain 2-oxo-1-[1-oxo-3-(2-trifluoromethylphenyl)-1,2-dihydroisoquinolin-7-yl]-pyrrolidin-3-carboxylic acid dimethylamide (7 mg, 70%) in the form of a colorless oil substance.

$^1$H-NMR (270 MHz, DMSO-$d_6$) δ (ppm): 2.23-2.31 (1H, m) 2.42-2.52 (1H, m), 3.33 (6H, s), 3.94-4.07 (2H, m), 4.27 (1H, t, J=7.9 Hz), 6.49 (1H, s), 7.63-7.78 (4H, m), 7.88 (1H, d, J=7.4 Hz), 8.11 (1H, dd, J=2.3, 8.8 Hz), 8.36 (1H, d, J=2.3 Hz), (1H, brs)

ESI (LC-MS positive mode) m/z 444 (M+H).

Example 2-55

7-(3-Morpholin-4-ylmethyl-2-oxopyrrolidin-1-yl)-3-(2-trifluoromethylphenyl)-2H-isoquinolin-1-one

[Formula 167]

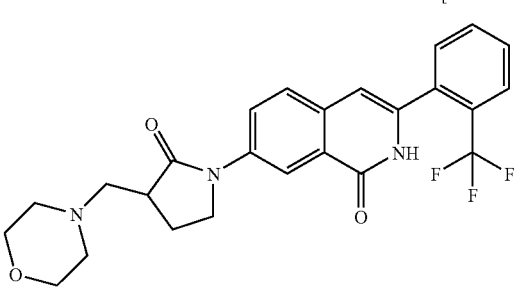

Methanesulfonyl chloride (0.023 ml, 0.299 mmol) and triethylamine (0.03 ml, 0.299 mmol) were added at −20° C. to a dichloromethane solution (2 ml) that contained the 7-(3-hydroxymethyl-2-oxopyrrolidin-1-yl)-3-(2-trifluoromethylphenyl)-2H-isoquinolin-1-one (80 mg, 199 mmol) obtained in Example 1-46. The obtained mixture was stirred at −20° C. for 2 hours. Thereafter, a saturated ammonium chloride aqueous solution was added to the reaction solution, and the obtained mixture was then extracted with ethyl acetate. The extract was dried over anhydrous sodium sulfate, and the solvent was then distilled away under reduced pressure. The obtained residue was purified by silica gel column chromatography (methylene chloride:methanol=30:1->20:1), so as to obtain methanesulfonic acid 2-oxo-1-[1-oxo-3-(2-trifluoromethylphenyl)-1,2-dihydroisoquinolin-7-yl]-pyrrolidin-3-ylmethyl ester (38 mg, 40%) in the form of a colorless oil substance.

Morpholine (0.024 ml, 0.29 mmol) and triethylamine (0.040 ml, 0.29 mmol) were added to a THF solution (1 ml) that contained the obtained methanesulfonic acid 2-oxo-1-[1-oxo-3-(2-trifluoromethylphenyl)-1,2-dihydroisoquinolin-7-yl]-pyrrolidin-3-ylmethyl ester (14 mg, 0.029 mmol). The obtained mixture was heated to reflux for 16 hours. Thereafter, a saturated ammonium chloride aqueous solution was added to the reaction solution, and the obtained mixture was then extracted with ethyl acetate. The extract was dried over anhydrous sodium sulfate, and the solvent was then distilled away under reduced pressure. The obtained residue was purified by silica gel column chromatography (methylene chloride:methanol=100:1->30:1), so as to obtain 7-(3-morpholin-4-ylmethyl-2-oxo-pyrrolidin-1-yl)-3-(2-trifluoromethylphenyl)-2H-isoquinolin-1-one (3 mg, 22%) in the form of a colorless oil substance.

$^1$H-NMR (270 MHz, CDCl$_3$) δ (ppm): 2.16-2.20 (1H, m), 2.37-2.67 (6H, m), 2.85-2.95 (2H, m), 3.64-3.74 (4H, m), 3.93-3.99 (2H, m), 6.52 (1H, s), 7.26-7.68 (4H, m), 7.82 (1H, d, J=8.8 Hz), 8.07 (1H, d, J=2.5 Hz), 8.64 (1H, dd, J=2.5, 8.8 Hz)

ESI (LC-MS positive mode) m/z 472 (M+H).

The following compounds (Examples 2-56 and 2-57) were synthesized by a method similar to that of Example 2-55.

Example 2-56

7-(2-Oxo-3-piperidin-1-ylmethylpyrrolidin-1-yl)-3-(2-trifluoromethylphenyl)-2H-isoquinolin-1-one

[Formula 168]

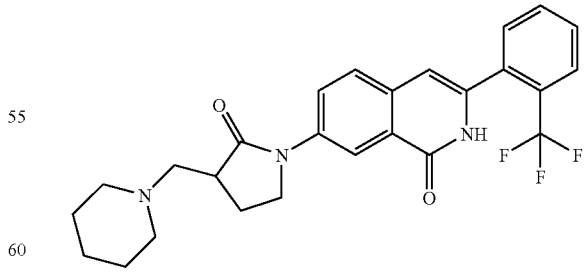

$^1$H-NMR (270 MHz, CDCl$_3$) δ (ppm): 1.43-1.49 (2H, m), 1.56-1.62 (4H, m), 2.09-2.16 (1H, m), 2.43-2.62 (6H, m), 2.88-2.94 (2H, m), 3.91-3.97 (2H, m), 6.51 (1H, s), 7.26-7.67 (4H, m), 7.82 (1H, d, J=8.7 Hz), 8.06 (1H, d, J=2.3 Hz), 8.66 (1H, dd, J=2.3, 8.7 Hz)

ESI (LC-MS positive mode) m/z 470 (M+H).

Example 2-57

7-[3-(4-Hydroxypiperidin-1-ylmethyl)-2-oxopyrrolidin-1-yl]-3-(2-trifluoromethylphenyl)-2H-isoquinolin-1-one

[Formula 169]

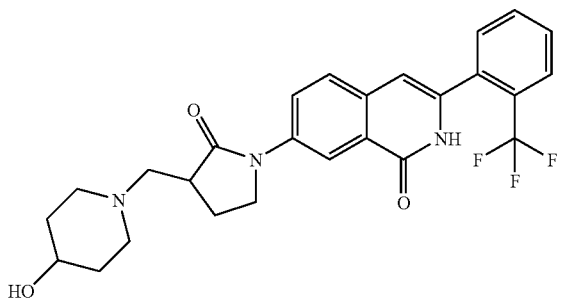

$^1$H-NMR (270 MHz, CDCl$_3$) δ (ppm): 1.52-1.73 (2H, m), 1.86-1.94 (2H, m), 2.07-2.44 (4H, m), 2.61 (1H, dd, J=10.0, 14.0 Hz), 2.74-2.95 (4H, m), 3.65-3.74 (1H, m), 3.92-3.98 (2H, m), 6.51 (1H, s), 7.55-7.68 (4H, m), 7.82 (1H, d, J=8.9 Hz), 8.06 (1H, d, J=2.4 Hz), 8.64 (1H, dd, J=2.4, 8.9 Hz)

ESI (LC-MS positive mode) m/z 486 (M+H).

Example 2-58

7-((3R,4R)-3,4-Dihydroxy-2-oxopyrrolidin-1-yl)-3-(2-trifluoromethylphenyl)-2H-isoquinolin-1-one Step A
(4R,5R)-5-Hydroxymethyl-2,2-dimethyl-[1,3]dioxolane-4-carboxylic acid [1-oxo-3-(2-trifluoromethylphenyl)-1,2-dihydroisoquinolin-7-yl]amide

[Formula 170]

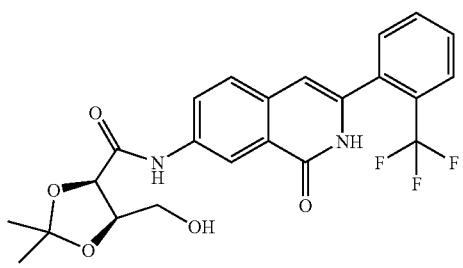

Ethyl magnesium bromide (1 M THF solution, 8.2 ml, 8.22 mmol) was added at −78° C. to 10 ml of an anhydrous THF solution that contained the 7-amino-3-(2-trifluoromethylphenyl)-2H-isoquinolin-1-one (1.0 g, 3.29 mmol) obtained in step C of Example 1-1. The obtained mixture was stirred for 30 minutes. Thereafter, 10 ml of an anhydrous THF solution that contained (−)-2,3-isopropyliden-D-erythronolactone (520 mg, 3.29 mmol) was added to the reaction solution, and the obtained mixture was then stirred at −78° C. for 14 hours. Thereafter, the temperature of the reaction solution was returned to a room temperature, and ethyl magnesium bromide (8.2 ml, 8.2 mmol) was further added thereto. The obtained mixture was stirred at a room temperature for 2 hours. Thereafter, a saturated ammonium chloride aqueous solution was added to the reaction solution, so as to separate an organic layer. A water layer was then extracted with ethyl acetate. The organic layer was mixed with the extract. The mixture was then washed with water and a saturated saline solution, and was then dried over anhydrous sodium sulfate. The solvent was distilled away under reduced pressure, so as to obtain (4R,5R)-5-hydroxymethyl-2,2-dimethyl-[1,3]dioxolan-4-carboxylic acid [1-oxo-3-(2-trifluoromethylphenyl)-1,2-dihydroisoquinolin-7-yl]amide (1.5 g, 99%).

$^1$H-NMR (Bruker, 300 MHz, CDCl$_3$) δ: 1.47 (s, 3H), 1.68 (s, 3H), 3.06-3.10 (m, 1H), 3.77-3.88 (m, 2H), 4.64-4.68 (m, 1H), 4.76 (d, J=7.60 Hz, 1H), 6.51 (s, 1H), 7.54-7.70 (m, 4H), 7.82 (d, J=8.07 Hz, 1H), 8.21 (s, 1H), 8.34 (dd, J=8.67 Hz, 2.34 Hz, 1H). 8.63 (s, 1H), 8.71 (s, 1H)

Mass (Micromass, Quttromicro) (ESI+): m/z 485.88 (M+Na).

Step B (4R,5S)-5-Bromomethyl-2,2-dimethyl-[1,3]dioxolane-4-carboxylic acid [1-oxo-3-(2-trifluoromethylphenyl)-1,2-dihydroisoquinolin-7-yl]amide

[Formula 171]

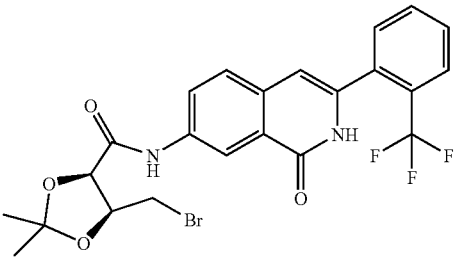

The (4R,5R)-5-hydroxymethyl-2,2-dimethyl-[1,3]dioxolan-4-carboxylic acid [1-oxo-3-(2-trifluoromethylphenyl)-1,2-dihydroisoquinolin-7-yl]amide (1.5 g, 3.24 mmol) obtained in step A was dissolved in an anhydrous methylene chloride solution (30 ml). Thereafter, triphenylphosphine (2.21 g, 8.43 mmol) and carbon tetrabromide (2.80 g, 8.43 mmol) were added to the solution, and the obtained mixture was stirred at a room temperature for 3 hours. Thereafter, the solvent was distilled away. The obtained residue was purified by silica gel column chromatography (methylene chloride:methanol=50:1), so as to obtain (4R,5S)-5-bromomethyl-2,2-dimethyl-[1,3]dioxolan-4-carboxylic acid [1-oxo-3-(2-trifluoromethylphenyl)-1,2-dihydroisoquinolin-7-yl]amide (3.0 g).

$^1$H-NMR (Bruker, 300 MHz, CDCl$_3$) δ: 1.48 (s, 3H), 1.73 (s, 3H), 3.43-3.49 (m, 1H), 3.79 (dd, J=11.1 Hz, 2.57 Hz, 1H), 4.72-4.78 (m, 2H), 6.51 (s, 1H), 7.44-7.70 (m, 4H), 7.81 (d, J=7.70 Hz, 1H), 7.20 (d, J=2.39 Hz, 1H), 8.33 (dd, J=8.51 Hz, 2.31 Hz, 1H), 8.65 (s, 1H), 8.92 (brs, 1H)

Mass (Micromass, Quttromicro) (ESI+): m/z 547.10 & 549.18 (M+Na).

Step C

7-((3aR,6aR)-2,2-Dimethyl-4-oxotetrahydro-[1,3]dioxolo[4,5-c]pyrrol-5-yl)-3-(2-trifluoromethylphenyl)-2H-isoquinolin-1-one

[Formula 172]

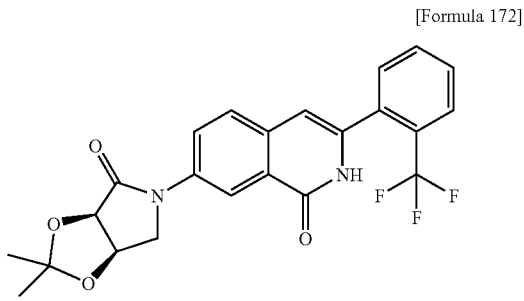

The (4R,5S)-5-bromomethyl-2,2-dimethyl-[1,3]dioxolan-4-carboxylic acid [1-oxo-3-(2-trifluoromethylphenyl)-1,2-dihydroisoquinolin-7-yl]amide (3.0 g, 5.71 mmol) obtained in step B was dissolved in anhydrous DMF (50 ml), and potassium carbonate (3.95 g, 28.6 mmol) was then added thereto. The obtained mixture was stirred at a room temperature for 2 hours. Thereafter, the solvent was distilled away. Water and ethyl acetate were added to the obtained residue. An organic layer was separated, and a water layer was extracted with ethyl acetate. The organic layer was mixed with the extract. The obtained mixture was washed with water and a saturated saline solution, and was then dried over anhydrous sodium sulfate. The solvent was distilled away under reduced pressure. The obtained residue was purified by silica gel column chromatography (methylene chloride:methanol=70:1 to 20:1), so as to obtain 640 mg of 7-((3aR,6aR)-2,2-dimethyl-4-oxotetrahydro-[1,3]dioxolo[4,5-c]pyrrol-5-yl)-3-(2-trifluoromethylphenyl)-2H-isoquinolin-1-one (25%).

$^1$H-NMR (Bruker, 300 MHz, CDCl$_3$) δ: 1.45 (s, 3H), 1.50 (s, 3H), 4.05-4.20 (m, 2H), 4.84-4.93 (m, 2H), 6.52 (s, 1H), 7.55-7.70 (m, 4H), 7.82 (d, J=7.19 Hz, 1H), 8.06 (d, J=2.29 Hz, 1H), 8.68 (dd, J=8.77 Hz, 2.20 Hz, 1H), 8.85 (brs, 1H)

Mass (Micromass, Quttromicro) (ESI+): m/z 467.20 (M+Na).

Step D

7-((3R,4R)-3,4-Dihydroxy-2-oxopyrrolidin-1-yl)-3-(2-trifluoromethylphenyl)-2H-isoquinolin-1-one

[Formula 173]

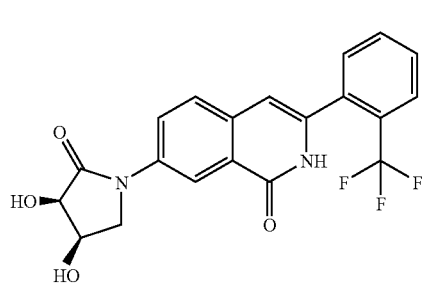

The 7-((3aR,6aR)-2,2-dimethyl-4-oxotetrahydro-[1,3]dioxolo[4,5-c]pyrrol-5-yl)-3-(2-trifluoromethylphenyl)-2H-isoquinolin-1-one (630 mg, 1.42 mmol) obtained in step C was dissolved in THF (15 ml). Thereafter, 1 N hydrochloric acid (8.1 ml, 8.1 mmol) was added to the solution. The obtained mixture was stirred for 4 hours, while gently heating. Thereafter, the reaction solution was cooled to 0° C., and a 1 N sodium hydroxide aqueous solution was added thereto until liquid property became pH 8. An organic layer was separated, and a water layer was extracted with ethyl acetate. The organic layer was mixed with the extract. The mixture was washed with water and a saturated saline solution, and was then dried over anhydrous sodium sulfate. Thereafter, the solvent was distilled away under reduced pressure. The obtained residue was purified by silica gel column chromatography (methylene chloride:methanol), so as to obtain 36.7 mg of 7-((3R,4R)-3,4-dihydroxy-2-oxopyrrolidin-1-yl)-3-(2-trifluoromethylphenyl)-2H-isoquinolin-1-one (7%).

$^1$H-NMR (Bruker, 300 MHz, DMSO-d$_6$) δ: 3.65 (d, J=10.64 Hz, 1H), 4.03 (dd, J=10.58 Hz, 2.83 Hz, 1H), 4.33-4.36 (m, 2H), 5.22 (d, J=2.70 Hz, 1H), 5.67 (d, J=6.89 Hz, 1H), 6.48 (s, 1H), 7.62-7.80 (m, 4H), 7.87 (d, J=7.69 Hz, 1H), 8.15 (dd, J=8.79 Hz, 2.27 Hz, 1H), 8.39 (d, J=1.85 Hz, 1H), 11.58 (s, 1H)

Mass (Micromass, Quttromicro) (ESI+): m/z 405.24 (M+H).

Example 2-59

7-(5-Hydroxymethyl)-3-methyl-2-oxoimidazolidin-1-yl)-3-(2-trifluoromethylphenyl)-2H-isoquinolin-1-one

[Formula 174]

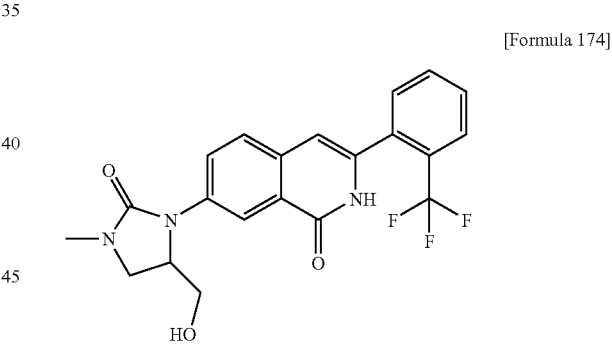

10% Pd—C (5 mg) was added to a methanol solution (3 ml) that contained 5-(hydroxymethyl)-3-methyl-2-oxo-1-imidazolidin carboxylic acid phenyl methyl ester (32 mg, 0.12 mmol), which is a known compound described in a publication (Beck, Gerhard; DE3337181). Thereafter, the obtained mixture was stirred in a hydrogen atmosphere for 2 hours. The reaction solution was filtered through celite, and the filtrate was then concentrated, without being purified. Using the 7-iodo-3-(2-trifluoromethylphenyl)-2H-isoquinolin-1-one (20 mg, 0.048 mmol) obtained in step D of Example 1-1, the captioned compound was synthesized by a reaction similar to step E of Example 1-1.

$^1$H-NMR (500 MHz, CDCl$_3$) δ (ppm): 2.59 (1H, brs), 2.93 (3H, s), 3.55-3.58 (1H, m), 3.63-3.67 (1H, m), 3.81-3.87 (2H, m), 4.5-4.6 (1H, m), 6.52 (1H, s), 7.29-7.61 (3H, m), 7.64-7.67 (1H, m), 7.81 (1H, d, J=7.5 Hz), 7.99 (1H, d, J=2 Hz), 8.56 (1H, dd, J=2, 8.5 Hz), 8.71 (1H, brs)

ESI (LC-MS positive mode) m/z 418 (M+H).

Example 2-60

7-((R)-4-Benzyloxymethyl-2-oxoimidazolidin-1-yl)-3-(2-trifluoromethylphenyl)-2H-isoquinolin-1-one

[Formula 175]

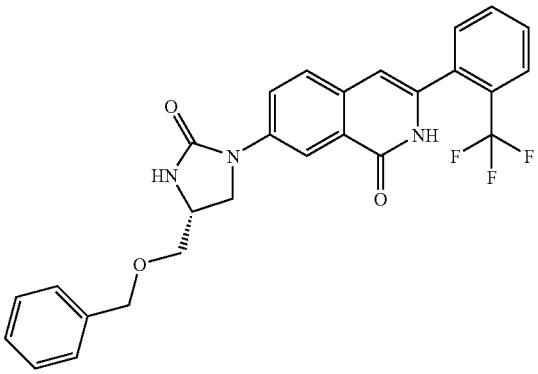

[(1S)-1-Formyl-2-(phenylmethoxy)ethyl]carbamic acid 1,1-dimethyl ethyl ester (410 mg, 1.48 mmol), which is a known compound described in a publication (Murray, William V; Tetrahedron Letters, vol. 43(41), p. 7389 (2002)), the 7-amino-3-(2-trifluoromethylphenyl)-2H-isoquinolin-1-one (450 mg, 1.48 mmol) obtained in step C of Example 1-1, and acetic acid (3 ml) were mixed. Thereafter, sodium cyanotrihydroborate (465 mg, 7.4 mmol) was added to the mixture under cooling on ice. The temperature of the obtained mixture was increased to a room temperature, and the mixture was then stirred for 3 hours. Thereafter, a saturated sodium bicarbonate aqueous solution was added to the reaction solution, and the mixture was then extracted with dichloromethane. The extract was dried over anhydrous sodium sulfate, and was then concentrated. The obtained residue was purified by silica gel column chromatography (ethyl acetate:hexane=1:1), so as to obtain a yellow foaming substance. TFA (0.5 ml) was added to a dichloromethane solution (3 ml) that contained this yellow foaming substance (50 mg, 0.088 mmol), and the obtained mixture was then stirred at a room temperature for 3 hours. Thereafter, the reaction solution was concentrated, and the compound of interest was synthesized by a reaction similar to step B of Example 1-35.

$^1$H-NMR (500 MHz, CDCl$_3$) δ (ppm): 3.52-3.56 (1H, m) 3.58-3.61 (1H, m), 3.73-3.76 (1H, m), 4.06-4.10 (1H, m), 4.12-4.16 (1H, m), 4.59 (2H, s), 5.07 (1H, s), 6.51 (1H, s), 7.26-7.55 (5H, m), 7.56-7.57 (2H, m), 7.60-7.63 (1H, m), 7.66-7.68 (1H, m), 7.81-7.82 (2H, m), 8.42 (1H, brs), 8.72 (1H, dd, J=2.5, 9 Hz)

ESI (LC-MS positive mode) m/z 494 (M+H).

Example 2-61

7-((R)-4-Hydroxymethyl-2-oxoimidazolidin-1-yl)-3-(2-trifluoromethylphenyl)-2H-isoquinolin-1-one

[Formula 176]

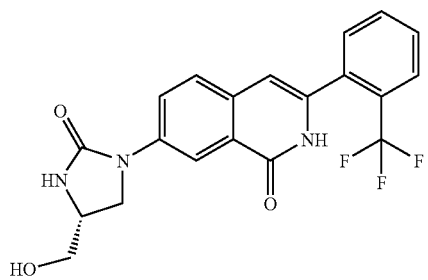

Using the 7-((R)-4-benzyloxymethyl-2-oxoimidazolidin-1-yl)-3-(2-trifluoromethylphenyl)-2H-isoquinolin-1-one prepared in Example 2-61 as a raw material, the captioned compound was synthesized by a reaction similar to that of Example 1-36.

$^1$H-NMR (400 MHz, DMSO-d$_6$) δ (ppm): 3.40-3.51 (2H, m) 3.71-3.78 (2H, m), 4.00-4.04 (1H, m), 4.98 (1H, t, J=5.37 Hz), 6.43 (1H, s), 7.24 (1H, s), 7.62-7.64 (2H, m), 7.68-7.72 (1H, m), 7.75-7.79 (1H, m), 7.86 (1H, d, J=7.33 Hz), 8.12 (1H, d, J=2.44 Hz), 8.21 (1H, dd, J=2.44, 8.79 Hz), 11.48 (1H, brs)

ESI (LC-MS positive mode) m/z 404 (M+H).

Example 2-62

7-(3-Methyl-2-oxotetrahydropyrimidin-1-yl)-3-(2-trifluoromethylphenyl)-2H-isoquinolin-1-one Step A 7-(3-Bromopropylamino)-3-(2-trifluoromethylphenyl)-2H-isoquinolin-1-one

[Formula 177]

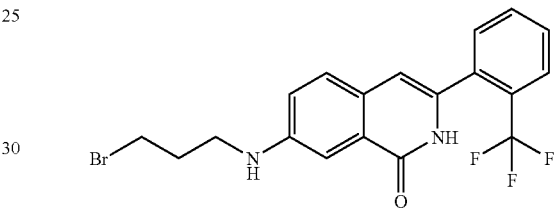

Triphenylphosphine (940 mg, 3.59 mmol) and carbon tetrabromide (1.19 g, 3.59 mmol) were added to a methylene chloride solution (10 ml) that contained the 7-(3-hydroxypropylamino)-3-(2-trifluoromethylphenyl)-2H-isoquinolin-1-one (500 mg, 1.38 mmol) obtained in step B of Example 1-49. The obtained mixture was stirred at a room temperature for 3 hours. The reaction solvent was distilled away, and the obtained residue was purified by silica gel column chromatography (ethyl acetate:hexane=1:2 to 1:1), so as to obtain 7-(3-bromopropylamino)-3-(2-trifluoromethylphenyl)-2H-isoquinolin-1-one (245 mg, 42%).

$^1$H-NMR (Bruker, 300 MHz, CDCl$_3$) δ: 2.23 (quintet, J=6.50 Hz, 2H), 3.46-3.56 (m, 4H), 6.43 (s, 1H), 7.03 (dd, J=8.31 Hz, 2.56 Hz, 1H), 7.39-7.71 (m, 5H), 7.80 (d, J=7.11 Hz, 1H), 8.58 (brs, 1H)

Mass (Micromass, Quttromicro) (ESI+): m/z 425.15 & 427.26 (M+H).

Step B 7-(3-Methylaminopropylamino)-3-(2-trifluoromethylphenyl)-2H-isoquinolin-1-one

[Formula 178]

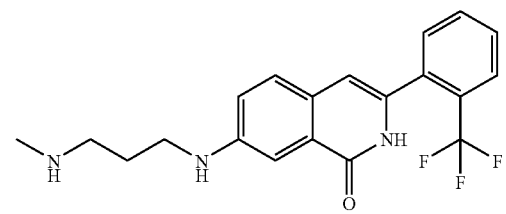

Methylamine (40% methanol solution) was added to the 7-(3-bromopropylamino)-3-(2-trifluoromethylphenyl)-2H-isoquinolin-1-one (245 mg, 0.576 mmol) obtained in step A, and the obtained mixture was then stirred at a room temperature for 3 hours. Thereafter, the reaction solvent was distilled away, and the obtained residue was purified by amino silica gel column chromatography (methylene chloride:methanol=20:1), so as to obtain 142 mg of 7-(3-methylaminopropylamino)-3-(2-trifluoromethylphenyl)-2H-isoquinolin-1-one (66%).

$^1$H-NMR (Bruker, 300 MHz, CDCl$_3$) δ: 1.87 (quintet, J=6.48 Hz, 2H), 2.45 (s, 3H), 2.77 (t, J=6.48 Hz, 2H), 3.34 (t, J=6.48 Hz, 2H), 6.42 (s, 1H), 7.01 (dd, J=8.43 Hz, 2.25 Hz, 1H), 7.37 (d, J=8.75 Hz, 1H), 7.47-7.66 (m, 4H), 7.79 (d, J=7.29 Hz, 1H)

Mass (Micromass, Quttromicro, ESI+): m/z 376.03 (M+H).

Step C 7-(3-Methyl-2-oxotetrahydropyrimidin-1-yl)-3-(2-trifluoromethylphenyl)-2H-isoquinolin-1-one

[Formula 179]

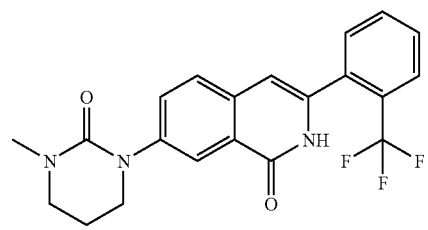

Phosgene (294 µl, 0.559 mmol) was added at 0° C. to an anhydrous methylene chloride solution (2 ml) that contained the 7-(3-methylaminopropylamino)-3-(2-trifluoromethylphenyl)-2H-isoquinolin-1-one (70 mg, 0.186 mmol) obtained in step B. The obtained mixture was stirred for 10 minutes. Thereafter, triethylamine (156 µl, 0.112 mmol) was added to the reaction solution, and the obtained mixture was then stirred for 30 minutes. Thereafter, water was added to the reaction solution. An organic layer was separated, and a water layer was then extracted with methylene chloride. The organic layer was mixed with the extract. The obtained mixture was washed with water and a saturated saline solution, and was then dried over anhydrous sodium sulfate. The solvent was distilled away under reduced pressure. The obtained residue was purified by amino silica gel column chromatography (methylene chloride:methanol=40:1), so as to obtain 7-(3-methyl-2-oxotetrahydropyrimidin-1-yl)-3-(2-trifluoromethylphenyl)-2H-isoquinolin-1-one (10.2 mg, 14%).

$^1$H-NMR (Bruker, 300 MHz, CDCl$_3$) δ: 2.17 (quintet, J=6.03 Hz, 2H), 3.03 (s, 3H), 3.42 (t, J=6.05 Hz, 2H), 3.84 (t, J=5.75 Hz, 2H), 6.49 (s, 1H), 7.48-7.66 (m, 4H), 7.81 (d, J=7.22 Hz, 1H), 7.88 (dd, J=8.87 Hz, 2.27 Hz, 1H), 8.09 (d, J=2.27 Hz, 1H), 8.64 (brs, 1H)

Mass (Micromass, Quttromicro) (ESI+): m/z 402.26 (M+H).

Example 2-63

Benzyl 3-oxo-4-[1-oxo-3-(2-trifluoromethylphenyl)-1,2-dihydroisoquinolin-7-yl]piperazine-1-carboxylate

[Formula 180]

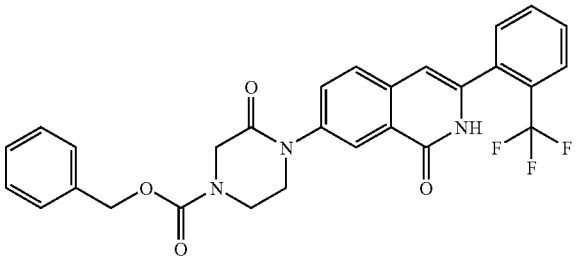

Using the 7-iodo-3-(2-trifluoromethylphenyl)-2H-isoquinolin-1-one as a raw material, the captioned compound was synthesized by a reaction similar to step D of Example 1-1.

$^1$H-NMR (270 MHz, CDCl$_3$) δ (ppm): 3.65-3.72 (4H, m), 4.37 (2H, s), 5.21 (2H, s), 6.52 (1H, s), 7.34-7.41 (6H, m), 7.52-7.81 (6H, m), 8.18 (1H, s), 9.75 (1H, brs)

ESI (LC-MS positive mode) m/z 522 (M+H).

Example 2-64

7-(2-Oxopiperazin-1-yl)-3-(2-trifluoromethylphenyl)-2H-isoquinolin-1-one

[Formula 181]

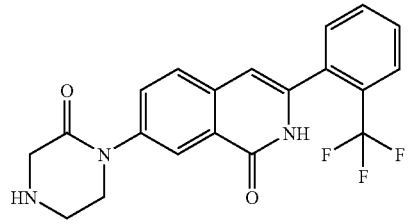

Using the 3-oxo-4-[1-oxo-3-(2-trifluoromethylphenyl)-1,2-dihydroisoquinolin-7-yl]piperazin-1-carboxylic acid benzyl obtained in Example 2-63, the captioned compound was synthesized by a method similar to that of Example 2-39.

$^1$H-NMR (270 MHz, DMSO-d$_6$) δ (ppm): 3.32 (4H, brs), 3.43 (2H, s), 6.51 (1H, s), 7.62-7.82 (5H, m), 7.88 (1H, d, J=7.9 Hz), 8.12 (1H, s), 11.63 (1H, brs)

ESI (LC-MS positive mode) m/z 388 (M+H).

Example 2-65

7-[(R)-5-((S)-1,2-Dihydroxyethyl)-2-oxooxazolidin-3-yl]-3-(2-trifluoromethylphenyl)-2H-isoquinolin-1-one

[Formula 182]

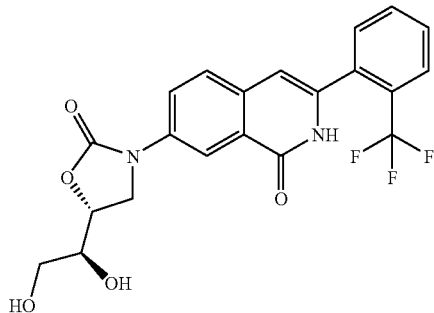

Using (L)-(+)-erythrose as a raw material, the captioned compound was synthesized by a method similar to that of Example 1-39.

$^1$H-NMR (300 MHz, CDCl$_3$) δ (ppm): 3.30-3.50 (1H, m) 3.60-3.80 (1H, m), 3.80-3.92 (1H, m), 3.93-4.02 (1H, m), 4.11 (1H, t, J=9.1 Hz), 4.29 (1H, dd, J=6.8, 9.4 Hz), 4.60-4.70 (1H, m), 6.45 (1H, s), 7.47-7.63 (5H, m), 7.74 (1H, d, J=7.4 Hz), 7.91 (1H, d, J=2.0 Hz), 8.44 (1H, dd, J=2.5, 8.8 Hz), 8.66 (1H, brs)

ESI (LC-MS positive mode) m/z 435 (M+H).

Example 2-66

7-[(R)-5-((R)-1,2-Dihydroxyethyl)-2-oxooxazolidin-3-yl]-3-(2-trifluoromethylphenyl)-2H-isoquinolin-1-one

[Formula 183]

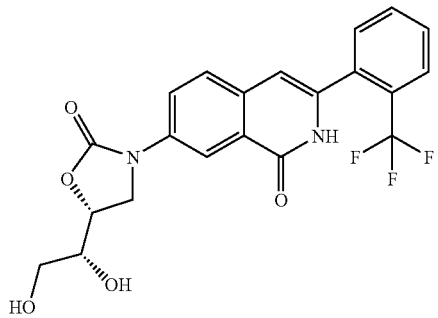

Using the 7-[(R)-5-((S)-1,2-dihydroxyethyl)-2-oxooxazolidin-3-yl]-3-(2-trifluoromethylphenyl)-2H-isoquinolin-1-one obtained in Example 2-65 as a raw material, the captioned compound was synthesized by a reaction similar to that of Example 2-50.

$^1$H-NMR (Bruker, 300 MHz, MeOH-d$_4$) δ: 3.71-3.77 (m, 3H), 4.15-4.20 (m, 1H), 4.31 (t, J=8.74 Hz, 1H), 4.88-4.94 (m, 1H), 6.62 (s, 1H), 7.60-7.88 (m, 5H), 8.27 (d, J=2.22 Hz, 1H), 8.33 (dd, J=8.77 Hz, 2.34 Hz, 1H).

Mass (Micromass, Quttromicro) (ESI–): m/z 433.43 (M–H).

Example 2-67

7-(5,5-Bishydroxymethyl-2-oxooxazolidin-3-yl)-3-(2-trifluoromethylphenyl)-2H-isoquinolin-1-one Step A 7-[(5-Hydroxy-2,2-dimethyl-[1,3]dioxan-5-ylmethyl)amino]-3-(2-trifluoromethylphenyl)-2H-isoquinolin-1-one

[Formula 184]

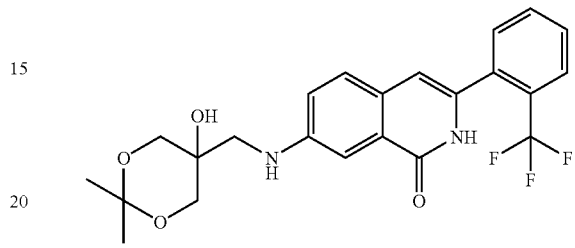

6,6-Dimethyl-1,5,7-trioxaspiro[2.5]octane (292 mg, 2.03 mmol) prepared according to a known method described in publications (EP227338, for example) and the 7-amino-3-(2-trifluoromethylphenyl)-2H-isoquinolin-1-one (154 mg, 0.506 mmol) obtained in step C of Example 1-1 were dissolved in ethanol (4 ml). The obtained mixture was stirred at a room temperature for 4 hours and then stirred under heating to reflux for 18 hours. Thereafter, lithium bromide (0.2 mg, mmol) was added to the reaction solution at a room temperature, and the obtained mixture was then stirred for 3 hours. Thereafter, the reaction solution was concentrated, and water was then added thereto, followed by extraction with ethyl acetate. The extract was washed with water and a saturated saline solution, and was then dried over anhydrous sodium sulfate. The solvent was distilled away under reduced pressure. The obtained residue was purified by silica gel column chromatography (methylene chloride:methanol=40:1 to 20:1), so as to obtain 7-[(5-hydroxy-2,2-dimethyl-[1,3]dioxan-5-ylmethyl)amino]-3-(2-trifluoromethylphenyl)-2H-isoquinolin-1-one (163 mg, 72%).

$^1$H-NMR (Bruker, 300 MHz, CDCl$_3$) δ: 1.47 (s, 6H), 3.27 (s, 2H), 3.74 (d, J=11.87 Hz, 2H), 3.92 (d, J=11.60 Hz, 2H), 6.45 (s, 1H), 7.08 (dd, J=8.55 Hz, 2.70 Hz, 1H), 7.40 (d, J=8.59 Hz, 1H), 7.50-7.67 (m, 4H), 7.80 (d, J=7.40 Hz, 1H), 8.86 (brs, 1H)

Mass (Micromass, Quttromicro) (ESI+): m/z 471.23 (M+Na).

Step B 7-(8,8-Dimethyl-2-oxo-1,7,9-trioxa-3-azaspiro[4.5]deca-3-yl)-3-(2-trifluoromethylphenyl)-2H-isoquinolin-1-one

[Formula 185]

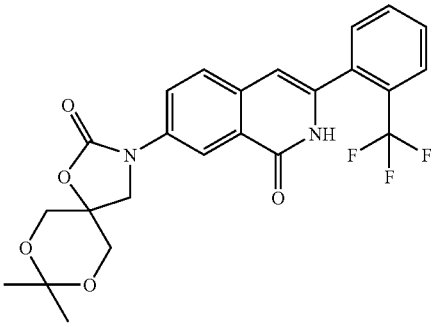

The 7-[(5-hydroxy-2,2-dimethyl-[1,3]dioxan-5-ylmethyl)amino]-3-(2-trifluoromethylphenyl)-2H-isoquinolin-1-one (163 mg, 0.366 mmol) obtained in step A was dissolved in anhydrous THF (3 ml). Thereafter, tetraethylamine (306 μl, 2.19 mmol) and phosgene (115 μl, 1.10 mmol) were added thereto under cooling on ice. The obtained mixture was stirred at a room temperature for 26 hours. Thereafter, water was added to the reaction solution, and the mixture was then extracted with ethyl acetate. The extract was washed with water and a saturated saline solution, and was then dried over anhydrous sodium sulfate. The solvent was distilled away under reduced pressure. The obtained residue was purified by silica gel column chromatography (methylene chloride:methanol=40:1), so as to obtain 7-(8,8-dimethyl-2-oxo-1,7,9-trioxa-3-azaspiro[4.5]deca-3-yl)-3-(2-trifluoromethylphenyl)-2H-isoquinolin-1-one (22 mg, 13%).

$^1$H-NMR (Bruker, 300 MHz, CDCl$_3$) δ: 1.48 (s, 3H), 1.54 (s, 3H), 3.87 (d, J=11.82 Hz, 2H), 4.09 (d, J=11.86 Hz, 2H), 4.18 (s, 2H), 6.52 (s, 1H), 7.55-7.68 (m, 4H), 7.81-7.84 (m, 1H), 7.99 (d, J=2.72 Hz, 1H), 8.55 (dd, J=8.84 Hz, 2.53 Hz, 1H), 8.83 (brs, 1H)

Mass (Micromass, Quttromicro) (ESI+): m/z 497.30 (M+Na).

Step C 7-(5,5-Bishydroxymethyl-2-oxooxazolidin-3-yl)-3-(2-trifluoromethylphenyl)-2H-isoquinolin-1-one

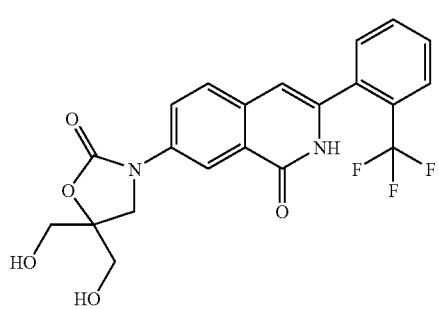

[Formula 186]

The 7-(8,8-dimethyl-2-oxo-1,7,9-trioxa-3-azaspiro[4.5]deca-3-yl)-3-(2-trifluoromethylphenyl)-2H-isoquinolin-1-one (22 mg, 0.0464 mmol) obtained in step B was dissolved in anhydrous THF (2 ml). Thereafter, 1 N hydrochloric acid (264 μl, 0.264 mmol) was added to the solution. The obtained mixture was stirred at a room temperature for 18 hours. Thereafter, a 1 N sodium hydroxide aqueous solution was added to the reaction solution, so that the reaction solution was neutralized to pH 8. The solvent was distilled away, and the obtained residue was purified by silica gel column chromatography (methylene chloride:methanol=30:1 to 10:1), so as to obtain 7-(5,5-bishydroxymethyl-2-oxooxazolidin-3-yl)-3-(2-trifluoromethylphenyl)-2H-isoquinolin-1-one (7.6 mg, 38%).

$^1$H-NMR (300 MHz, MeHO-d$_4$) δ (ppm): 3.71 (2H, d, J=12.1 Hz), 3.80 (2H, d, J=12.1 Hz), 4.11 (2H, s), 6.61 (1H, s), 7.58-7.87 (5H, m), 8.28-8.34 (2H, m)

ESI (LC-MS positive mode) m/z 435 (M+H).

Example 2-68

7-[3-(2-Hydroxyethyl)-5-oxoimidazolidin-1-yl]-3-(2-trifluoromethylphenyl)-2H-isoquinolin-1-one Step A 2-Chloro-N-[1-oxo-3-(2-trifluoromethylphenyl)-1,2-dihydroisoquinolin-7-yl]acetamide

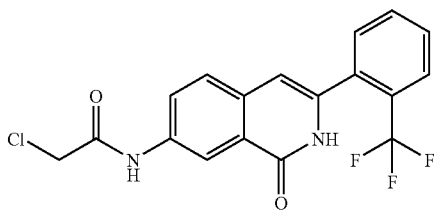

[Formula 187]

The 7-amino-3-(2-trifluoromethylphenyl)-2H-isoquinolin-1-one (100 mg, 0.329 mmol) obtained in step C of Example 1-1 was dissolved in benzene (2 ml). Thereafter, chloroacetic acid chloride (29 μl, 0.362 mmol) and pyridine (80 μl, 0.986 mmol) were added to the solution, and the obtained mixture was stirred at a room temperature for 4 hours. Thereafter, the reaction solution was washed with 1 N hydrochloric acid, and was then extracted with ethyl acetate. The extract was dried over anhydrous sodium sulfate. The solvent was distilled away under reduced pressure. The obtained residue was suspended in and washed with cold ethyl acetate, and a solid was collected by filtration, so as to obtain 2-chloro-N-[1-oxo-3-(2-trifluoromethylphenyl)-1,2-dihydroisoquinolin-7-yl]acetamide (70 mg, 56%).

$^1$H-NMR (Bruker, 300 MHz, DMSO-d$_6$) δ: 4.31 (s, 2H), 6.45 (s, 1H), 7.62-7.92 (m, 7H), 8.53 (s, 1H), 10.61 (s, 1H)

Mass (Micromass, Quttromicro) (ESI+): m/z 381.53 (M+H).

Step B 2-(2-Hydroxyethylamino)-N-[1-oxo-3-(2-trifluoromethylphenyl)-1,2-dihydroisoquinolin-7-yl]acetamide

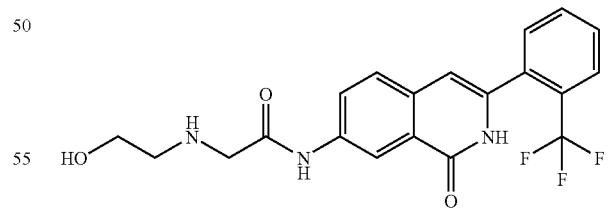

[Formula 188]

Ethanolamine (22 μl, 0.368 mmol) and triethylamine (128 μl) were added to an ethanol solution (2 ml) that contained the 2-chloro-N-[1-oxo-3-(2-trifluoromethylphenyl)-1,2-dihydroisoquinolin-7-yl]acetamide (70 mg, 0.184 mmol) obtained in step A. The obtained mixture was stirred at 70° C. for 18 hours. Thereafter, water was added to the reaction solution, and the mixture was then extracted with ethyl acetate. The extract was washed with water and a saturated saline solution, and was then dried over anhydrous sodium sulfate. Thereafter, the solvent was distilled away under reduced pressure. The obtained residue was purified by silica gel column chromatography (methylene chloride:methanol=10:1), so as to obtain 2-(2-hydroxyethylamino)-N-[1-oxo-3-(2-trifluoromethylphenyl)-1,2-dihydroisoquinolin-7-yl]acetamide (19 mg, 26%).

¹H-NMR (Bruker, 300 MHz, MeOH-$d_4$) δ: 2.89 (t, J=5.36 Hz, 2H), 3.60 (s, 2H), 3.73 (t, J=5.14 Hz, 2H), 6.57 (s, 1H), 7.58-7.76 (m, 4H), 7.84 (d, J=7.87 Hz, 1H), 8.01 (dd, J=8.56 Hz, 2.31 Hz, 1H), 8.59 (d, J=2.23 Hz, 1H)

Mass (Micromass, Quttromicro) (ESI+): m/z 406.56 (M+H).

Step C

7-[3-(2-Hydroxyethyl)-5-oxoimidazolidin-1-yl]-3-(2-trifluoromethylphenyl)-2H-isoquinolin-1-one

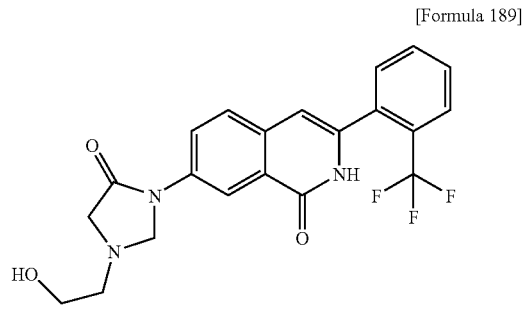

[Formula 189]

A 37% formalin aqueous solution (3.8 μl, 0.0469 mmol) was added to an ethanol solution (2 ml) that contained the 2-(2-hydroxyethylamino)-N-[1-oxo-3-(2-trifluoromethylphenyl)-1,2-dihydroisoquinolin-7-yl]acetamide (19 mg, 0.0469 mmol) obtained in step B. The obtained mixture was stirred under heating to reflux for 3 hours. Thereafter, water was added to the reaction solution, and the mixture was then extracted with ethyl acetate. The extract was washed with water and a saturated saline solution, and was then dried over anhydrous sodium sulfate. Thereafter, the solvent was distilled away under reduced pressure. The obtained residue was purified by silica gel column chromatography (methylene chloride:methanol=25:1), so as to obtain 7-[3-(2-hydroxyethyl)-5-oxoimidazolidin-1-yl]-3-(2-trifluoromethylphenyl)-2H-isoquinolin-1-one (5.2 mg, 27%).

¹H-NMR (300 MHz, MeOH-$d_4$) δ (ppm): 2.89 (2H, t, J=5.5 Hz), 3.61 (2H, s), 3.75 (2H, t, J=5.5 Hz), 4.83 (2H, s), 6.62 (1H, s), 7.62-7.86 (5H, m), 8.25 (1H, dd, J=2.4, 8.7 Hz), 8.31 (1H, d, J=2.3 Hz)

ESI (LC-MS positive mode) m/z 418 (M+H).

The following compounds (Examples 2-69 to 2-72) were synthesized by a reaction similar to that of Example 1-19.

Example 2-69

7-((R)-5-Hydroxymethyl-2-oxooxazolidin-3-yl)-3-(3-trifluoromethylphenyl)-2H-isoquinolin-1-one

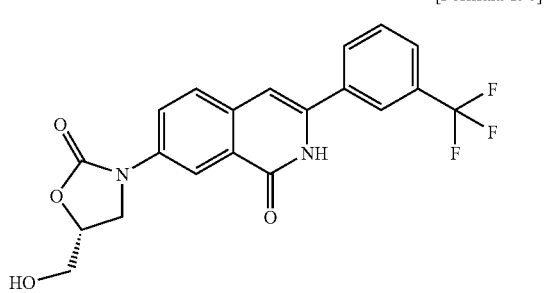

[Formula 190]

¹H-NMR (Bruker, 300 MHz, DMSO-$d_6$) δ: 3.56-3.75 (m, 2H), 3.96 (dd, J=8.74, 6.17 Hz, 1H), 4.22 (t, J=8.99 Hz, 1H), 4.71-4.79 (m, 1H), 5.23 (t, J=5.56 Hz, 1H), 7.08 (s, 1H), 7.70-7.80 (m, 3H), 8.09 (dd, J=8.74, 2.30 Hz, 2H), 8.15 (s, 1H), 8.27 (d, J=2.35 Hz, 1H), 11.73 (brs, 1H)

Mass (Micromass, Quttromicro) (ESI-): m/z 403.28 (M-H).

Example 2-70

7-((R)-5-Hydroxymethyl-2-oxooxazolidin-3-yl)-3-naphthalen-1-yl-2H-isoquinolin-1-one

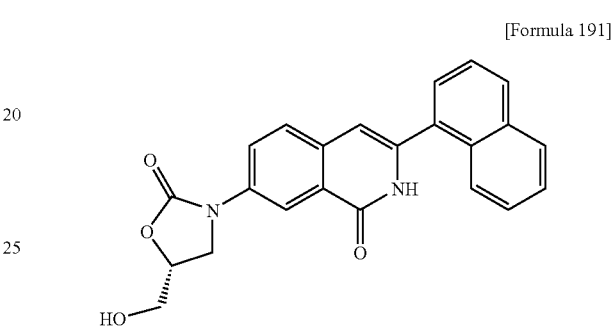

[Formula 191]

¹H-NMR (Bruker, 300 MHz, DMSO-$d_6$) δ: 3.58-3.76 (m, 2H), 3.98 (dd, J=8.38, 5.96 Hz, 1H), 4.23 (t, J=8.96 Hz, 1H), 4.72-4.80 (m, 1H), 5.24 (t, J=4.99 Hz, 1H), 6.66 (s, 1H), 7.53-7.65 (m, 4H), 7.76 (d, J=9.15 Hz, 2H), 7.89-7.93 (m, 1H), 8.01-8.12 (m, 3H), 8.29 (d, J=2.41 Hz, 1H), 11.66 (brs, 1H)

Mass (Micromass, Quttromicro) (ESI-): m/z 385.21 (M-H).

Example 2-71

3-Furan-2-yl-7-((R)-5-hydroxymethyl-2-oxooxazolidin-3-yl)-2H-isoquinolin-1-one

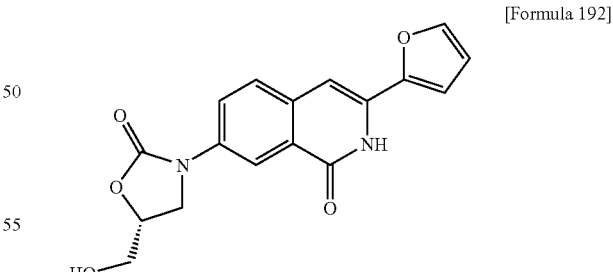

[Formula 192]

¹H-NMR (Bruker, 300 MHz, DMSO-$d_6$) δ: 3.58-3.72 (m, 2H), 3.95 (dd, J=8.84, 6.60 Hz, 1H), 4.20 (t, J=8.72 Hz, 1H), 4.70-4.78 (m, 1H), 5.23 (brs, 1H), 6.66 (dd, J=3.42, 1.43 Hz, 1H), 6.95 (s, 1H), 7.34 (d, J=3.45 Hz, 1H), 7.77 (d, J=8.34 Hz, 1H), 7.84 (s, 1H), 8.03 (dd, J=8.82, 2.31 Hz, 1H), 8.24 (s, 1H), 11.55 (brs, 1H)

Mass (Micromass, Quttromicro) (ESI+): m/z 349.48 (M+Na).

Example 2-72

7-((R)-5-Hydroxymethyl-2-oxooxazolidin-3-yl)-3-thiophen-2-yl-2H-isoquinolin-1-one

[Formula 193]

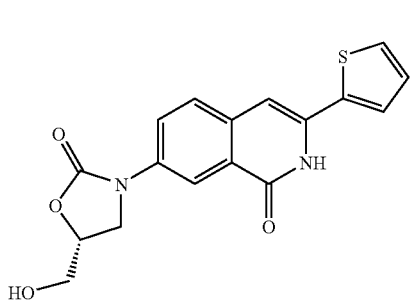

$^1$H-NMR (Bruker, 300 MHz, DMSO-d$_6$) δ: 3.57-3.73 (m, 2H), 3.95 (dd, J=9.13, 6.33 Hz, 1H), 4.20 (t, J=9.16 Hz, 1H), 4.71-4.76 (m, 1H), 5.21 (brs, 1H), 6.88 (s, 1H), 7.16 (dd, J=4.98, 3.79 Hz, 1H), 7.65 (d, J=5.01 Hz, 1H), 7.76 (d, J=8.78 Hz, 1H), 7.82 (d, J=3.51 Hz, 1H), 8.04 (dd, J=8.87, 2.65 Hz, 1H), 8.23 (d, J=2.66 Hz, 1H), 11.60 (brs, 1H)

Mass (Micromass, Quttromicro) (ESI+): m/z 365.22 (M+Na).

Example 2-73

7-((S)-5-Dimethylaminomethyl-2-oxooxazolidin-3-yl)-3-(2-trifluoromethylphenyl)-2H-isoquinolin-1-one

[Formula 194]

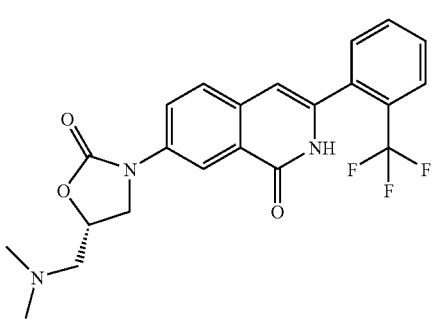

The captioned compound was synthesized by a method similar to that of Example 2-22.

$^1$H-NMR (300 MHz, CDCl$_3$) δ (ppm): 2.36 (6H, s), 2.69-2.76 (2H, m), 4.00 (1H, dd, J=7.1, 9.3 Hz), 4.21 (1H, d, J=8.8 Hz), 4.78-4.84 (1H, m), 6.53 (1H, s), 7.54-7.68 (4H, m), 7.82 (1H, d, J=7.8 Hz), 7.95 (1H, d, J=2.5 Hz), 8.61 (1H, dd, J=2.5, 8.8 Hz), 8.78 (1H, brs)

ESI (LC-MS positive mode) m/z 432 (M+H).

The following compounds given in Examples 2-75 and 2-76 were synthesized by a reaction similar to that of Example 1-19.

Example 2-75

7-((R)-5-Hydroxymethyl-2-oxooxazolidin-3-yl)-3-(4-trifluoromethylphenyl)-2H-isoquinolin-1-one

[Formula 195]

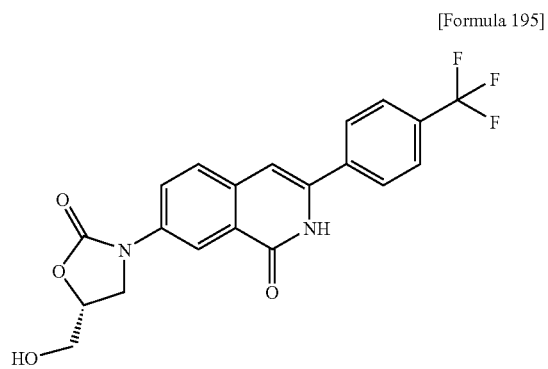

$^1$H-NMR (Bruker, 300 MHz, DMSO-d$_6$) δ: 3.57-3.75 (m, 2H), 3.96 (dd, J=8.41, 5.95 Hz, 1H), 4.22 (t, J=8.95 Hz, 1H), 4.71-4.79 (m, 1H), 5.23 (t, J=5.74 Hz, 1H), 7.06 (s, 1H), 7.78-7.86 (m, 3H), 8.01 (d, J=8.32 Hz, 2H), 8.10 (dd, J=8.78, 2.66 Hz, 1H), 8.27 (d, J=2.30 Hz, 1H), 11.67 (brs, 1H)

Mass (Micromass, Quttromicro) (ESI+): m/z 427.32 (M+Na).

Example 2-76

7-((R)-5-Hydroxymethyl-2-oxooxazolidin-3-yl)-3-(3-methylthiophen-2-yl)-2H-isoquinolin-1-one

[Formula 196]

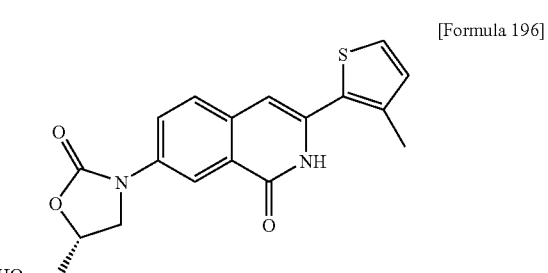

$^1$H-NMR (Bruker, 300 MHz, DMSO-d$_6$) δ: 2.31 (s, 3H) 3.57-3.74 (m, 2H), 3.95 (dd, J=8.78, 6.48 Hz, 1H), 4.20 (t, J=8.84 Hz, 1H), 4.71-4.78 (m, 1H), 5.22 (t, J=4.36 Hz, 1H), 6.62 (s, 1H), 7.01 (d, J=5.09 Hz, 1H), 7.56 (d, J=5.44 Hz, 1H), 7.74 (d, J=8.82 Hz, 1H), 8.07 (dd, J=8.79, 2.79 Hz, 1H), 8.23 (d, J=2.21 Hz, 1H), 11.38 (brs, 1H)

Mass (Micromass, Quttromicro) (ESI+): m/z 379.36 (M+Na).

Example 2-77

7-(3-Oxomorpholin-4-yl)-3-(2-trifluoromethylphenyl)-2H-isoquinolin-1-one

Step A

7-[2-(tert-Butyldimethylsilanyloxy)ethylamino]-3-(2-trifluoromethylphenyl)-2H-isoquinolin-1-one

[Formula 197]

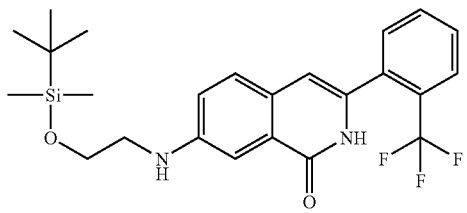

(tert-Butyldimethylsilanyloxy)acetaldehyde (93.9 µL, 0.493 mmol) and acetic acid (169 µL, 2.96 mmol) were added to a methanol solution (30 ml) that contained the 7-amino-3-(2-trifluoromethylphenyl)-2H-isoquinolin-1-one (150 mg, 0.493 mmol) prepared in step C of Example 1-1. The obtained solution was cooled to 0° C., and sodium cyanoborate (1M THF solution, 1.48 mL, 1.48 mmol) was then added thereto. The obtained mixture was stirred at a room temperature for 18 hours. The reaction solution was poured into a mixed solution of ethyl acetate and a saturated sodium bicarbonate aqueous solution. An organic layer was dried over anhydrous sodium sulfate, and the solvent was then distilled away under reduced pressure. The obtained residue was purified by silica gel column chromatography (methylene chloride:methanol=40:1), so as to obtain 7-[2-(tert-butyldimethylsilanyloxy)ethylamino]-3-(2-trifluoromethylphenyl)-2H-isoquinolin-1-one (210 mg, 92%).

$^1$H-NMR (300 MHz, CDCl$_3$) δ (ppm): 0.09 (6H, s), 0.92 (9H, s), 3.36 (2H, t, J=5.15 Hz), 3.88 (2H, t, J=5.16 Hz), 6.44 (1H, s), 7.06 (1H, dd, J=8.54, 2.66 Hz), 7.40 (1H, d, J=8.57 Hz), 7.52-7.67 (4H, m), 7.80 (1H, d, J=6.87 Hz), 8.58 (1H, brs)

Mass (Micromass, Quttromicro) (ESI+): m/z 463.39 (M+H).

Step B 7-(2-Hydroxyethylamino)-3-(2-trifluoromethylphenyl)-2H-isoquinolin-1-one

[Formula 198]

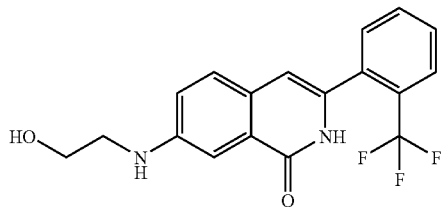

TBAF (1 M THF solution, 88.2 µL, 0.882 mmol) was added to a THF solution (4 mL) that contained the 7-[2-(tert-butyldimethylsilanyloxy)ethylamino]-3-(2-trifluoromethylphenyl)-2H-isoquinolin-1-one (204 mg, 0.441 mmol) obtained in step A, and the obtained mixture was then stirred at a room temperature for 1 hour. Thereafter, the reaction solution was poured into a mixed solution of ethyl acetate and a saturated ammonium chloride aqueous solution. An organic layer was dried over anhydrous sodium sulfate, and the solvent was then distilled away under reduced pressure. The obtained residue was purified by silica gel column chromatography (methylene chloride:methanol=40:1 to 10:1), so as to obtain 7-(2-hydroxyethylamino)-3-(2-trifluoromethylphenyl)-2H-isoquinolin-1-one (173 mg, quant).

$^1$H-NMR (300 MHz, CDCl$_3$) δ (ppm): 3.44 (2H, t, J=5.00 Hz), 3.91 (2H, t, J=5.02 Hz), 6.44 (1H, s), 7.05 (1H, dd, J=8.55, 2.59 Hz), 7.39 (1H, d, J=8.61 Hz), 7.51-7.66 (4H, m), 7.79 (1H, d, J=7.30 Hz), 8.64 (1H, brs)

Mass (Micromass, Quttromicro) (ESI+): m/z 371.30 (M+Na).

Step C

2-{(2-Bromoacetyl)-1-[1-oxo-3-(2-trifluoromethylphenyl)-1,2-dihydroisoquinolin-7-yl]amino}ethyl bromoacetate

[Formula 199]

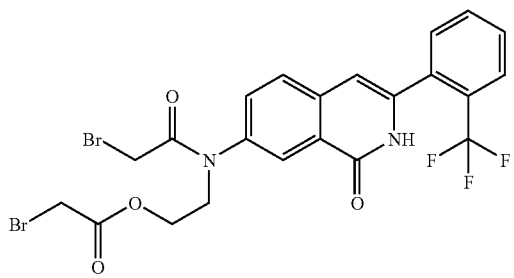

Sodium hydride (60% in mineral oil, 39 mg, 0.976 mmol) was added to an anhydrous DMF solution (3 mL) that contained the 7-(2-hydroxyethylamino)-3-(2-trifluoromethylphenyl)-2H-isoquinolin-1-one (170 mg, 0.488 mmol) obtained in step B. Thereafter, bromoacetyl bromide (213 µL, 2.44 mmol) was added thereto, and the obtained mixture was then stirred at a room temperature for 15 hours. Thereafter, a saturated ammonium chloride aqueous solution was added to the reaction solution, and the obtained reaction solution was extracted with ethyl acetate. The extract was dried over anhydrous sodium sulfate, and the solvent was then distilled away under reduced pressure. The obtained residue was purified by preparative HPLC, so as to obtain 2-{(2-bromoacetyl)-1-[1-oxo-3-(2-trifluoromethylphenyl)-1,2-dihydroisoquinolin-7-yl]amino}ethyl bromoacetate (24 mg, 8.3%).

$^1$H-NMR (300 MHz, CDCl$_3$) δ (ppm): 3.69 (2H, s), 3.81 (2H, s), 4.07 (2H, t, J=5.21 Hz), 4.40 (2H, t, J=5.26 Hz), 6.57 (1H, s), 7.57-7.74 (5H, m), 7.85 (1H, d, J=7.67 Hz), 8.30 (1H, s), 9.59 (1H, brs)

Mass (Micromass, Quttromicro) (ESI+): m/z 612.77 and 614.85 (M+Na)

Step D 7-(3-Oxomorpholin-4-yl)-3-(2-trifluoromethylphenyl)-2H-isoquinolin-1-one

[Formula 200]

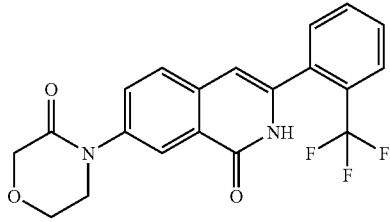

Potassium carbonate (28 mg, 0.203 mmol) was added to a methanol solution (2 mL) that contained the 2-{(2-bromoacetyl)-1-[1-oxo-3-(2-trifluoromethylphenyl)-1,2-dihydroisoquinolin-7-yl]amino}ethyl bromoacetate (24 mg, 0.0407 mmol) obtained in step C. The obtained mixture was stirred at a room temperature for 4 hours. Thereafter, the reaction solution was poured into a mixed solution of ethyl acetate and water, and the obtained mixture was then extracted with ethyl acetate. The extract was dried over anhydrous sodium sulfate, and the solvent was then distilled away under reduced pressure. The obtained residue was purified by preparative thin layer chromatography (methylene chloride:methanol=20:1), so as to obtain 7-(3-oxomorpholin-4-yl)-3-(2-trifluoromethylphenyl)-2H-isoquinolin-1-one (4.5 mg, 25%).

$^1$H-NMR (300 MHz, CDCl$_3$) δ (ppm): 3.88-3.92 (2H, m), 4.07-4.10 (2H, m), 4.39 (2H, s), 6.53 (1H, s), 7.54-7.71 (4H, m), 7.81-7.87 (2H, m), 8.25 (1H, d, J=2.25 Hz), 8.83 (1H, brs)

Mass (Micromass, Quttromicro) (ESI+): m/z 411.05 (M+Na)

Example 3-1

(R)-2-Oxo-3-[1-oxo-3-(2-trifluoromethylphenyl)-1,2-dihydroisoquinolin-7-yl]oxazolidin-5-ylmethyl methylaminoacetate hydrochloride Step A (R)-2-Oxo-3-[1-oxo-3-(2-trifluoromethylphenyl)-1,2-dihydroisoquinolin-7-yl]oxazolidin-5-ylmethyl N-tert-butoxycarbonyl-N-methyl-aminoacetate

[Formula 201]

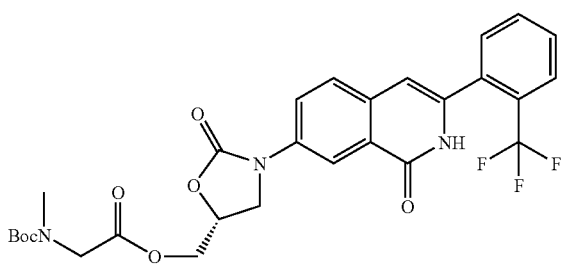

The 7-((R)-5-hydroxymethyl-2-oxooxazolidin-3-yl)-3-(2-trifluoromethylphenyl)-2H-isoquinolin-1-one (800 mg, 1.98 mmol) obtained in step B of Example 1-14 was dissolved in methylene chloride (10 ml). Thereafter, Boc-sar-OH (449 mg, 2.37 mmol), N,N-dimethylaminopyridine (73 mg, 0.59 mmol), and WSCI (493 mg, 2.57 mmol) were added at 0° C. to the solution. The obtained mixture was stirred at a room temperature for 15 hours. Thereafter, the reaction mixture was concentrated under reduced pressure, and the obtained residue was then purified by silica gel chromatography (methylene chloride:methanol=20:1), so as to obtain N-tert-butoxycarbonyl-N-methylaminoacetic acid (R)-2-oxo-3-[1-oxo-3-(2-trifluoromethylphenyl)-1,2-dihydroisoquinolin-7-yl]oxazolidin-5-ylmethyl ester (1.14 g, 100%) in the form of a colorless foaming substance.

$^1$H-NMR (CDCl$_3$) δ: 1.38-1.48 (9H, m), 2.91 (3H, s), 3.46-3.54 (1H, m), 3.93-4.06 (3H, m), 4.22-4.51 (2H, m), 4.88-5.02 (1H, m), 6.53 (1H, s), 7.50-7.74 (5H, m), 7.83 (1H, d, J=8.9 Hz), 7.91-7.98 (1H, m)

ESI (LC-MS positive mode) m/z 576 (M+H).

Step B (R)-2-Oxo-3-[1-oxo-3-(2-trifluoromethylphenyl)-1,2-dihydroisoquinolin-7-yl]oxazolidin-5-ylmethyl methylaminoacetate hydrochloride

[Formula 202]

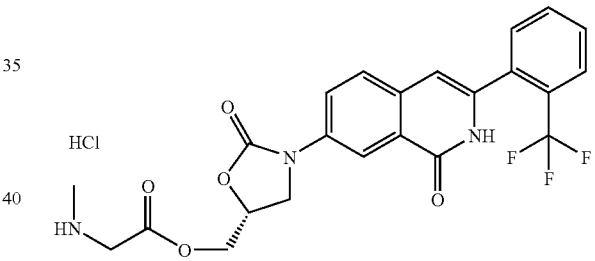

A 4 N hydrochloric acid-ethyl acetate solution (5 ml, 20 mmol) was added at 0° C. to a methylene chloride solution (10 ml) that contained the N-tert-butoxycarbonyl-N-methylaminoacetic acid (R)-2-oxo-3-[1-oxo-3-(2-trifluoromethylphenyl)-1,2-dihydroisoquinolin-7-yl]oxazolidin-5-ylmethyl ester (1.15 g, 2.0 mmol) obtained in step A. The obtained mixture was stirred at a room temperature for 5 hours. Thereafter, ether was added to the reaction mixture, so that powders were completely precipitated and collected by filtration. The filtrate was washed with ether and hexane, and was then dried under reduced pressure, so as to obtain methylaminoacetic acid (R)-2-oxo-3-[1-oxo-3-(2-trifluoromethylphenyl)-1,2-dihydroisoquinolin-7-yl]oxazolidin-5-ylmethyl ester hydrochloride (967 mg, 95%) in the form of white powders.

$^1$H-NMR (DMSO-d$_6$) δ: 2.55-2.65 (3H, m), 3.95-4.12 (2H, m), 4.24-4.40 (1H, m), 4.48-4.58 (2H, m), 4.98-5.12 (1H, m), 6.50 (1H, s), 7.55-7.93 (5H, m), 8.10 (1H, dd, J=8.6, 2.4 Hz), 8.21 (1H, d, J=2.4 Hz), 9.19 (2H, brs), 11.60 (1H, brs)

ESI (LC-MS positive mode) m/z 476 (M+H).

Example 3-2

(R)-2-Oxo-3-[1-oxo-3-(2-trifluoromethylphenyl)-1,2-dihydroisoquinolin-7-yl]oxazolidin-5-ylmethyl aminoacetate hydrochloride

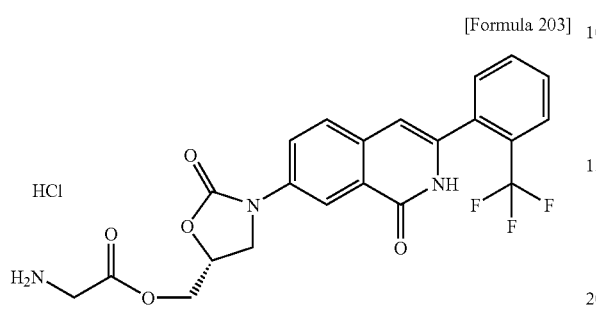

[Formula 203]

The captioned compound was synthesized by a method similar to that of Example 3-1 with the exception that Boc-Gly-OH was used instead of Boc-Sar-OH.

$^1$H-NMR (DMSO-d$_6$) δ: 3.84-4.96 (1H, m), 3.06-4.08 (1H, m), 4.23-4.37 (1H, m), 4.48-4.56 (2H, m), 4.95-5.10 (1H, m), 6.50 (1H, s), 7.58-7.93 (1H, m), 8.10 (1H, dd, J=8.7, 2.5 Hz), 8.21 (1H, d, J=2.5 Hz), 8.35 (3H, brs), 11.63 (1H, s)

ESI (LC-MS positive mode) m/z 462 (M+H).

Example 3-3

(R)-2-Oxo-3-[1-oxo-3-(2-trifluoromethylphenyl)-1,2-dihydroisoquinolin-7-yl]oxazolidin-5-ylmethyl(S)-2-aminopropionate hydrochloride

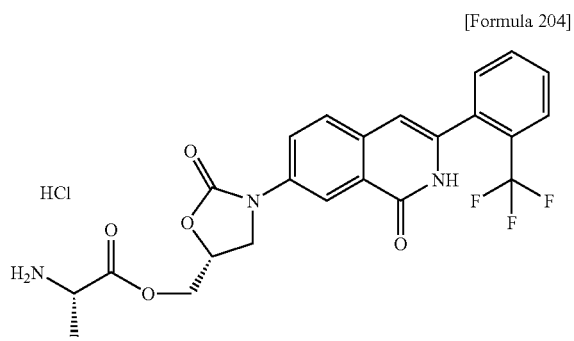

[Formula 204]

The captioned compound was synthesized by a method similar to that of Example 3-1 with the exception that L-Boc-Ala-OH was used instead of Boc-Sar-OH.

$^1$H-NMR (DMSO-d$_6$) δ: 1.38 (3H, d, J=7.1 Hz), 4.0-4.10 (1H, m), 4.10-4.24 (1H, m), 4.28-4.38 (1H, m), 4.38-4.69 (2H, m), 4.97-5.12 (1H, m), 6.50 (1H, s), 7.58-7.93 (1H, m), 8.10 (1H, dd, J=8.7, 2.4 Hz), 8.22 (1H, d, J=2.5 Hz), 8.46 (3H, brs), (1H, s)

ESI (LC-MS positive mode) m/z 476 (M+H).

Example 3-4

(R)-2-Oxo-3-[1-oxo-3-(2-trifluoromethylphenyl)-1,2-dihydroisoquinolin-7-yl]oxazolidin-5-ylmethyl(S)-pyrrolidine-2-carboxylate hydrochloride

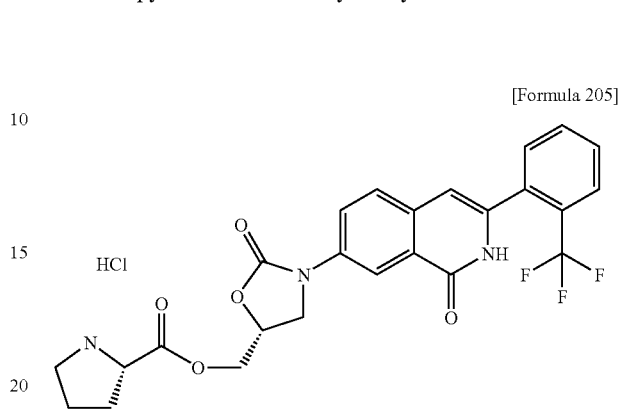

[Formula 205]

The captioned compound was synthesized by a method similar to that of Example 3-1 with the exception that L-Boc-Pro-OH was used instead of Boc-Sar-OH.

$^1$H-NMR (DMSO-d$_6$) δ: 1.81-2.07 (3H, m), 2.12-2.30 (1H, m), 3.11-3.32 (1H, m), 4.03-4.17 (1H, m), 4.25-4.39 (1H, m), 4.39-4.50 (2H, m), 4.53-4.68 (1H, m), 4.99-5.13 (1H, m), 6.50 (1H, s), 7.55-7.93 (5H, m), 8.10 (1H, dd, J=8.7, 2.5 Hz), 8.23 (1H, d, J=2.5 Hz), 9.09 (1H, brs), 10.06 (1H, brs), 11.63 (1H, brs)

ESI (LC-MS positive mode) m/z 502 (M+H).

Example 3-5

(R)-2-Oxo-3-[1-oxo-3-(2-trifluoromethylphenyl)-1,2-dihydroisoquinolin-7-yl]oxazolidin-5-ylmethyl(S)-2-aminobutanoate hydrochloride

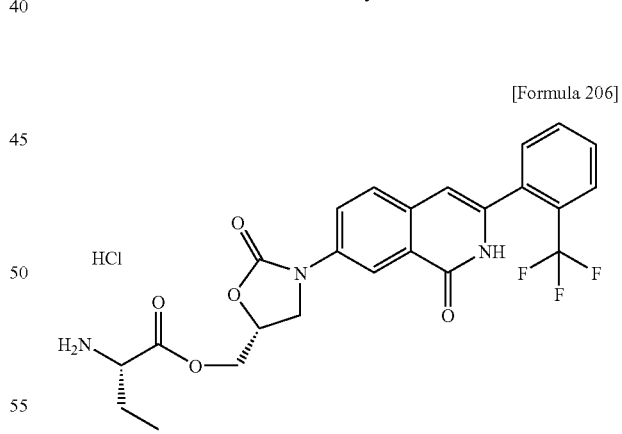

[Formula 206]

The captioned compound was synthesized by a method similar to that of Example 3-1 with the exception that L-Boc-Abu-OH was used instead of Boc-Sar-OH.

$^1$H-NMR (DMSO-d$_6$) δ: 0.75-1.00 (3H, m), 1.73-1.90 (1H, m), 3.95-4.12 (1H, m), 4.35-4.49 (1H, m), 4.39-4.50 (1H, m), 4.58-4.70 (1H, m), 5.00-5.11 (1H, m), 6.50 (1H, s), 7.58-7.92 (1H, m), 8.09 (1H, dd, J=8.7, 2.5 Hz), 8.22 (1H, d, J=2.5 Hz), 8.52 (3H, brs), 11.63 (1H, brs)

ESI (LC-MS positive mode) m/z 490 (M+H).

Example 3-6

(R)-2-Oxo-3-[1-oxo-3-(2-trifluoromethylphenyl)-1,2-dihydroisoquinolin-7-yl]oxazolidin-5-ylmethyl(S)-2-aminopentanoate hydrochloride

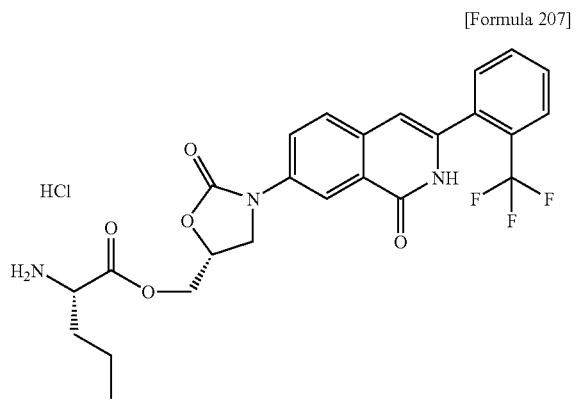

[Formula 207]

The captioned compound was synthesized by a method similar to that of Example 3-1 with the exception that L-Boc-Nva-OH was used instead of Boc-Sar-OH.

$^1$H-NMR (DMSO-d$_6$) δ: 0.79 (1H, t, J=8.1 Hz), 1.1-1.72 (4H, m), 3.90-4.12 (2H, m), 4.25-4.34 (1H, m), 4.34-4.48 (1H, m), 4.58-4.70 (1H, m), 4.98-5.12 (1H, m), 6.50 (1H, s), 7.54-7.93 (5H, m), 8.10 (1H, dd, J=8.7, 2.5 Hz), 8.23 (1H, d, J=2.5 Hz), 8.54 (3H, brs), 11.62 (1H, brs)

ESI (LC-MS positive mode) m/z 504 (M+H).

Example 3-7

(R)-2-Oxo-3-[1-oxo-3-(2-trifluoromethylphenyl)-1,2-dihydroisoquinolin-7-yl]oxazolidin-5-ylmethyl(S)-2-amino-4-methyl-pentanoate hydrochloride

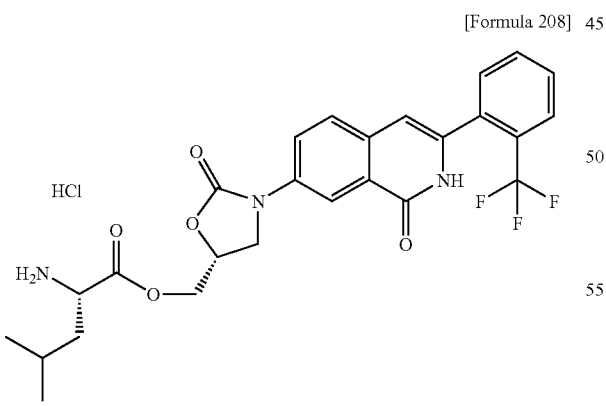

[Formula 208]

The captioned compound was synthesized by a method similar to that of Example 3-1 with the exception that L-Boc-Leu-OH was used instead of Boc-Sar-OH.

$^1$H-NMR (DMSO-d$_6$) δ: 0.7-0.84 (6H, m), 1.52-1.63 (2H, m), 1.63-1.79 (1H, m), 3.92-4.14 (2H, m), 4.28-4.46 (2H, m), 4.60-4.69 (1H, m), 5.00-5.13 (1H, m), 6.50 (1H, s), 7.58-7.93 (5H, m), 8.11 (1H, dd, J=8.7, 2.5 Hz), 8.23 (1H, d, J=2.5 Hz), 8.48 (3H, brs), 11.62 (1H, brs)

ESI (LC-MS positive mode) m/z 518 (M+H).

Example 3-8

(R)-2-Oxo-3-[1-oxo-3-(2-trifluoromethylphenyl)-1,2-dihydroisoquinolin-7-yl]oxazolidin-5-ylmethyl(2S,3S)-2-amino-3-methylpentanoate hydrochloride

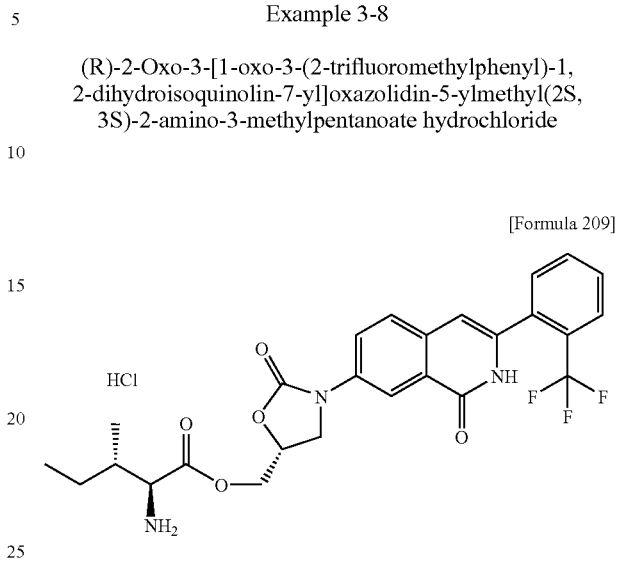

[Formula 209]

The captioned compound was synthesized by a method similar to that of Example 3-1 with the exception that L-Boc-ILe-OH was used instead of Boc-Sar-OH.

$^1$H-NMR (DMSO-d$_6$) δ: 0.72-0.95 (6H, m), 1.17-1.50 (1H, m), 1.80-1.95 (1H, m), 3.94-4.09 (1H, m), 4.26-4.48 (2H, m), 4.58-4.70 (1H, m), 5.0-5.13 (1H, m), 6.50 (1H, s), 7.58-7.93 (5H, m), 8.11 (1H, dd, J=8.7, 2.5 Hz), 8.22 (1H, d, J=2.5 Hz), 8.50 (2H, brs), 11.63 (1H, brs)

ESI (LC-MS positive mode) m/z 518 (M+H).

Example 3-9

(R)-2-Oxo-3-[1-oxo-3-(2-trifluoromethylphenyl)-1,2-dihydroisoquinolin-7-yl]oxazolidin-5-ylmethyl(S)-2-amino-3-methyl-butanoate hydrochloride

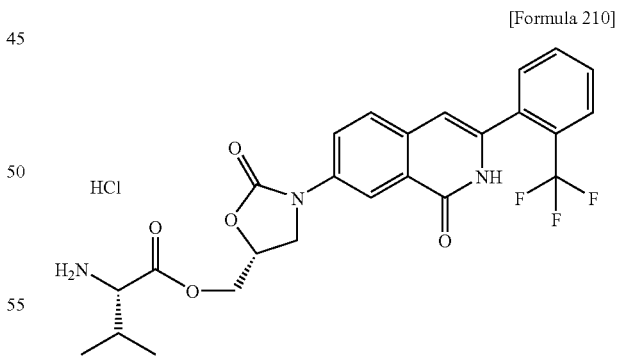

[Formula 210]

The captioned compound was synthesized by a method similar to that of Example 3-1 with the exception that L-Boc-Val-OH was used instead of Boc-Sar-OH.

$^1$H-NMR (DMSO-d$_6$) δ: 0.96 (6H, t, J=7.4 Hz), 1.20-1.30 (1H, m), 3.92-4.08 (2H, m), 4.26-4.52 (2H, m), 4.60-4.70 (1H, m), 4.99-5.12 (1H, m), 6.50 (1H, s), 7.55-7.96 (5H, m), 8.10 (1H, d, J=2.5, 8.7 Hz), 8.21 (1H, d, J=2.5 Hz), 11.63 (1H, brs)

ESI (LC-MS positive mode) m/z 504 (M+H).

Example 3-10

(R)-2-Oxo-3-[1-oxo-3-(2-trifluoromethylphenyl)-1,2-dihydroisoquinolin-7-yl]oxazolidin-5-ylmethyl(S)-2-aminohexanoate hydrochloride

[Formula 211]

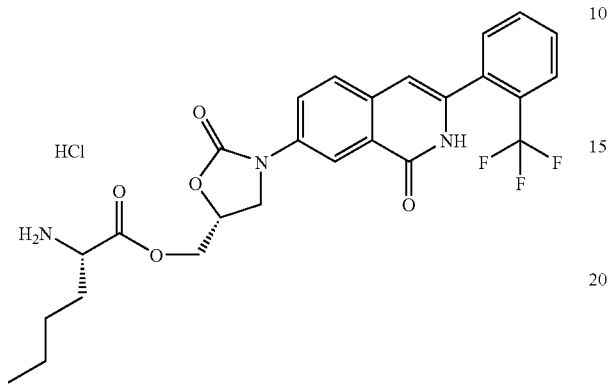

The captioned compound was synthesized by a method similar to that of Example 3-1 with the exception that L-Boc-Nle-OH was used instead of Boc-Sar-OH.

$^1$H-NMR (DMSO-$d_6$) δ: 0.86 (1H, t, J=8.1 Hz), 1.55-1.80 (6H, m), 3.90-4.12 (2H, m), 4.24-4.36 (1H, m), 4.33-4.49 (1H, m), 4.58-4.70 (1H, m), 4.98-5.12 (1H, m), 6.50 (1H, s), 7.54-7.93 (5H, m), 8.11 (1H, dd, J=8.7, 2.5 Hz), 8.24 (1H, d, J=2.5 Hz), 8.54 (3H, brs), 11.62 (1H, brs)

ESI (LC-MS positive mode) m/z 518 (M+H).

Example 3-11

(R)-2-Oxo-3-[1-oxo-3-(2-trifluoromethylphenyl)-1,2-dihydroisoquinolin-7-yl]oxazolidin-5-ylmethyl dimethylaminoacetate hydrochloride

[Formula 212]

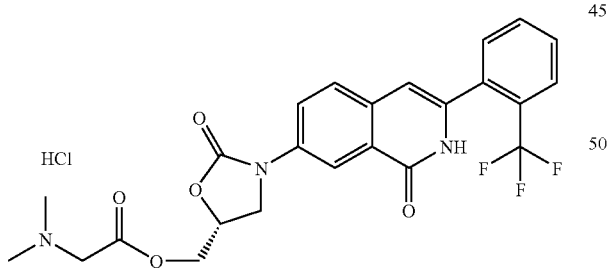

Using N,N-dimethyl-Gly-OH instead of Boc-Sar-OH, a condensation reaction was carried out by a method similar to step A of Example 3-1. The reaction mixture was concentrated under reduced pressure, and the obtained residue was purified by silica gel chromatography (methylene chloride:methanol=20:1). Thereafter, 2 equivalent weight of a 4 N hydrochloric acid-ethyl acetate solution was added thereto at 0° C. in methylene chloride, and the obtained mixture was then stirred for 30 minutes. Thereafter, ether was added to the reaction mixture, so that powders were completely precipitated and collected by filtration. The filtrate was washed with ether and hexane, and was then dried under reduced pressure, so as to obtain (R)-2-oxo-3-[1-oxo-3-(2-trifluoromethylphenyl)-1,2-dihydroisoquinolin-7-yl]oxazolidin-5-ylmethyl ester hydrochloride in the form of white powders.

$^1$H-NMR (DMSO-$d_6$) δ: 2.84 (6H, s), 4.0-4.10 (1H, m), (2H, s), 4.44-4.60 (2H, s), 5.0-5.12 (1H, s), 6.50 (1H, s), 7.57-7.94 (5H, m), 8.10 (1H, dd, J=8.7, 2.4 Hz), 8.22 (1H, d, J=2.4 Hz), 10.52 (1H, brs), 11.63 (1H, brs)

ESI (LC-MS positive mode) m/z 490 (M+H).

Example 3-12

(R)-2-Oxo-3-[1-oxo-3-(2-trifluoromethylphenyl)-1,2-dihydroisoquinolin-7-yl]oxazolidin-5-ylmethyl 3-aminopropionate hydrochloride

[Formula 213]

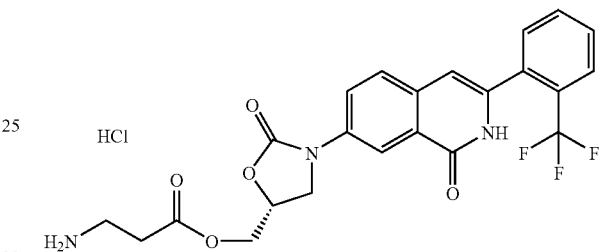

The captioned compound was synthesized by a method similar to that of Example 3-1 with the exception that Boc-beta-Ala-OH was used instead of Boc-Sar-OH.

$^1$H-NMR (DMSO-$d_6$) δ: 2.73 (2H, t, J=8.1 Hz), 2.91-3.10 (2H, m), 3.95-4.08 (1H, m), 4.22-4.48 (3H, m), 4.85-5.10 (1H, m), 6.50 (1H, s), 7.58-7.93 (5H, m), 7.97 (3H, brs), 8.09 (1H, dd, J=8.7, 2.5 Hz), 8.23 (1H, d, J=2.5 Hz), 11.63 (1H, brs)

ESI (LC-MS positive mode) m/z 476 (M+H).

Example 3-13

(R)-2-Oxo-3-[1-oxo-3-(2-trifluoromethylphenyl)-1,2-dihydroisoquinolin-7-yl]oxazolidin-5-ylmethyl(S)-2-amino-3-phenylpropionate hydrochloride

[Formula 214]

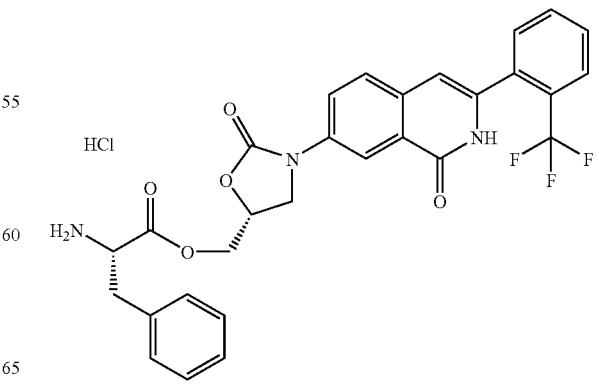

The captioned compound was synthesized by a method similar to that of Example 3-1 with the exception that L-Boc-Phe-OH was used instead of Boc-Sar-OH.

$^1$H-NMR (DMSO-d$_6$) δ: 3.06-3.24 (2H, m), 3.83-3.98 (1H, m), 4.17-4.31 (1H, m), 4.31-4.55 (3H, m), 4.85-5.00 (1H, m), 6.50 (1H, s), 7.14-7.38 (5H, m), 7.59-7.93 (5H, m), 8.09 (1H, dd, J=8.7, 2.5 Hz), 8.19 (1H, d, J=2.5 Hz), 8.63 (3H, s), (1H, brs)

ESI (LC-MS positive mode) m/z 552 (M+H).

Example 3-14

(R)-2-Oxo-3-[1-oxo-3-(2-trifluoromethylphenyl)-1,2-dihydroisoquinolin-7-yl]oxazolidin-5-ylmethyl 4-aminobutanoate hydrochloride

[Formula 215]

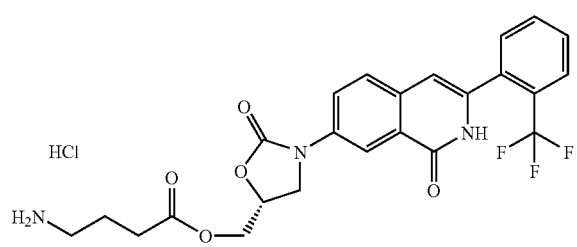

The captioned compound was synthesized by a method similar to that of Example 3-1 with the exception that L-Boc-gamma-Abu-OH was used instead of Boc-Sar-OH.

$^1$H-NMR (DMSO-d$_6$) δ: 1.79-1.90 (2H, m), 2.42-2.55 (2H, m), 2.68-2.89 (2H, m), 3.91-4.12 (1H, m), 4.24-4.46 (2H, m), 4.92-5.09 (1H, m), 6.50 (1H, s), 7.54-8.0 (8H, m), 8.09 (1H, dd, J=8.9, 2.5 Hz), 8.23 (1H, d, J=2.5 Hz), 11.63 (1H, brs)

ESI (LC-MS positive mode) m/z 490 (M+H).

Example 3-15

(R)-2-Oxo-3-[1-oxo-3-(2-trifluoromethylphenyl)-1,2-dihydroisoquinolin-7-yl]oxazolidin-5-ylmethyl 3-methylaminopropionate hydrochloride

[Formula 216]

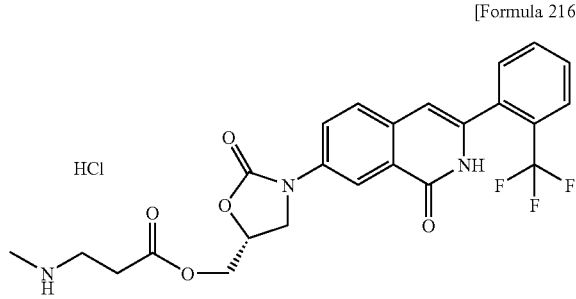

The captioned compound was synthesized by a method similar to that of Example 3-1 with the exception that Boc-N-methyl-beta-Ala-OH was used instead of Boc-Sar-OH.

$^1$H-NMR (DMSO-d$_6$) δ: 2.69 (2H, t, J=8.1 Hz), 2.82 (2H, t, J=8.1 Hz), 2.98-3.18 (3H, m), 3.95-4.13 (1H, m), 4.23-4.48 (3H, m), 4.95-5.12 (1H, s), 6.50 (1H, s), 7.56-7.95 (5H, m), 8.09 (1H, dd, J=8.7, 2.4 Hz), 8.24 (1H, d, J=2.4 Hz), 8.94 (2H, brs), 11.63 (1H, s)

ESI (LC-MS positive mode) m/z 490 (M+H).

Example 3-16

(R)-2-Oxo-3-[1-oxo-3-(2-trifluoromethylphenyl)-1,2-dihydroisoquinolin-7-yl]oxazolidin-5-ylmethyl 3-dimethylaminopropionate hydrochloride

[Formula 217]

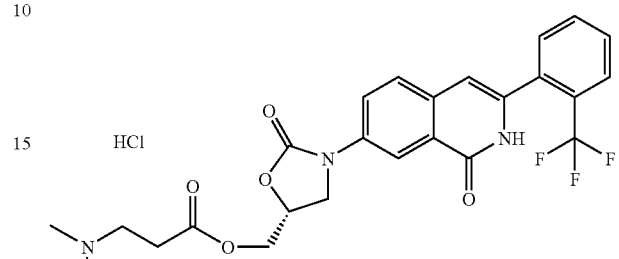

The captioned compound was synthesized by a method similar to that of Example 3-1 with the exception that Boc-N,N-dimethyl-beta-Ala-OH was used instead of Boc-Sar-OH.

$^1$H-NMR (DMSO-d$_6$) δ: 2.68-2.78 (3H, m), 2.81-2.98 (1H, m), 3.20-3.35 (2H, m), 3.95-4.08 (1H, m), 4.22-4.43 (3H, m), 4.92-5.09 (1H, m), 6.50 (1H, s), 7.57-7.95 (5H, m), 8.10 (1H, dd, J=8.7, 2.5 Hz), 8.23 (1H, d, J=2.5 Hz), 11.63 (1H, s)

ESI (LC-MS positive mode) m/z 504 (M+H).

Example 3-17

Sodium 3-{(R)-2-oxo-3-[1-oxo-3-(2-trifluoromethylphenyl)-1,2-dihydroisoquinolin-7-yl]oxazolidin-5-ylmethoxycarbonyl}propionate Step A 3-{(R)-2-Oxo-3-[1-oxo-3-(2-trifluoromethylphenyl)-1,2-dihydroisoquinolin-7-yl]oxazolidin-5-ylmethoxycarbonyl}propionic acid

[Formula 218]

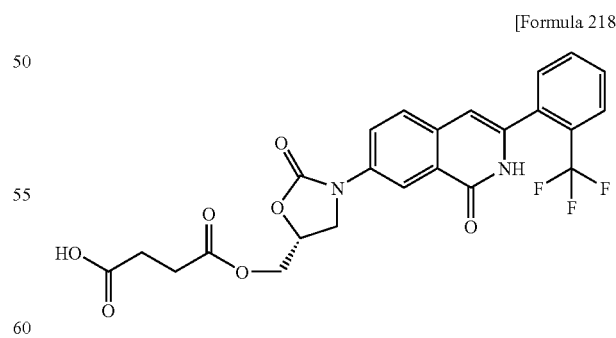

The 7-((R)-5-hydroxymethyl-2-oxooxazolidin-3-yl)-3-(2-trifluoromethylphenyl)-2H-isoquinolin-1-one (50 mg, 0.12 mmol) obtained in step B of Example 1-14 was dissolved in pyridine (3 ml). Thereafter, succinic anhydride (14 mg, 0.14 mmol) was added to the solution, and the obtained mixture was then stirred at 50° C. for 6 hours. Thereafter, succinic anhydride (24 mg, 0.25 mmol) was further added to the reaction solution, and the obtained mixture was then stirred at 50° C. for 15 hours. Thereafter, 1 N hydrochloric acid was added to the reaction mixture, and precipitated powders were collected by filtration. The obtained filtrate was washed with water. The resultant was subjected to air-drying, and was then dried under reduced pressure, so as to obtain 3-{(R)-2-oxo-3-[1-oxo-3-(2-trifluoromethylphenyl)-1,2-dihydroisoquinolin-7-yl]oxazolidin-5-ylmethoxycarbonyl}propionic acid (46 mg, 74%) in the form of white powders.

¹H-NMR (CDCl₃) δ: 2.63 (4H, s), 4.03-4.24 (2H, m), (2H, m), 4.84-5.00 (1H, m), 6.59 (1H, s), 7.42-7.74 (4H, m), 7.81 (1H, d, J=7.6 Hz), 7.97 (1H, s), 8.61 (1H, dd, J=8.9, 2.3 Hz), 10.08 (1H, brs)

ESI (LC-MS positive mode) m/z 505 (M+H).

Step B

Sodium 3-{(R)-2-oxo-3-[1-oxo-3-(2-trifluoromethylphenyl)-1,2-dihydroisoquinolin-7-yl]oxazolidin-5-ylmethoxycarbonyl}propionate

[Formula 219]

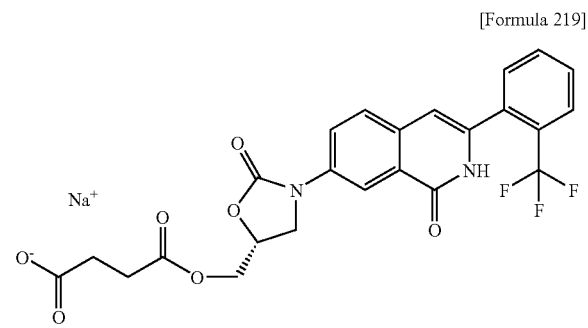

The 3-{(R)-2-oxo-3-[1-oxo-3-(2-trifluoromethylphenyl)-1,2-dihydroisoquinolin-7-yl]oxazolidin-5-ylmethoxycarbonyl}propionic acid (44 mg, 0.09 mmol) obtained in step A was dissolved in ethyl acetate. The obtained solution, a 1 N-sodium hydroxide aqueous solution (79 μl, 0.08 mmol), and water were placed in a separatory funnel, and the obtained mixture was then fully shaken. Thereafter, the water layer thereof was freeze-dried, so as to obtain 3-{(R)-2-oxo-3-[1-oxo-3-(2-trifluoromethylphenyl)-1,2-dihydroisoquinolin-7-yl]oxazolidin-5-ylmethoxycarbonyl}sodium propionate (24 mg, 58%) in the form of white powders.

¹H-NMR (DMSO-d₆) δ: 2.11 (2H, t, J=7.0 Hz), 2.39 (2H, t, J=7.0 Hz), 3.96-4.09 (1H, m), 4.18-4.35 (2H, m), 4.90-5.05 (1H, m), 6.49 (1H, s), 7.55-7.91 (5H, m), 8.08 (1H, dd, J=2.5, 8.7 Hz), 8.24 (1H, d, J=2.5 Hz)

ESI (LC-MS positive mode) m/z 505 (M+H).

Example 3-18

Sodium 2-{(R)-2-oxo-3-[1-oxo-3-(2-trifluoromethylphenyl)-1,2-dihydroisoquinolin-7-yl]oxazolidin-5-ylmethoxycarbonyl}benzoate

[Formula 220]

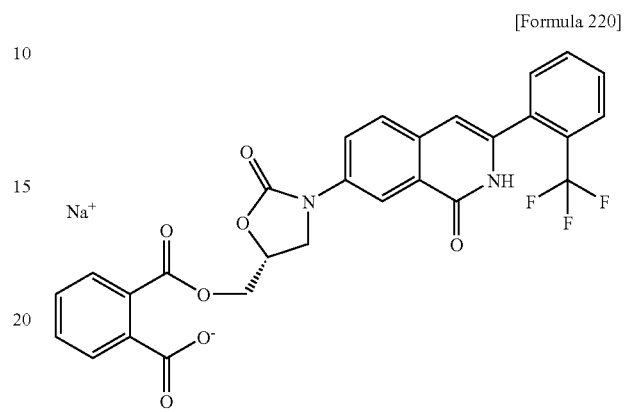

The captioned compound was synthesized by a method similar to that of Example 3-17 with the exception that phthalic anhydride was used instead of succinic anhydride.

¹H-NMR (DMSO-d₆) δ: 4.26 (1H, d, J=7.9 Hz), 4.43 (1H, d, J=4.0 Hz), 5.0-5.12 (1H, m), 6.49 (1H, s), 7.15-7.40 (4H, m), 7.60-7.93 (5H, m), 8.05 (1H, dd, J=8.7, 2.5 Hz), 8.29 (1H, d, J=2.5 Hz)

ESI (LC-MS positive mode) m/z 553 (M+H).

Example 3-19

(R)-2-Oxo-3-[1-oxo-3-(2-trifluoromethylphenyl)-1,2-dihydroisoquinolin-7-yl]oxazolidin-5-ylmethyl 2-aminoethylsuccinamate hydrochloride

[Formula 221]

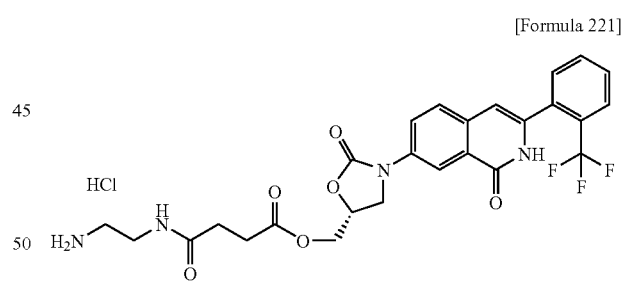

The 3-{(R)-2-oxo-3-[1-oxo-3-(2-trifluoromethylphenyl)-1,2-dihydroisoquinolin-7-yl]oxazolidin-5-ylmethoxycarbonyl}propionic acid obtained in step B of Example 3-17 and tert-butyl N-(2-aminoethyl)-carbamate were condensed with WSCI, and the reaction mixture was then concentrated under reduced pressure. The obtained residue was purified by silica gel chromatography (methylene chloride:methanol=20:1), and the compound of interest was then synthesized by a method similar to step B of Example 3-1.

¹H-NMR (DMSO-d₆) δ: 2.23-2.65 (6H, m), 2.83 (2H, t, J=5.4 Hz), 3.9-4.04 (1H, m), 4.21-4.39 (2H, m), 4.90-5.06 (1H, m), 6.50 (1H, s), 7.58-7.92 (5H, m), 7.94 (1H, brs), 8.03-8.20 (2H, m), 8.23 (1H, d, J=2.5 Hz), 11.63 (1H, brs)

ESI (LC-MS positive mode) m/z 547 (M+H).

Example 3-20

(S)-2-Oxo-3-[1-oxo-3-(2-trifluoromethylphenyl)-1,2-dihydroisoquinolin-7-yl]oxazolidin-5-ylmethyl methylaminoacetate hydrochloride

[Formula 222]

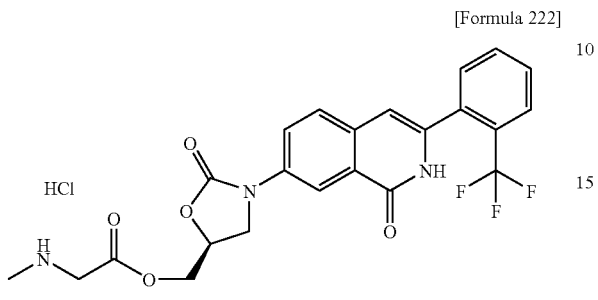

The 7-((S)-5-hydroxymethyl-2-oxooxazolidin-3-yl)-3-(2-trifluoromethylphenyl)-2H-isoquinolin-1-one obtained in step B of Example 1-13 was used instead of the 7-((R)-5-hydroxymethyl-2-oxooxazolidin-3-yl)-3-(2-trifluoromethylphenyl)-2H-isoquinolin-1-one obtained in step B of Example 1-14. Using this compound, the captioned compound was synthesized by a method similar to that of Example 3-1.

$^1$H-NMR (DMSO-$d_6$) δ: 2.55-2.65 (3H, m), 3.95-4.12 (2H, m), 4.24-4.40 (1H, m), 4.48-4.58 (2H, m), 4.98-5.12 (1H, m), 6.50 (1H, s), 7.55-7.93 (5H, m), 8.10 (1H, dd, J=8.6, 2.4 Hz), 8.21 (1H, d, J=2.4 Hz), 9.19 (2H, brs), 11.60 (1H, brs)

ESI (LC-MS positive mode) m/z 476 (M+H).

Example 3-21

(S)-2-Oxo-3-[1-oxo-3-(2-trifluoromethylphenyl)-1,2-dihydroisoquinolin-7-yl]oxazolidin-5-ylmethyl dimethylaminoacetate hydrochloride

[Formula 223]

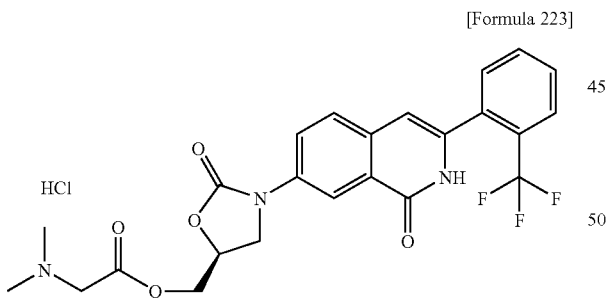

The 7-((S)-5-hydroxymethyl-2-oxooxazolidin-3-yl)-3-(2-trifluoromethylphenyl)-2H-isoquinolin-1-one obtained in step B of Example 1-13 was used instead of the 7-((R)-5-hydroxymethyl-2-oxooxazolidin-3-yl)-3-(2-trifluoromethylphenyl)-2H-isoquinolin-1-one obtained in step B of Example 1-14. Using this compound, the captioned compound was synthesized by a method similar to that of Example 3-11.

$^1$H-NMR (DMSO-$d_6$) δ: 2.84 (6H, s), 4.0-4.10 (1H, m), 4.15-4.38 (2H, s), 4.44-4.60 (2H, s), 5.0-5.12 (1H, s), 6.50 (1H, s), 7.57-7.94 (5H, m), 8.10 (1H, dd, J=8.7, 2.4 Hz), 8.22 (1H, d, J=2.4 Hz), 10.52 (1H, brs), 11.63 (1H, brs)

ESI (LC-MS positive mode) m/z 490 (M+H).

Example 3-22

(S)-2-Oxo-3-[1-oxo-3-(2-trifluoromethylphenyl)-1,2-dihydro-isoquinolin-7-yl]-oxazolidin-5-ylmethyl(S)-2-amino-3-methylbutyrate hydrochloride

[Formula 224]

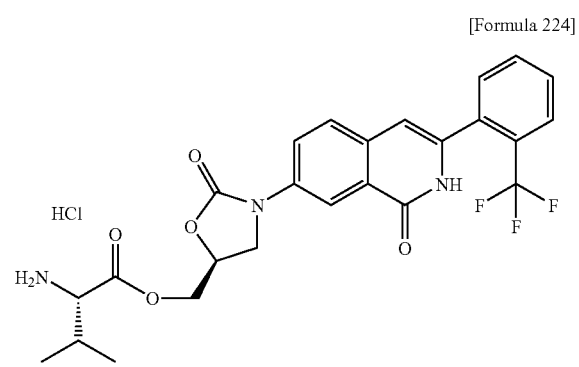

The 7-((S)-5-hydroxymethyl-2-oxooxazolidin-3-yl)-3-(2-trifluoromethylphenyl)-2H-isoquinolin-1-one obtained in step B of Example 1-13 was used instead of the 7-((R)-5-hydroxymethyl-2-oxooxazolidin-3-yl)-3-(2-trifluoromethylphenyl)-2H-isoquinolin-1-one obtained in step B of Example 1-14. Using this compound, the captioned compound was synthesized by a method similar to that of Example 3-9.

$^1$H-NMR (270 MHz, DMSO-$d_6$) δ (ppm): 0.93 (3H, d, J=6.9 Hz), 0.94 (3H, d, J=6.9 Hz), 2.14-2.21 (1H, m), 3.93 (1H, brs), 4.02 (1H, dd, J=6.3, 9.1 Hz), 4.35 (1H, t, J=9.3 Hz), 4.48-4.61 (2H, m), 5.03-5.12 (1H, m), 6.51 (1H, s), 7.63-7.90 (5H, m), 8.09 (1H, dd, J=2.3, 8.8 Hz), 8.23 (1H, d, J=2.3 Hz), 8.70 (1H, brs), 11.65 (1H, brs)

ESI (LC-MS positive mode) m/z 504 (M+H).

Example 3-23

(R)-2-Oxo-3-[1-oxo-3-trifluoromethylphenyl)-1,2-dihydro-isoquinolin-7-yl]-oxazolidin-5-ylmethyl 2-amino-2-methyl-propionate hydrochloride

[Formula 225]

The captioned compound was synthesized by a method similar to that of Example 3-1 with the exception that Boc-alfa-dimethyl-Gly-OH was used instead of Boc-Sar-OH.

$^1$H-NMR (270 MHz, DMSO-$d_6$) δ (ppm): 1.42 (3H, s), 1.46 (3H, s), 4.07 (1H, dd, J=6.1, 8.6 Hz), 4.35 (1H, dd, J=4.4, 12.2 Hz), 4.59 (1H, dd, J=2.6, 12.2 Hz), 5.02-5.11 (1H, m), 6.51 (1H, s), 7.63-7.89 (5H, m), 8.10 (1H, dd, J=2.5, 8.8 Hz), 8.22 (1H, d, J=2.5 Hz), 8.71 (2H, brs), 11.64 (1H, brs)

ESI (LC-MS positive mode) m/z 490 (M+H).

Example 3-24

(R)-2-Oxo-3-[1-oxo-3-(2-trifluoromethylphenyl)-1,2-dihydro-isoquinolin-7-yl]-oxazolidin-5-ylmethyl 2-methyl-2-methylamino-propionate hydrochloride

[Formula 226]

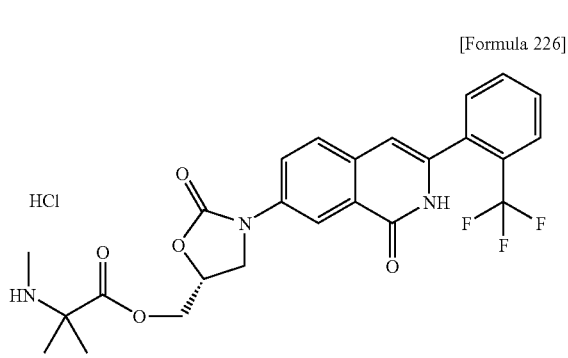

The captioned compound was synthesized by a method similar to that of Example 3-1 with the exception that Boc-alfa-dimethyl-Sar-OH was used instead of Boc-Sar-OH.

$^1$H-NMR (270 MHz, DMSO-$d_6$) δ (ppm): 1.46 (3H, s), 1.50 (3H, s), 2.50 (3H, brs), 4.12 (1H, t, J=6.1 Hz), 4.35 (1H, t, J=9.0 Hz), 4.47 (1H, dd, J=4.4, 12.3 Hz), 4.61 (1H, d, J=12.3 Hz), 6.51 (1H, s), 7.64-7.90 (5H, m), 8.10 (1H, dd, J=2.3, 8.7 Hz), 8.25 (1H, d, J=2.3 Hz), 9.88 (1H, brs), 11.66 (1H, brs)

ESI (LC-MS positive mode) m/z 504 (M+H).

Example 3-25

(R)-2-Oxo-3-[1-oxo-3-(2-trifluoromethylphenyl)-1,2-dihydro-isoquinolin-7-yl]-oxazolidin-5-ylmethyl 1-amino-cyclopentanecarboxylate hydrochloride

[Formula 227]

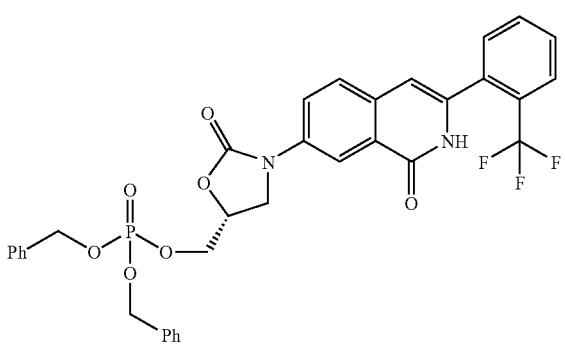

The captioned compound was synthesized by a method similar to that of Example 3-1 with the exception that Boc-alfa-cyclopentyl-Sar-OH was used instead of Boc-Sar-OH.

$^1$H-NMR (270 MHz, DMSO-$d_6$) δ (ppm): 1.50-2.17 (8H, m), 4.09 (1H, t, J=5.6 Hz), 4.36 (1H, t, J=9.3 Hz), 4.45 (1H, dd, J=3.9, 12.2 Hz), 4.58 (1H, d, J=12.2 Hz), 5.10 (1H, brs), 6.51 (1H, s), 7.64-7.90 (5H, m), 8.10 (1H, dd, J=2.5, 8.7 Hz), 8.24 (1H, d, J=2.5 Hz), 8.81 (2H, brs), 11.66 (1H, brs)

ESI (LC-MS positive mode) m/z 516 (M+H)

Example 3-26

Dibenzyl phosphoate (R)-2-oxo-3-[1-oxo-3-(2-trifluoromethylphenyl)-1,2-dihydroisoquinolin-7-yl]-oxazolidin-5-ylmethyl ester

[Formula 228]

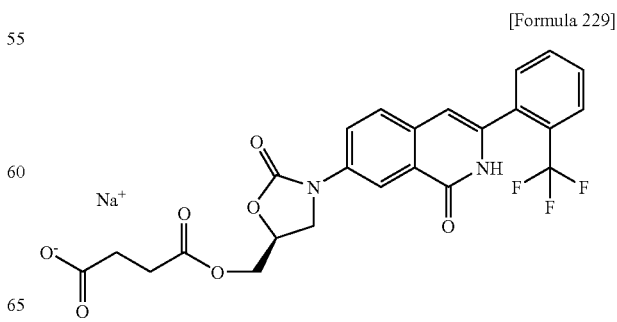

The 7-((R)-5-hydroxymethyl-2-oxooxazolidin-3-yl)-3-(2-trifluoromethylphenyl)-2H-isoquinolin-1-one (150 mg, 0.37 mmol) obtained in step B of Example 1-14 was dissolved in acetonitrile (5 ml). Thereafter, N,N-diisopropylethylamine ml, 2.96 mmol), carbon tetrachloride (0.706 ml, 7.4 mmol), N,N-dimethylaminopyridine (14 mg, 0.22 mmol), and dibenzyl phosphite (0.410 ml, 1.86 mmol) were added to the solution. The obtained mixture was stirred at 50° C. for 15 hours. Thereafter, the reaction mixture was concentrated under reduced pressure. The obtained residue was purified by silica gel chromatography (hexane:ethyl acetate=1:5), so as to obtain phosphate dibenzyl ester (R)-2-oxo-3-[1-oxo-3-(2-trifluoromethylphenyl)-1,2-dihydroisoquinolin-7-yl]-oxazolidin-5-ylmethyl ester (85 mg, 34%) in the form of a colorless foaming substance.

$^1$H-NMR (DMSO-$d_6$) δ: 3.56-3.80 (1H, m), 3.85-4.02 (1H, m), 4.13-4.26 (1H, m), 4.73-4.86 (1H, m), 5.22-5.35 (4H, m), 6.52 (1H, s), 7.20-7.40 (10H, m), 7.55-7.95 (5H, m), 8.11 (1H, dd, J=8.7, 2.5 Hz), 8.25 (1H, d, J=2.5 Hz), 11.62 (1H, brs)

ESI (LC-MS positive mode) m/z 665 (M+H).

Example 4-1

Sodium 3-{(R)-2-oxo-3-[1-oxo-3-(2-trifluoromethylphenyl)-1,2-dihydroisoquinolin-7-yl]oxazolidin-5-ylmethoxycarbonyl}propionate

[Formula 229]

The title compound was synthesized by a method similar to that of Example 3-17 using 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (DMSO-$d_6$) δ: 2.11 (2H, t, J=7.0 Hz), 2.39 (2H, t, J=7.0 Hz), 3.96-4.09 (1H, m), 4.18-4.35 (2H, m), 4.90-5.05 (1H, m), 6.49 (1H, s), 7.55-7.91 (5H, m), 8.08 (1H, dd, J=2.5, 8.7 Hz), 8.24 (1H, d, J=2.5 Hz)

ESI (LC-MS positive mode) m/z 505 (M+H)

Example 4-2

Sodium 2-{(S)-2-oxo-3-[1-oxo-3-(2-trifluoromethylphenyl)-1,2-dihydroisoquinolin-7-yl]oxazolidin-5-ylmethoxycarbonyl}benzoate

[Formula 230]

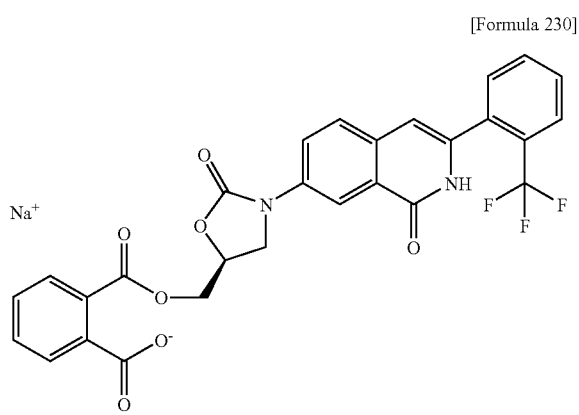

The title compound was synthesized by a method similar to that of Example 3-17 using phthalic anhydride instead of succinic anhydride and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (DMSO-$d_6$) δ: 4.26 (1H, d, J=7.9 Hz), 4.43 (1H, d, J=4.0 Hz), 5.0-5.12 (1H, m), 6.49 (1H, s), 7.15-7.40 (4H, m), 7.60-7.93 (5H, m), 8.05 (1H, dd, J=8.7, 2.5 Hz), 8.29 (1H, d, J=2.5 Hz)

ESI (LC-MS positive mode) m/z 553 (M+H)

Example 4-3

Sodium 3-{(R)-2-oxo-3-[1-oxo-3-(2-trifluoromethylphenyl)-1,2-dihydroisoquinolin-7-yl]oxazolidin-5-ylmethoxycarbonyl}butanoate

[Formula 231]

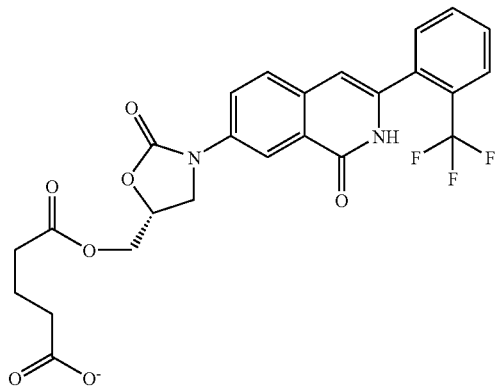

The title compound was synthesized by a method similar to that of Example 3-17 using glutaric anhydride instead of succinic anhydride.

$^1$H-NMR (DMSO-$d_6$) δ: 1.66 (2H, quint, J=8.0 Hz), 1.83 (2H, t, J=8.0 Hz), 2.33 (2H, t, J=8.0 Hz), 3.94-4.00 (1H, m), 4.21-4.38 (3H, m), 4.89-5.07 (1H, m), 6.48 (1H, s), 7.60-7.90 (5H, m), 8.07 (1H, dd, J=2.5, 8.7 Hz), 8.23 (1H, d, J=2.5 Hz)

ESI (LC-MS positive mode) m/z 519(M+H).

Example 4-4

Sodium (Z)-3-{(R)-2-oxo-3-[1-oxo-3-(2-trifluoromethylphenyl)-1,2-dihydroisoquinolin-7-yl]oxazolidin-5-ylmethoxycarbonyl}acrylate

[Formula 232]

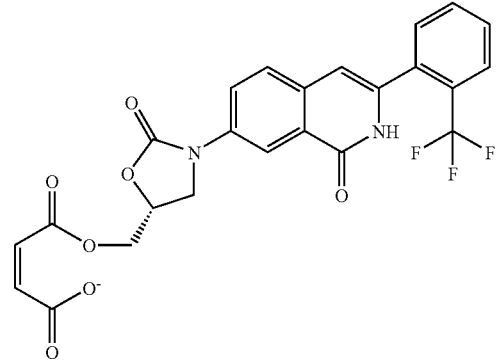

The title compound was synthesized by a method similar to that of Example 3-17 using maleic anhydride instead of succinic anhydride.

$^1$H-NMR (DMSO-$d_6$) δ: 3.96-4.05 (1H, m), 4.25-4.49 (3H, m), 4.98-5.10 (1H, m), 6.15 (1H, d, J=12.0 Hz), 6.49 (1H, s), 6.75 (1H, d, J=12.0 Hz), 7.60-8.11 (5H, m), 8.08 (1H, dd, J=2.5, 8.7 Hz), 8.23 (1H, d, J=2.5 Hz)

ESI (LC-MS positive mode) m/z 503 (M+H)

Example 4-5

Sodium 2-(1-methyl-1-{(S)-2-oxo-3-[1-oxo-3-(2-trifluoromethylphenyl)-1,2-dihydroisoquinolin-7-yl]oxazolidin-5-ylethoxycarbonyl}propionate

[Formula 233]

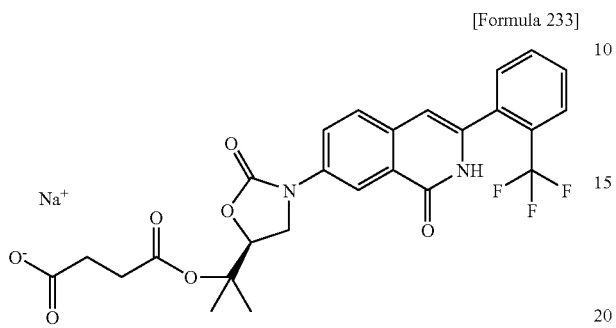

The title compound was synthesized by a method similar to that of Example 3-17 using 7-[(S)-5-(1-hydroxy-1-methyl-ethyl)-2-oxooxazolidin-3-yl]-3-(2-trifluoromethylphenyl)-2H-isoquinolin-1-one obtained in Step B of Example 2-11 instead of 7-((R)-5-hydroxymethyl-2-oxooxazolidin-3-yl)-3-(2-trifluoromethylphenyl)-2H-isoquinolin-1-one obtained in Step B of Example 1-14. However, condensation was carried out in a pyridine solvent under reflux (115° C.), not at a reaction temperature of 50° C.

$^1$H-NMR (DMSO-$d_6$) δ: 1.60 (6H, s), 2.05 (2H, t, J=6.8 Hz), 2.28 (2H, t, J=6.8 Hz), 4.21 (2H, d, J=7.7 Hz), 4.83 (1H, t, J=7.6 Hz), 6.50 (1H, s), 7.59-7.92 (5H, m), 8.14 (1H, dd, J=8.7, 2.5 Hz), 8.29 (1H, d, J=2.5 Hz)

ESI (LC-MS positive mode) m/z 533(M+H).

Example 4-6

Sodium 2-(1-methyl-1-{(S)-2-oxo-3-[1-oxo-3-(2-trifluoromethylphenyl)-1,2-dihydroisoquinolin-7-yl]oxazolidin-5-ylethoxycarbonyl}benzoate

[Formula 234]

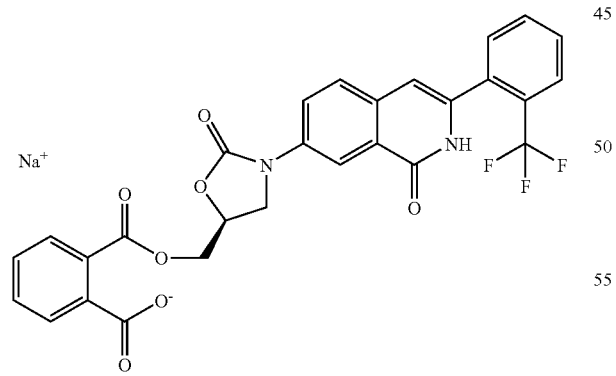

The title compound was synthesized by a method similar to that of Example 3-17 using phthalic anhydride instead of succinic anhydride and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14. However, condensation was carried out in a pyridine solvent under reflux (115° C.), not at a reaction temperature of 50° C.

$^1$H-NMR (DMSO-$d_6$) δ: 1.60 (3H, s), 1.66 (3H, s), (1H, m), 4.52-4.61 (1H, m), 4.80-4.91 (1H, m), 6.49 (1H, s), 7.20-7.32 (4H, m), 7.48-7.90 (5H, m), 8.07 (1H, dd, J=8.7, 2.5 Hz), 8.45 (1H, d, J=2.5 Hz).

ESI (LC-MS positive mode) m/z 581 (M+H)

Example 4-7

1-{(R)-2-Oxo-3-[1-oxo-3-(2-trifluoromethylphenyl)-1,2-dihydroisoquinolin-7-yl]-oxazolidin-5-ylmethyl}(S)-2-aminosuccinate

[Formula 235]

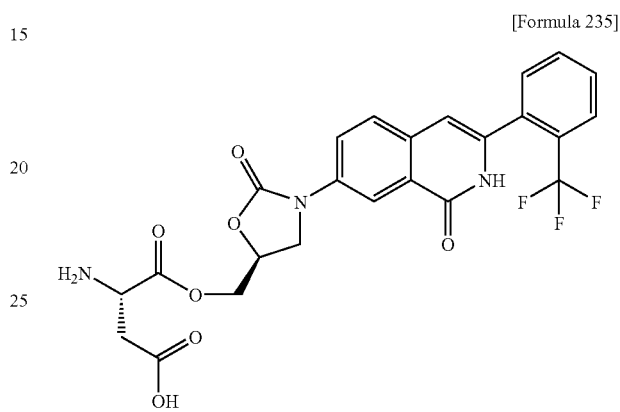

Condensation was carried out by a method similar to that of Example 3-1 using (L)-Z-Asp(OBzl)-OH instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14, and deprotection was carried out by a method similar to that of Example 1-36 using a 10% Pd—C catalyst in a hydrogen atmosphere to synthesize the title compound.

$^1$H-NMR (DMSO-$d_6$) δ: 2.76-2.85 (2H, m), 3.92-4.05 (1H, m), 4.22-4.33 (2H, m), 4.40-4.55 (2H, m), 4.90-5.02 (1H, m), 6.48 (1H, s), 7.55-7.90 (5H, m), 8.09 (1H, dd, J=2.5, 8.7 Hz), 8.17 (1H, d, J=2.5 Hz)

ESI (LC-MS positive mode) m/z 520 (M+H)

Example 4-8

(R)-2-Oxo-3-[1-oxo-3-(2-trifluoromethylphenyl)-1,2-dihydroisoquinolin-7-yl]oxazolidin-5-ylmethyl(S)-2-amino-3-hydroxypropionate trifluoroacetic acid

[Formula 236]

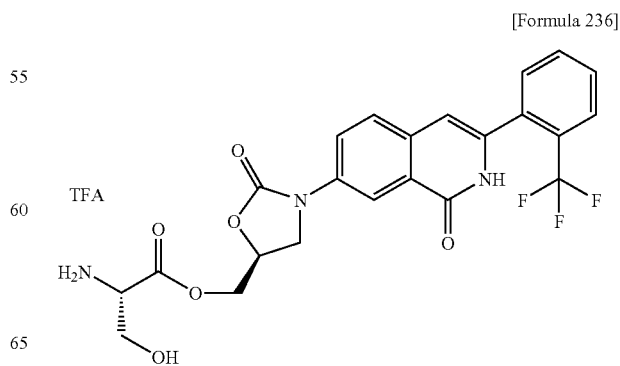

The title compound was synthesized by a method similar to that of Example 3-1 using (L)-Boc-Ser(t-Bu)-OH instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (DMSO-$d_6$) δ: 3.37 (1H, dd, J=3.4, 11.7 Hz), 3.85 (1H, dd, J=4.4, 11.7 Hz), 4.03 (1H, dd, J=6.5, 9.0 Hz), 4.22 (1H, brs), 4.32 (1H, t, J=9.2 Hz), 4.49 (1H, dd, J=5.4, 12.2 Hz), 4.55 (1H, dd, J=2.9, 12.2 Hz), 4.55 (1H, dd, J=2.9, 12.2 Hz), 5.00-5.09 (1H, brs), 6.51 (1H, s), 7.63 (1H, d, J=7.3 Hz), 7.70-7.81 (3H, m), 7.88 (1H, d, J=7.3 Hz), 8.10 (1H, dd, J=2.4, 8.8 Hz), 8.23 (1H, d, J=2.4 Hz), 8.45 (2H, brs), 11.63 (1H, brs)

ESI (LC-MS positive mode) m/z 492 (M+H)

Example 4-9

(R)-2-Oxo-3-[1-oxo-3-(2-trifluoromethylphenyl)-1,2-dihydroisoquinolin-7-yl]oxazolidin-5-ylmethyl(2S,3R)-2-amino-3-hydroxybutanoate trifluoroacetate

[Formula 237]

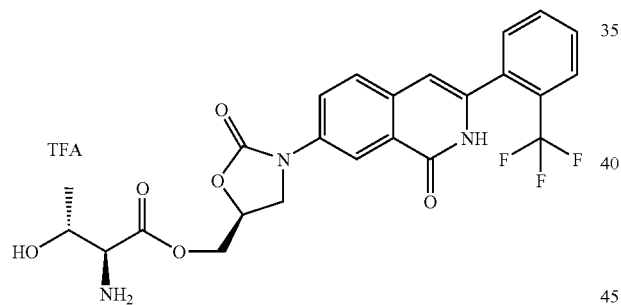

The title compound was synthesized by a method similar to that of Example 3-1 using (L)-Boc-Thr(t-Bu)-OH instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (DMSO-$d_6$) δ: 1.20 (3H, d, J=6.3 Hz), 4.02 (2H, t, J=6.8 Hz), 4.14-4.17 (1H, m), 4.32 (1H, t, J=8.8 Hz), 4.49 (1H, dd, J=5.4, 12.2 Hz), 4.54 (1H, dd, J=2.9, 12.2 Hz), 5.04 (1H, brs), 6.51 (1H, s), 7.63 (1H, d, J=7.8 Hz), 7.70-7.81 (3H, m), 7.87 (1H, d, J=7.3 Hz), 8.09 (1H, dd, J=2.5, 8.8 Hz), 8.22 (1H, d, J=2.5 Hz), 8.34 (2H, brs), 11.63 (1H, brs)

ESI (LC-MS positive mode) m/z 506 (M+H)

Example 4-10

Sodium (Z)-3-{(S)-2-oxo-3-[1-oxo-3-(2-trifluoromethylphenyl)-1,2-dihydroisoquinolin-7-yl]oxazolidin-5-ylmethoxycarbonyl}acrylate

[Formula 238]

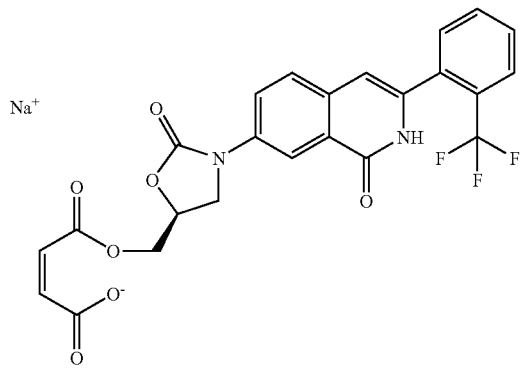

The title compound was synthesized by a method similar to that of Example 3-17 using maleic anhydride instead of succinic anhydride and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (DMSO-$d_6$) δ: 3.96-4.05 (1H, m), 4.25-4.49 (3H, m), 4.98-5.10 (1H, m), 6.15 (1H, d, J=12.0 Hz), 6.49 (1H, s), 6.75 (1H, d, J=12.0 Hz), 7.60-8.11 (5H, m), 8.08 (1H, dd, J=2.5, 8.7 Hz), 8.23 (1H, d, J=2.5 Hz)

ESI (LC-MS positive mode) m/z 503 (M+H)

Example 4-11

Sodium (Z)-3-{(S)-2-oxo-3-[1-oxo-3-(2-trifluoromethylphenyl)-1,2-dihydroisoquinolin-7-yl]oxazolidin-5-ylmethoxycarbonyl}acrylate

[Formula 239]

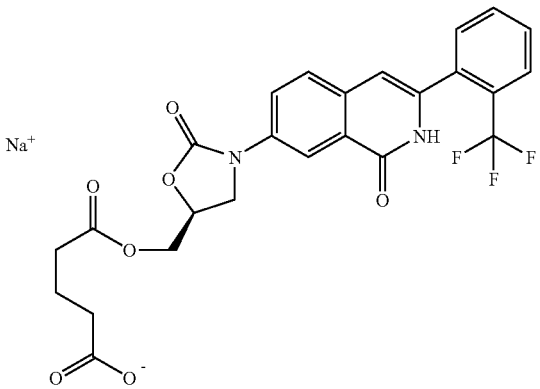

The title compound was synthesized by a method similar to that of Example 3-17 using glutaric anhydride instead of succinic anhydride and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (DMSO-d$_6$) δ: 1.66 (2H, quint, J=8.0 Hz), 1.83 (2H, t, J=8.0 Hz), 2.33 (2H, t, J=8.0 Hz), 3.94-4.00 (1H, m), 4.21-4.38 (3H, m), 4.89-5.07 (1H, m), 6.48 (1H, s), 7.60-7.90 (5H, m), 8.07 (1H, dd, J=2.5, 8.7 Hz), 8.23 (1H, d, J=2.5 Hz)

ESI (LC-MS positive mode) m/z 519 (M+H)

Example 4-12

Sodium 2-{(S)-2-oxo-3-[1-oxo-3-(2-trifluoromethylphenyl)-1,2-dihydroisoquinolin-7-yl]oxazolidin-5-ylmethoxycarbonyl}benzoate

[Formula 240]

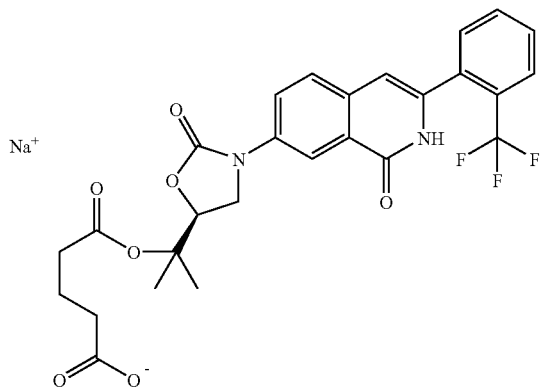

The title compound was synthesized by a method similar to that of Example 3-17 using glutaric anhydride instead of succinic anhydride and 7-[(S)-5-(1-hydroxy-1-methylethyl)-2-oxooxazolidin-3-yl]-3-(2-trifluoromethylphenyl)-2H-isoquinolin-1-one obtained in Step B of Example 2-11 instead of 7-((R)-5-hydroxymethyl-2-oxooxazolidin-3-yl)-3-(2-trifluoromethylphenyl)-2H-isoquinolin-1-one obtained in Step B of Example 1-14. However, condensation was carried out in a pyridine solvent under reflux (115° C.), not at a reaction temperature of 50° C.

$^1$H-NMR (DMSO-d$_6$) δ: 1.60 (6H, s), 1.55-1.70 (2H, m), (2H, m), 2.19-2.31 (2H, m), 4.08-4.35 (2H, m), 4.74-4.84 (1H, m), 6.49 (1H, s), 7.59-7.91 (5H, m), 8.12 (1H, dd, J=8.8, 2.6 Hz), 8.30 (1H, d, J=2.6 Hz)

ESI (LC-MS positive mode) m/z 457 (M+H)

Example 4-13

Sodium 3-{(S)-2-oxo-3-[1-oxo-3-(2-trifluoromethylphenyl)-1,2-dihydroisoquinolin-7-yl]oxazolidin-5-ylmethoxycarbonyl}-(S)-2-hydroxypropionate Step A 3-{(S)-2-Oxo-3-[1-oxo-3-(2-trifluoromethylphenyl)-1,2-dihydroisoquinolin-7-yl]oxazolidin-5-ylmethyl} ((R)-2,2-dimethyl-5-oxo-[1,3]dioxolan-4-yl)acetate

[Formula 241]

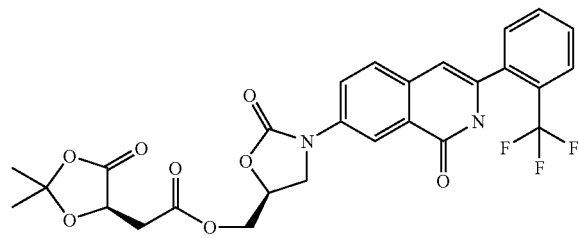

Condensation was carried out by a method similar to that of Step A of Example 3-1 using (R)-2,2-dimethyl-5-oxo-1,3-dioxolane-4-acetic acid instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14 to synthesize the title compound.

$^1$H-NMR (CDCl$_3$) δ: 1.52 (3H, s), 1.58 (3H, s), 2.78-3.05 (2H, m), 4.02 (1H, dd, J=9.2, 6.3 Hz), 4.28 (1H, t, J=9.2 Hz), 4.34-4.58 (2H, m), 4.66-4.75 (1H, m), 4.91-5.02 (1H, m), 6.52 (1H, s), 7.52-7.84 (5H, m), 7.93 (1H, d, J=2.5 Hz), 8.51 (1H, dd, J=8.9, 2.5 Hz), 9.28 (1H, s)

ESI (LC-MS positive mode) m/z 561 (M+H).

Step B

Sodium 3-{(S)-2-oxo-3-[1-oxo-3-(2-trifluoromethylphenyl)-1,2-dihydroisoquinolin-7-yl]oxazolidin-5-ylmethoxycarbonyl}-(S)-2-hydroxypropionate

[Formula 242]

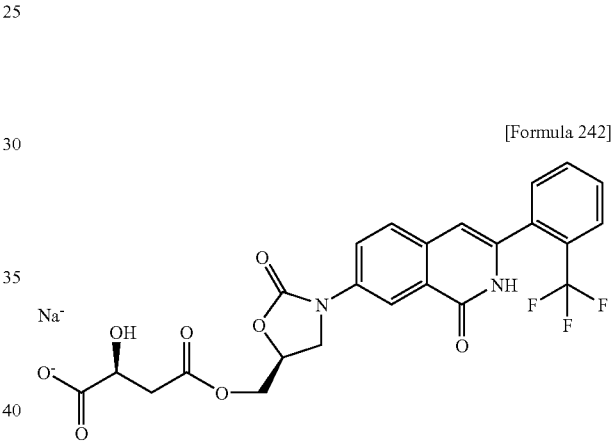

Water (1 mL) and acetic acid (0.102 mL, 1.8 mmol) were added to a solution of 3-{(S)-2-oxo-3-[1-oxo-3-(2-trifluoromethylphenyl)-1,2-dihydroisoquinolin-7-yl]oxazolidin-5-ylmethyl} ((R)-2,2-dimethyl-5-oxo-[1,3]dioxolan-4-yl)acetate obtained in Step A (50 mg, 0.09 mmol) in THF (1 mL) at 0° C., and the mixture was stirred under reflux for five hours. The reaction mixture was concentrated under reduced pressure and purified by preparative TLC (Merck 1.13792: dichloromethane methanol=5:1) to obtain 3-{(S)-2-oxo-3-[1-oxo-3-(2-trifluoromethylphenyl)-1,2-dihydroisoquinolin-7-yl]oxazolidin-5-ylmethoxycarbonyl}-(S)-2-hydroxypropionic acid (28 mg, 60%) as a white solid. The product was converted into a sodium salt by a method similar to that of Step B of Example 3-17 to synthesize the title compound.

$^1$H-NMR (DMSO-d$_6$) δ: 2.21 (1H, dd, J=14.7, 9.4 Hz), 2.68 (1H, dd, J=14.7, 4.1 Hz), 3.79 (1H, dd, J=9.4, 4.1 Hz), 3.99-4.05 (1H, m), 4.23-4.34 (3H, m), 4.92-5.02 (1H, m), 6.49 (1H, s), 7.59-7.90, 8.05 (1H, dd, J=8.7, 2.5 Hz), 8.24 (1H, d, J=2.5 Hz)

ESI (LC-MS positive mode) m/z 521 (M+H)

Example 4-14

Sodium 3-{(S)-2-oxo-3-[1-oxo-3-(2-trifluoromethylphenyl)-1,2-dihydroisoquinolin-7-yl]oxazolidin-5-ylmethoxycarbonyl}ethanoate

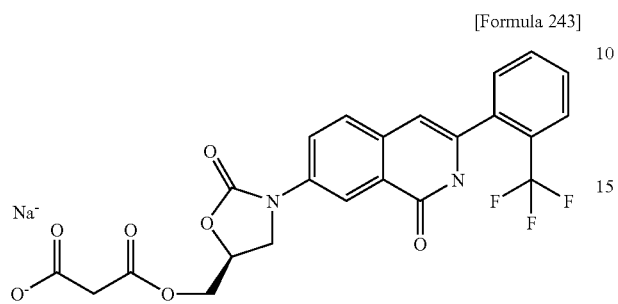

[Formula 243]

Condensation and deprotection were carried out by a method similar to that of Example 3-1 using mono-t-butyl malonate instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14. The product was converted into a sodium salt by a method similar to that of Step B of Example 3-17 to synthesize the title compound.

$^1$H-NMR (DMSO-$d_6$) δ: 3.50 (2H, s), 3.91-4.43 (3H, m), 4.88-5.05 (1H, m), 6.49 (1H, s), 7.60-7.89 (5H, m), 8.03-8.09 (1H, m), 8.23 (1H, t, J=3.0 Hz).

ESI (LC-MS positive mode) m/z 491 (M+H)

Example 4-15

Sodium 3-{(S)-2-oxo-3-[1-oxo-3-(2-trifluoromethylphenyl)-1,2-dihydroisoquinolin-7-yl]oxazolidin-5-ylmethoxycarbonyl}ethanoate

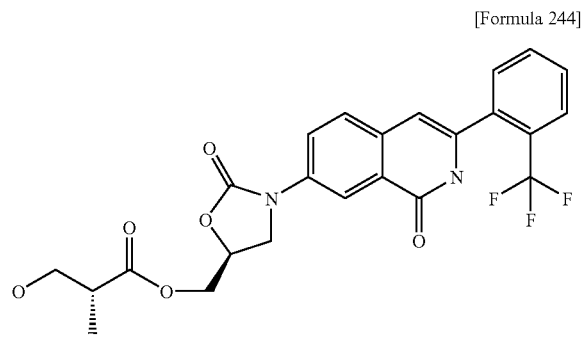

[Formula 244]

Condensation was carried out by a method similar to that of Step A of Example 3-1 using (R)-2,2-dimethyl-1,3-dioxolane-4-carboxylic acid instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14, and deprotection was carried out by a method similar to that of Step B of Example 4-13 to synthesize the title compound.

$^1$H-NMR (DMSO-$d_6$) δ: 3.51-3.60 (2H, m), 3.92-4.13 (2H, m), 4.23-4.47 (3H, m), 4.95-5.04 (1H, m), 6.49 (1H, s), (5H, m), 8.08 (1H, dd, J=8.7, 2.5 Hz), 8.22 (1H, d, J=2.5 Hz), 11.64 (1H, s).

ESI (LC-MS positive mode) m/z 493 (M+H)

Example 4-16

(S)-2-Oxo-3-[1-oxo-3-(2-trifluoromethylphenyl)-1,2-dihydroisoquinolin-7-yl]oxazolidin-5-ylmethyl 3-hydroxy-2-hydroxymethyl-2-methylpropionate

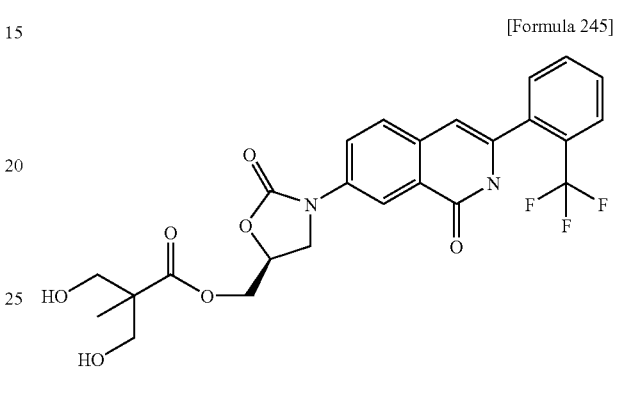

[Formula 245]

Step A

Benzyl 3-benzyloxy-2-benzyloxymethyl-2-methylpropionate

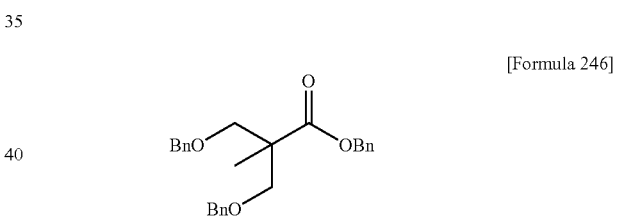

[Formula 246]

2,2-Bis(hydroxymethyl)propionic acid (500 mg, 3.73 mmol) was added to a solution of sodium hydride (55%: 488 mg, 11.2 mmol) in DMF (5 mL) at 0° C., and the mixture was stirred at room temperature for 15 hours. 1 N hydrochloric acid was added to the mixture under ice-cooling, followed by extraction with ethyl acetate. The extract was dried over anhydrous magnesium sulfate, and the solvent was evaporated under reduced pressure. The resulting residue was purified by silica gel column chromatography (hexane:ethyl acetate=20:1, then 9:1) to obtain benzyl 3-benzyloxy-2-benzyloxymethyl-2-methylpropionate (518 mg, yield: 34%) as a colorless oil.

$^1$H-NMR (CDCl$_3$) δ: 1.27 (3H, s), 3.65 (4H, s), 4.49 (4H, s), 5.15 (2H, s), 7.19-7.40 (15H, m)

ESI (LC-MS positive mode) m/z 405 (M+H).

Step B (S)-2-Oxo-3-[1-oxo-3-(2-trifluoromethylphenyl)-1,2-dihydroisoquinolin-7-yl]oxazolidin-5-ylmethyl 3-hydroxy-2-hydroxymethyl-2-methylpropionate 1 N Aqueous sodium hydroxide (2.6 mL) was added to a solution of benzyl 3-benzyloxy-2-benzyloxymethyl-2-methylpropionate obtained in Step A (350 mg, 0.87 mmol) in THF (2.6 mL), and the mixture was stirred under reflux for three hours. Water and ethyl acetate were added to the mixture to separate the aqueous layer. 1 N hydrochloric acid was added to the aqueous layer to make the aqueous layer acidic, followed by extraction with ethyl acetate. The extract was dried over anhydrous magnesium sulfate, and the solvent was evaporated under reduced pressure. From the resulting residue, crude 3-benzyloxy-2-benzyloxymethyl-2-methylpropionic acid (95 mg) was obtained as a colorless oil without purification. Condensation was carried out by a method similar to that of Example 3-1 using 3-benzyloxy-2-benzyloxymethyl-2-methylpropionic acid obtained above instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14, and deprotection was carried out by a method similar to that of Example 1-36 using a 10% Pd—C catalyst in a hydrogen atmosphere to synthesize the title compound.

$^1$H-NMR (DMSO-d$_6$) δ: 0.98 (3H, s), 3.30-3.49 (3H, m), 3.92-4.03 (1H, m), 4.21-4.37 ((3H, m), 4.60-4.77 (2H, m), 4.92-5.04 (1H, m), 6.48 (1H, s), 7.57-7.91 (5H, m), 8.06 (1H, dd, J=8.7, 2.4 Hz), 8.23 (1H, d, J=2.4 Hz), 11.62 (1H, s).

ESI (LC-MS positive mode) m/z 521 (M+H)

Example 4-17

(S)-2-Oxo-3-[1-oxo-3-(2-trifluoromethylphenyl)-1,2-dihydroisoquinolin-7-yl]oxazolidin-5-ylmethyl 3-hydroxy-2,2-bishydroxymethylpropionate

[Formula 247]

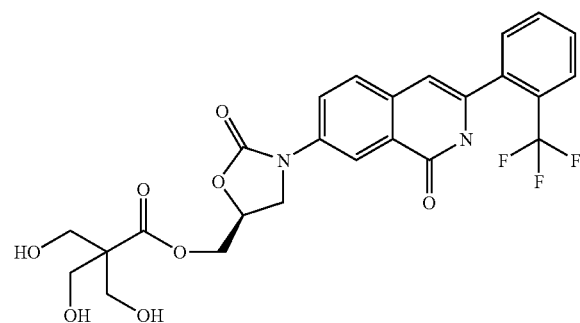

Step A

3-Benzyloxy-2,2-bis(benzyloxymethyl)propan-1-ol

[Formula 248]

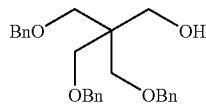

Sodium hydride (440 mg, 11.01 mmol) and benzyl bromide (1.3 mL, 11.01 mmol) were added to 20 mL of a solution of pentaerythritol (500 mg, 3.67 mmol) in DMF, and the mixture was stirred at room temperature for 14 hours. Aqueous saturated ammonium chloride was added to the mixture, followed by extraction with ethyl acetate. The extract was washed with saturated saline and then dried over anhydrous sodium sulfate, and the solvent was evaporated under reduced pressure. The resulting residue was purified by silica gel column chromatography (hexane:ethyl acetate=5:1) to obtain 3-benzyloxy-2,2-bis(benzyloxymethyl)propan-1-ol (560 mg, 38%) as a colorless oil.

$^1$H-NMR (CDCl$_3$) δ: 3.57 (6H, s), 3.78 (2H, s), 4.49 (6H, s), 7.28-7.37 (15H, m)

ESI (LC-MS positive mode) m/z 407 (M+H)

Step B

3-Benzyloxy-2,2-bis(benzyloxymethyl)propionic acid

[Formula 249]

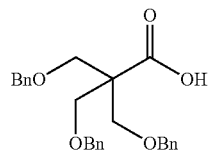

A Jones reagent (0.984 mmol) was added to 5 mL of a solution of 3-benzyloxy-2,2-bis(benzyloxymethyl)propan-1-ol (200 mg, 0.492 mmol) obtained in the Step A in acetone under ice-cooling, and the mixture was stirred at room temperature for one hour. Water was added to the mixture, followed by extraction with ethyl acetate. The extract was washed with saturated saline and then dried over anhydrous sodium sulfate, and the solvent was evaporated under reduced pressure to obtain 3-benzyloxy-2,2-bis(benzyloxymethyl) propionic acid (206 mg, 100%) as a colorless solid.

$^1$H-NMR (CDCl$_3$) δ: 3.73 (6H, s), 4.51 (6H, s), 7.27-7.33 (15H, m)

ESI (LC-MS positive mode) m/z 421 (M+H)

Step C (S)-2-Oxo-3-[1-oxo-3-(2-trifluoromethylphenyl)-1,2-dihydroisoquinolin-7-yl]oxazolidin-5-ylmethyl 3-hydroxy-2,2-bishydroxymethylpropionate Condensation was carried out by a method similar to that of Example 3-1 using 3-benzyloxy-2,2-bis(benzyloxymethyl) propionic acid obtained in Step B instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14, and deprotection was carried out by a method similar to that of Example 1-36 using a 10% Pd—C catalyst in a hydrogen atmosphere to synthesize the title compound.

$^1$H-NMR (CD$_3$OD) δ: 3.70 (3H, s), 3.71 (3H, s), 4.13 (1H, dd, J=5.6, 9.1 Hz), 4.35 (1H, t, J=9.1 Hz), 4.44 (2H, d, J=3.3 Hz), 5.02-5.08 (1H, m), 6.61 (1H, d, J=7.6 Hz), 7.66-7.77 (3H, m), 7.85 (1H, d, J=6.9 Hz), 8.26-8.31 (2H, m)

ESI (LC-MS positive mode) m/z 537 (M+H)

Example 4-18

(S)-2-Oxo-3-[1-oxo-3-(2-trifluoromethylphenyl)-1,2-dihydroisoquinolin-7-yl]oxazolidin-5-ylmethyl(2-aminoacetyl)methylaminoacetate hydrochloride

[Formula 250]

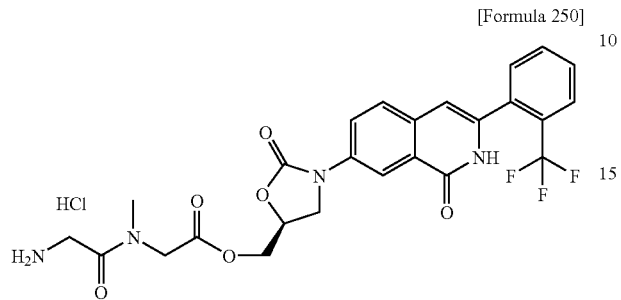

The title compound was synthesized by a method similar to that of Example 3-1 using Boc-Gly-Sar-OH instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (270 MHz, DMSO-$d_6$) δ (ppm): 2.88 (1H, s), 3.00 (2H, s), 3.80-4.04 (3H, m), 4.24-4.34 (3H, m), 4.41-4.45 (2H, m), 4.9-5.1 (1H, m), 6.51 (1H, s), 7.64 (1H, d, J=7.42 Hz), 7.69-7.82 (3H, m), 7.86-7.89 (1H, m), 8.07-8.14 (3H, m), 8.22-8.23 (1H, m), 11.64 (1H, brs)

ESI (LC-MS positive mode) m/z 533 (M+H)

Example 4-19

(S)-2-Oxo-3-[1-oxo-3-(2-trifluoromethylphenyl)-1,2-dihydroisoquinolin-7-yl]oxazolidin-5-ylmethyl 2-aminoacetylaminoacetate hydrochloride

[Formula 251]

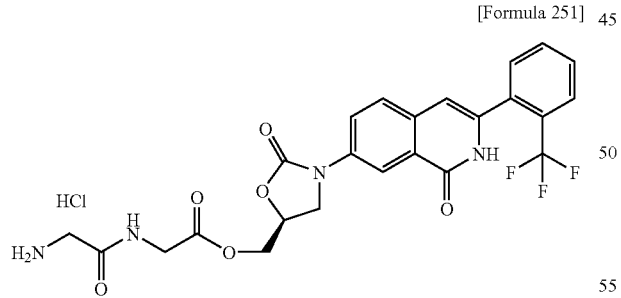

The title compound was synthesized by a method similar to that of Example 3-1 using Boc-Gly-Gly-OH instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (400 MHz, DMSO-$d_6$) δ (ppm): 3.60-3.64 (2H, m), 3.98-4.06 (3H, m), 4.27-4.32 (1H, m), 4.38-4.46 (2H, m), 4.98-5.04 (1H, m), 6.50 (1H, s), 7.63 (1H, d, J=7.32 Hz), 7.7-7.8 (3H, m), 7.88 (1H, d, J=6.84 Hz), 8.07-8.1 (3H, m), 8.23 (1H, d, J=2.44 Hz), 8.85 (1H, t, J=5.86 Hz), 11.6 (1H, brs)

ESI (LC-MS positive mode) m/z 519 (M+H)

Example 4-20

5-{(S)-2-Oxo-3-[1-oxo-3-(2-trifluoromethylphenyl)-1,2-dihydroisoquinolin-7-yl]oxazolidin-5-ylmethyl} (S)-2-[(S)-2-amino-3-(1H-indol-3-yl)propionylamino]-pentanedioate,

[Formula 252]

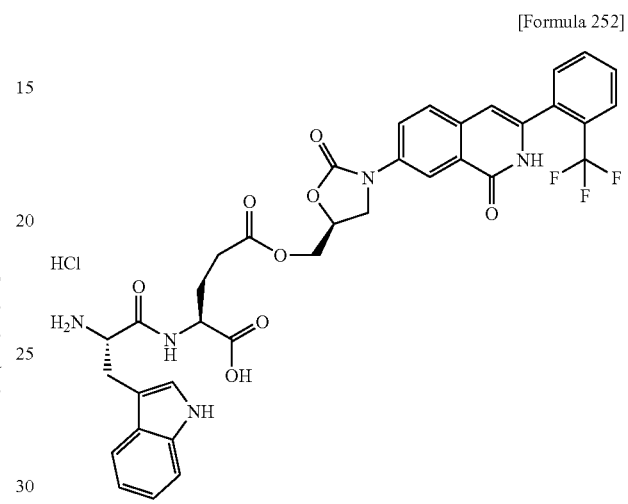

The title compound was synthesized by a method similar to that of Example 3-1 using Boc-Trp-Glu(OH)-OtBu instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (400 MHz, DMSO-$d_6$) δ (ppm): 1.80-1.95 (1H, m), 2.05-2.15 (1H, m), 2.45-2.47, 2.98-3.04 (1H, m), 3.17-3.23, 3.39-3.51, 3.97-4.00 (2H, m), 4.27-4.40 (4H, m), 4.9-5.0 (1H, m), 6.49 (1H, s), 6.99-7.03 (1H, m), 7.08-7.11 (1H, m), 7.23 (1H, m), 7.37 (1H, d, J=8.30 Hz), 7.63 (1H, d, J=7.81 Hz), 7.69-7.80 (4H, m), 7.88 (1H, d, J=7.81 Hz), 8.08 (1H, dd, J=2.44, 8.79 Hz), 8.23 (1H, d, J=2.44 Hz), 8.77 (brs), 10.99 (1H, brs)

ESI (LC-MS positive mode) m/z 742 (M+H)

Example 4-21

(S)-2-Oxo-3-[1-oxo-3-(2-trifluoromethylphenyl)-1,2-dihydroisoquinolin-7-yl]oxazolidin-5-ylmethyl[2-(2-hydroxyethoxy)ethyl]carbamate

[Formula 253]

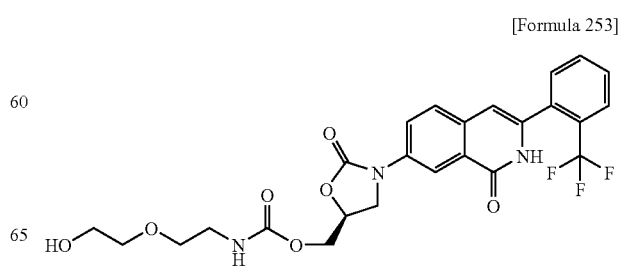

The title compound was synthesized by a method similar to that of Example 4-23 using 2-(2-aminoethoxy)ethanol instead of DL-3-amino-1,2-propanediol.

¹H-NMR (CDCl₃) δ: 3.32 (2H, dd, J=5.1, 10.0 Hz), 3.44-3.51 (4H, m), 3.64 (2H, t, J=4.8 Hz), 4.02 (1H, dd, J=6.6, 9.1 Hz), 4.21 (1H, t, J=9.1 Hz), 4.32 (1H, dd, J=4.6, 12.2 Hz), 4.40 (1H, dd, J=3.7, 12.2 Hz), 4.84-4.93 (1H, m), 6.11 (1H, t, J=5.3 Hz), 6.49 (1H, s), 7.52-7.67 (4H, m), 7.77 (1H, d, J=7.4 Hz), 7.92 (1H, d, J=2.3 Hz), 8.42 (1H, dd, J=2.3, 8.9 Hz), 9.83 (1H, brs)

ESI (LC-MS positive mode) m/z 536 (M+H)

Example 4-22

(R)-2-Oxo-3-[1-oxo-3-(2-trifluoromethylphenyl)-1,2-dihydroisoquinolin-7-yl]oxazolidin-5-ylmethyl(2,3-dihydroxypropyl)carbamate

[Formula 254]

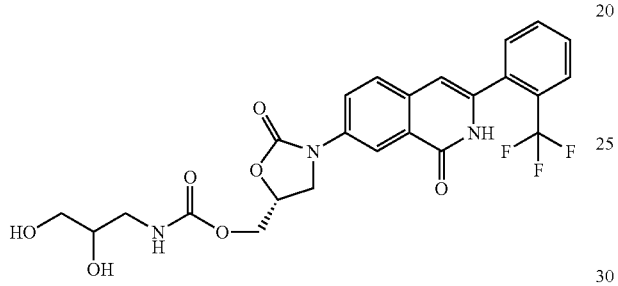

The title compound was synthesized by a method similar to that of Example 4-23 using 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxo-oxazolidin-3-yl)-3-(2-trifluoromethylphenyl)-2H-isoquinolin-1-one obtained in Step B of Example 1-14.

¹H-NMR (CDCl₃) δ: 2.75-3.40 (5H, m), 3.40-3.61 (1H, m) 3.82-4.33 (3H, m), 4.45-4.60 (1H, m), 4.65-4.75 (1H, m), 4.83-5.02 (1H, m), 6.48 (1H, s), 7.23 (1H, t, J=5.7 Hz), 7.55-7.91 (5H, m), 8.06 (1H, dd, J=8.7, 2.5 Hz), 8.23 (1H, d, J=2.5 Hz), 11.63 (1H, s)

ESI (LC-MS positive mode) m/z 522 (M+H)

Example 4-23

(S)-2-Oxo-3-[1-oxo-3-(2-trifluoromethylphenyl)-1,2-dihydroisoquinolin-7-yl]oxazolidin-5-ylmethyl(2,3-dihydroxypropyl)carbamate

[Formula 255]

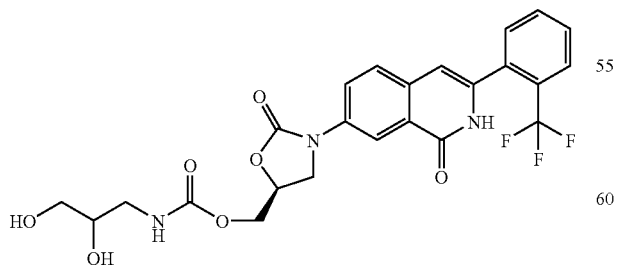

4-Nitrophenyl chloroformate (100 mg, 0.5 mmol) was added to a solution of 7-((S)-5-hydroxymethyl-2-oxooxazolidin-3-yl)-3-(2-trifluoromethylphenyl)-2H-isoquinolin-1-one obtained in Step B of Example 1-13 (40 mg, 0.10 mmol) in pyridine (1 mL), and the mixture was stirred at room temperature for 17 hours. DL-3-amino-1,2-propanediol (180 mg, 1.98 mmol) was added to the reaction mixture which was then stirred at room temperature for five hours. 1 N Hydrochloric acid was added to the mixture under ice-cooling, followed by extraction with ethyl acetate and washing with saturated saline. The extract was dried over anhydrous magnesium sulfate, and the solvent was evaporated under reduced pressure. The resulting residue was purified by silica gel column chromatography (methylene chloride:methanol=10:1) to obtain (S)-2-oxo-3-[1-oxo-3-(2-trifluoromethylphenyl)-1,2-dihydroisoquinolin-7-yl]oxazolidin-5-ylmethyl((2,3-dihydroxypropyl)carbamate (23 mg, yield: 45%) as a colorless oil.

¹H-NMR (DMSO-d₆) δ: 2.75-3.40 (5H, m), 3.40-3.61 (1H, m), 3.82-4.33 (3H, m), 4.45-4.60 (1H, m), 4.65-4.75 (1H, m), 4.83-5.02 (1H, m), 6.48 (1H, s), 7.23 (1H, t, J=5.7 Hz), 7.55-7.91 (5H, m), 8.06 (1H, dd, J=8.7, 2.5 Hz), 8.23 (1H, d, J=2.5 Hz), 11.63 (1H, s).

ESI (LC-MS positive mode) m/z 522 (M+H)

Example 4-24

(S)-2-Oxo-3-[1-oxo-3-(2-trifluoromethylphenyl)-1,2-dihydroisoquinolin-7-yl]oxazolidin-5-ylmethyl(2-hydroxy-1-hydroxymethylethyl)carbamate

[Formula 256]

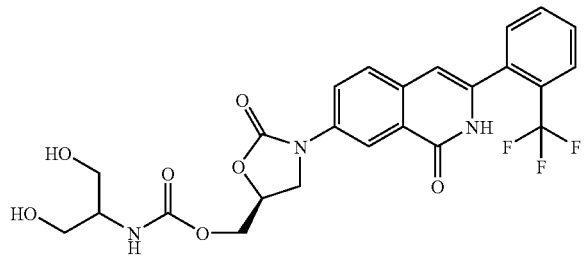

The title compound was synthesized by a method similar to that of Example 4-23 using 2-aminopropane-1,3-diol instead of DL-3-amino-1,2-propanediol.

¹H-NMR (DMSO-d₆) δ: 3.28-3.45 (2H, m), 3.90-4.01 (1H, m), 4.15-4.36 (4H, m), 4.52-4.65 (1H, m), 6.49 (1H, s), 6.98 (1H, d, J=7.6 Hz), 7.60-7.91 (5H, m), 8.08 (1H, dd, J=8.8, 2.4 Hz), 8.23 (1H, d, J=2.4 Hz), 11.62 (1H, s).

ESI (LC-MS positive mode) m/z 522 (M+H)

Example 4-25

(S)-2-Oxo-3-[1-oxo-3-(2-trifluoromethylphenyl)-1,2-dihydroisoquinolin-7-yl]oxazolidin-5-ylmethyl[(2R,3S)-2,3,4-trihydroxybutyl]carbamate

[Formula 257]

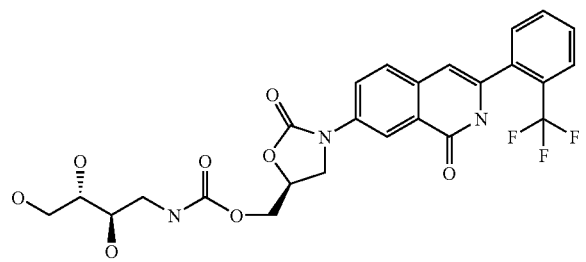

The title compound was synthesized by a method similar to that of Example 4-23 using (2S,3R)-4-aminobutane-1,2,3-triol instead of DL-3-amino-1,2-propanediol.

$^1$H-NMR (CD$_3$OD) δ: 3.08-3.35 (2H, m), 3.46-3.72 (4H, m), 4.03-4.13 (1H, m), 4.25-4.48 (3H, m), 4.92-5.05 (1H, m), 6.60 (1H, s), 7.55-7.88 (5H, m), 8.26 (2H, dd, J=4.5, 2.4 Hz)

ESI (LC-MS positive mode) m/z 522 (M+H)

Example 4-26

(S)-2-Oxo-3-[1-oxo-3-(2-trifluoromethylphenyl)-1,2-dihydroisoquinolin-7-yl]oxazolidin-5-ylmethyl[(2S,3R,4R,5R)-2,3,4,5,6-pentahydroxyhexyl]carbamate

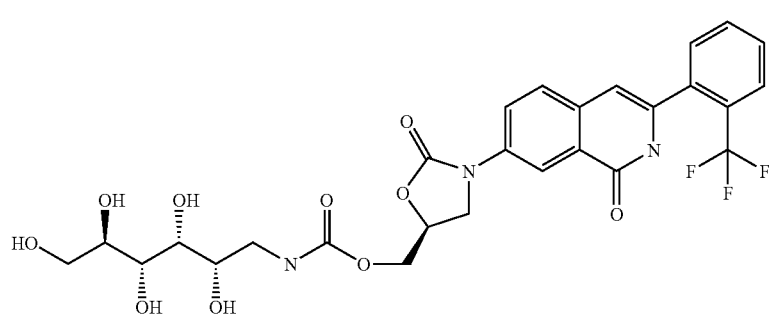

[Formula 258]

The title compound was synthesized by a method similar to that of Example 4-23 using D-glucamine instead of DL-3-amino-1,2-propanediol.

$^1$H-NMR (CD$_3$OD) δ: 3.05-3.41 (2H, m), 3.53-3.86 (6H, m), 4.00-4.13 (1H, m), 4.24-4.48 (3H, m), 4.92-5.06 (1H, m), 6.61 (1H, s), 7.55-7.89 (5H, m), 8.27 (2H, d, J=7.3 Hz).

ESI (LC-MS positive mode) m/z 612 (M+H)

Example 4-27

Ethyl {(R)-2-oxo-3-[1-oxo-3-(2-trifluoromethylphenyl)-1,2-dihydroisoquinolin-7-yl]oxazolidin-5-ylmethoxycarbonylamino}acetate

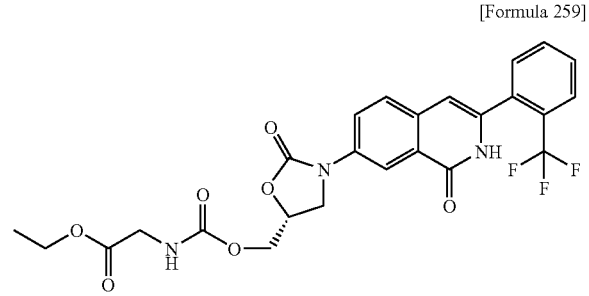

[Formula 259]

Ethyl isocyanatoacetate (6.6 μL, 0.059 mmol) and triethylamine (10.3 μL, 0.074 mmol) were added to a solution of 7-((R)-5-hydroxymethyl-2-oxooxazolidin-3-yl)-3-(2-trifluoromethylphenyl)-2H-isoquinolin-1-one obtained in Step B of Example 1-14 (20 mg, 0.050 mmol) in dichloromethane, and the mixture was stirred at room temperature for four hours. Aqueous saturated ammonium chloride was added to the mixture, followed by extraction with dichloromethane. The extract was dried over anhydrous sodium sulfate, and then the solvent was evaporated under reduced pressure. The resulting residue was purified by aminosilica gel column chromatography (methylene chloride:methanol=50:1) to obtain 24 mg (92%) of ethyl{(R)-2-oxo-3-[1-oxo-3-(2-trifluoromethylphenyl)-1,2-dihydroisoquinolin-7-yl]oxazolidin-5-ylmethoxycarbonylamino}acetate as a colorless oil.

$^1$H-NMR (CDCl$_3$) δ: 1.27 (3H, t, J=7.8 Hz), 3.93 (1H, dd, J=1.8, 5.7 Hz), 3.99 (1H, d, J=5.3 Hz), 4.04-4.28 (4H, m), 4.36 (1H, dd, J=4.9, 12.2 Hz), 4.50 (1H, dd, J=3.8, 12.2 Hz), 4.87-4.96 (1H, m), 6.49 (1H, s), 7.52-7.68 (4H, m), 7.80 (1H, d, J=7.6 Hz), 7.89 (1H, d, J=2.5 Hz), 8.49 (1H, dd, J=2.5, 8.7 Hz), 9.49 (1H, brs)

ESI (LC-MS positive mode) m/z 534 (M+H)

Example 4-28

Ethyl carbonate (R)-2-oxo-3-[1-oxo-3-(2-trifluoromethylphenyl)-1,2-dihydroisoquinolin-7-yl]oxazolidin-5-ylmethyl ester

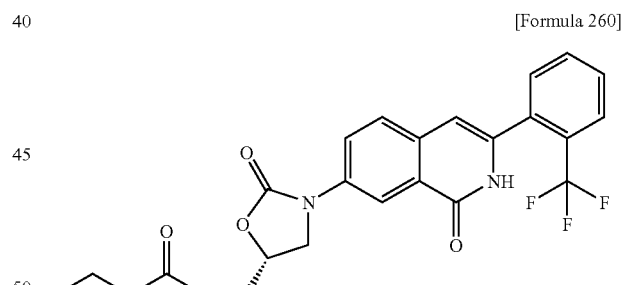

[Formula 260]

Ethyl chloroformate (5.7 μL, 0.059 mmol) and triethylamine (10.3 μL, 0.074 mmol) were added to a solution of 7-((R)-5-hydroxymethyl-2-oxooxazolidin-3-yl)-3-(2-trifluoromethylphenyl)-2H-isoquinolin-1-one obtained in Step B of Example 1-14 (20 mg, 0.050 mmol) in dichloromethane, and the mixture was stirred at room temperature for 18 hours. Aqueous saturated ammonium chloride was added to the mixture, followed by extraction with dichloromethane. The extract was dried over anhydrous sodium sulfate, and then the solvent was evaporated under reduced pressure. The resulting residue was purified by aminosilica gel column chromatography (methylene chloride:methanol=50:1) to obtain 4 mg (17%) of ethyl carbonate (R)-2-oxo-3-[1-oxo-3-(2-trifluoromethylphenyl)-1,2-dihydroisoquinolin-7-yl]oxazolidin-5-ylmethyl ester as a colorless oil.

$^1$H-NMR (CDCl$_3$) δ: 1.32 (3H, t, J=7.1 Hz), 4.06 (1H, dd, J=6.5, 9.3 Hz), 4.23 (2H, dd, J=7.3, 14.3 Hz), 4.40 (1H, dd, J=4.8, 12.0 Hz), 4.47 (2H, dd, J=4.3, 12.0 Hz), 4.93-4.99 (1H, m), 6.53 (1H, s), 7.55-7.68 (1H, m), 7.83 (1H, dd, J=1.5, 7.2 Hz), 7.94 (1H, d, J=2.5 Hz), 8.58 (1H, dd, J=2.5, 8.9 Hz), 8.67 (1H, brs)

ESI (LC-MS positive mode) m/z 477 (M+H)

Example 4-29

(S)-2-oxo-3-[1-oxo-3-(2-trifluoromethylphenyl)-1,2-dihydroisoquinolin-7-yl]oxazolidin-5-ylmethyl nicotinate hydrochloride

[Formula 261]

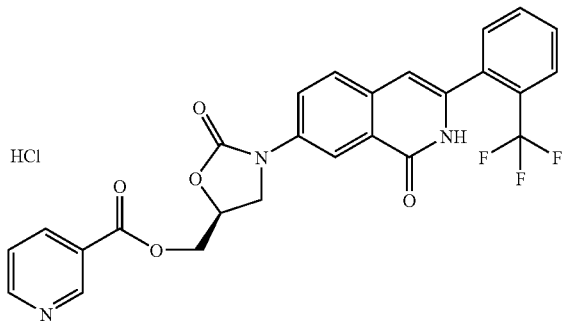

The title compound was synthesized by a condensation method similar to that of Step A of Example 3-1 using nicotinic acid instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (DMSO-d$_6$) δ: 4.18 (1H, dd, J=6.3, 9.2 Hz), 4.37-4.43 (1H, m), 4.62 (1H, dd, J=4.8, 12.5 Hz), 4.69 (1H, dd, J=2.9, 12.2 Hz), 5.13-5.21 (1H, m), 6.50 (1H, s), 7.64-7.82 (5H, m), 7.88 (1H, d, J=7.6 Hz), 8.11 (1H, d, J=8.6 Hz), 8.25 (1H, s), 8.37 (1H, d, J=7.6 Hz), 8.85 (1H, d, J=5.0 Hz), 9.09 (1H, s), 11.63 (1H, brs)

ESI (LC-MS positive mode) m/z 510 (M+H)

Example 4-30

(S)-2-Oxo-3-[1-oxo-3-(2-trifluoromethylphenyl)-1,2-dihydroisoquinolin-7-yl]oxazolidin-5-ylmethyl acetoxyacetate

[Formula 262]

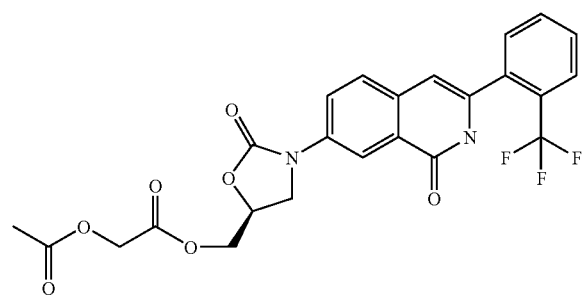

The title compound was synthesized by a condensation method similar to that of Step A of Example 3-1 using acetoxyacetic acid instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (CDCl$_3$) δ: 2.09 (3H, s), 4.00 (1H, dd, J=6.4, 9.4 Hz), 4.27 (1H, t, J=9.2 Hz), 4.45 (1H, dd, J=4.9, 12.2 Hz), 4.52 (1H, dd, J=3.8, 12.2 Hz), 4.64 (2H, s), 4.93-5.02 (1H, m), 6.51 (1H, s), 7.55-7.69 (4H, m), 7.80 (1H, d, J=7.4 Hz), 7.94 (1H, d, J=2.5 Hz), 8.49 (1H, dd, J=2.5, 8.8 Hz), 9.48 (1H, brs)

ESI (LC-MS positive mode) m/z 505 (M+H)

Example 4-31

(S)-2-Oxo-3-[1-oxo-3-(2-trifluoromethylphenyl)-1,2-dihydroisoquinolin-7-yl]oxazolidin-5-ylmethyl(2-methoxyethoxy)acetate

[Formula 263]

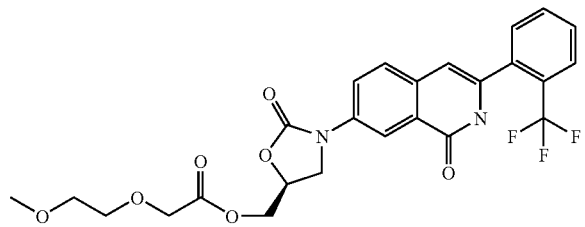

The title compound was synthesized by a condensation method similar to that of Step A of Example 3-1 using (2-methoxyethoxy)acetic acid instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (CDCl$_3$) δ: 3.32 (3H, s), 3.51 (2H, t, J=4.3 Hz), 3.68 (2H, t, J=4.3 Hz), 4.00 (1H, dd, J=6.3, 9.2 Hz), 4.20 (2H, s), 4.27 (1H, t, J=9.2 Hz), 4.38 (1H, dd, J=4.9, 12.2 Hz), 4.49 (1H, dd, J=4.0, 12.2 Hz), 4.91-4.99 (1H, m), 6.50 (1H, s), 7.52-7.69 (4H, m), 7.79 (1H, d, J=8.9 Hz), 7.91 (1H, d, J=2.5 Hz), 8.54 (1H, dd, J=2.5, 8.9 Hz), 8.72 (1H, brs)

ESI (LC-MS positive mode) m/z 521 (M+H)

Example 4-32

(S)-2-Oxo-3-[1-oxo-3-(2-trifluoromethylphenyl)-1,2-dihydroisoquinolin-7-yl]oxazolidin-5-ylmethyl[2-(2-methoxyethoxy)ethoxy]acetate

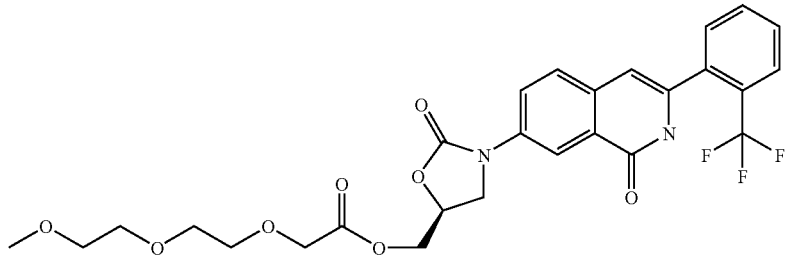

[Formula 264]

The title compound was synthesized by a condensation method similar to that of Step A of Example 3-1 using 2-(2-methoxyethoxy)ethoxyacetic acid instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14.

$^1$H-NMR (CDCl$_3$) δ: 3.35 (3H, s), 3.51-3.55 (2H, m), 3.59-3.66 (4H, m), 3.70-3.74 (2H, m), 4.00 (1H, dd, J=6.3, 9.3 Hz), 4.22 (2H, d, J=0.5 Hz), 4.28 (1H, t, J=9.2 Hz), 4.42 (1H, dd, J=5.1, 12.2 Hz), 4.51 (1H, dd, J=2.8, 12.2 Hz), 4.93-4.99 (1H, m), 6.52 (1H, s), 7.56-7.70 (4H, m), 7.80 (1H, d, J=6.9 Hz), 7.92 (1H, d, J=2.5 Hz), 8.51 (1H, dd, J=2.5, 8.9 Hz), 9.33 (1H, brs)

ESI (LC-MS positive mode) m/z 565 (M+H)

Example 4-33

(S)-2-Oxo-3-[1-oxo-3-(2-trifluoromethylphenyl)-1,2-dihydroisoquinolin-7-yl]oxazolidin-5-ylmethyl[2-(2-{2-[2-(2-methoxyethoxy)ethoxy]ethoxy}ethoxy)ethoxy]acetate

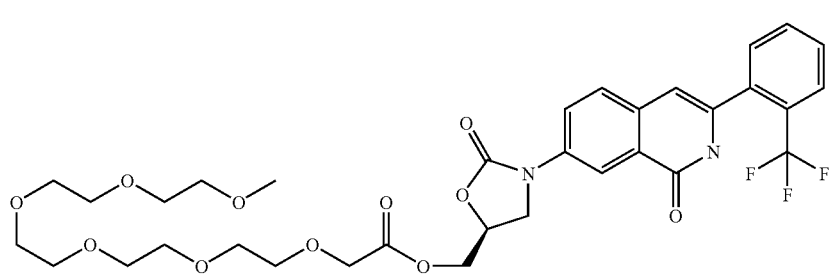

[Formula 265]

The title compound was synthesized by a condensation method similar to that of Step A of Example 3-1 using [2-(2-{2-[2-(2-methoxyethoxy)ethoxy]ethoxy}ethoxy)ethoxy]acetic acid instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14. However, [2-(2-{2-[2-(2-methoxyethoxy)ethoxy]ethoxy}ethoxy)ethoxy]acetic acid was synthesized by a method similar to that of Step A of Example 4-39 using pentaethylene glycol monomethyl ether instead of pentaethylene glycol monobenzyl ether.

$^1$H-NMR (CDCl$_3$) δ: 3.36 (3H, s), 3.52-3.75 (20H, m), 4.01 (1H, dd, J=6.2, 9.4 Hz), 4.22 (2H, s), 4.29 (1H, t, J=9.1 Hz), 4.42 (1H, dd, J=5.1, 12.2 Hz), 4.51 (1H, dd, J=3.9, 12.2 Hz), 4.96-5.01 (1H, m), 6.53 (1H, s), 7.56-7.71 (1H, m), 7.81 (1H, d, J=6.8 Hz), 7.94 (1H, d, J=2.5 Hz), 8.53 (1H, dd, J=2.5, 8.9 Hz), 9.16 (1H, brs)

ESI (LC-MS positive mode) m/z 697 (M+H)

Example 4-34

(S)-2-Oxo-3-[1-oxo-3-(2-trifluoromethylphenyl)-1,2-dihydroisoquinolin-7-yl]oxazolidin-5-ylmethyl {2-[2-(2-methoxyethoxy)ethoxy]ethoxy}acetate

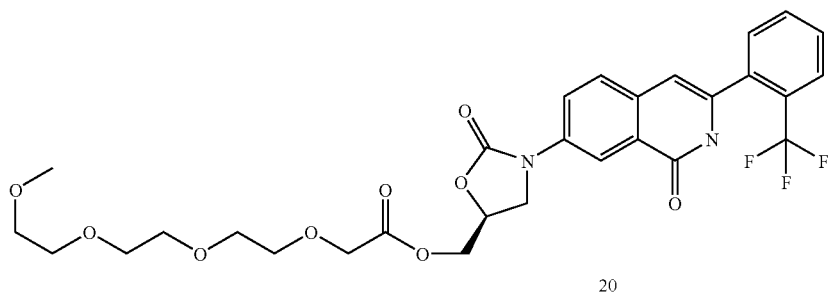

[Formula 266]

The title compound was synthesized by a condensation method similar to that of Step A of Example 3-1 using {2-[2-(2-methoxyethoxy)ethoxy]ethoxy}acetic acid instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14. However, {2-[2-(2-methoxyethoxy)ethoxy]ethoxy}acetic acid was synthesized by a method similar to that of Step A of Example 4-39 using triethylene glycol monomethyl ether instead of pentaethylene glycol monobenzyl ether.

$^1$H-NMR (CDCl$_3$) δ: 3.35 (3H, s), 3.51-3.75 (12H, m), 4.01 (1H, dd, J=6.2, 9.2 Hz), 4.17-4.32 (3H, m), 4.42 (1H, dd, J=5.1, 12.2 Hz), 4.51 (1H, dd, J=3.8, 12.2 Hz), 4.93-5.02 (1H, m), 6.52 (1H, s), 7.56-7.70 (4H, m), 7.81 (1H, d, J=6.8 Hz), 7.93 (1H, dd, J=2.5, 8.9 Hz), 9.19 (1H, brs)

ESI (LC-MS positive mode) m/z 608 (M+H)

Example 4-35

(S)-2-Oxo-3-[1-oxo-3-(2-trifluoromethylphenyl)-1,2-dihydroisoquinolin-7-yl]oxazolidin-5-ylmethyl(2-{2-[2-(2-methoxyethoxy)ethoxy]ethoxy}ethoxy)acetate

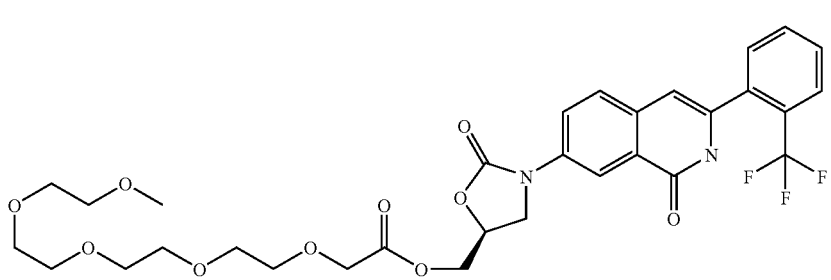

[Formula 267]

The title compound was synthesized by a condensation method similar to that of Step A of Example 3-1 using (2-{2-[2-(2-methoxyethoxy)ethoxy]ethoxy}ethoxy)acetic acid instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14. However, (2-{2-[2-(2-methoxyethoxy)ethoxy]ethoxy}ethoxy)acetic acid was synthesized by a method similar to that of Step A of Example 4-39 using tetraethylene glycol monomethyl ether instead of pentaethylene glycol monobenzyl ether.

$^1$H-NMR (CDCl$_3$) δ: 3.36 (3H, s), 3.52-3.75 (16H, m), 4.02 (1H, dd, J=6.4, 9.4 Hz), 4.17-4.33 (3H, m), 4.42 (1H, dd, J=5.1, 12.2 Hz), 4.51 (1H, dd, J=4.0, 12.2 Hz), 4.94-5.03 (1H, m), 6.53 (1H, s), 7.56-7.71 (4H, m), 7.82 (1H, d, J=7.4 Hz), 7.94 (1H, d, J=2.5 Hz), 8.54 (1H, dd, J=2.5, 8.9 Hz), 9.09 (1H, brs)

ESI (LC-MS positive mode) m/z 653 (M+H)

Example 4-36

(S)-2-Oxo-3-[1-oxo-3-(2-trifluoromethylphenyl)-1,2-dihydroisoquinolin-7-yl]oxazolidin-5-ylmethyl {2-[2-(2-{2-[2-(2-methoxyethoxy)ethoxy]ethoxy}ethoxy)ethoxy]ethoxy}acetate

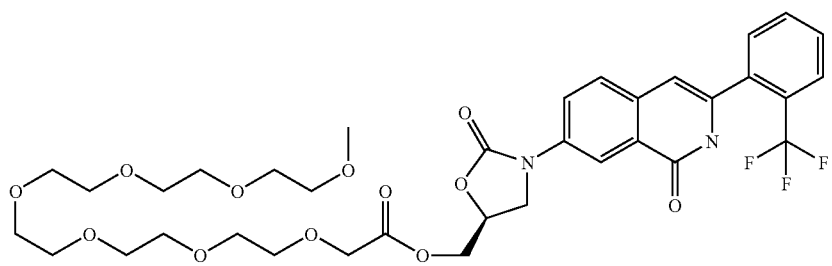

[Formula 268]

The title compound was synthesized by a condensation method similar to that of Step A of Example 3-1 using {2-[2-(2-{2-[2-(2-methoxyethoxy)ethoxy]ethoxy}ethoxy)ethoxy]ethoxy}acetic acid instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14. However, {2-[2-(2-{2-[2-(2-methoxyethoxy)ethoxy]ethoxy}ethoxy)ethoxy]ethoxy}acetic acid was synthesized by a method similar to that of Step A of Example 4-39 using hexaethylene glycol monomethyl ether instead of pentaethylene glycol monobenzyl ether.

$^1$H-NMR (CDCl$_3$) δ: 3.36 (3H, s), 3.52-3.75 (24H, m), 4.02 (1H, dd, J=4.9, 12.2 Hz), 4.17-4.33 (3H, m), 4.41 (1H, dd, J=4.9, 12.2 Hz), 4.51 (1H, dd, J=4.0, 12.2 Hz), 4.94-5.00 (1H, m), 6.53 (1H, s), 7.55-7.71 (4H, m), 7.82 (1H, d, J=7.2 Hz), 7.94 (1H, d, J=2.3 Hz), 8.57 (1H, dd, J=2.3, 8.8 Hz), 8.74 (1H, brs)

ESI (LC-MS positive mode) m/z 741 (M+H)

Example 4-37

(S)-2-Oxo-3-[1-oxo-3-(2-trifluoromethylphenyl)-1,2-dihydroisoquinolin-7-yl]oxazolidin-5-ylmethyl[2-(2-hydroxyethoxy)ethoxy]acetate

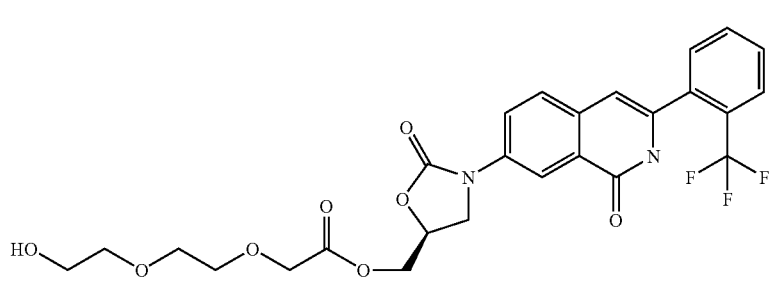

[Formula 269]

The title compound was synthesized by a method similar to that of Example 4-39 using diethylene glycol monobenzyl ether instead of pentaethylene glycol monobenzyl ether.

$^1$H-NMR (CDCl$_3$) δ: 3.56-3.76 (8H, m), 4.05 (1H, dd, J=6.2, 9.2 Hz), 4.22 (2H, s), 4.29 (1H, t, J=9.2 Hz), 4.43 (1H, dd, J=4.9, 12.2 Hz), 4.52 (1H, dd, J=3.8, 12.2 Hz), 4.94-5.03 (1H, m), 6.53 (1H, s), 7.55-7.71 (1H, m), 7.81 (1H, d, J=7.1 Hz), 7.95 (1H, d, J=2.5 Hz), 8.55 (1H, dd, J=2.5, 8.9 Hz), 8.95 (1H, brs)

ESI (LC-MS positive mode) m/z 551 (M+H)

Example 4-38

(S)-2-Oxo-3-[1-oxo-3-(2-trifluoromethylphenyl)-1,2-dihydroisoquinolin-7-yl]oxazolidin-5-ylmethyl {2-[2-(2-hydroxyethoxy)ethoxy]ethoxy}acetate

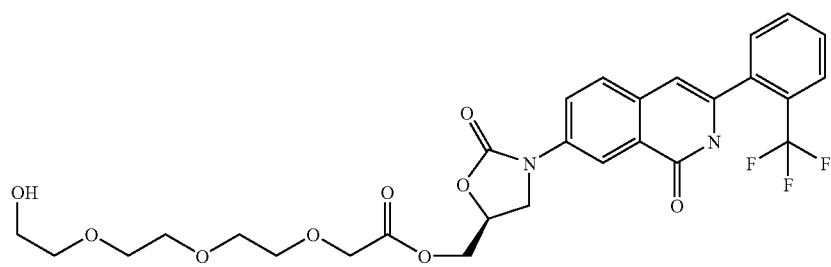

[Formula 270]

The title compound was synthesized by a method similar to that of Example 4-39 using triethylene glycol monobenzyl ether instead of pentaethylene glycol monobenzyl ether.

$^1$H-NMR (CDCl$_3$) δ: 3.56-3.77 (12H, m), 4.04 (1H, dd, J=6.2, 9.3 Hz), 4.17-4.35 (3H, m), 4.42 (1H, dd, J=5.0, 12.2 Hz), 4.52 (1H, dd, J=3.9, 12.2 Hz), 4.94-5.03 (1H, m), 6.53 (1H, s), 7.55-7.71 (4H, m), 7.82 (1H, d, J=7.6 Hz), 7.95 (1H, d, J=2.5 Hz), 8.55 (1H, dd, J=2.5, 8.9 Hz), 8.92 (1H, s)

ESI (LC-MS positive mode) m/z 595 (M+H)

Example 4-39

(S)-2-Oxo-3-[1-oxo-3-(2-trifluoromethylphenyl)-1,2-dihydroisoquinolin-7-yl]oxazolidin-5-ylmethyl[2-(2-{2-[2-(2-hydroxyethoxy)ethoxy]ethoxy}ethoxy)ethoxy]acetate

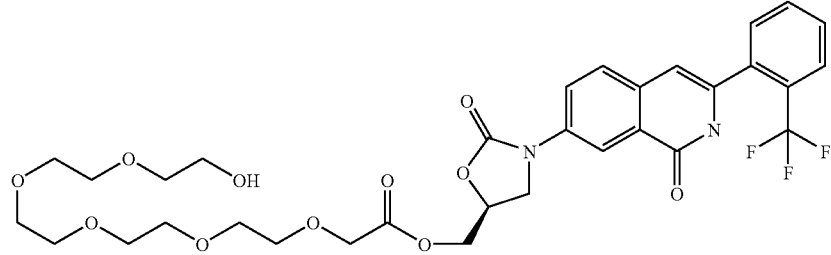

[Formula 271]

Step A

[2-(2-{2-[2-(2-Benzyloxyethoxy)ethoxy]ethoxy}ethoxy)ethoxy]acetic acid

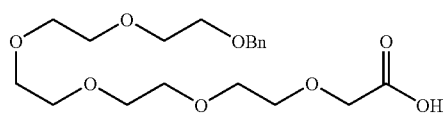

[Formula 272]

Metal sodium (115 mg, 5.0 mmol) was added to pentaethylene glycol monobenzyl ether (328 mg, 1.0 mmol), and the mixture was stirred at 90° C. for three hours. Chloroacetic acid (47 mg, 0.5 mmol) was added to the mixture which was then stirred at 90° C. for 16 hours. Water was added to the mixture which was then washed with ethyl acetate. Next, the aqueous layer was made acidic by 1 N hydrochloric acid, followed by extraction with ethyl acetate. The extract was dried over anhydrous sodium sulfate, and then the solvent was evaporated under reduced pressure to obtain 390 mg of crude [2-(2-{2-[2-(2-benzyloxyethoxy)ethoxy]ethoxy}ethoxy)ethoxy]acetic acid in the form of a reddish brown substance.

Step B (S)-2-Oxo-3-[1-oxo-3-(2-trifluoromethylphenyl)-1,2-dihydroisoquinolin-7-yl]oxazolidin-5-ylmethyl[2-(2-{2-[2-(2-hydroxyethoxy)ethoxy]ethoxy}ethoxy)ethoxy]acetate Condensation was carried out by a method similar to that of Example 3-1 using crude [2-(2-{2-[2-(2-benzyloxyethoxy)ethoxy]ethoxy}ethoxy)ethoxy]acetic acid obtained in Step A instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14, and deprotection was carried out by a method similar to that of Example 1-36 using a 10% Pd—C catalyst in a hydrogen atmosphere to synthesize the title compound.

$^1$H-NMR (CDCl$_3$) δ: 3.55-3.75 (20H, m), 4.02 (1H, dd, J=6.2, 9.2 Hz), 4.22-4.33 (3H, m), 4.42 (1H, dd, J=5.0, 12.2 Hz), 4.51 (1H, dd, J=3.7, 12.2 Hz), 4.94-5.03 (1H, m), 6.52 (1H, s), 7.56-7.70 (4H, m), 7.80 (1H, d, J=7.4 Hz), 7.94 (1H, d, J=2.3 Hz), 8.51 (1H, dd, J=2.3, 8.9 Hz), 9.40 (1H, brs)

ESI (LC-MS positive mode) m/z 683 (M+H)

Example 4-40

(S)-2-Oxo-3-[1-oxo-3-(2-trifluoromethylphenyl)-1,2-dihydroisoquinolin-7-yl]oxazolidin-5-ylmethyl {2-[2-(2-{2-[2-(2-hydroxyethoxy)ethoxy]ethoxy}ethoxy)ethoxy]ethoxy}acetate

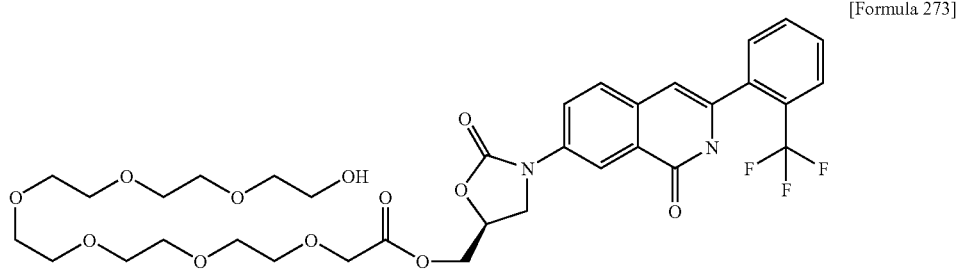

[Formula 273]

The title compound was synthesized by a method similar to that of Example 4-39 using hexaethylene glycol monobenzyl ether instead of pentaethylene glycol monobenzyl ether.

¹H-NMR (CDCl₃) δ: 3.56-3.75 (24H, m), 4.02 (1H, dd, J=6.3, 9.2 Hz), 4.15-4.37 (3H, m), 4.42 (1H, dd, J=5.0, 12.2 Hz), 4.51 (1H, dd, 3.8, 12.2 Hz), 4.92-5.02 (1H, m), 6.53 (1H, s), 7.56-7.70 (4H, m), 7.81 (1H, d, J=6.9 Hz), 7.95 (1H, d, J=2.5 Hz), 8.52 (1H, dd, J=2.5, 8.9 Hz), 9.30 (1H, brs)

ESI (LC-MS positive mode) m/z 727 (M+H)

Example 4-41

2-[2-(2-Methoxy-1-methylethoxy)-1-methylethoxy]-1-methylethyl carbonate (S)-2-oxo-3-[1-oxo-3-(2-trifluoromethylphenyl)-1,2-dihydroisoquinolin-7-yl]oxazolidin-5-ylmethyl ester

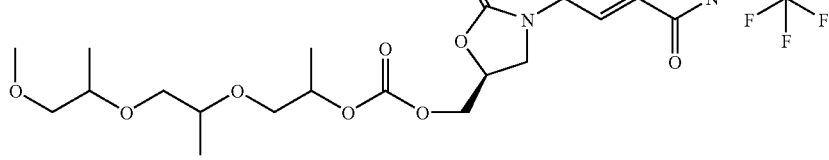

[Formula 274]

The title compound was synthesized by a method similar to that of Example 4-45 using 2-[2-(2-methoxy-1-methylethoxy)-1-methylethoxy]-1-methylethanol instead of hexaethylene glycol monobenzyl ether.

¹H-NMR (CDCl₃) δ: 1.12 (6H, d, J=5.1 Hz), 1.26-1.31 (3H, m), 3.27-3.63 (9H, m), 3.35 (3H, s), 4.04 (1H, dd, J=6.6, 9.2 Hz), 4.26 (1H, t, J=9.0 Hz), 4.39-4.50 (2H, m), 4.86-4.98 (1H, m), 6.51 (1H, s), 7.55-7.70 (4H, m), 7.81 (1H, d, J=7.3 Hz), 7.92 (1H, d, J=2.5 Hz), 8.53 (1H, dd, J=2.5, 8.7 Hz), 9.23 (1H, brs)

ESI (LC-MS positive mode) m/z 637 (M+H)

Example 4-42

2-(2-Hydroxyethoxy)ethyl carbonate (S)-2-oxo-3-[1-oxo-3-(2-trifluoromethylphenyl)-1,2-dihydroisoquinolin-7-yl]oxazolidin-5-ylmethyl ester

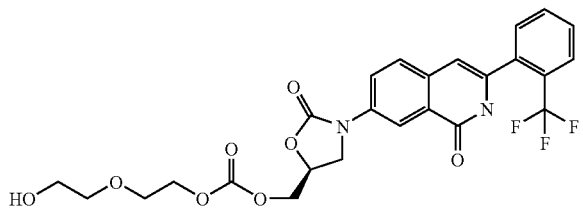

[Formula 275]

The title compound was synthesized by a method similar to that of Example 4-45 using diethylene glycol monobenzyl ether instead of hexaethylene glycol monobenzyl ether.

¹H-NMR (CDCl₃) δ: 3.59 (4H, dd, J=3.8, 8.6 Hz), 3.71 (4H, dd, 3.3, 5.4 Hz), 4.07 (1H, dd, 6.4, 9.0 Hz), 4.23-4.34 (1H, m), 4.42 (1H, dd, J=4.7, 12.0 Hz), 4.51 (1H, dd, J=4.0, 12.0 Hz), 4.92-5.01 (1H, m), 6.52 (1H, s), 7.52-7.69 (4H, m), 7.80 (1H, d, J=7.6 Hz), 7.91 (1H, d, J=2.5 Hz), 8.52 (1H, dd, J=2.5, 8.7 Hz)

ESI (LC-MS positive mode) m/z 537 (M+H).

Example 4-43

2-[2-(2-Hydroxyethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester

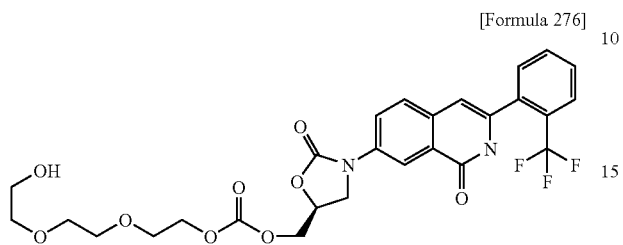

[Formula 276]

The title compound was synthesized by a method similar to that of Example 4-45 using triethylene glycol monobenzyl ether instead of hexaethylene glycol monobenzyl ether.

$^1$H-NMR (CDCl$_3$) δ: 3.57-3.73 (12H, m), 4.08 (1H, dd, J=6.6, 9.2 Hz), 4.24-4.34 (1H, m), 4.42 (1H, dd, J=4.8, 11.9 Hz), 4.49 (1H, dd, J=4.2, 11.9 Hz), 4.93-5.02 (1H, m), 6.52 (1H, s), 7.55-7.69 (4H, m), 7.79 (1H, d, J=7.4 Hz), 7.92 (1H, d, J=2.3 Hz), 8.51 (1H, dd, J=2.3, 11.0 Hz)

ESI (LC-MS positive mode) m/z 581 (M+H)

Example 4-44

2-{2-[2-(2-Hydroxyethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester

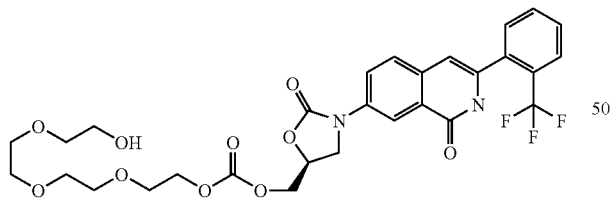

[Formula 277]

The title compound was synthesized by a method similar to that of Example 4-45 using tetraethylene glycol monobenzyl ether instead of hexaethylene glycol monobenzyl ether.

$^1$H-NMR (CDCl$_3$) δ: 3.57-3.79 (16H, m), 4.07 (1H, dd, J=6.8, 9.2 Hz), 4.25-4.34 (1H, m), 4.41 (1H, dd, J=4.9, 11.9 Hz), 4.49 (1H, dd, J=4.3, 11.9 Hz), 4.92-5.02 (1H, m), 6.52 (1H, s), 7.55-7.70 (4H, m), 7.81 (1H, d, J=7.6 Hz), 7.94 (1H, s), 8.54 (1H, d, J=8.9 Hz)

ESI (LC-MS positive mode) m/z 625 (M+H)

Example 4-45

2-[2-(2-{2-[2-(2-Hydroxyethoxy)ethoxy]ethoxy}ethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester

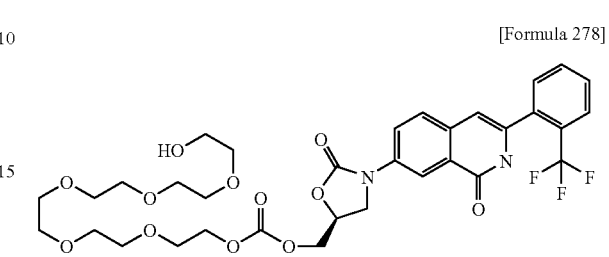

[Formula 278]

4-Nitrophenyl chloroformate was added to 1 mL of a solution of 7-((S)-5-hydroxymethyl-2-oxooxazolidin-3-yl)-3-(2-trifluoromethylphenyl)-2H-isoquinolin-1-one obtained in Step B of Example 1-13 (30 mg, 0.074 mmol) in pyridine, and the mixture was stirred at room temperature for six hours. Hexaethylene glycol monobenzyl ether (138 mg, 0.370 mmol) was added to the mixture which was then stirred at 60° C. for 14 hours. 1 N hydrochloric acid was added to the mixture, followed by extraction with ethyl acetate. The extract was washed with saturated saline and then dried over anhydrous sodium sulfate, and then the solvent was evaporated under reduced pressure. The resulting residue was purified by silica gel column chromatography (methylene chloride:methanol=50:1) to obtain 2-[2-(2-{2-[2-(2-benzyloxyethoxy)ethoxy]ethoxy}ethoxy)ethoxy]ethyl carbonate (S)-2-oxo-3-[1-oxo-3-(2-trifluoromethylphenyl)-1,2-dihydroisoquinolin-7-yl]-oxazolidin-5-ylmethyl ester (22 mg, yield: 37%) as a colorless oil. The product was deprotected by a method similar to that of Example 1-36 using a 10% Pd—C catalyst in a hydrogen atmosphere to synthesize the title compound.

$^1$H-NMR (CDCl$_3$) δ: 3.57-3.74 (24H, m), 4.07 (1H, dd, J=6.4, 9.2 Hz), 4.25-4.34 (1H, m), 4.41 (1H, dd, J=4.8, 11.9 Hz), 4.49 (1H, dd, J=4.3, 11.9 Hz), 4.93-5.01 (1H, m), 6.53 (1H, s), 7.56-7.68 (4H, m), 7.81 (1H, d, J=7.4 Hz), 7.93 (1H, d, J=2.5 Hz), 8.55 (1H, dd, J=2.5, 9.8 Hz), 9.14 (1H, brs)

ESI (LC-MS positive mode) m/z 713 (M+H)

Example 4-46

(S)-2-Oxo-3-[1-oxo-3-(2-trifluoromethylphenyl)-1,2-dihydroisoquinolin-7-yl]oxazolidin-5-ylmethyl carbonate 1,4,7,10-tetraoxacyclododec-2-ylmethyl ester

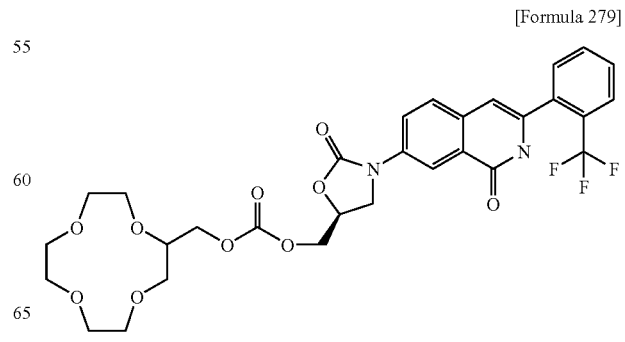

[Formula 279]

The title compound was synthesized by a method similar to that of Example 4-45 using 1,4,7,10-tetraoxacyclododec-2-ylmethyl alcohol instead of hexaethylene glycol monobenzyl ether.

$^1$H-NMR (CDCl$_3$) δ: 3.55-3.92 (16H, m), 4.05 (1H, dd, J=6.4, 8.2 Hz), 4.13-4.31 (2H, m), 4.38-4.52 (2H, m), 4.92-5.01 (1H, m), 6.52 (1H, s), 7.55-7.71 (4H, m), 7.82 (1H, d, J=7.4 Hz), 7.93 (1H, d, J=2.3 Hz), 8.55 (1H, dd, J=2.3, 8.7 Hz), 8.86 (1H, brs)

ESI (LC-MS positive mode) m/z 637 (M+H)

Example 4-47

2-(2-Hydroxy-1-hydroxymethylethoxy)ethyl carbonate (S)-2-oxo-3-[1-oxo-3-(2-trifluoromethylphenyl)-1,2-dihydroisoquinolin-7-yl]oxazolidin-5-ylmethyl ester

[Formula 280]

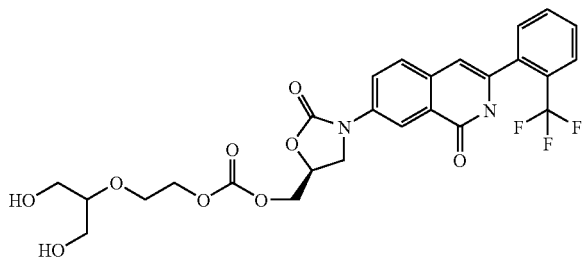

Step A tert-Butyldimethyl-[2-(2-phenyl-[1,3]dioxan-5-yloxy)ethoxy]silane

[Formula 281]

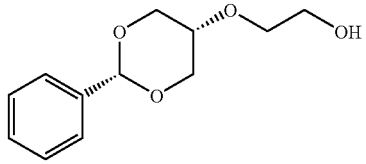

Sodium hydride (133 mg, 3.32 mmol) was added to 5 mL of a solution of cis-1,3-O-benzylideneglycerol (300 mg, 1.66 mmol) in DMF, and the mixture was stirred at room temperature for two hours. (2-bromoethoxy)-tert-butyldimethylsilane (534 μl, 3.32 mmol) was added to the mixture which was then stirred at room temperature for two hours. Aqueous saturated ammonium chloride was added to the mixture, followed by extraction with ethyl acetate. The extract was washed with saturated saline and then dried over anhydrous sodium sulfate, and the solvent was evaporated under reduced pressure to obtain a crude product, tert-butyldimethyl-[2-(2-phenyl-[1,3]dioxan-5-yloxy)ethoxy]silane (343 mg) as a colorless oil.

Step B 2-(2-Phenyl-[1,3]dioxan-5-yloxy)ethanol

[Formula 282]

A solution of TBAF in 1 M-THF (1 mL, 1.00 mmol) was added to 5 mL of a solution of crude tert-butyldimethyl-[2-(2-phenyl-[1,3]dioxan-5-yloxy)ethoxy]silane (343 mg, 1.01 mmol) obtained in Step A in THF, and the mixture was stirred at room temperature for 16 hours. Aqueous saturated ammonium chloride was added to the mixture, followed by extraction with ethyl acetate. The extract was washed with saturated saline and then dried over anhydrous sodium sulfate, and the solvent was evaporated under reduced pressure. The resulting residue was purified by silica gel column chromatography (methylene chloride:methanol=50:1) to obtain 2-(2-phenyl-[1,3]dioxan-5-yloxy)ethanol (39 mg, yield: 17%) as a colorless oil.

$^1$H-NMR (CDCl$_3$) δ: 3.33 (1H, t, J=1.5 Hz), 3.67 (2H, J=4.0 Hz), 3.78 (2H, t, J=4.0 Hz), 4.06 (2H, dd, J=1.5, 12.7 Hz), 4.35 (2H, dd, J=1.5, 12.7 Hz), 5.57 (1H, s), 7.34-7.37 (3H, m), 7.48-7.52 (2H, m)

ESI (LC-MS positive mode) m/z 225 (M+H).

Step C 2-(2-Hydroxy-1-hydroxymethylethoxy)ethyl carbonate (S)-2-oxo-3-[1-oxo-3-(2-trifluoromethylphenyl)-1,2-dihydroisoquinolin-7-yl]oxazolidin-5-ylmethyl ester The title compound was synthesized by a method similar to that of Example 4-45 using 2-(2-phenyl-[1,3]dioxan-5-yloxy)-ethanol obtained in Step B instead of hexaethylene glycol monobenzyl ether.

$^1$H-NMR (CDCl$_3$) δ: 3.49 (1H, dt, J=9.6, 4.8 Hz), 3.61-3.84 (6H, m), 4.06-4.34 (4H, m), 4.42 (1H, dd, J=4.6, 11.9 Hz), 4.51 (1H, dd, J=4.3, 11.9 Hz), 4.92-5.01 (1H, m), 6.52 (1H, s), 7.52-7.69 (4H, m), 7.79 (1H, m), 7.92 (1H, d, J=2.6 Hz), 8.50 (1H, dd, J=2.6, 8.9 Hz), 9.19 (1H, brs)

ESI (LC-MS positive mode) m/z 567 (M+H).

Example 4-48

2-{2-[2-(2-{2-[2-(2-{2-[2-(2-Hydroxyethoxy)ethoxy]ethoxy}ethoxy)ethoxy]ethoxy}ethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester

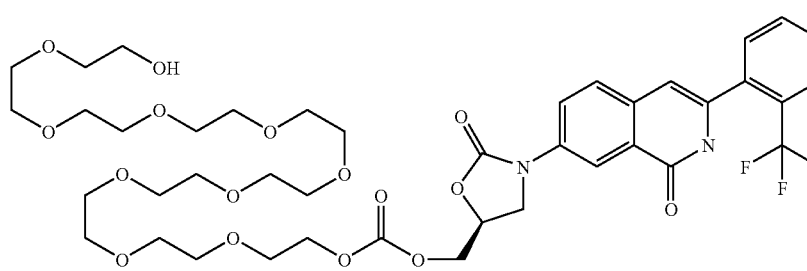

[Formula 283]

Step A

Decaethylene Glycol Monobenzyl Ether

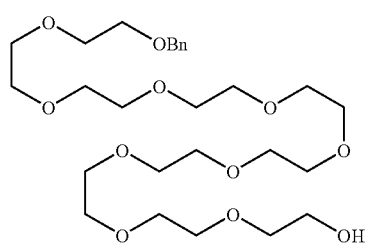

[Formula 284]

Sodium hydride (35 mg, 0.872 mmol) and benzyl bromide (52 μl, 0.436 mmol) were added to 5 mL of a solution of commercially available decaethylene glycol (200 mg, 0.436 mmol) in THF, and the mixture was stirred at room temperature for 16 hours. Aqueous saturated ammonium chloride was added to the mixture, followed by extraction with ethyl acetate. The extract was washed with saturated saline and then dried over anhydrous sodium sulfate, and the solvent was evaporated under reduced pressure to obtain 168 mg of crude decaethylene glycol monobenzyl ether as a colorless oil.

Step B

2-{2-[2-(2-{2-[2-(2-{2-[2-(2-Hydroxyethoxy)ethoxy]ethoxy}ethoxy)ethoxy]ethoxy}ethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester The title compound was synthesized by a method similar to that of Example 4-45 using decaethylene glycol monobenzyl ether instead of hexaethylene glycol monobenzyl ether.

$^1$H-NMR (CDCl$_3$) δ: 3.45-3.47 (40H, m), 4.07 (1H, t, J=9.3 Hz), 4.28-4.33 (1H, m), 4.41 (1H, dd, J=4.6, 12.0 Hz), 4.47 (1H, dd, J=4.4, 12.0 Hz), 4.92-5.00 (1H, m), 6.55 (1H, s), 7.55-7.70 (4H, m), 7.82 (1H, d, J=7.8 Hz), 7.96 (1H, d, J=2.0 Hz), 8.57 (1H, dd, J=2.0, 8.7 Hz)

ESI (LC-MS positive mode) m/z 889 (M+H)

Example 4-49

2-{2-[2-(2-{2-[2-(2-{2-[2-(2-Methoxyethoxy)ethoxy]ethoxy}ethoxy)ethoxy]ethoxy}ethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester

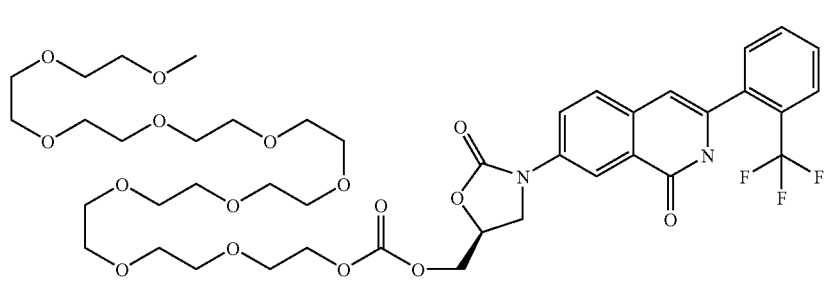

[Formula 285]

The title compound was synthesized by a method similar to that of Example 4-45 using decaethylene glycol monomethyl ether instead of hexaethylene glycol monobenzyl ether.

$^1$H-NMR (CDCl$_3$) δ: 3.37 (3H, s), 3.48-3.74 (40H, m), 4.06 (1H, dd, J=6.6, 9.2 Hz), 4.24-4.34 (1H, m), 4.41 (1H, dd, J=4.5, 12.0 Hz), 4.48 (1H, dd, J=4.3, 12.0 Hz), 4.92-5.01 (1H, m), 6.53 (1H, s), 7.54-7.71 (4H, m), 7.82 (1H, d, J=7.3 Hz), 7.95 (1H, d, J=2.5 Hz), 8.57 (1H, dd, J=2.5, 8.9 Hz)

ESI (LC-MS positive mode) m/z 903 (M+H).

Example 4-50

2-[2-(2-Hydroxyethoxy)ethoxy]-1-[2-(2-hydroxyethoxy)ethoxymethyl]ethyl carbonate (S)-2-oxo-3-[1-oxo-3-(2-trifluoromethylphenyl)-1,2-dihydroisoquinolin-7-yl]oxazolidin-5-ylmethyl ester

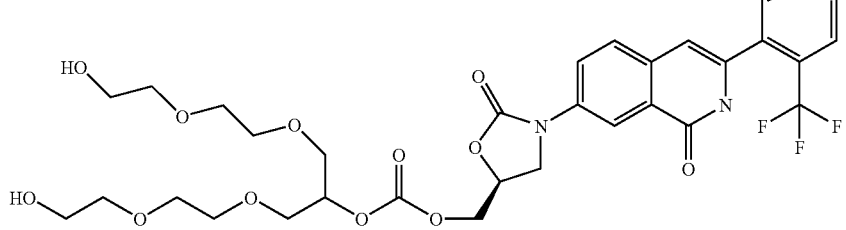

Step A

2-[2-(2-Benzyloxyethoxy)ethoxy]-1-[2-(2-benzyloxyethoxy)ethoxymethyl]ethanol

[Formula 287]

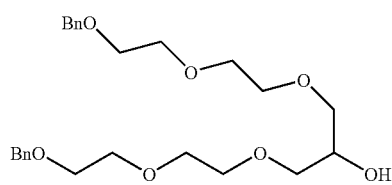

A solution of n-butyl lithium in THF (1.6 N, 1.59 mL, 2.55 mmol) was added to 10 mL of a solution of diethylene glycol monobenzyl ether (500 mg, 2.55 mmol) in THF at −78° C., and the mixture was stirred for 15 minutes. Then, DL-epichlorohydrin (0.1 mL, 1.28 mmol) was added thereto. The mixture was stirred at room temperature for one hour and under reflux for one hour. Next, the THF solvent was evaporated under reduced pressure, and the residue was stirred at 100° C. without a solvent to complete the reaction. Aqueous saturated ammonium chloride was added to the residue, followed by extraction with ethyl acetate. The extract was washed with saturated saline and then dried over anhydrous magnesium sulfate, and the solvent was evaporated under reduced pressure. The resulting residue was purified by preparative liquid chromatography (water:acetonitrile=1:1, 0.05% TFA) to obtain 2-[2-(2-benzyloxyethoxy)ethoxy]-1-[2-(2-benzyloxyethoxy)ethoxymethyl]ethanol (129 mg, yield: 23%) as a colorless oil.

Step B

2-[2-(2-Hydroxyethoxy)ethoxy]-1-[2-(2-hydroxyethoxy)ethoxymethyl]ethyl carbonate (S)-2-oxo-3-[1-oxo-3-(2-trifluoromethylphenyl)-1,2-dihydroisoquinolin-7-yl]oxazolidin-5-ylmethyl ester The title compound was synthesized by a method similar to that of Example 4-45 using 2-[2-(2-benzyloxyethoxy)ethoxy]-1-[2-(2-benzyloxyethoxy)ethoxymethyl]ethanol obtained in Step A instead of hexaethylene glycol monobenzyl ether.

$^1$H-NMR (DMSO-d$_6$) δ: 3.33-3.60 (20H, m), 3.90-4.01 (1H, m), 4.18-4.63 (5H, m), 4.81-4.93 (1H, m), 6.48 (1H, s), (5H, m), 8.05 (1H, dd, J=8.7, 2.5 Hz), 8.22 (1H, d, J=2.5 Hz), 11.61 (1H, s)

ESI (LC-MS positive mode) m/z 699 (M+H).

Example 4-51

2-[2-(2-Hydroxyethoxy)ethoxy]-1-{2-[2-(2-hydroxyethoxy)ethoxy]-1-[2-(2-hydroxyethoxy)ethoxymethyl]ethoxymethyl}ethyl carbonate (S)-2-oxo-3-[1-oxo-3-(2-trifluoromethylphenyl)-1,2-dihydroisoquinolin-7-yl]oxazolidin-5-ylmethyl ester Another name: 1-[2-(2-hydroxyethoxy)ethoxy]-3-{1,3-bis[2-(2-hydroxyethoxy)ethoxy]prop-2-yloxy}prop-2-yl carbonate (S)-2-oxo-3-[1-oxo-3-(2-trifluoromethylphenyl)-1,2-dihydroisoquinolin-7-yl]oxazolidin-5-ylmethyl ester

[Formula 288]

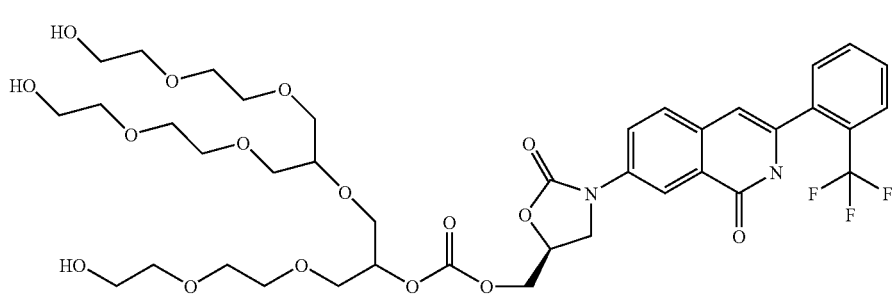

Step A

1-[2-(2-Benzyloxyethoxy)ethoxy]-3-{1,3-bis[2-(2-benzyloxyethoxy)ethoxy]prop-2-yloxy}propan-2-ol

[Formula 289]

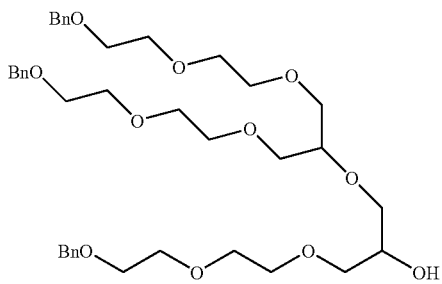

The title compound (52 mg, 9%) as a colorless oil was obtained as a by-product of Step A of Example 4-50.

Step B

1-[2-(2-Hydroxyethoxy)ethoxy]-3-{1,3-bis[2-(2-hydroxyethoxy)ethoxy]prop-2-yloxy}prop-2-yl carbonate (S)-2-oxo-3-[1-oxo-3-(2-trifluoromethylphenyl)-1,2-dihydroisoquinolin-7-yl]oxazolidin-5-ylmethyl ester The title compound was synthesized by a method similar to that of Example 4-45 using the compound obtained in Step A instead of hexaethylene glycol monobenzyl ether.

$^1$H-NMR (DMSO-$d_6$) δ: 3.32-3.73 (35H, m), 3.90-4.00 (1H, m), 4.12-4.65 (4H, m), 4.77-4.87 (1H, m), 4.94-5.12 (1H, m), 6.47 (1H, s), 7.58-7.89 (5H, m), 8.00-8.10 (1H, m), 8.18-8.25 (1H, m)

ESI (LC-MS positive mode) m/z 861 (M+H)

Example 4-52

2-(2-Hydroxyethoxy)-1-(2-hydroxyethoxymethyl)ethyl carbonate (S)-2-oxo-3-[1-oxo-3-(2-trifluoromethylphenyl)-1,2-dihydroisoquinolin-7-yl]oxazolidin-5-ylmethyl ester

[Formula 290]

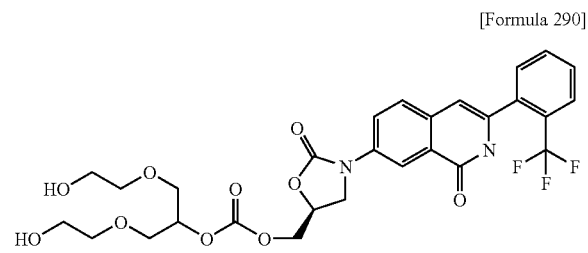

The title compound was synthesized by a method similar to that of Example 4-50 using 2-(2-benzyloxyethoxy)-1-(2-benzyloxyethoxymethyl)ethanol instead of 2-[2-(2-benzyloxyethoxy)ethoxy]-1-[2-(2-benzyloxyethoxy)ethoxymethyl]ethanol.

$^1$H-NMR (DMSO-$d_6$) δ: 3.30-3.64 (12H, m), 3.92-4.01 (1H, m), 4.22-4.68 (5H, m), 4.81-4.92 (1H, m), 4.95-5.06 (1H, m), 6.48 (1H, s), 7.58-7.90 (5H, m), 8.05 (1H, dd, J=8.7, 2.4 Hz), 8.22 (1H, d, J=2.4 Hz), 11.62 (1H, s).

ESI (LC-MS positive mode) m/z 611 (M+H).

Example 4-53

2-{2-[2-(2-Hydroxyethoxy)ethoxy]ethoxy}-1-{2-[2-(2-hydroxyethoxy)ethoxy]ethoxymethyl}ethyl carbonate (S)-2-oxo-3-[1-oxo-3-(2-trifluoromethylphenyl)-1,2-dihydroisoquinolin-7-yl]oxazolidin-5-ylmethyl ester

[Formula 291]

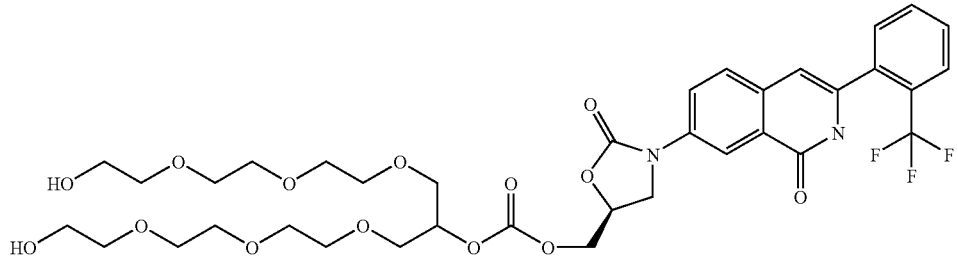

The title compound was synthesized by a method similar to that of Example 4-50 using 2-{2-[2-(2-hydroxyethoxy)ethoxy]ethoxy}-1-{2-[2-(2-hydroxyethoxy)ethoxy]ethoxymethyl}ethanol instead of 2-[2-(2-benzyloxyethoxy)ethoxy]-1-[2-(2-benzyloxyethoxy)ethoxymethyl]ethanol.

$^1$H-NMR (DMSO-$d_6$) δ: 3.30-3.59 (28H, m), 3.90-4.02 (1H, m), 4.18-4.71 (5H, m), 4.81-4.92 (1H, m), 4.95-5.06 (1H, m), 6.47 (1H, s), 7.58-7.89 (5H, m), 8.05 (1H, dd, J=8.7, 2.4 Hz), 8.21 (1H, d, J=2.4 Hz).

ESI (LC-MS positive mode) m/z 787 (M+H).

Example 4-54

2-{2-[2-(2-{2-[2-(2-Hydroxyethoxy)ethoxy]ethoxy}ethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester

[Formula 292]

The title compound was synthesized by a method similar to that of Example 4-45 using heptaethylene glycol monobenzyl ether instead of hexaethylene glycol monobenzyl ether. However, heptaethylene glycol monobenzyl ether was synthesized by a method similar to that of Step A of Example 4-48 using heptaethylene glycol instead of decaethylene glycol.

$^1$H-NMR (CDCl$_3$) δ: 3.57-3.73 (28H, m), 4.04-4.12 (1H, m), 4.25-4.34 (1H, m), 4.38-4.51 (2H, m), 4.93-5.01 (1H, m), 7.57-7.69 (4H, m), 7.82 (1H, d, J=7.1 Hz), 7.95 (1H, s), 8.59 (1H, d, J=8.9 Hz)

ESI (LC-MS positive mode) m/z 757 (M+H)

Example 4-55

2-(2-{2-[2-(2-{2-[2-(2-Hydroxyethoxy)ethoxy]ethoxy}ethoxy)ethoxy]ethoxy}ethoxy)-ethyl carbonate (S)-2-oxo-3-[1-oxo-3-(2-trifluoromethylphenyl)-1,2-dihydroisoquinolin-7-yl]oxazolidin-5-ylmethyl ester

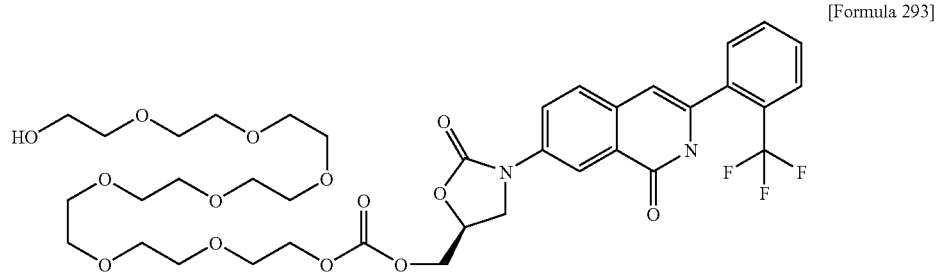

[Formula 293]

The title compound was synthesized by a method similar to that of Example 4-45 using octaethylene glycol monobenzyl ether instead of hexaethylene glycol monobenzyl ether. However, octaethylene glycol monobenzyl ether was synthesized by a method similar to that of Step A of Example 4-48 using octaethylene glycol instead of decaethylene glycol.

$^1$H-NMR (CDCl$_3$) δ: 3.58-3.81 (32H, m), 4.07 (1H, dd, J=6.6, 9.1 Hz), 4.25-4.34 (1H, m), 4.41 (1H, dd, J=4.6, 11.9 Hz), 4.49 (1H, dd, J=4.4, 11.9 Hz), 4.94-5.02 (1H, m), 6.57 (1H, s), 7.56-7.72 (4H, m), 7.83 (1H, d, J=7.4 Hz), 7.95 (1H, d, J=2.3 Hz), 8.58 (1H, dd, J=2.3, 8.9 Hz)

ESI (LC-MS positive mode) m/z 801 (M+H)

Example 4-56

2-[2-(2-{2-[2-(2-{2-[2-(2-Hydroxyethoxy)ethoxy]ethoxy}ethoxy)ethoxy]ethoxy}ethoxy)-ethoxy]ethyl carbonate (S)-2-oxo-3-[1-oxo-3-(2-trifluoromethylphenyl)-1,2-dihydroisoquinolin-7-yl]oxazolidin-5-ylmethyl ester

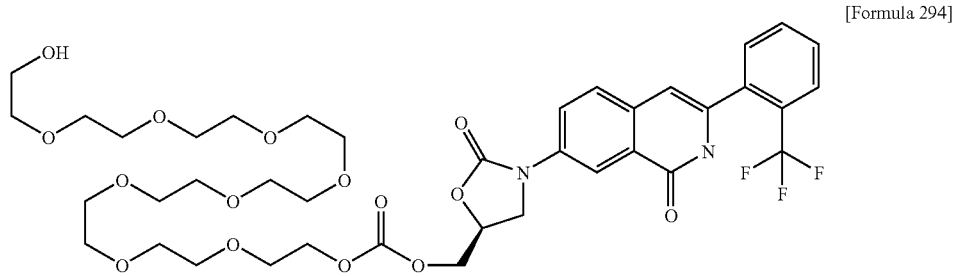

[Formula 294]

The title compound was synthesized by a method similar to that of Example 4-45 using nonaethylene glycol monobenzyl ether instead of hexaethylene glycol monobenzyl ether. However, nonaethylene glycol monobenzyl ether was synthesized by a method similar to that of Step A of Example 4-48 using nonaethylene glycol instead of decaethylene glycol.

$^1$H-NMR (CDCl$_3$) δ: 3.59-3.72 (36H, m), 4.07 (1H, dd, J=6.4, 8.9 Hz), 4.25-4.34 (1H, m), 4.41 (1H, dd, J=4.6, 12.0 Hz), 4.48 (1H, dd, J=3.8, 12.0 Hz), 4.94-5.02 (1H, m), 6.55 (1H, s), 7.55-7.71 (4H, m), 7.82 (1H, d, J=7.6 Hz), 7.95 (1H, s), 8.59 (1H, dd, J=2.3, 8.7 Hz), 8.89 (1H, brs)

ESI (LC-MS positive mode) m/z 845 (M+H)

Example 4-57

(S)-2-Oxo-3-[1-oxo-3-(2-trifluoromethylphenyl)-1,2-dihydroisoquinolin-7-yl]-oxazolidin-5-ylmethyl(2-{2-[2-(2-{2-[2-(2-{2-[2-(2-methoxyethoxy)ethoxy]ethoxy}ethoxy)ethoxy]ethoxy}ethoxy)-ethoxy]ethoxy}ethoxy)acetate

[Formula 295]

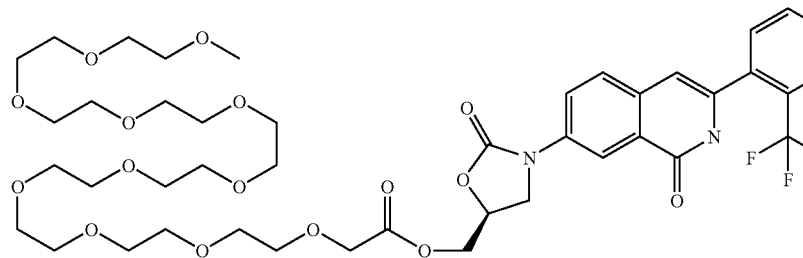

The title compound was synthesized by a condensation method similar to that of Step A of Example 3-1 using (2-{2-[2-(2-{2-[2-(2-{2-[2-(2-methoxy-ethoxy)ethoxy]ethoxy}ethoxy)ethoxy]ethoxy}ethoxy)ethoxy]-ethoxy}ethoxy)acetic acid instead of Boc-Sar-OH and 7-((S)-5-hydroxymethyl-2-oxooxazolidin-3-yl)-3-(2-trifluoromethylphenyl)-2H-isoquinolin-1-one obtained in Step B of Example 1-13 instead of 7-((R)-5-hydroxymethyl-2-oxooxazolidin-3-yl)-3-(2-trifluoromethylphenyl)-2H-isoquinolin-1-one obtained in Step B of Example 1-14. However, (2-{2-[2-(2-{2-[2-(2-{2-[2-(2-methoxy-ethoxy)ethoxy]ethoxy}ethoxy)ethoxy]ethoxy}ethoxy)ethoxy]-ethoxy}ethoxy)acetic acid was synthesized by a method similar to that of Step A of Example 4-39 using decaethylene glycol monomethyl ether instead of pentaethylene glycol monobenzyl ether.

$^1$H-NMR (CDCl$_3$) δ: 3.37 (3H, s), 3.53-3.73 (40H, m), 4.02 (1H, dd, J=6.3, 9.2 Hz), 4.18-4.34 (3H, m), 4.42 (1H, dd, J=4.8, 12.2 Hz), 4.51 (1H, dd, J=3.7, 12.2 Hz), 4.95-5.04 (1H, m), 6.52 (1H, s), 7.58-7.72 (4H, m), 7.82 (1H, d, J=8.1 Hz), 7.95 (1H, d, J=2.3 Hz), 8.53 (1H, dd, J=2.3, 8.9 Hz), 9.28 (1H, brs)

FAB-MS (positive mode) m/z 939 (M+Na).

Test Example 1

Measurement of Cell Growth Inhibitory Activity

Several representative examples of the compound group of the present invention were measured in terms of cell growth inhibitory activity.

Cancer cell growth inhibitory activity was measured using Cell Counting Kit-8 manufactured by Dojindo Laboratories. The human colon cancer cell line HCT116 obtained from American Type Culture Collection (Virginia, U.S.A) was inoculated in a 96-well culture plate at a concentration of 2,000 cells/well. Thereafter, a certain concentration of compound was added thereto, and the obtained mixture was then cultured at 37° C. in 5% CO$_2$, 95% air for 4 days. On the 4$^{th}$ day of the culture, a Cell Counting Kit-8 solution was added to the culture product, and absorbance (measurement wavelength: 450 nm; reference wavelength: 615 nm) was measured in accordance with protocols included with the kit. Thereafter, 50% growth inhibitory concentration (IC50) was calculated.

The results are shown in Table 6.

TABLE 6

| Compound No. | Cell growth inhibitory activity (HCT116) IC50 (μM) |
|---|---|
| 9 | 0.53 |
| 11 | 0.45 |

TABLE 6-continued

| Compound No. | Cell growth inhibitory activity (HCT116) IC50 (μM) |
|---|---|
| 15 | 0.11 |
| 14 | 0.30 |
| 35 | 0.96 |
| 36 | 0.31 |
| 29 | 0.091 |
| 32 | 0.53 |
| 33 | 0.29 |
| 27 | 0.021 |
| 8 | 0.20 |

Test Example 2

Measurement of Antitumor Effect

A representative example of the compound group of the present invention was measured in terms of antitumor effect.

Such antitumor effect was examined, using a tumor-bearing mouse produced by transplanting the human colon cancer cell line HCT116 obtained from American Type Culture Collection (Virginia, U.S.A) into the inguinal subcutis of a BALB/c nude mouse purchased from Charles River Laboratories Japan, Inc. The purchased nude mouse was quarantined for 1 week. Thereafter, approximately 5×10$^6$ HCT116 cells were transplanted subcutaneously. When the size of a tumor thereof became 200 mm$^3$, the mouse was subjected to the present experiment.

Each compound was suspended in a solution to be administered, and 0.2 ml of the solution was orally administered. Such administration was carried out twice in total, that is, on the initiation date of administration and 7 days after the first administration. The antitumor effect was calculated as a tumor growth inhibition by comparing the agent-treated group with a control group in terms of tumor growth, on 14 days after the initiation date of administration.

Tumor growth inhibition (TGI)=(1−the tumor growth amount of agent-treated group/the tumor growth amount of control group)×100(%)

The results are shown in Table 7.

TABLE 7

| Compound No. | Dose (mg/kg) | Antitumor effect TGI (%) obtained 14 days after administration |
|---|---|---|
| 14 | 300 | 113 |

Test Example 3

Measurement of Solubility

Several representative examples of the compound group of the present invention were measured in terms of solubility.

Measurement was carried out by preparing a four-point calibration curve (4,000 μM, 1,000 μM, 250 μM, and 31.3 μM) according to the internal standard method. A sample solution (100% DMSO) was freeze-dried, and each solution was then added thereto. The obtained mixture was stirred for 2 hours. Thereafter, a solution in which the sample had been dissolved was filtrated, and the filtrate was then analyzed with an analyzer. As an analysis method, the filtrate was measured by HPLC (HPLC). As dissolving solutions, a saline solution or a 50 mM sodium citrate-HCl buffer (pH 4.0) solution were used. The results are shown in Table 8.

TABLE 8

| Compound No. | Solubility |
|---|---|
| B20 | >2 mM* |
| B9 | >2 mM* |
| C6 | >2 mM |
| C39 | >2 mM |
| C45 | >2 mM |

*solubility in 50 mM sodium citrate-HCl buffer (pH 4.0) solution

The invention claimed is:

1. A compound represented by the following formula (1):

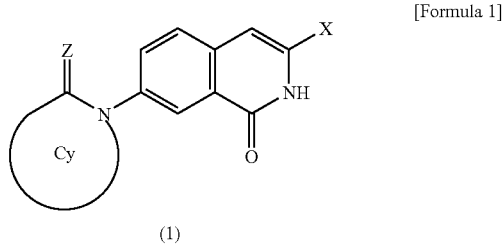

[Formula 1]

(1)

wherein X represents an aryl group or heteroaryl group, wherein the aryl group or heteroaryl group may be substituted with one or more substituents selected from Group A;
wherein Group A consists of a $C_{1-8}$ alkyl group (wherein the alkyl group may be substituted with one or more substituents selected from a halogen atom, an aryl group, a heteroaryl group, —$OR^{11}$, and —$NR^{12}R^{13}$), a $C_{2-7}$ alkenyl group (wherein the $C_{2-7}$ alkenyl group may be substituted with one or more substituents selected from a halogen atom, a $C_{1-8}$ alkyl group, an aryl $C_{1-6}$ alkyl group, an aryl group, and a heteroaryl group), a $C_{2-7}$ alkynyl group (wherein the $C_{2-7}$ alkynyl group may be substituted with one or more substituents selected from a halogen atom, a $C_{1-8}$ alkyl group, an aryl $C_{1-6}$ alkyl group, an aryl group, and a heteroaryl group), a halogen atom, a hydroxyl group, an aryl group, a heteroaryl group, a cyano group, an amino group (wherein the nitrogen atom of the amino group may be substituted with one or two substituents selected from a $C_{1-8}$ alkyl group, which may be substituted with —$OR^{11}$ or —$NR^{12}R^{13}$, an aryl group, an aryl $C_{1-6}$ alkyl group, and a heteroaryl group), —$S(O)_{n1}R^{14}$ (wherein n1 represents an integer from 0 to 2), a $C_{1-6}$ alkoxy group (wherein the alkoxy group may be substituted with one or more groups selected from an aryl group, a heteroaryl group, —$OR^{11}$, —$NR^{12}R^{13}$, and a halogen atom), a 4- to 7-membered heterocyclyl group (wherein the heterocyclyl group may be substituted with one or more substituents selected from a $C_{1-8}$ alkyl group, an aryl group, an aryl $C_{1-6}$ alkyl group, and a heteroaryl group), an aryloxy group, a heteroaryloxy group, and a $C_{1-6}$ alkylenedioxy group;
wherein each of $R^{11}$, $R^{12}$, $R^{13}$, and $R^{14}$ is independently selected from a hydrogen atom, a $C_{1-8}$ alkyl group (wherein the alkyl group may be substituted with one or more substituents selected from a hydroxyl group, a $C_{1-6}$ alkoxy group, an aryl $C_{1-6}$ alkoxy group, an aryl group, and a heteroaryl group), an aryl group, and a heteroaryl group; or $R^{12}$ and $R^{13}$, together with nitrogen to which they bind, may form a 4- to 7-membered heterocyclic ring containing at least one nitrogen atom;
Z represents O, S, or NRa, wherein Ra represents a hydrogen atom, a $C_{1-8}$ alkyl group, an aryl $C_{1-6}$ alkyl group, an aryl group, or a heteroaryl group;
Cy represents a 4- to 7-membered monocyclic heterocyclic ring or a 8- to 10-membered condensed heterocyclic ring, wherein the carbon atom(s) of the heterocyclic ring may be substituted with one or more substituents selected from Group Q1, and when the heterocyclic ring contains —NH—, the nitrogen atom may be substituted with a substituent selected from Group Q2;
wherein Group Q1 consists of a $C_{1-8}$ alkyl group, which may be substituted with one or more substituents selected from Group B, a $C_{2-7}$ alkenyl group, which may be substituted with one or more substituents selected from Group B, a hydroxyl group, a $C_{1-6}$ alkoxy group (wherein the alkoxy group may be substituted with one or more substituents selected from a halogen atom, a hydroxyl group, a $C_{1-6}$ alkoxy group, an amino group, a $C_{1-6}$ alkylamino group, a di($C_{1-6}$ alkyl)amino group, an aryl group, and a heteroaryl group), a $C_{1-6}$ alkylcarbonyl group, —$CONR^{21}R^{22}$, a carboxy group, a $C_{1-6}$ alkoxycarbonyl group, which may be substituted with an aryl group, an aryloxy group, a heteroaryloxy group, an amino group, a $C_{1-6}$ alkylamino group, a di($C_{1-6}$ alkyl) amino group, a 4- to 7-membered heterocyclyl group (wherein the heterocyclyl group may be substituted with one or two substituents selected from a $C_{1-8}$ alkyl group, an aryl group, an aryl $C_{1-6}$ alkyl group, and a heteroaryl group), an oxo group, and a thioxo group;

wherein each of $R^{21}$ and $R^{22}$ is independently selected from a hydrogen atom, a $C_{1-8}$ alkyl group (wherein the alkyl group may be substituted with one or more substituents selected from a halogen atom, a hydroxyl group, a $C_{1-6}$ alkoxy group, an aryl group, an amino group, a $C_{1-6}$ alkylamino group, and a di($C_{1-6}$ alkyl)amino group), an aryl group, and a heteroaryl group; or $R^{21}$ and $R^{22}$, together with a nitrogen atom to which they bind, may form a 4- to 7-membered heterocyclyl group containing at least one nitrogen atom (wherein the heterocyclyl group may be substituted with one or more substituents selected from a hydroxyl group, a $C_{1-8}$ alkyl group (wherein the alkyl group may be substituted with one or more substituents selected from a hydroxyl group, a $C_{1-8}$ alkoxy group, and an aryl group), an aryl group, and a heteroaryl group);

wherein Group Q2 consists of a $C_{1-8}$ alkyl group (wherein the alkyl group may be substituted with one or more substituents selected from a halogen atom, a hydroxyl group, a $C_{1-6}$ alkoxy group, an amino group, a $C_{1-6}$ alkylamino group, a di($C_{1-6}$ alkyl)amino group, an aryl group, and a heteroaryl group), a $C_{1-6}$ alkoxycarbonyl group, an aryl $C_{1-6}$ alkoxycarbonyl group, an aryl group, and a heteroaryl group;

wherein Group B consists of a halogen atom, an aryl group, a heteroaryl group, an oxo group, a $C_{1-6}$ alkylcarbonyl group, a $C_{1-6}$ alkylaminocarbonyl group, a di($C_{1-6}$ alkyl) aminocarbonyl group, a $C_{1-6}$ alkoxycarbonyl group, an azido group, —$OR^{31}$, —$NR^{32}R^{33}$, and —$S(O)_{n2}R^{39}$ (wherein n2 represents an integer from 0 to 2);

wherein $R^{31}$ is selected from a hydrogen atom, —PO($OR^{41}$)$OR^{42}$, a $C_{1-8}$ alkyl group (wherein the alkyl group may be substituted with one or more substituents selected from a halogen atom, a hydroxyl group, a $C_{1-6}$ alkoxy group, which may be substituted with a $C_{1-6}$ alkoxy group, an aryl group, and —$NR^{34}R^{35}$), an aryl group, a heteroaryl group, a $C_{1-6}$ alkylcarbonyl group, a $C_{2-7}$ alkenylcarbonyl group, a $C_{3-8}$ cycloalkylcarbonyl group (wherein the $C_{1-6}$ alkylcarbonyl group, $C_{2-7}$ alkenylcarbonyl group, and $C_{3-8}$ cycloalkylcarbonyl group may be substituted with one or more substituents selected from a hydroxyl group, —$NR^{37}R^{38}$, an aryl group, which may be substituted with a hydroxyl group, a heteroaryl group, a mercapto group, a $C_{1-6}$ alkylthio group, a guanidyl group, a carboxy group, a $C_{1-6}$ alkoxycarbonyl group, a $C_{1-6}$ alkylcarbonyloxy group, an aryl $C_{1-6}$ alkoxy group, an aminocarbonyl group, a $C_{1-6}$ alkylaminocarbonyl group, and a di($C_{1-6}$ alkyl)aminocarbonyl group (wherein the $C_{1-6}$ alkylaminocarbonyl group and di ($C_{1-6}$ alkyl)aminocarbonyl group may be substituted with one or more substituents selected from an amino group, a $C_{1-6}$ alkylamino group, and a di($C_{1-6}$ alkyl)amino group), and —(OCHR$^{74}$CH$_2$)$_l$—OR$^{73}$ (wherein l represents an integer from 1 to 20)), an arylcarbonyl group, a heteroarylcarbonyl group, a 4- to 12-membered heterocyclyl carbonyl group (wherein the arylcarbonyl group, heteroarylcarbonyl group, and heterocyclyl carbonyl group may be substituted with one or more substituents selected from a hydroxyl group, a carboxy group, a $C_{1-6}$ alkyl group, a $C_{1-6}$ alkoxycarbonyl group, a $C_{1-6}$ alkylcarbonyl group (wherein the $C_{1-6}$ alkoxycarbonyl group and $C_{1-6}$ alkylcarbonyl group may be substituted with one or more substituents selected from a hydroxyl group, —$NR^{84}R^{85}$, and a carboxy group)), a $C_{1-6}$ alkoxycarbonyl group (wherein the $C_{1-6}$ alkoxycarbonyl group may be substituted with one or more 4- to 12-membered heterocyclyl groups), —$CONR^{71}R^{72}$, —$CO(OCHR^{76}CH_2)_k$—$OR^{75}$ (wherein k represents an integer from 1 to 20), and —$S(O)_{n3}R^{81}$ (wherein n3 represents an integer of 1 or 2));

each of $R^{32}$, $R^{33}$, $R^{34}$, $R^{35}$, $R^{37}$, $R^{38}$, $R^{71}$, $R^{72}$, $R^{84}$, and $R^{85}$ is independently selected from a hydrogen atom, a $C_{1-8}$ alkyl group (wherein the alkyl group may be substituted with one or more substituents selected from a halogen atom, a hydroxyl group, a $C_{1-6}$ alkoxy group, —(OCH$_2$CH$_2$)$_m$—OH (wherein m represents an integer from 1 to 20), a $C_{1-6}$ alkoxycarbonyl group, an aryl group, an amino group, a $C_{1-6}$ alkylamino group, and a di($C_{1-6}$ alkyl)amino group), —$S(O)_{n4}R^{83}$ (wherein n4 represents an integer of 1 or 2), a $C_{1-6}$ alkylcarbonyl group (wherein the $C_{1-6}$ alkylcarbonyl group may be substituted with one or more substituents selected from an amino group, a $C_{1-6}$ alkylamino group, a di($C_{1-6}$ alkyl)amino group, an aminocarbonyl group, an aryl group, which may be substituted with a hydroxyl group, a heteroaryl group, a hydroxyl group, a mercapto group, a $C_{1-6}$ alkylthio group, a guanidyl group, and a carboxy group), a $C_{1-6}$ alkylaminocarbonyl group, a $C_{1-6}$ alkoxycarbonyl group, a 4- to 7-membered heterocyclyl carbonyl group, an aryl group, and a heteroaryl group; or $R^{32}$ and $R^{33}$, $R^{34}$ and $R^{35}$, $R^{37}$ and $R^{38}$, and $R^{84}$ and $R^{85}$, together with a nitrogen atom to which they bind, may form a 4- to 7-membered heterocyclyl group containing at least one nitrogen atom (wherein the heterocyclyl group may be substituted with one or more substituents selected from a hydroxyl group, a $C_{1-8}$ alkyl group (wherein the alkyl group may be substituted with one or more substituents selected from a hydroxyl group, a $C_{1-8}$ alkoxy group, and an aryl group), a $C_{1-8}$ alkoxy group (wherein the alkoxy group may be substituted with one or more substituents selected from a hydroxyl group, a $C_{1-8}$ alkoxy group, and an aryl group), an aryl group, and a heteroaryl group);

each of $R^{39}$ and $R^{83}$ is independently selected from a hydrogen atom, a $C_{1-8}$ alkyl group (wherein the alkyl group may be substituted with one or more substituents selected from a hydroxyl group, a $C_{1-6}$ alkoxy group, an aryl $C_{1-6}$ alkoxy group, an aryl group, and a heteroaryl group), a $C_{2-8}$ alkenyl group, a $C_{3-6}$ cycloalkyl group, an aryl group, and a heteroaryl group;

each of $R^{41}$ and $R^{42}$ is independently selected from a hydrogen atom, an aryl $C_{1-6}$ alkyl group, and a $C_{1-8}$ alkyl group;

each of $R^{73}$ and $R^{75}$ is independently selected from a hydrogen atom, a $C_{1-6}$ alkyl group, which may be substituted with one or more hydroxyl groups, and an aryl $C_{1-6}$alkyl group;

each occurrence of $R^{74}$ and $R^{76}$ is independently selected from a hydrogen atom, a $C_{1-6}$ alkyl group, a $C_{1-6}$ alkyl group, which is substituted with a hydroxyl group(s), and —CH$_2$(OCH$_2$CH$_2$)$_i$—OR$^{80}$ (wherein i represents an integer from 1 to 20);

$R^{80}$ is selected from a hydrogen atom, an aryl $C_{1-6}$ alkyl group, and a $C_{1-6}$ alkyl group, which may be substituted with one or more hydroxyl groups; and $R^{81}$ represents a $C_{1-6}$ alkyl group, or a pharmaceutically acceptable salt thereof.

2. The compound or pharmaceutically acceptable salt thereof according to claim 1, wherein the carbon atom(s) of Cy are substituted with one or two groups selected from a hydroxyl group, and the groups —C(=O)—OR⁵⁰, —CR⁵¹R⁵²—OR⁵³, —CR^zR^qCR⁵¹R⁵²—OR⁵³, —C(=O)—NR⁵⁴R⁵⁵, and —CR⁵¹R⁵²—NR⁵⁶R⁵⁷;

R⁵⁰ represents a hydrogen atom or a C₁₋₆ alkyl group (wherein the alkyl group may be substituted with a hydroxyl group or a C₁₋₆ alkoxy group);

each of R⁵¹ and R⁵² is independently selected from a hydrogen atom, a C₁₋₃ alkyl group (wherein the alkyl group may be substituted with one or more substituents selected from a hydroxyl group and an amino group), and a C₂₋₃ alkenyl group;

each of R^z and R^q is independently selected from a hydrogen atom and a C₁₋₃ alkyl group;

R⁵³ represents a hydrogen atom, a C₁₋₆ alkyl group (wherein the alkyl group may be substituted with 1 to 3 substituents selected from an aryl group, a hydroxyl group, a C₁₋₆ alkoxy group, a C₁₋₆ alkoxy C₁₋₆ alkoxy group, and —NR^xR^y), a C₁₋₆ alkylcarbonyl group (wherein the alkylcarbonyl group may be substituted with 1 to 3 substituents selected from a hydroxyl group, a C₁₋₃ alkoxy group, an aryl group, —NR⁶¹R⁶², a carboxy group, —CONR⁶³R⁶⁴, and —(OCHR⁷⁴CH₂)ₗ—OR⁷³ (wherein R⁷³, R⁷⁴, and l are the same as those defined in claim 1)), an arylcarbonyl group or a 4- to 7-membered heterocyclyl carbonyl group (wherein the arylcarbonyl group and heterocyclyl carbonyl group may be substituted with one or more substituents selected from a carboxy group, a C₁₋₆ alkoxycarbonyl group, and a C₁₋₆ alkylcarbonyl group (wherein the C₁₋₆ alkoxycarbonyl group and C₁₋₆ alkylcarbonyl group may be substituted with one or more substituents selected from —NR⁶¹R⁶², a carboxy group, and a hydroxyl group)), or —CO(OCHR⁷⁶CH₂)ₖ—OR⁷⁵ (wherein R⁷⁵, R⁷⁶, and k are the same as those defined in claim 1), each of R⁵⁴ and R⁵⁵ is independently selected from a hydrogen atom and a C₁₋₆ alkyl group (wherein the alkyl group may be substituted with a hydroxyl group or an amino group); or R⁵⁴ and R⁵⁵, together with a nitrogen atom to which they bind, may form a 4- to 7-membered heterocyclic ring (wherein the heterocyclic ring may be substituted with 1 to 3 substituents selected from a hydroxyl group and a hydroxy C₁₋₆ alkyl group);

each of R⁵⁶ and R⁵⁷ is independently selected from a hydrogen atom, a C₁₋₆alkyl group (wherein the alkyl group may be substituted with a hydroxyl group or an amino group), and a C₁₋₆ alkylsulfonyl group (wherein the alkylsulfonyl group may be substituted with a hydroxyl group or an amino group); or R⁵⁶ and R⁵⁷, together with a nitrogen atom to which they bind, may form a 4- to 7-membered heterocyclic ring (wherein the heterocyclic ring may be substituted with 1 to 3 substituents selected from a hydroxyl group and a hydroxy C₁₋₆ alkyl group);

each of R⁶¹ and R⁶² is independently selected from a hydrogen atom, a C₁₋₆ alkyl group, and a C₁₋₆ alkylcarbonyl group (wherein the alkylcarbonyl group may be substituted with 1 to 3 substituents selected from a hydroxyl group, a C₁₋₃ alkoxy group, an aryl group, an amino group, a C₁₋₆ alkylamino group, a di(C₁₋₆ alkyl)amino group, and a carboxy group); or R⁶¹ and R⁶², together with a nitrogen atom to which they bind, may form a 4- to 7-membered heterocyclic ring;

each of R^x and R^y is independently selected from a hydrogen atom and a C₁₋₆ alkyl group, and each of R⁶³ and R⁶⁴ is independently selected from a hydrogen atom and a C₁₋₆ alkyl group (wherein the alkyl group may be substituted with a hydroxyl group or an amino group);

or R^x and R^y, or R⁶³ and R⁶⁴, together with a nitrogen atom to which they bind, may form a 4- to 7-membered heterocyclic ring.

3. The compound or pharmaceutically acceptable salt thereof according to claim 1,
wherein Cy represents a heterocyclic ring selected from the following group:

[Formula 2]

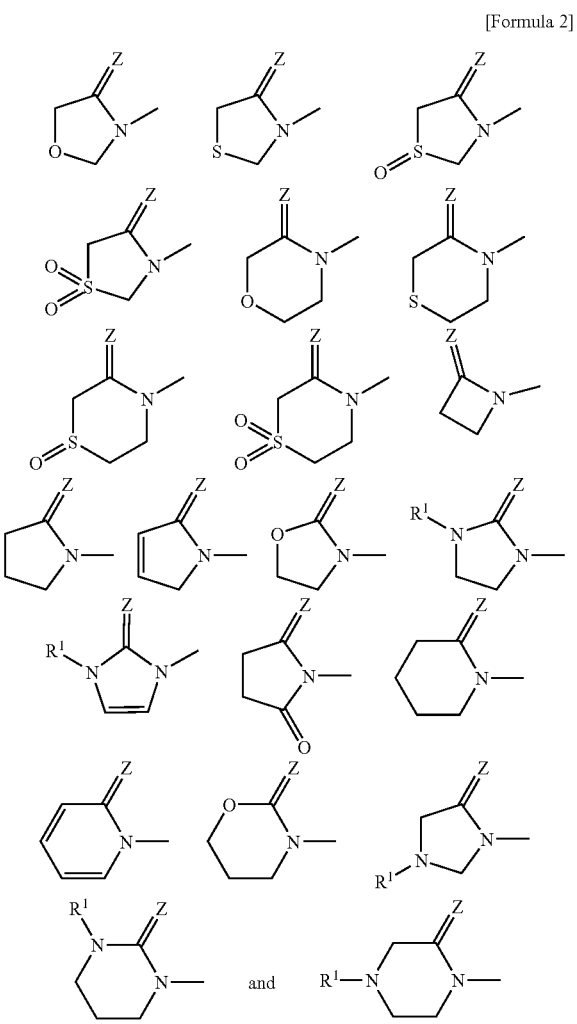

wherein the carbon atom(s) of the heterocyclic ring may be substituted with one or more substituents selected from Group Q1; and R¹ represents a hydrogen atom, a C₁₋₈ alkyl group (wherein the alkyl group may be substituted with one or more substituents selected from a halogen atom, a hydroxyl group, a C₁₋₆ alkoxy group, an amino group, a C₁₋₆ alkylamino group, a di(C₁₋₆ alkyl)amino group, an aryl group, and a heteroaryl group), a C₁₋₆ alkoxycarbonyl group, an aryl C₁₋₆ alkoxycarbonyl group, an aryl group, or a heteroaryl group.

4. The compound or pharmaceutically acceptable salt thereof according to claim 3, wherein Cy represents a heterocyclic ring selected from the following group:

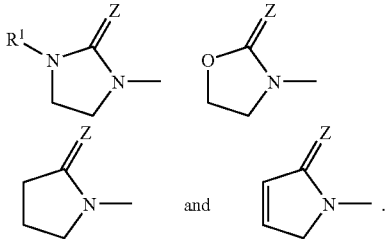

[Formula 3]

5. The compound or pharmaceutically acceptable salt thereof according to claim 1,
wherein X represents an aryl group, wherein the aryl group may be substituted with one or more substituents selected from Group A1;
wherein Group A1 consists of a $C_{1-8}$ alkyl group (wherein the alkyl group may be substituted with one or more substituents selected from a halogen atom and —$NR^{12}R^{13}$), a halogen atom, a hydroxyl group, an aryl group, an amino group (wherein the nitrogen atom of the amino group may be substituted with one or two substituents selected from a $C_{1-8}$ alkyl group and an aryl group), —$SR^{14}$, a $C_{1-6}$ alkoxy group (wherein the alkoxy group may be substituted with one or more substituents selected from —$OR^{11}$ and a halogen atom), and a 4- to 7-membered heterocyclyl group (wherein the heterocyclyl group may be substituted with one or two substituents selected from $C_{1-8}$ alkyl groups);
wherein each of $R^{11}$, $R^{12}$, $R^{13}$, and $R^{14}$ is independently selected from a hydrogen atom, a $C_{1-8}$ alkyl group, and an aryl group; or $R^{12}$ and $R^{13}$, together with nitrogen to which they bind, may form a 4- to 7-membered heterocyclic ring containing at least one nitrogen atom.

6. The compound or pharmaceutically acceptable salt thereof according to claim 1, wherein Z represents O.

7. The compound or pharmaceutically acceptable salt thereof according to claim 1,
wherein the substituent(s) on the ring carbon atom(s) of Cy are selected from a hydroxyl group, a $C_{1-8}$ alkyl group (wherein the alkyl group may be substituted with one or more substituents selected from a hydroxyl group, a $C_{1-6}$ alkylamino group, a di($C_{1-6}$ alkyl)amino group, a 4- to 7-membered heterocyclyl group containing at least one nitrogen atom (wherein the heterocyclyl group may be substituted with a hydroxyl group, or a $C_{1-6}$ alkyl group, which may be substituted with a hydroxyl group), a $C_{1-6}$ alkylcarbonyloxy group (wherein the $C_{1-6}$ alkylcarbonyloxy group may be substituted with one or two substituents selected from a hydroxyl group and —(OCH$_2$CH$_2$)$_l$—OR$^{73}$ (wherein R$^{73}$ and l are the same as those defined in claim 1)), —OCO(OCHR$^{76}$CH$_2$)$_k$—OR$^{75}$ (wherein R$^{75}$, R$^{76}$, and k are the same as those defined in claim 1)), and —CONR$^{91}$R$^{92}$;
wherein each of $R^{91}$ and $R^{92}$ is selected from a hydrogen atom and a $C_{1-6}$ alkyl group; or $R^{91}$ and $R^{92}$, together with nitrogen to which they bind, may form a 4- to 7-membered heterocyclic ring containing at least one nitrogen atom (wherein the heterocyclic ring may be substituted with a hydroxyl group).

8. The compound or pharmaceutically acceptable salt thereof according to claim 1, wherein the substituent(s) on the ring carbon atom(s) of Cy are selected from a hydroxyl group, a hydroxymethyl group, and a 1-hydroxy-1-methylethyl group.

9. The compound or pharmaceutically acceptable salt thereof according to claim 1, wherein the substituent(s) on the ring carbon atom(s) of Cy are —CH$_2$—OCOCH$_2$—(OCH$_2$CH$_2$)$_l$—OR$^{73}$ (wherein R$^{73}$ and l are the same as those defined in claim 1), a propionyloxymethyl group, which is substituted with one or two hydroxyl groups, or —CH$_2$—OCO(OCHR$^{76}$CH$_2$)$_k$—OR$^{75}$ (wherein R$^{75}$, R$^{76}$, and k are the same as those defined in claim 1).

10. The compound or pharmaceutically acceptable salt thereof according to claim 1, wherein a substituent on the ring nitrogen atom of Cy is selected from $C_{1-8}$ alkyl groups (wherein the alkyl group may be substituted with a hydroxyl group).

11. The compound or pharmaceutically acceptable salt thereof according to claim 1, wherein X represents an aryl group, wherein the aryl group may be substituted with one or more substituents selected from a halogen atom, a $C_{1-6}$ alkyl group, a halo $C_{1-6}$ alkyl group, a $C_{1-6}$ alkoxy group, a halo $C_{1-6}$ alkoxy group, an aryl group, and a 4- to 7-membered heterocyclyl group.

12. The compound or pharmaceutically acceptable salt thereof according to claim 1, wherein X represents an aryl group, wherein the aryl group may be substituted with an ethyl group, a trifluoromethyl group, a trifluoromethoxy group, an ethoxy group, a propoxy group, a phenyl group, or a morpholinyl group.

13. The compound or pharmaceutically acceptable salt thereof according to claim 1, which compound is selected from:
7-(2-Oxoazetidin-1-yl)-3-(2-trifluoromethylphenyl)-2H-isoquinolin-1-one,
7-(2-Oxopiperidin-1-yl)-3-(2-trifluoromethylphenyl)-2H-isoquinolin-1-one,
7-(2-Oxo-2H-pyridin-1-yl)-3-(2-trifluoromethylphenyl)-2H-isoquinolin-1-one,
7-((R)-4-Hydroxy-2-oxopyrrolidin-1-yl)-3-(2trifluoromethylphenyl)-2H-isoquinolin-1-one,
7-((S)-4-Hydroxy-2-oxopyrrolidin-1-yl)-3-(2-trifluoromethylphenyl)-2H-isoquinolin-1-one,
7-(4-Methoxy-2-oxo-2,5-dihydropyrrol-1-yl)-3-(2-trifluoromethylphenyl)-2H-isoquinolin-1-one,
7-((S)-2-Hydroxymethyl-5-oxopyrrolidin-1-yl)-3-(2-trifluoromethylphenyl)-2H-isoquinolin-1-one,
7-(4-Benzyloxy-2-oxo-2,5-dihydropyrrol-1-yl)-3-(2-trifluoromethylphenyl)-2H-isoquinolin-1-one,
7-[3-(2-Hydroxyethyl)-2-oxoimidazolidin-1-yl]-3-(2-trifluoromethylphenyl)-2H-isoquinolin-1-one,
7-((R)-4-Hydroxymethyl-2-oxazolidin-3-yl)-3-(2-trifluoromethylphenyl)-2H-isoquinolin-1-one,
(R)-2-Oxo-3-[1-oxo-3-(2-trifluoromethylphenyl)-1,2-dihydroisoquinolin-7-yl]oxazolidin-4-ylmethyl benzoate,
7-(5-Chloromethyl-2-oxooxazolidin-3-yl)-3-(2-trifluoromethylphenyl)-2H-isoquinolin-1-one,
7-((S)-5-Hydroxymethyl-2-oxooxazolidin-3-yl)-3-(2-trifluoromethylphenyl)-2H-isoquinolin-1-one,
7-((R)-5-Hydroxymethyl-2-oxooxazolidin-3-yl)-3-(2-trifluoromethylphenyl)-2H-isoquinolin-1-one,
7-(2-Oxopyrrolidin-1-yl)-3-(2-trifluoromethylphenyl)-2H-isoquinolin-1-one,
7-((R)-2-Hydroxymethyl-5-oxopyrrolidin-1-yl)-3-(2trifluoromethylphenyl)-2H-isoquinolin-1-one,
7-(2-Oxooxazolidin-3-yl)-3-(2-trifluoromethylphenyl)-2H-isoquinolin-1-one, 7-(3-Methyl-2-oxo-2,3-dihydroimidazol-1-yl)-3-(2-trifluoromethylphenyl)-2H-isoquinolin-1-one,
7-((R)-5-Hydroxymethyl-2-oxooxazolidin-3-yl)-3-(2-morpholin-4-ylphenyl)-2H-isoquinolin-1-one,
7-((R)-5-Hydroxymethyl-2-oxooxazolidin-3-yl)-3-(2-methoxyphenyl)-2H-isoquinolin-1-one,
7-((R)-5-Hydroxymethyl-2-oxooxazolidin-3-yl)-3-o-tolyl-2H-isoquinolin-1-one,
7-((R)-5-Hydroxymethyl-2-oxooxazolidin-3-yl)-3-(2-trifluoromethoxyphenyl)-2H-isoquinolin-1-one,
3-Biphenyl-2-yl-7-((R)-5-hydroxymethyl-2-oxooxazolidin-3-yl)-2H-isoquinolin-1-one,
3-(2-Ethylphenyl)-7-((R)-5-hydroxymethyl-2-oxooxazolidin-3-yl)-2H-isoquinolin-1-one,
3-(2,6-Dimethoxyphenyl)-7-((R)-5-hydroxymethyl-2-oxooxazolidin-3-yl)-2H-isoquinolin-1-one,
3-(2-Fluorophenyl)-7-((S)-5-hydroxymethyl-2-oxooxazolidin-3-yl)-2H-isoquinolin-1-one,
7-((S)-5-Hydroxymethyl-2-oxooxazolidin-3-yl)-3-(2-trifluoromethoxyphenyl)-2H-isoquinolin-1-one,
7-((S)-5-Hydroxymethyl-2-oxooxazolidin-3-yl)-3-(2-morpholin-4ylphenyl)-2H-isoquinolin-1-one,
7-[5-(2-Hydroxyethyl)-2-oxooxazolidin-3-yl]-3-(2-trifluoromethylphenyl)-2H-isoquinolin-1-one,
7-(5-Azidomethyl-2-oxooxazolidin-3-yl)-3-(2-trifluoromethylphenyl)-2H-isoquinolin-1-one,
7-(5-Aminomethyl-2-oxooxazolidin-3-yl)-3-(2-trifluoromethylphenyl)-2H-isoquinolin-1-one,
N-{2-Oxo-3-[1-oxo-3-(2-trifluoromethylphenyl)-1,2-dihydroisoquinolin-7-yl]oxazolidin-5-ylmethyl}acetamide,
7-(5-Morpholin-4-ylmethyl-2-oxooxazolidin-3-yl)-3-(2-trifluoromethylphenyl)-2H-isoquinolin-1-one,
7-[5-(4-Hydroxypiperidin-1-ylmethyl)-2-oxooxazolidin-3-yl]-3-(2-trifluoromethylphenyl)-2H-isoquinolin-1-one,
7-((R)-4-Benzyloxymethyl-3-methyl-2-oxoimidazolidin-1-yl)-3-(2-trifluoromethylphenyl)-2H-isoquinolin-1-one,
7-((R)-4-Hydroxymethyl-3-methyl-2-oxoimidazolidin-1-yl)-3-(2-trifluoromethylphenyl)-2H-isoquinolin-1-one,
3-(2-Ethylphenyl)-7-((S)-5-hydroxymethyl-2-oxooxazolidin-3-yl)-2H-isoquinolin-1-one,
7-[(S)-5-(2-Hydroxyethyl)-2-oxooxazolidin-3-yl]-3-(2-trifluoromethylphenyl)-2H-isoquinolin-1-one,
7-[(S)-5-((R)-1,2-Dihydroxyethyl)-2-oxooxazolidin-3-yl]-3-(2-trifluoromethylphenyl)-2H-isoquinolin-1-one,
3-{2-[2-(2-Benzyloxyethoxy)ethoxy]phenyl}-7-((R)-5hydroxymethyl-2-oxooxazolidin-3-yl)-2H-isoquinolin-1-one,
3-{2-[2-(2-Hydroxyethoxy)ethoxy]phenyl}-7-((R)-5-hydroxymethyl-2-oxooxazolidin-3-yl)-2H-isoquinolin-1-one,
3-{2-[2-(2-Hydroxyethoxy)ethoxy]phenyl}-7-((S)-5-hydroxymethyl-2-oxooxazolidin-3-yl)-2H-isoquinolin-1-one,
3-(2,6-Bistrifluoromethylphenyl)-7-((R)-5-hydroxymethyl-2-oxooxazolidin-3-yl)-2H-isoquinolin-1-one,
7-[5-(2-Hydroxy-1-hydroxymethylethyl)-2-oxooxazolidin-3-yl]-3-(2-trifluoromethylphenyl)-2H-isoquinolin-1-one,
Ethyl 2-oxo-1-[1-oxo-3-(2-trifluoromethylphenyl)-1,2-dihydroisoquinolin-7-yl]pyrrolidine-3-carboxylate,
7-(3-Hydroxymethyl-2-oxopyrrolidin-1-yl)-3-(2-trifluoromethylphenyl)-2H-isoquinolin-1-one,
7-((R)-5-Hydroxymethyl-2-oxooxazolidin-3-yl)-3-(2-isobutylphenyl)-2H-isoquinolin-1-one,
3-(2-Allylphenyl)-7-((R)-5-hydroxymethyl-2-oxooxazolidin-3-yl)-2H-isoquinolin-1-one,
7-(2-Oxo-[1,3]oxazinan-3-yl)-3-(2-trifluoromethylphenyl)-2H-isoquinolin-1-one,
7-(4-Hydroxy-2-oxo-2,5-dihydropyrrol-1-yl)-3-(2-trifluoromethylphenyl)-2H-isoquinolin-1-one,
1-[1-Oxo-3-(2-trifluoromethylphenyl)-1,2-dihydroisoquinolin-7-yl]pyrrolidine-2,5-dione,
Ethyl 2-oxo-3-[1-oxo-3-(2-trifluoromethylphenyl)-1,2-dihydroisoquinolin-7-yl]oxazolidine-5-carboxylate,
Methyl 2-oxo-3-[1-oxo-3-(2-trifluoromethylphenyl)-1,2-dihydroisoquinolin-7-yl]oxazolidine-5-carboxylate,
7-[5-(1-Hydroxy-1-methylethyl)-2-oxooxazolidin-3-yl]-3-(2-trifluoromethylphenyl)-2H-isoquinolin-1-one,
2-Oxo-3-[1-oxo-3-(2-trifluoromethylphenyl)-1,2-dihydroisoquinolin-7-yl]oxazolidine-5-carboxylic acid,
2-Oxo-3-[1-oxo-3-(2-trifluoromethylphenyl)-1,2-dihydroisoquinolin-7-yl]oxazolidine-5-carboxylic acid amide,
2-Oxo-3-[1-oxo-3-(2-trifluoromethylphenyl)-1,2-dihydroisoquinolin-7-yl]oxazolidine-5-carboxylic acid methylamide,
2-Oxo-3-[1-oxo-3-(2-trifluoromethylphenyl)-1,2-dihydroisoquinolin-7-yl]oxazolidine-5-carboxylic acid dimethylamide,
2-Oxo-3-[1-oxo-3-(2-trifluoromethylphenyl)-1,2-dihydroisoquinolin-7-yl]oxazolidine-5-carboxylic acid (2-hydroxyethyl)amide,
7-[5-(Morpholine-4-carbonyl)-2-oxooxazolidin-3-yl]-3-(2-trifluoromethylphenyl)-2H-isoquinolin-1-one,
7-[5-(4-Hydroxypiperidine-1-carbonyl)-2-oxooxazolidin-3-yl]-3-(2-trifluoromethylphenyl)-2H-isoquinolin-1-one,
7-[(S)-5-(1-Hydroxy-1-methylethyl)-2-oxooxazolidin-3-yl]-3-(2-trifluoromethylphenyl)-2H-isoquinolin-1-one,
7-[(R)-5-(1-Hydroxy-1-methylethyl)-2-oxooxazolidin-3-yl]-3-(2-trifluoromethylphenyl)-2H-isoquinolin-1-one,
(S)-2-Oxo-3-[1-oxo-3-(2-trifluoromethylphenyl)-1,2-dihydroisoquinolin-7-yl]oxazolidine-5-carboxylic acid amide,
(R)-2-Oxo-3-[1-oxo-3-(2-trifluoromethylphenyl)-1,2-dihydroisoquinolin-7-yl]oxazolidine-5-carboxylic acid amide,
7-[(S)-5-(4-Hydroxypiperidine-1-carbonyl)-2-oxooxazolidin-3-yl]-3-(2-trifluoromethylphenyl)-2H-isoquinolin-1-one,
7-[(R)-5-(4-Hydroxypiperidine-1-carbonyl)-2-oxooxazolidin-3-yl]-3-(2-trifluoromethylphenyl)-2H-isoquinolin-1-one,
7-[(R)-5-(2-Methoxyethoxymethyl)-2-oxooxazolidin-3-yl]-3-(2-trifluoromethylphenyl)-2H-isoquinolin-1-one,
7-((R)-5-Methoxymethyl-2-oxooxazolidin-3-yl)-3-(2-trifluoromethylphenyl)-2H-isoquinolin-1-one,
7-{(R)-5-[2-(2-Methoxyethoxy)ethoxymethyl]-2-oxooxazolidin-3-yl}-3-(2-trifluoromethylphenyl)-2H-isoquinolin-1-one,
7-[(R)-5-(2-Morpholin-4-ylethoxymethyl)-2-oxooxazolidin-3-yl]-3-(2-trifluoromethylphenyl)-2H-isoquinolin-1-one,
7-((R)-5-Benzyloxymethyl-2-oxooxazolidin-3-yl)-3-(2-trifluoromethylphenyl)-2H-isoquinolin-1-one,
7-((S)-2-oxo-5-piperidin-1-ylmethyloxazolidin-3-yl)-3-(2-trifluoromethylphenyl)-2H-isoquinolin-1-one,
7-[(S)-5-((S)-2-Hydroxymethylpyrrolidin-1-ylmethyl)-2-oxooxazolidin-3-yl]-3-(2-trifluoromethylphenyl)-2H-isoquinolin-1-one, 7-[(S)-5-((S)-3-Hydroxypiperidin-1-ylmethyl)-2-oxooxazolidin-3-yl]-3-(2-trifluoromethylphenyl)-2H-isoquinolin-1-one, 7-[(S)-5-((R)-3-Hydroxypiperidin-1-ylmethyl)-2-oxooxazolidin-3-yl]-3-(2-trifluoromethylphenyl)-2H-isoquinolin-1-one, 7-[(S)-5-((R)-2-Hydroxymethylpyrrolidin-1-ylmethyl)-2-oxooxazolidin-3-yl]-3-(2-trifluoromethylphenyl)-2H-isoquinolin-1-one, 7-[(S)-5-(4-Hydroxymethylpiperidin-1-ylmethyl)-2-oxooxazolidin-3-yl]-3-(2-trifluoromethylphenyl)-2H-isoquinolin-1-one, 7-[(S)-5-(4-Methoxypiperidin-1-ylmethyl)-2-oxooxazolidin-3-yl]-3-(2-trifluoromethylphenyl)-2H-isoquinolin-1-one, 7-((S)-5-Morpholin-4-ylmethyl-2-oxooxazolidin-3-yl)-3-(2-trifluoromethylphenyl)-2H-isoquinolin-1-one, 7-[(S)-(4-Hydroxypiperidin-1-ylmethyl)-2-oxooxazolidin-3-yl]-3-(2-trifluoromethylphenyl)-2H-isoquinolin-1-one, N-{(R)-2-Oxo-3-[1-oxo-3-(2-trifluoromethylphenyl)-1,2-dihydroisoquinolin-7-yl]oxazolidin-5-ylmethyl}methanesulfonamide, Ethanesulfonic acid {(R)-2-oxo-3-[1-oxo-3-(2-trifluoromethylphenyl)-1,2-dihydroisoquinolin-7-yl]oxazolidin-5-ylmethyl}amide, Propane-1-sulfonic acid {(R)-2-oxo-3-[1-oxo-3-(2trifluoromethylphenyl)-1,2-dihydroisoquinolin-7-yl]oxazolidin-5-ylmethyl}amide, Propane-2-sulfonic acid {(R)-2-oxo-3-[1-oxo-3-(2-trifluoromethylphenyl)-1,2-dihydroisoquinolin-7-yl]oxazolidin-5-ylmethyl}amide, Pentane-1-sulfonic acid {(R)-2-oxo-3-[1-oxo-3-(2-trifluoromethylphenyl)-1,2-dihydroisoquinolin-7-yl]oxazolidin-5-ylmethyl}amide, N-{(R)-2-Oxo-3-[1-oxo-3-(2-trifluoromethylphenyl)-1,2-dihydroisoquinolin-7-yl]oxazolidin-5-ylmethyl}benzenesulfonamide, Ethenesulfonic acid {(R)-2-oxo-3-[1-oxo-3-(2-trifluoromethylphenyl)-1,2-dihydroisoquinolin-7-yl]oxazolidin-5-ylmethyl}amide, 2-Hydroxyethanesulfonic acid {(R)-2-oxo-3-[1-oxo-3-(2-trifluoromethylphenyl)-1,2-dihydroisoquinolin-7-yl]oxazolidin-5-ylmethyl}}amide, 7-((R)-5-Hydroxymethyl-2-oxooxazolidin-3-yl)-3-(2-propylphenyl)-2H-isoquinolin-1-one, 7-((R)-5-Hydroxymethyl-2-oxooxazolidin-3-yl)-3-[2-(2-methylallyl)phenyl]-2H-isoquinolin-1-one, 7-((R)-5-Hydroxymethyl-2-oxooxazolidin-3-yl)-3-(2-propoxyphenyl)-2H-isoquinolin-1-one, 7-((R)-5-Hydroxymethyl-2-oxooxazolidin-3-yl)-3-[2-(2methoxyethoxy)phenyl]-2H-isoquinolin-1-one, 3-(2-Ethoxyphenyl)-7-((R)-5-hydroxymethyl-2-oxooxazolidin-3-yl)-2H-isoquinolin-1-one, 3-[2-(2,3-Dihydroxy-2-methylpropyl)phenyl]-7-((R)-5-hydroxymethyl-2-oxooxazolidin-3-yl)-2H-isoquinolin-1-one, 7-((R)-5-Hydroxymethyl-2-oxooxazolidin-3-yl)-3-[2-(2-hydroxypropyl)phenyl]-2H-isoquinolin-1-one, 3-(1-Ethyl-1H-benzimidazol-2-yl)-7-((R)-5-hydroxymethyl-2-oxooxazolidin-3-yl)-2H-isoquinolin-1-one, 7-((R)-5-Hydroxymethyl-2-oxooxazolidin-3-yl)-3-(2-methylsulfanylphenyl)-2H-isoquinolin-1-one, 7-((R)-5-Hydroxymethyl-2-oxooxazolidin-3-yl)-3-(2-methanesulfonylphenyl)-2H-isoquinolin-1-one, 7-(4-Hydroxy-5-hydroxymethyl-2-oxooxazolidin-3-yl)-3-(2-trifluoromethylphenyl)-2H-isoquinolin-1-one, 7-[(S)-5-((S)-1,2-Dihydroxyethyl)-2-oxooxazolidin-3-yl]-3-(2-trifluoromethylphenyl)-2H-isoquinolin-1-one, Cyclopropanesulfonic acid {(R)-2-oxo-3-[1-oxo-3-(2-trifluoromethylphenyl)-1,2-dihydroisoquinolin-7-yl]oxazolidin-5-ylmethyl}amide, 7-(4-Hydroxymethyl-2-oxopyrrolidin-1-yl)-3-(2-trifluoromethylphenyl)-2H-isoquinolin-1-one, 7-((S)-3-Hydroxy-2-oxopyrrolidin-1-yl)-3-(2-trifluoromethylphenyl)-2H-isoquinolin-1-one, 2-oxo-1-[1-oxo-3-(2-trifluoromethylphenyl)-1,2-dihydroisoquinolin-7-yl]pyrrolidine-3-carboxylic acid dimethylamide, 7-(3-Morpholin-4-ylmethyl-2-oxopyrrolidin-1-yl)-3-(2-trifluoromethylphenyl)-2H-isoquinolin-1-one, 7-(2-Oxo-3-piperidin-1-ylmethylpyrrolidin-1-yl)-3-(2-trifluoromethylphenyl)-2H-isoquinolin-1-one, 7-[3-(4-Hydroxypiperidin-1-ylmethyl)-2-oxopyrrolidin-1-yl]-3-(2-trifluoromethylphenyl)-2H-isoquinolin-1-one, 7-((3R,4R)-3,4-Dihydroxy-2-oxopyrrolidin-1-yl)-3-(2-trifluoromethylphenyl)-2H-isoquinolin-1-one, 7-(5-Hydroxymethyl)-3-methyl-2-oxoimidazolidin-1-yl)-3-(2-trifluoromethylphenyl)-2H-isoquinolin-1-one, 7-((R)-4-Benzyloxymethyl-2-oxoimidazolidin-1-yl)-3-(2-trifluoromethylphenyl)-2H-isoquinolin-1-one, 7-((R)-4-Hydroxymethyl-2-oxoimidazolidin-1-yl)-3-(2-trifluoromethylphenyl)-2H-isoquinolin-1-one, 7-(3-Methyl-2-oxotetrahydropyrimidin-1-yl)-3-(2-trifluoromethylphenyl)-2H-isoquinolin-1-one, Benzyl 3-oxo-4-[1-oxo-3-(2-trifluoromethylphenyl)-1,2-dihydroisoquinolin-7-yl]piperazine-1-carboxylate, 7-(2-oxopiperazin-1-yl)-3-(2-trifluoromethylphenyl)-2H-isoquinolin-1-one, 7-[(R)-5-((S)-1,2-Dihydroxyethyl)-2-oxooxazolidin-3-yl]-3-(2-trifluoromethylphenyl)-2H-isoquinolin-1-one, 7-[(R)-5-((R)-1,2-Dihydroxyethyl)-2-oxooxazolidin-3-yl]-3-(2-trifluoromethylphenyl)-2H-isoquinolin-1-one, 7-(5,5-Bishydroxymethyl-2-oxooxazolidin-3-yl)-3-(2-trifluoromethylphenyl)-2H-isoquinolin-1-one, 7-[3-(2-Hydroxyethyl)-5-oxoimidazolidin-1-yl]-3-(2-trifluoromethylphenyl)-2H-isoquinolin-1-one, 7-((R)-5-Hydroxymethyl-2-oxooxazolidin-3-yl)-3-(3-trifluoromethylphenyl)-2H-isoquinolin-1-one, 7-((R)-5-Hydroxymethyl-2-oxooxazolidin-3-yl)-3-naphthalen-1-yl-2H-isoquinolin-1-one, 3-Furan-2-yl-7-((R)-5-hydroxymethyl-2-oxooxazolidin-3-yl)-2H-isoquinolin-1-one, 7-((R)-5-Hydroxymethyl-2-oxooxazolidin-3-yl)-3-thiophen-2-yl-2H-isoquinolin-1-one, 7-((S)-5-Dimethylaminomethyl-2-oxooxazolidin-3-yl)-3-(2-trifluoromethylphenyl)-2H-isoquinolin-1-one, 7-[(S)-5-(1-Hydroxy-1-vinylallyl)-2-oxooxazolidin-3-yl]-3-(2-trifluoromethylphenyl)-2H-isoquinolin-1-one, 7-((R)-5-Hydroxymethyl-2-oxooxazolidin-3-yl)-3-(4-trifluoromethylphenyl)-2H-isoquinolin-1-one, 7-((R)-5-Hydroxymethyl-2-oxooxazolidin-3-yl)-3-(3-methylthiophen-2-yl)-2H-isoquinolin-1-one, 7-(3-oxomorpholin-4-yl)-3-(2-trifluoromethylphenyl)-2H-isoquinolin-1-one, (R)-2-oxo-3-[1-oxo-3-(2-trifluoromethylphenyl)-1,2-dihydroisoquinolin-7-yl]oxazolidin-5-ylmethyl methylaminoacetate, (R)-2-oxo-3-[1-oxo-3-(2-trifluoromethylphenyl)-1,2-dihydroisoquinolin-7-yl]oxazolidin-5-ylmethyl aminoacetate, (R)-2-oxo-3-[1-oxo-3-(2-trifluoromethylphenyl)-1,2-di-hydroisoquinolin-7-yl]oxazolidin-5-ylmethyl(S)-2-aminopropionate,
(R)-2-Oxo-3-[1-oxo-3-(2-trifluoromethylphenyl)-1,2-di-hydroisoquinolin-7-yl]oxazolidin-5-ylmethyl(S)-pyr-rolidine-2-carboxylate,
(R)-2-Oxo-3-[1-oxo-3-(2-trifluoromethylphenyl)-1,2-di-hydroisoquinolin-7-yl]oxazolidin-5-ylmethyl(S)-2-aminobutanoate,
(R)-2-Oxo-3-[1-oxo-3-(2-trifluoromethylphenyl)-1,2-di-hydroisoquinolin-7-yl]oxazolidin-5-ylmethyl(S)-2-aminopentanoate,
(R)-2-Oxo-3-[1-oxo-3-(2-trifluoromethylphenyl)-1,2-di-hydroisoquinolin-7-yl]oxazolidin-5-ylmethyl(S)-2-amino-4-methyl-pentanoate,
(R)-2-Oxo-3-[1-oxo-3-(2-trifluoromethylphenyl)-1,2-di-hydroisoquinolin-7-yl]oxazolidin-5-ylmethyl(2S,3S)-2-amino-3-methylpentanoate,
(R)-2-Oxo-3-[1-oxo-3-(2-trifluoromethylphenyl)-1,2-di-hydroisoquinolin-7-yl]oxazolidin-5-ylmethyl(S)-2-amino-3-methyl-butanoate,
(R)-2-Oxo-3-[1-oxo-3-(2-trifluoromethylphenyl)-1,2-di-hydroisoquinolin-7-yl]oxazolidin-5-ylmethyl(S)-2-aminohexanoate,
(R)-2-Oxo-3-[1-oxo-3-(2-trifluoromethylphenyl)-1,2-di-hydroisoquinolin-7-yl]oxazolidin-5-ylmethyl dimethy-laminoacetate,
(R)-2-Oxo-3-[1-oxo-3-(2-trifluoromethylphenyl)-1,2-di-hydroisoquinolin-7-yl]oxazolidin-5-ylmethyl 3-amino-propionate,
(R)-2-Oxo-3-[1-oxo-3-(2-trifluoromethylphenyl)-1,2-di-hydroisoquinolin-7-yl]oxazolidin-5-ylmethyl(S)-2-amino-3-phenylpropionate,
(R)-2-Oxo-3-[1-oxo-3-(2-trifluoromethylphenyl)-1,2-di-hydroisoquinolin-7-yl]oxazolidin-5-ylmethyl 4-ami-nobutanoate,
(R)-2-Oxo-3-[1-oxo-3-(2-trifluoromethylphenyl)-1,2-di-hydroisoquinolin-7-yl]oxazolidin-5-ylmethyl 3-methy-laminopropionate,
(R)-2-Oxo-3-[1-oxo-3-(2-trifluoromethylphenyl)-1,2-di-hydroisoquinolin-7-yl]oxazolidin-5-ylmethyl 3-dim-ethylaminopropionate,
3-{(R)-2-Oxo-3-[1-oxo-3-(2-trifluoromethylphenyl)-1,2-dihydroisoquinolin-7-yl]oxazolidin-5-ylmethoxycarbonyl}propionic acid,
2-{(R)-2-Oxo-3-[1-oxo-3-(2-trifluoromethylphenyl)-1,2-dihydroisoquinolin-7-yl]oxazolidin-5-ylmethoxycarbonyl}benzoic acid,
(R)-2-Oxo-3-[1-oxo-3-(2-trifluoromethylphenyl)-1,2-di-hydroisoquinolin-7-yl]oxazolidin-5-ylmethyl 2-amino-ethylsuccinamate,
(S)-2-Oxo-3-[1-oxo-3-(2-trifluoromethylphenyl)-1,2-di-hydroisoquinolin-7-yl]oxazolidin-5-ylmethyl methy-laminoacetate,
(S)-2-Oxo-3-[1-oxo-3-(2-trifluoromethylphenyl)-1,2-di-hydroisoquinolin-7-yl]oxazolidin-5-ylmethyl dimethy-laminoacetate,
(S)-2-Oxo-3-[1-oxo-3-(2-trifluoromethylphenyl)-1,2-di-hydroisoquinolin-7-yl]oxazolidin-5-ylmethyl(S)-2-amino-3-methylbutyrate,
(R)-2-Oxo-3-[1-oxo-3-trifluoromethylphenyl]-1,2-dihy-droisoquinolin-7-yl]-oxazolidin-5-ylmethyl 2-amino-2-methylpropionate,
(R)-2-Oxo-3-[1-oxo-3-(2-trifluoromethylphenyl)-1,2-di-hydroisoquinolin-7-yl]oxazolidin-5-ylmethyl 2-me-thyl-2-(methylamino)propionate,
(R)-2-Oxo-3-[1-oxo-3-(2-trifluoromethylphenyl)-1,2-di-hydroisoquinolin-7-yl]oxazolidin-5-ylmethyl 1-amino-cyclopentanecarboxylate,
Dibenzyl phosphoate (R)-2-oxo-3-[1-oxo-3-(2-trifluo-romethylphenyl)-1,2-dihydroisoquinolin-7-yl]-oxazo-lidin-5-ylmethyl ester,
3-{(S)-2-Oxo-3-[1-oxo-3-(2-trifluoromethylphenyl)-1,2-dihydroisoquinolin-7-yl]oxazolidin-5-ylmethoxycarbonyl}propionic acid,
2-{(S)-2-Oxo-3-[1-oxo-3-(2-trifluoromethylphenyl)-1,2-dihydroisoquinolin-7-yl]oxazolidin-5-ylmethoxycarbonyl}benzoic acid,
3-{(R)-2-Oxo-3-[1-oxo-3-(2-trifluoromethylphenyl)-1,2-dihydroisoquinolin-7-yl]oxazolidin-5-ylmethoxycarbonyl}butanoic acid,
(Z)-3-{(R)-2-Oxo-3-[1-oxo-3-(2-trifluoromethylphenyl)-1,2-dihydroisoquinolin-7-yl]oxazolidin-5-ylmethoxycarbonyl}acrylic acid,
2-(1-Methyl-1-{(S)-2-oxo-3-[1-oxo-3-(2-trifluorometh-ylphenyl)-1,2-dihydroisoquinolin-7-yl]oxazolidin-5-ylethoxycarbonyl}propionic acid,
2-(1-Methyl-1-{(S)-2-oxo-3-[1-oxo-3-(2-trifluorometh-ylphenyl)-1,2-dihydroisoquinolin-7-yl]oxazolidin-5-ylethoxycarbonyl}benzoic acid,
1-{(R)-2-Oxo-3-[1-oxo-3-(2-trifluoromethylphenyl)-1,2-dihydroisoquinolin-7-yl]-oxazolidin-5-ylmethyl}(S)-2-amino succinate,
(R)-2-Oxo-3-[1-oxo-3-(2-trifluoromethylphenyl)-1,2-di-hydroisoquinolin-7-yl]oxazolidin-5-ylmethyl(S)-2-amino-3-hydroxypropionate,
(R)-2-Oxo-3-[1-oxo-3-(2-trifluoromethylphenyl)-1,2-di-hydroisoquinolin-7-yl]oxazolidin-5-ylmethyl(2S,3R)-2-amino-3-hydroxybutanoate,
(Z)-3-{(S)-2-Oxo-3-[1-oxo-3-(2-trifluoromethylphenyl)-1,2-dihydroisoquinolin-7-yl]oxazolidin-5-ylmethoxycarbonyl}acrylic acid,
3-{(S)-2-Oxo-3-[1-oxo-3-(2-trifluoromethylphenyl)-1,2-dihydroisoquinolin-7-yl]oxazolidin-5-ylmethoxycarbonyl}butanoic acid,
2-(1-Methyl-1-{(S)-2-oxo-3-[1-oxo-3-(2-trifluorometh-ylphenyl)-1,2-dihydroisoquinolin-7-yl]oxazolidin-5-ylethoxycarbonyl}butanoic acid,
3-{(S)-2-Oxo-3-[1-oxo-3-(2-trifluoromethylphenyl)-1,2-dihydroisoquinolin-7-yl]oxazolidin-5-ylmethoxycar-bonyl}-(S)-2-hydroxypropionic acid,
3-{(S)-2-Oxo-3-[1-oxo-3-(2-trifluoromethylphenyl)-1,2-dihydroisoquinolin-7-yl]oxazolidin-5-ylmethoxycarbonyl}ethanoic acid,
(S)-2-Oxo-3-[1-oxo-3-(2-trifluoromethylphenyl)-1,2-di-hydroisoquinolin-7-yl]oxazolidin-5-ylmethyl(R)-2,3-dihydroxypropionate,
(S)-2-Oxo-3-[1-oxo-3-(2-trifluoromethylphenyl)-1,2-di-hydroisoquinolin-7-yl]oxazolidin-5-ylmethyl 3-hy-droxy-2-hydroxymethyl-2-methylpropionate,
(S)-2-Oxo-3-[1-oxo-3-(2-trifluoromethylphenyl)-1,2-di-hydroisoquinolin-7-yl]oxazolidin-5-ylmethyl 3-hy-droxy-2,2-bishydroxymethylpropionate,
(S)-2-Oxo-3-[1-oxo-3-(2-trifluoromethylphenyl)-1,2-di-hydroisoquinolin-7-yl]oxazolidin-5-ylmethyl(2-ami-noacetyl)methylaminoacetate,
(S)-2-Oxo-3-[1-oxo-3-(2-trifluoromethylphenyl)-1,2-di-hydroisoquinolin-7-yl]oxazolidin-5-ylmethyl 2-ami-noacetylaminoacetate,
5-{(S)-2-Oxo-3-[1-oxo-3-(2-trifluoromethylphenyl)-1,2-dihydroisoquinolin-7-yl]oxazolidin-5-ylmethyl}(S)-2-[(S)-2-amino-3-(1H-indol-3-yl)-propionylamino]-pen-tanedioate, (S)-2-Oxo-3-[1-oxo-3-(2-trifluoromethylphenyl)-1,2-dihydroisoquinolin-7-yl]oxazolidin-5-ylmethyl[2-(2-hydroxyethoxy)ethyl]carbamate, (R)-2-Oxo-3-[1-oxo-3-(2-trifluoromethylphenyl)-1,2-dihydroisoquinolin-7-yl]oxazolidin-5-ylmethyl(2,3-dihydroxypropyl)carbamate, (S)-2-Oxo-3-[1-oxo-3-(2-trifluoromethylphenyl)-1,2-dihydroisoquinolin-7-yl]oxazolidin-5-ylmethyl(2,3-dihydroxypropyl)carbamate, (S)-2-Oxo-3-[1-oxo-3-(2-trifluoromethylphenyl)-1,2-dihydroisoquinolin-7-yl]oxazolidin-5-ylmethyl(2-hydroxy-1-hydroxymethylethyl)carbamate, (S)-2-Oxo-3-[1-oxo-3-(2-trifluoromethylphenyl)-1,2-dihydroisoquinolin-7-yl]oxazolidin-5-ylmethyl[(2R,3S)-2,3,4-trihydroxybutyl]carbamate, (S)-2-Oxo-3-[1-oxo-3-(2-trifluoromethylphenyl)-1,2-dihydroisoquinolin-7-yl]oxazolidin-5-ylmethyl[(2S,3R,4R,5R)-2,3,4,5,6-pentahydroxyhexyl]carbamate, Ethyl{(R)-2-oxo-3-[1-oxo-3-(2-trifluoromethylphenyl)-1,2-dihydroisoquinolin-7-yl]oxazolidin-5-ylmethoxycarbonylamino}acetate, Ethyl carbonate (R)-2-oxo-3-[1-oxo-3-(2-trifluoromethylphenyl)-1,2-dihydroisoquinolin-7-yl]oxazolidin-5-ylmethyl ester, (S)-2-Oxo-3-[1-oxo-3-(2-trifluoromethylphenyl)-1,2-dihydroisoquinolin-7-yl]oxazolidin-5-ylmethyl nicotinate, (S)-2-Oxo-3-[1-oxo-3-(2-trifluoromethylphenyl)-1,2-dihydroisoquinolin-7-yl]oxazolidin-5-ylmethyl acetoxyacetate, (S)-2-Oxo-3-[1-oxo-3-(2-trifluoromethylphenyl)-1,2-dihydroisoquinolin-7-yl]oxazolidin-5-ylmethyl(2methoxyethoxy)acetate, (S)-2-Oxo-3-[1-oxo-3-(2-trifluoromethylphenyl)-1,2-dihydroisoquinolin-7-yl]oxazolidin-5-ylmethyl[2-(2-methoxyethoxy)ethoxy]acetate, (S)-2-Oxo-3-[1-oxo-3-(2-trifluoromethylphenyl)-1,2-dihydroisoquinolin-7-yl]oxazolidin-5-ylmethyl[2-(2-{2-[2-(2-methoxyethoxy)ethoxy]ethoxy}ethoxy)ethoxy]acetate, (S)-2-Oxo-3-[1-oxo-3-(2-trifluoromethylphenyl)-1,2-dihydroisoquinolin-7-yl]oxazolidin-5-ylmethyl {2-[2-(2-methoxyethoxy)ethoxy]ethoxy}acetate, (S)-2-Oxo-3-[1-oxo-3-(2-trifluoromethylphenyl)-1,2-dihydroisoquinolin-7-yl]oxazolidin-5-ylmethyl(2-{2-[2-(2-methoxyethoxy)ethoxy]ethoxy}ethoxy)acetate, (S)-2-Oxo-3-[1-oxo-3-(2-trifluoromethylphenyl)-1,2-dihydroisoquinolin-7-yl]oxazolidin-5-ylmethyl {2-[2-(2-{2-[2-(2-methoxyethoxy)ethoxy]ethoxy}ethoxy)ethoxy]ethoxy}-acetate, (S)-2-Oxo-3-[1-oxo-3-(2-trifluoromethylphenyl)-1,2-dihydroisoquinolin-7-yl]oxazolidin-5-ylmethyl[2-(2-hydroxyethoxy)ethoxy]acetate, (S)-2-Oxo-3-[1-oxo-3-(2-trifluoromethylphenyl)-1,2-dihydroisoquinolin-7-yl]oxazolidin-5-ylmethyl {2-[2-(2-hydroxyethoxy)ethoxy]ethoxy}acetate, (S)-2-Oxo-3-[1-oxo-3-(2-trifluoromethylphenyl)-1,2-dihydroisoquinolin-7-yl]oxazolidin-5-ylmethyl[2-(2-{2-[2-(2-hydroxyethoxy)ethoxy]ethoxy}ethoxy)ethoxy]acetate, (S)-2-Oxo-3-[1-oxo-3-(2-trifluoromethylphenyl)-1,2-dihydroisoquinolin-7-yl]oxazolidin-5-ylmethyl {2-[2-(2-{2-[2-(2-hydroxyethoxy)ethoxy]ethoxy}ethoxy)-ethoxy]ethoxy}acetate, 2-[2-(2-Methoxy-1-methylethoxy)-1-methylethoxy]-1-methylethyl carbonate (S)-2-oxo-3-[1-oxo-3-(2-trifluoromethylphenyl)-1,2-dihydroisoquinolin-7-yl]oxazolidin-5-ylmethyl ester, 2-(2-Hydroxyethoxy)ethyl carbonate (S)-2-oxo-3-[1-oxo-3-(2-trifluoromethylphenyl)-1,2-dihydroisoquinolin-7-yl]oxazolidin-5-ylmethyl ester, 2-[2-(2-Hydroxyethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester, 2-{2-[2-(2-Hydroxyethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester, 2-[2-(2-{2-[2-(2-Hydroxyethoxy)ethoxy]ethoxy}ethoxy)-ethoxy]ethyl carbonate (S)-2-oxo-3-[1-oxo-3-(2-trifluoromethylphenyl)-1,2-dihydroisoquinolin-7-yl]oxazolidin-5-ylmethyl ester, (S)-2-Oxo-3-[1-oxo-3-(2-trifluoromethylphenyl)-1,2-dihydroisoquinolin-7-yl]oxazolidin-5-ylmethyl carbonate 1,4,7,10-tetraoxacyclododec-2-ylmethyl ester, 2-(2-Hydroxy-1-hydroxymethylethoxy)ethyl carbonate (S)-2-oxo-3-[1-oxo-3-(2-trifluoromethylphenyl)-1,2-dihydroisoquinolin-7-yl]oxazolidin-5-ylmethyl ester, 2-{2-[2-(2-{2-[2-(2-{2-[2-(2-Hydroxyethoxy)ethoxy]ethoxy}ethoxy)ethoxy]ethoxy}ethoxy)-ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester, 2-{2-[2-(2-{2-[2-(2-{2-[2-(2-Methoxyethoxy)ethoxy]ethoxy}ethoxy)ethoxy]ethoxy}ethoxy)-ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester, 2-[2-(2-Hydroxyethoxy)ethoxy]-1-[2-(2-hydroxyethoxy)ethoxymethyl]ethyl carbonate (S)-2-oxo-3-[1-oxo-3-(2-trifluoromethylphenyl)-1,2-dihydroisoquinolin-7-yl]oxazolidin-5-ylmethyl ester, 2-[2-(2-Hydroxyethoxy)ethoxy]-1-{2-[2-(2-hydroxyethoxy)ethoxy]-1-[2-(2-hydroxyethoxy)ethoxymethyl]ethoxymethyl}ethyl carbonate (S)-2-oxo-3-[1-oxo-3-(2-trifluoromethylphenyl)-1,2-dihydroisoquinolin-7-yl]oxazolidin-5-ylmethyl ester, 2-(2-Hydroxyethoxy)-1-(2-hydroxyethoxymethyl)ethyl carbonate (S)-2-oxo-3-[1-oxo-3-(2-trifluoromethylphenyl)-1,2-dihydroisoquinolin-7-yl]oxazolidin-5-ylmethyl ester, 2-{2-[2-(2-Hydroxyethoxy)ethoxy]ethoxy}-1-{2-[2-(2-hydroxyethoxy)ethoxy]ethoxymethyl}ethyl carbonate (S)-2-oxo-3-[1-oxo-3-(2-trifluoromethylphenyl)-1,2-dihydroisoquinolin-7-yl]oxazolidin-5-ylmethyl ester, 2-{2-[2-(2-{2-[2-(2-Hydroxyethoxy)ethoxy]ethoxy}-ethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester, 2-(2-{2-[2-(2-{2-[2-(2-Hydroxyethoxy)ethoxy]ethoxy}-ethoxy)ethoxy]ethoxy}ethoxy)ethyl carbonate (S)-2-oxo-3-[1-oxo-3-(2-trifluoromethylphenyl)-1,2-dihydroisoquinolin-7-yl]oxazolidin-5-ylmethyl ester, 2-[2-(2-{2-[2-(2-{2-[2-(2-Hydroxyethoxy)ethoxy]-ethoxy}ethoxy)ethoxy]ethoxy}ethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester, (2-{2-[2-(2-{2-[2-(2-{2-[2-(2-methoxyethoxy)ethoxy]-ethoxy}ethoxy)ethoxy]ethoxy}ethoxy)ethoxy] ethoxy}ethoxy)-acetic acid (S)-2-oxo-3-[1-oxo-3-(2- trifluoromethylphenyl)-1,2-dihydroisoquinolin-7-yl]
oxazolidin-5-ylmethyl ester,
1-Methyl-1-{(S)-2-oxo-3-[1-oxo-3-(2-trifluoromethylphenyl)-1,2-dihydroisoquinolin-7-yl]oxazolidin-5-yl}ethyl aminoacetate,
1-Methyl-1-{(S)-2-oxo-3-[1-oxo-3-(2-trifluoromethylphenyl)-1,2-dihydroisoquinolin-7-yl]oxazolidin-5-yl}ethyl methylaminoacetate,
1-Methyl-1-{(S)-2-oxo-3-[1-oxo-3-(2-trifluoromethylphenyl)-1,2-dihydroisoquinolin-7-yl]oxazolidin-5-yl}ethyl dimethylaminoacetate,
1-Methyl-1-{(S)-2-oxo-3-[1-oxo-3-(2-trifluoromethylphenyl)-1,2-dihydroisoquinolin-7-yl]oxazolidin-5-yl}ethyl 4-aminobutanoate,
1-Methyl-1-{(S)-2-oxo-3-[1-oxo-3-(2-trifluoromethylphenyl)-1,2-dihydroisoquinolin-7-yl]oxazolidin-5-yl}ethyl(S)-2-aminopropionate,
1-Methyl-1-{(S)-2-oxo-3-[1-oxo-3-(2-trifluoromethylphenyl)-1,2-dihydroisoquinolin-7-yl]oxazolidin-5-yl}ethyl(S)-2-amino-3-methylbutanoate,
1-Methyl-1-{(S)-2-oxo-3-[1-oxo-3-(2-trifluoromethylphenyl)-1,2-dihydroisoquinolin-7-yl]oxazolidin-5-yl}ethyl(S)-pyrrolidine-2-carboxylate,
1-Methyl-1-{(S)-2-oxo-3-[1-oxo-3-(2-trifluoromethylphenyl)-1,2-dihydroisoquinolin-7-yl]oxazolidin-5-yl}ethyl [(2-aminoacetyl)methylamino]acetate,
1-Methyl-1-{(S)-2-oxo-3-[1-oxo-3-(2-trifluoromethylphenyl)-1,2-dihydroisoquinolin-7-yl]oxazolidin-5-yl}ethyl(S)-1-(2-aminoacetyl)pyrrolidine-2-carboxylate,
(E)-3-{(R)-2-Oxo-3-[1-oxo-3-(2-trifluoromethylphenyl)-1,2-dihydroisoquinolin-7-yl]oxazolidin-5-ylmethoxycarbonyl}acrylic acid,
1-{(R)-2-Oxo-3-[1-oxo-3-(2-trifluoromethylphenyl)-1,2-dihydroisoquinolin-7-yl]oxazolidin-5-ylmethyl}(S)-2-aminopentanedionate,
(S)-2-Oxo-3-[1-oxo-3-(2-trifluoromethylphenyl)-1,2-dihydroisoquinolin-7-yl]oxazolidin-5-ylmethyl(2S,3R,4S,5R)-3,4,5,6-tetrahydroxytetrahydropyrane-2-carboxylate,
(2-{2-[2-(2-{2-[2-(2-methoxyethoxy)ethoxy]ethoxy}ethoxy)ethoxy]ethoxy}ethoxy)acetic acid (S)-2-oxo-3-[1-oxo-3-(2-trifluoromethylphenyl)-1,2-dihydroisoquinolin-7-yl]oxazolidin-5-ylmethyl ester,
[2-(2-{2-[2-(2-{2-[2-(2-methoxyethoxy)ethoxy]ethoxy}ethoxy)ethoxy]ethoxy}ethoxy)-ethoxy]acetic acid (S)-2-oxo-3-[1-oxo-3-(2-trifluoromethylphenyl)-1,2-dihydroisoquinolin-7-yl]oxazolidin-5-ylmethyl ester,
{2-[2-(2-{2-[2-(2-{2-[2-(2-methoxyethoxy)ethoxy]ethoxy}ethoxy)ethoxy]ethoxy}ethoxy)-ethoxy]ethoxy}acetic acid (S)-2-oxo-3-[1-oxo-3-(2-trifluoromethylphenyl)-1,2-dihydroisoquinolin-7-yl]oxazolidin-5-ylmethyl ester,
[2-(2-{2-[2-(2-{2-[2-(2-{2-[2-(2-methoxyethoxy)ethoxy]ethoxy}ethoxy)ethoxy]ethoxy}ethoxy)-ethoxy]ethoxy}ethoxy)ethoxy]acetic acid (S)-2-oxo-3-[1-oxo-3-(2-trifluoromethylphenyl)-1,2-dihydroisoquinolin-7-yl]oxazolidin-5-ylmethyl ester,
{2-[2-(2-{2-[2-(2-{2-[2-(2-{2-[2-(2-methoxyethoxy)ethoxy]ethoxy}ethoxy)ethoxy]ethoxy}ethoxy)-ethoxy]ethoxy}ethoxy)ethoxy]ethoxy}acetic acid (S)-2-oxo-3-[1-oxo-3-(2-trifluoromethylphenyl)-1,2-dihydroisoquinolin-7-yl]oxazolidin-5-ylmethyl ester,
2-[2-(2-{2-[2-(2-{2-[2-(2-{2-[2-(2-Methoxyethoxy)ethoxy]ethoxy)ethoxy]ethoxy}ethoxy)-ethoxy]ethoxy}ethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester,
2-(2-{2-[2-(2-{2-[2-(2-{2-[2-(2-Methoxyethoxy)ethoxy]ethoxy}ethoxy)ethoxy]ethoxy}ethoxy)-ethoxy]ethoxy}ethoxy)ethyl carbonate (S)-2-oxo-3-[1-oxo-3-(2-trifluoromethylphenyl)-1,2-dihydroisoquinolin-7-yl]oxazolidin-5-ylmethyl ester,
2-[2-(2-{2-[2-(2-{2-[2-(2-Methoxyethoxy)ethoxy]ethoxy}ethoxy)ethoxy]ethoxy}ethoxy)-ethoxy]ethyl carbonate (S)-2-oxo-3-[1-oxo-3-(2-trifluoromethylphenyl)-1,2-dihydroisoquinolin-7-yl]oxazolidin-5-ylmethyl ester,
2-(2-{2-[2-(2-{2-[2-(2-Methoxyethoxy)ethoxy]ethoxy}ethoxy)ethoxy]ethoxy}ethoxy)-ethyl carbonate (S)-2-oxo-3-[1-oxo-3-(2-trifluoromethylphenyl)-1,2-dihydroisoquinolin-7-yl]oxazolidin-5-ylmethyl ester,
2-{2-[2-(2-{2-[2-(2-Methoxyethoxy)ethoxy]ethoxy}ethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester,
2-[2-(2-{2-[2-(2-Methoxyethoxy)ethoxy]ethoxy}ethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester,
2-(2-{2-[2-(2-Methoxyethoxy)ethoxy]ethoxy}ethoxy)ethyl carbonate (S)-2-oxo-3-[1-oxo-3-(2-trifluoromethylphenyl)-1,2-dihydroisoquinolin-7-yl]oxazolidin-5-ylmethyl ester,
2-{2-[2-(2-Methoxyethoxy)ethoxy]ethoxy}ethyl carbonate (S)-2-oxo-3-[1-oxo-3-(2-trifluoromethylphenyl)-1,2-dihydroisoquinolin-7-yl]oxazolidin-5-ylmethyl ester,
2-[2-(2-Methoxyethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester,
2-(2-Methoxyethoxy)ethyl carbonate (S)-2-oxo-3-[1-oxo-3-(2-trifluoromethylphenyl)-1,2-dihydroisoquinolin-7-yl]oxazolidin-5-ylmethyl ester,
2-Methoxyethyl carbonate (S)-2-oxo-3-[1-oxo-3-(2trifluoromethylphenyl)-1,2-dihydroisoquinolin-7-yl]oxazolidin-5-ylmethyl ester,
(S)-2-Oxo-3-[1-oxo-3-(2-trifluoromethylphenyl)-1,2-dihydroisoquinolin-7-yl]oxazolidin-5-ylmethyl(2-{2-[2-(2-{2-[2-(2-hydroxyethoxy)ethoxy]ethoxy}ethoxy)ethoxy]ethoxy}ethoxy)acetate,
(S)-2-Oxo-3-[1-oxo-3-(2-trifluoromethylphenyl)-1,2-dihydroisoquinolin-7-yl]oxazolidin-5-ylmethyl[2-(2-{2-[2-(2-{2-[2-(2-hydroxyethoxy)ethoxy]ethoxy}ethoxy)ethoxy]-ethoxy}ethoxy)-ethoxy]acetate,
(S)-2-Oxo-3-[1-oxo-3-(2-trifluoromethylphenyl)-1,2-dihydroisoquinolin-7-yl]oxazolidin-5-ylmethyl {2-[2-(2-{2-[2-(2-{2-[2-(2-hydroxyethoxy)ethoxy]ethoxy}ethoxy)ethoxy]-ethoxy}ethoxy)ethoxy]ethoxy}acetate,
(S)-2-Oxo-3-[1-oxo-3-(2-trifluoromethylphenyl)-1,2-dihydroisoquinolin-7-yl]oxazolidin-5-ylmethyl(2-{2-[2-(2-{2-[2-(2-{2-[2-(2-hydroxyethoxy)ethoxy]ethoxy}ethoxy)-ethoxy]ethoxy}ethoxy)ethoxy]ethoxy}ethoxy)acetate,
(S)-2-Oxo-3-[1-oxo-3-(2-trifluoromethylphenyl)-1,2-dihydroisoquinolin-7-yl]oxazolidin-5-ylmethyl[2-(2-{2-[2-(2-{2-[2-(2-{2-[2-(2-hydroxyethoxy)ethoxy]ethoxy}ethoxy)-ethoxy]ethoxy}ethoxy)ethoxy]ethoxy}ethoxy)ethoxy]acetate,
(S)-2-Oxo-3-[1-oxo-3-(2-trifluoromethylphenyl)-1,2-dihydroisoquinolin-7-yl]oxazolidin-5-ylmethyl {2-[2-(2-{2-[2-(2-{2-[2-(2-{2-[2-(2-hydroxyethoxy)ethoxy]

ethoxy}-ethoxy)ethoxy]ethoxy}ethoxy)ethoxy]ethoxy}ethoxy)ethoxy]-ethoxy}acetate, 2-(2-{2-[2-(2-{2-[2-(2-{2-[2-(2-Hydroxyethoxy)ethoxy]ethoxy}ethoxy)ethoxy]ethoxy}ethoxy)-ethoxy]ethoxy}ethoxy)ethyl carbonate (S)-2-oxo-3-[1-oxo-3-(2-trifluoromethylphenyl)-1,2-dihydroisoquinolin-7-yl]oxazolidin-5-ylmethyl ester, and 2-[2-(2-{2-[2-(2-{2-[2-(2-{2-[2-(2-Hydroxyethoxy)ethoxy]ethoxy}ethoxy)ethoxy]ethoxy}ethoxy)-ethoxy]ethoxy}ethoxy)ethoxy]ethyl carbonate (S)-2-oxo-3-[1-oxo-3-(2-trifluoromethylphenyl)-1,2-dihydroisoquinolin-7-yl]oxazolidin-5-ylmethyl ester.

14. A pharmaceutical composition, which comprises, as an active ingredient, the compound, or pharmaceutically acceptable salt thereof according to claim 1.

15. A therapeutic or preventive agent used for malignant tumor, which comprises, as an active ingredient, the compound, or pharmaceutically acceptable salt thereof according to any claim 1.

16. The therapeutic or preventive agent according to claim 15, wherein the malignant tumor is solid cancer.

* * * * *